US009677869B2

(12) United States Patent
Berkeley et al.

(10) Patent No.: US 9,677,869 B2
(45) Date of Patent: Jun. 13, 2017

(54) SYSTEM AND METHOD FOR GENERATING A WIDE-FIELD OCT IMAGE OF A PORTION OF A SAMPLE

(71) Applicant: Perimeter Medical Imaging, Inc., Toronto (CA)

(72) Inventors: Andrew Berkeley, Woodstock (CA); David Rempel, Toronto (CA); Jason Silver, Toronto (CA)

(73) Assignee: PERIMETER MEDICAL IMAGING, INC., Toronto (CA)

( * ) Notice: Subject to any disclaimer, the term of this patent is extended or adjusted under 35 U.S.C. 154(b) by 15 days.

(21) Appl. No.: 14/649,697

(22) PCT Filed: Dec. 5, 2013

(86) PCT No.: PCT/CA2013/001010
§ 371 (c)(1),
(2) Date: Jun. 4, 2015

(87) PCT Pub. No.: WO2014/085911
PCT Pub. Date: Jun. 12, 2014

(65) Prior Publication Data
US 2016/0040976 A1 Feb. 11, 2016

Related U.S. Application Data

(60) Provisional application No. 61/733,837, filed on Dec. 5, 2012.

(51) Int. Cl.
*G01B 9/02* (2006.01)
*A61B 5/00* (2006.01)
(Continued)

(52) U.S. Cl.
CPC ........ *G01B 9/02041* (2013.01); *A61B 5/0066* (2013.01); *G01B 9/02091* (2013.01); *G01N 21/359* (2013.01); *G01N 21/4795* (2013.01)

(58) Field of Classification Search
CPC ............ A61B 3/102; A61B 2090/3735; A61B 5/0066; G01B 9/02041; G01B 9/02091; G01N 21/359; G01N 21/4795
See application file for complete search history.

(56) References Cited

U.S. PATENT DOCUMENTS

| 4,141,032 A | 2/1979 | Haeusler |
| 5,321,501 A | 6/1994 | Swanson et al. |

(Continued)

FOREIGN PATENT DOCUMENTS

| CA | 2729166 A1 | 12/2009 |
| EP | 1887312 A1 | 2/2008 |

(Continued)

OTHER PUBLICATIONS

International Preliminary Report on Patentability issued on Jun. 9, 2015 in relation to PCT/CA2013/001010, includes Written Opinion completed on Feb. 19, 2014.

(Continued)

*Primary Examiner* — Michael P Lapage
(74) *Attorney, Agent, or Firm* — Bereskin & Parr LLP/S.E.N.C.R.L., s.r.l.; Tony Orsi

(57) ABSTRACT

Various embodiments of systems and methods are described herein for obtaining wide field OCT images and other types of image data from at least one portion of a sample. Various embodiments of systems, and methods are described herein for assessing a degree of differentiation for a second region of an OCT image of a tissue sample with respect to another first. Various embodiments of a sample container are also described herein for containing a tissue sample and maintaining the tissue sample in a defined orientation during imaging or handling.

32 Claims, 70 Drawing Sheets

(51) Int. Cl.
*G01N 21/359* (2014.01)
*G01N 21/47* (2006.01)

(56) References Cited

U.S. PATENT DOCUMENTS

| | | |
|---|---|---|
| 5,373,971 A | 12/1994 | Laffy et al. |
| 5,836,877 A | 11/1998 | Zavislan |
| 5,920,390 A | 7/1999 | Farahi et al. |
| 5,975,697 A | 11/1999 | Podoleanu et al. |
| 5,978,695 A | 11/1999 | Greenwald et al. |
| 5,995,867 A | 11/1999 | Zavislan et al. |
| 6,034,804 A | 3/2000 | Bashkansky et al. |
| 6,053,613 A | 4/2000 | Wei et al. |
| 6,057,920 A | 5/2000 | Fercher et al. |
| 6,134,009 A | 10/2000 | Zavislan |
| 6,134,010 A | 10/2000 | Zavislan |
| 6,137,585 A | 10/2000 | Hitzenberger et al. |
| 6,174,291 B1 | 1/2001 | McMahon et al. |
| 6,225,107 B1 | 5/2001 | Nagle |
| 6,263,233 B1 | 7/2001 | Zavislan et al. |
| 6,288,784 B1 | 9/2001 | Hitzenberger et al. |
| 6,293,674 B1 | 9/2001 | Huang et al. |
| 6,304,373 B1 | 10/2001 | Zavislan |
| 6,307,634 B2 | 10/2001 | Hitzenberger et al. |
| 6,330,106 B1 | 12/2001 | Greenwald et al. |
| 6,360,115 B1 | 3/2002 | Greenwald et al. |
| 6,411,434 B1 | 6/2002 | Eastman et al. |
| 6,413,252 B1 | 7/2002 | Zavislan |
| 6,424,852 B1 | 7/2002 | Zavislan |
| 6,577,394 B1 | 6/2003 | Zavislan |
| 6,599,247 B1 | 7/2003 | Stetten |
| 6,608,684 B1 | 8/2003 | Gelikonov et al. |
| 6,636,755 B2 | 10/2003 | Toida |
| 6,668,186 B1 | 12/2003 | Zavislan et al. |
| 6,684,092 B2 | 1/2004 | Zavislan |
| 6,710,875 B1 | 3/2004 | Zavislan |
| 6,720,547 B1 | 4/2004 | Rajadhyaksha et al. |
| 6,726,325 B2 | 4/2004 | Xie et al. |
| 6,741,359 B2 | 5/2004 | Wei et al. |
| 6,745,067 B1 | 6/2004 | Zavislan et al. |
| 6,826,257 B2 | 11/2004 | Sayre et al. |
| 6,856,458 B2 | 2/2005 | Greenwald et al. |
| 6,922,250 B2 | 7/2005 | Fercher |
| 6,937,886 B2 | 8/2005 | Zavislan |
| 7,003,345 B1 | 2/2006 | Eastman |
| 7,047,064 B1 | 5/2006 | Zavislan et al. |
| 7,061,622 B2 | 6/2006 | Rollins et al. |
| 7,110,114 B2 | 9/2006 | Rajadhyaksha et al. |
| 7,126,693 B2 | 10/2006 | Everett et al. |
| 7,127,040 B2 | 10/2006 | Sayre et al. |
| 7,139,122 B1 | 11/2006 | Eastman et al. |
| 7,145,661 B2 | 12/2006 | Hitzenberger |
| 7,148,970 B2 | 12/2006 | de Boer |
| 7,190,464 B2 | 3/2007 | Alphonse |
| 7,190,990 B2 | 3/2007 | Zavislan et al. |
| 7,194,118 B1 | 3/2007 | Harris et al. |
| 7,225,010 B1 | 5/2007 | Zavislan |
| 7,227,630 B1 | 6/2007 | Zavislan et al. |
| 7,231,243 B2 | 6/2007 | Tearney et al. |
| 7,242,480 B2 | 7/2007 | Alphonse |
| 7,301,644 B2 | 11/2007 | Knighton et al. |
| 7,310,150 B2 | 12/2007 | Guillermo et al. |
| 7,321,394 B1 | 1/2008 | Grodevant |
| 7,330,270 B2 | 2/2008 | O'Hara et al. |
| 7,330,273 B2 | 2/2008 | Podoleanu et al. |
| 7,349,098 B2 | 3/2008 | Li |
| 7,355,716 B2 | 4/2008 | de Boer et al. |
| 7,365,856 B2 | 4/2008 | Everett et al. |
| 7,365,858 B2 | 4/2008 | Fang-Yen et al. |
| 7,365,859 B2 | 4/2008 | Yun et al. |
| 7,366,376 B2 | 4/2008 | Shishkov et al. |
| 7,382,464 B2 | 6/2008 | Everett et al. |
| 7,382,949 B2 | 6/2008 | Bouma et al. |
| 7,391,520 B2 | 6/2008 | Zhou et al. |
| 7,394,592 B2 | 7/2008 | Fox et al. |
| 7,400,410 B2 | 7/2008 | Baker et al. |
| 7,401,921 B2 | 7/2008 | Baker et al. |
| 7,418,169 B2 | 8/2008 | Tearney et al. |
| 7,450,243 B2 | 11/2008 | Marks et al. |
| 7,452,077 B2 | 11/2008 | Meyer et al. |
| 7,456,957 B2 | 11/2008 | Everett et al. |
| 7,466,423 B2 | 12/2008 | Podoleanu et al. |
| 7,474,407 B2 | 1/2009 | Gutin |
| 7,480,059 B2 | 1/2009 | Zhou et al. |
| 7,492,466 B2 | 2/2009 | Chan et al. |
| 7,508,525 B2 | 3/2009 | Zhou et al. |
| 7,515,266 B2 | 4/2009 | Rajadhyaksha et al. |
| 7,519,096 B2 | 4/2009 | Bouma et al. |
| 7,538,859 B2 | 5/2009 | Tearney et al. |
| 7,545,504 B2 | 6/2009 | Buckland et al. |
| 7,554,668 B2 | 6/2009 | Zhou et al. |
| 7,554,669 B2 | 6/2009 | Buckland et al. |
| 7,557,929 B2 | 7/2009 | Fang-Yen et al. |
| 7,557,931 B2 | 7/2009 | Toida |
| 7,567,349 B2 | 7/2009 | Tearney et al. |
| 7,573,627 B2 | 8/2009 | Mills et al. |
| 7,593,559 B2 | 9/2009 | Toth et al. |
| 7,602,501 B2 | 10/2009 | Ralston et al. |
| 7,616,986 B2 | 11/2009 | Seibel et al. |
| 7,623,908 B2 | 11/2009 | Boppart et al. |
| 7,631,970 B2 | 12/2009 | Wei |
| 7,643,152 B2 | 1/2010 | de Boer et al. |
| 7,643,153 B2 | 1/2010 | de Boer et al. |
| 7,643,154 B2 | 1/2010 | Kikawa et al. |
| 7,643,155 B2 | 1/2010 | Marks et al. |
| 7,659,990 B2 | 2/2010 | Knighton et al. |
| 7,668,342 B2 | 2/2010 | Everett et al. |
| 7,676,258 B2 | 3/2010 | Eastman |
| 7,695,140 B2 | 4/2010 | Fercher |
| 7,711,410 B2 | 5/2010 | Zavislan et al. |
| 7,719,692 B2 | 5/2010 | Izatt et al. |
| 7,724,786 B2 | 5/2010 | Bouma et al. |
| 7,731,362 B2 | 6/2010 | Gerlach |
| 7,733,497 B2 | 6/2010 | Yun et al. |
| 7,742,173 B2 | 6/2010 | Yun et al. |
| 7,742,174 B2 | 6/2010 | Izatt et al. |
| 7,755,769 B2 | 7/2010 | Everett et al. |
| 7,761,139 B2 | 7/2010 | Tearney et al. |
| 7,768,652 B2 | 8/2010 | Everett |
| 7,782,464 B2 | 8/2010 | Mujat et al. |
| 7,787,129 B2 | 8/2010 | Zysk et al. |
| RE41,633 E | 9/2010 | Zhou et al. |
| 7,796,270 B2 | 9/2010 | Yelin et al. |
| 7,797,119 B2 | 9/2010 | de Boer et al. |
| 7,798,647 B2 | 9/2010 | Meyer et al. |
| 7,813,609 B2 | 10/2010 | Petersen et al. |
| 7,813,788 B2 | 10/2010 | Zavislan et al. |
| 7,822,468 B2 | 10/2010 | Stamnes et al. |
| 7,830,525 B2 | 11/2010 | Buckland et al. |
| 7,843,572 B2 | 11/2010 | Tearney et al. |
| 7,847,949 B2 | 12/2010 | Tearney et al. |
| 7,847,951 B2 | 12/2010 | Buckland et al. |
| 7,848,791 B2 | 12/2010 | Schmitt et al. |
| 7,859,679 B2 | 12/2010 | Bouma et al. |
| 7,859,749 B2 | 12/2010 | Fox et al. |
| 7,864,822 B2 | 1/2011 | Bouma et al. |
| 7,864,996 B2 | 1/2011 | Hemmer et al. |
| 7,865,231 B2 | 1/2011 | Tearney et al. |
| 7,869,663 B2 | 1/2011 | Buckland et al. |
| 7,872,757 B2 | 1/2011 | de Boer et al. |
| 7,872,759 B2 | 1/2011 | Tearney et al. |
| 7,878,651 B2 | 2/2011 | O'Hara et al. |
| 7,884,945 B2 | 2/2011 | Srinivasan et al. |
| 7,903,257 B2 | 3/2011 | de Boer et al. |
| 7,909,463 B2 | 3/2011 | Dick et al. |
| 7,911,621 B2 | 3/2011 | Motaghiannezam et al. |
| 7,916,387 B2 | 3/2011 | Schmitt |
| 7,920,271 B2 | 4/2011 | Vakoc et al. |
| 7,924,429 B2 | 4/2011 | Knighton et al. |
| 7,929,146 B2 | 4/2011 | Izatt et al. |
| 7,933,021 B2 | 4/2011 | De Boer |
| 7,935,060 B2 | 5/2011 | Schmitt et al. |
| 7,945,312 B2 | 5/2011 | Hular et al. |
| 7,949,019 B2 | 5/2011 | Bouma et al. |

(56) References Cited

U.S. PATENT DOCUMENTS

| | | |
|---|---|---|
| 7,952,718 B2 | 5/2011 | Li et al. |
| 7,961,214 B2 | 6/2011 | Grodevant |
| 7,969,578 B2 | 6/2011 | Yun et al. |
| 7,982,879 B2 | 7/2011 | Desjardins et al. |
| 7,982,881 B2 | 7/2011 | Fercher et al. |
| 7,992,998 B2 | 8/2011 | Bergner et al. |
| 7,995,210 B2 | 8/2011 | Tearney et al. |
| 7,995,627 B2 | 8/2011 | Bouma et al. |
| 8,018,598 B2 | 9/2011 | Cense et al. |
| 8,032,200 B2 | 10/2011 | Tearney et al. |
| 8,040,524 B2 | 10/2011 | Ozawa |
| 8,040,608 B2 | 10/2011 | Evans et al. |
| 8,045,176 B2 | 10/2011 | Everett et al. |
| 8,050,747 B2 | 11/2011 | Tearney et al. |
| 8,054,468 B2 | 11/2011 | de Boer et al. |
| 8,064,989 B2 | 11/2011 | Brown et al. |
| 8,066,374 B2 | 11/2011 | Koschmieder et al. |
| 8,073,202 B2 | 12/2011 | Everett et al. |
| 8,079,711 B2 | 12/2011 | Stetson et al. |
| 8,081,316 B2 | 12/2011 | de Boer et al. |
| 8,085,408 B2 | 12/2011 | Everett et al. |
| 8,115,918 B2 | 2/2012 | Zavislan et al. |
| 8,115,935 B2 | 2/2012 | Everett et al. |
| 8,116,605 B2 | 2/2012 | Petersen et al. |
| 8,120,779 B2 | 2/2012 | Buckland et al. |
| 8,121,670 B2 | 2/2012 | Zavislan |
| 8,123,353 B2 | 2/2012 | Biernat et al. |
| 8,125,648 B2 | 2/2012 | Milner et al. |
| 8,128,229 B2 | 3/2012 | Meyer et al. |
| 8,149,418 B2 | 4/2012 | Tearney et al. |
| 8,149,506 B2 | 4/2012 | Eastman et al. |
| 8,150,496 B2 | 4/2012 | Tearney et al. |
| 8,162,140 B2 | 4/2012 | Hansen et al. |
| 8,174,702 B2 | 5/2012 | Tearney et al. |
| 8,175,685 B2 | 5/2012 | Yun et al. |
| 8,180,131 B2 | 5/2012 | Toth et al. |
| 8,184,351 B2 | 5/2012 | Mills et al. |
| 8,189,201 B2 | 5/2012 | Haisch et al. |
| 8,204,300 B2 | 6/2012 | Sugita et al. |
| 8,208,688 B2 | 6/2012 | Everett et al. |
| 8,208,995 B2 | 6/2012 | Tearney et al. |
| 8,208,996 B2 | 6/2012 | Meyer et al. |
| 8,211,020 B2 | 7/2012 | Stetten et al. |
| 8,218,152 B1 | 7/2012 | Marks et al. |
| 8,220,924 B2 | 7/2012 | Hanebuchi et al. |
| 8,223,143 B2 | 7/2012 | Dastmalchi et al. |
| 8,230,866 B2 | 7/2012 | Hauger et al. |
| 8,251,510 B2 | 8/2012 | Kobayashi et al. |
| 8,251,511 B2 | 8/2012 | Stetson et al. |
| 8,253,779 B2 | 8/2012 | Stetten |
| 8,260,401 B2 | 9/2012 | Herrmann et al. |
| 8,265,735 B2 | 9/2012 | Kato et al. |
| 8,287,126 B2 | 10/2012 | Hauger et al. |
| 8,289,522 B2 | 10/2012 | Tearney et al. |
| 8,300,309 B2 | 10/2012 | Haisch et al. |
| 8,301,227 B2 | 10/2012 | Phillips et al. |
| 8,319,974 B2 | 11/2012 | Knighton et al. |
| 8,325,419 B2 | 12/2012 | Schmitt |
| 8,332,016 B2 | 12/2012 | Stetson |
| 8,340,455 B2 | 12/2012 | Rolland et al. |
| 8,351,665 B2 | 1/2013 | Tearney et al. |
| 8,355,138 B2 | 1/2013 | Yun et al. |
| 8,363,958 B2 | 1/2013 | Everett et al. |
| 8,366,271 B2 | 2/2013 | Izatt et al. |
| 8,374,684 B2 | 2/2013 | Buckland et al. |
| 8,384,907 B2 | 2/2013 | Tearney et al. |
| 8,384,908 B2 | 2/2013 | Sugita et al. |
| 8,384,909 B2 | 2/2013 | Yun et al. |
| 8,388,135 B2 | 3/2013 | Hacker et al. |
| 8,390,819 B2 | 3/2013 | Suehira |
| 8,401,257 B2 | 3/2013 | Izatt et al. |
| 8,405,834 B2 | 3/2013 | Srinivasan et al. |
| 8,408,703 B2 | 4/2013 | Hacker et al. |
| 8,416,818 B2 | 4/2013 | Bouma et al. |
| 8,416,991 B2 | 4/2013 | Everett et al. |
| 8,422,023 B2 | 4/2013 | Podoleanu |
| 8,427,653 B2 | 4/2013 | Hacker et al. |
| 8,433,393 B2 | 4/2013 | Sharma et al. |
| 8,437,008 B2 | 5/2013 | Fercher et al. |
| 8,442,356 B2 | 5/2013 | Buckland et al. |
| 8,459,795 B2 | 6/2013 | Seesselberg et al. |
| 8,469,514 B2 | 6/2013 | Utsunomiya |
| 8,474,978 B2 | 7/2013 | Huang et al. |
| 8,478,384 B2 | 7/2013 | Schmitt et al. |
| 8,478,387 B2 | 7/2013 | Xu |
| 8,491,122 B2 | 7/2013 | Hacker et al. |
| 8,500,279 B2 | 8/2013 | Everett et al. |
| 8,500,280 B2 | 8/2013 | Hirose |
| 8,503,844 B2 | 8/2013 | Petersen et al. |
| 8,553,219 B2 | 10/2013 | Patil et al. |
| 8,559,012 B2 | 10/2013 | Tearney et al. |
| 8,564,787 B2 | 10/2013 | Yamakita |
| 8,567,948 B2 | 10/2013 | Kunath-Fandrei |
| 8,570,527 B2 | 10/2013 | Milner et al. |
| 8,581,643 B1 | 11/2013 | Schmitt |
| 8,582,934 B2 | 11/2013 | Adler et al. |
| 8,594,757 B2 | 11/2013 | Boppart et al. |
| 8,605,287 B2 | 12/2013 | Ko et al. |
| 8,606,343 B2 | 12/2013 | Zavislan |
| 8,622,548 B2 | 1/2014 | Guo et al. |
| 8,630,697 B2 | 1/2014 | Meyer et al. |
| 8,632,180 B2 | 1/2014 | Narasimha-Iyer |
| 8,632,181 B2 | 1/2014 | Bublitz et al. |
| 8,644,572 B2 | 2/2014 | Izatt et al. |
| 8,649,611 B2 | 2/2014 | Everett et al. |
| 2002/0028010 A1 | 3/2002 | Toida |
| 2003/0045798 A1 | 3/2003 | Hular et al. |
| 2003/0103212 A1 | 6/2003 | Westphal et al. |
| 2003/0199769 A1 | 10/2003 | Podoleanu et al. |
| 2004/0133112 A1 | 7/2004 | Rajadhyaksha |
| 2004/0239938 A1 | 12/2004 | Izatt |
| 2005/0004453 A1 | 1/2005 | Tearney et al. |
| 2005/0025797 A1 | 2/2005 | Wang et al. |
| 2005/0157386 A1 | 7/2005 | Greenwald et al. |
| 2005/0261568 A1 | 11/2005 | Hular et al. |
| 2006/0066869 A1 | 3/2006 | Ueno et al. |
| 2006/0072424 A1 | 4/2006 | Everett et al. |
| 2006/0090658 A1 | 5/2006 | Philips |
| 2006/0106304 A1 | 5/2006 | Eastman |
| 2006/0187462 A1* | 8/2006 | Srinivasan ............. A61B 3/102 356/479 |
| 2006/0229529 A1 | 10/2006 | Wright |
| 2007/0002276 A1 | 1/2007 | Hirohara et al. |
| 2007/0057211 A1 | 3/2007 | Bahlman et al. |
| 2007/0076213 A1 | 4/2007 | Kato |
| 2007/0179487 A1 | 8/2007 | Tearney et al. |
| 2007/0216909 A1* | 9/2007 | Everett ................ A61B 5/0059 356/479 |
| 2007/0232962 A1 | 10/2007 | Zumeris et al. |
| 2007/0236699 A1 | 10/2007 | Chou et al. |
| 2007/0276245 A1 | 11/2007 | Konofagou |
| 2007/0291277 A1 | 12/2007 | Everett et al. |
| 2008/0009728 A1 | 1/2008 | Malchow et al. |
| 2008/0221456 A1 | 9/2008 | Babchenko |
| 2009/0093798 A1 | 4/2009 | Charles |
| 2009/0177094 A1 | 7/2009 | Brown et al. |
| 2009/0221920 A1 | 9/2009 | Boppart et al. |
| 2009/0263040 A1* | 10/2009 | Rolland ............... A61B 5/0059 382/255 |
| 2009/0268161 A1* | 10/2009 | Hart ...................... A61B 3/102 351/208 |
| 2009/0270702 A1 | 10/2009 | Zeng et al. |
| 2009/0306520 A1 | 12/2009 | Schmitt et al. |
| 2010/0049055 A1 | 2/2010 | Freudenberg et al. |
| 2010/0113900 A1 | 5/2010 | Shakespeare et al. |
| 2010/0137710 A1 | 6/2010 | Zavislan et al. |
| 2010/0168586 A1 | 7/2010 | Hillman et al. |
| 2010/0198081 A1 | 8/2010 | Hanlin et al. |
| 2010/0228119 A1 | 9/2010 | Brennan et al. |
| 2010/0228123 A1 | 9/2010 | Brennan et al. |
| 2010/0228124 A1 | 9/2010 | Brennan et al. |
| 2010/0228132 A1 | 9/2010 | Brennan et al. |
| 2010/0228238 A1 | 9/2010 | Brennan et al. |
| 2010/0278405 A1 | 11/2010 | Kakadiaris et al. |

(56) References Cited

U.S. PATENT DOCUMENTS

| | | |
|---|---|---|
| 2011/0037987 A1 | 2/2011 | Gurny et al. |
| 2011/0098575 A1 | 4/2011 | Stamnes et al. |
| 2011/0199615 A1 | 8/2011 | Sugita |
| 2011/0228222 A1* | 9/2011 | Kobayashi ............ A61B 3/102 351/206 |
| 2011/0267340 A1* | 11/2011 | Kraus .................... A61B 3/102 345/419 |
| 2011/0282333 A1 | 11/2011 | Herekar et al. |
| 2011/0299034 A1* | 12/2011 | Walsh .................... A61B 3/102 351/206 |
| 2011/0319875 A1 | 12/2011 | Loesel et al. |
| 2012/0010494 A1 | 1/2012 | Teramura |
| 2012/0020893 A1 | 1/2012 | Elmaleh et al. |
| 2012/0022381 A1 | 1/2012 | Tearney et al. |
| 2012/0033227 A1 | 2/2012 | Bower et al. |
| 2012/0075638 A1 | 3/2012 | Rollins et al. |
| 2012/0095322 A1 | 4/2012 | Tsekos et al. |
| 2012/0140175 A1 | 6/2012 | Everett et al. |
| 2012/0189184 A1 | 7/2012 | Matsumoto et al. |
| 2012/0218557 A1 | 8/2012 | Sugita et al. |
| 2012/0230913 A1 | 9/2012 | Johnston et al. |
| 2012/0257165 A1 | 10/2012 | Suehira |
| 2012/0274897 A1* | 11/2012 | Narasimha-Iyer ..... A61B 3/102 351/206 |
| 2012/0274900 A1 | 11/2012 | Horn et al. |
| 2012/0299591 A1 | 11/2012 | Golan |
| 2012/0302862 A1 | 11/2012 | Yun et al. |
| 2012/0307056 A1 | 12/2012 | Zuzak et al. |
| 2013/0003074 A1 | 1/2013 | Kurosaka |
| 2013/0057873 A1 | 3/2013 | Brown, III et al. |
| 2013/0072769 A1 | 3/2013 | Zuckerman |
| 2013/0094720 A1 | 4/2013 | Stetson |
| 2013/0095519 A1 | 4/2013 | Backman et al. |
| 2013/0100404 A1 | 4/2013 | Narasimha-Iyer |
| 2013/0100455 A1 | 4/2013 | Tearney et al. |
| 2013/0138140 A1* | 5/2013 | Weaver ................... A61F 2/01 606/200 |
| 2013/0158393 A1 | 6/2013 | Papac et al. |
| 2013/0176532 A1 | 7/2013 | Sharma et al. |
| 2013/0176571 A1 | 7/2013 | Tearney et al. |
| 2013/0182318 A1 | 7/2013 | Eastman et al. |
| 2013/0194581 A1 | 8/2013 | Yoshida |
| 2013/0195336 A1 | 8/2013 | Uchida |
| 2013/0201449 A1 | 8/2013 | Walsh et al. |
| 2013/0287277 A1 | 10/2013 | Everett et al. |
| 2013/0345558 A1 | 12/2013 | Boppart et al. |
| 2014/0009741 A1 | 1/2014 | Levien et al. |
| 2014/0049632 A1 | 2/2014 | Hemmer |
| 2014/0055745 A1 | 2/2014 | Sato et al. |
| 2014/0063451 A1 | 3/2014 | Ono et al. |
| 2014/0063507 A1 | 3/2014 | Borycki et al. |
| 2014/0068513 A1 | 3/2014 | Sakagawa |
| 2014/0098373 A1 | 4/2014 | Milner et al. |

FOREIGN PATENT DOCUMENTS

| | | |
|---|---|---|
| EP | 1468245 B1 | 3/2011 |
| EP | 2325803 A1 | 5/2011 |
| JP | 2004344260 | 9/2004 |
| WO | 9503397 A1 | 2/1995 |
| WO | 2006004743 A2 | 1/2006 |
| WO | 2006078802 A1 | 7/2006 |
| WO | 2006079011 A1 | 7/2006 |
| WO | 2006079013 A1 | 7/2006 |
| WO | 2007091991 A2 | 8/2007 |
| WO | 2008000078 A1 | 1/2008 |
| WO | 2008109346 A1 | 9/2008 |
| WO | 2008151155 A2 | 12/2008 |
| WO | 2009149131 A1 | 12/2009 |
| WO | 2010085348 A1 | 7/2010 |
| WO | 2010114654 A1 | 10/2010 |
| WO | 2011094659 A2 | 8/2011 |
| WO | 2011140374 A1 | 11/2011 |
| WO | 2011144632 A1 | 11/2011 |
| WO | 2012004388 A1 | 1/2012 |
| WO | 2012146583 A1 | 11/2012 |
| WO | 2012177930 A1 | 12/2012 |
| WO | 2014085911 A1 | 6/2014 |

OTHER PUBLICATIONS

International Search Report mailed on Feb. 21, 2014 in relation to PCT/CA2013/001010.

Mujat, Mircea, R. Daniel Ferguson, Daniel X. Hammer, Christopher Gittins, and Nicusor Iftimia. Automated algorithm or breast tissue differentiation in optical coherence tomography. Journal of Biomedical Optics vol. 14(3), 034040 May/Jun. 2009).

DualAlign i2k Retina. Registering and Aligning Fundus Images. 2010 Topcon Medical Systems Inc. www.topconmedical.com.

Bing Qi et al. Dynamic focus control in high-speed optical coherence tomography based on a microelectromechanical mirror. Optics Communications 232 (2004) www.elsevier.com/locate/optcom. Jan. 9, 2004.

Nicusor Iftimia et al. Fluorescence-guided optical coherence tomography imaging for colon cancer screening: a preliminary mouse study. Medical optics and biotechnology. 2011 Optical Society of America. Jan. 1, 2012 / vol. 3, No. 1 / Biomedical Optics Express.

Dirk J. Faber et al. Quantitative Measurement of Attenuation Coefficients of Weakly Scattering Media Using Optical Coherence Tomography. Modeling the OCT Signal. Chapter 2. Published in Optics Express 12(19) 4353-4365 (2004).

Abstract. Schmitt JM et al. Optical-coherence tomography of a dense tissue: statistics of attenuation and packscattering. Biomedical Engineering and Instrumentation Program, NCRR, National Institutes of Health, Bethesda, MD 20892, USA. Phys Med Biol. Oct. 1994;39(10):1705-20. Accessed at http://www.ncbi.nlm.nih.gov/pubmed/15551540 on Oct. 25, 2013.

Freek J. van der Meer. Vascular Applications of Quantitative Optical Coherence Tomography. Faculty of Medicine. 2005.http://dare.uva.nl/record/167556. University of Amsterdam. UvA-DARE (Digital Academic Repository).

Abstract. FJ Van Der Meer et al. Localized Measurement of Optical Attenuation Coefficients of Atherosclerotic Plaque Constituents by Quantitative Optical Coherence Tomography. Laser Center Academic Medical Center, Amsterdam, The Netherlands. Accessed on Oct. 28, 2013.

Extended European Search Report received in connection to co-pending European patent application No. 13 860 624.9 on Dec. 23, 2016.

Supplementary Partial European Search Report, search completed Sep. 16, 2016, in relation to European Patent Application No. EP 13 86 0624.

Jae-Ho Han et al. "Common-Path Fourier-Domain Optical Coherence Tomography in Ophthalmology Applications", Life Science Systems and Applications Workshop, 2009, LISSA 2009. pp. 163-169.

Ashavini M. Pavaskar: "Tools for creating wide-field views of the human retina using Optical Coherence Tomography", Jan. 1, 2011, Retrieved from the Internet: URL: http://epublications.marquette.edu/cgi/viewcontent.cgi?article=1105&context=theses_open [retrieved on Aug. 3, 2016].

* cited by examiner

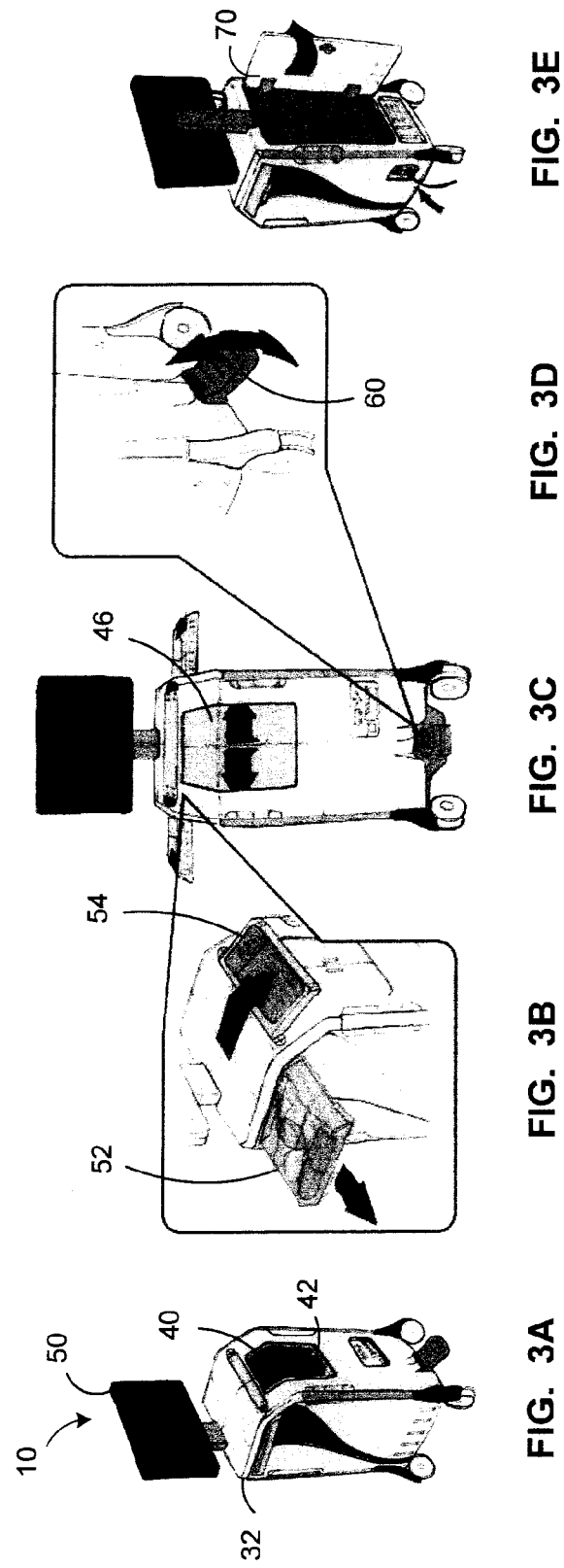

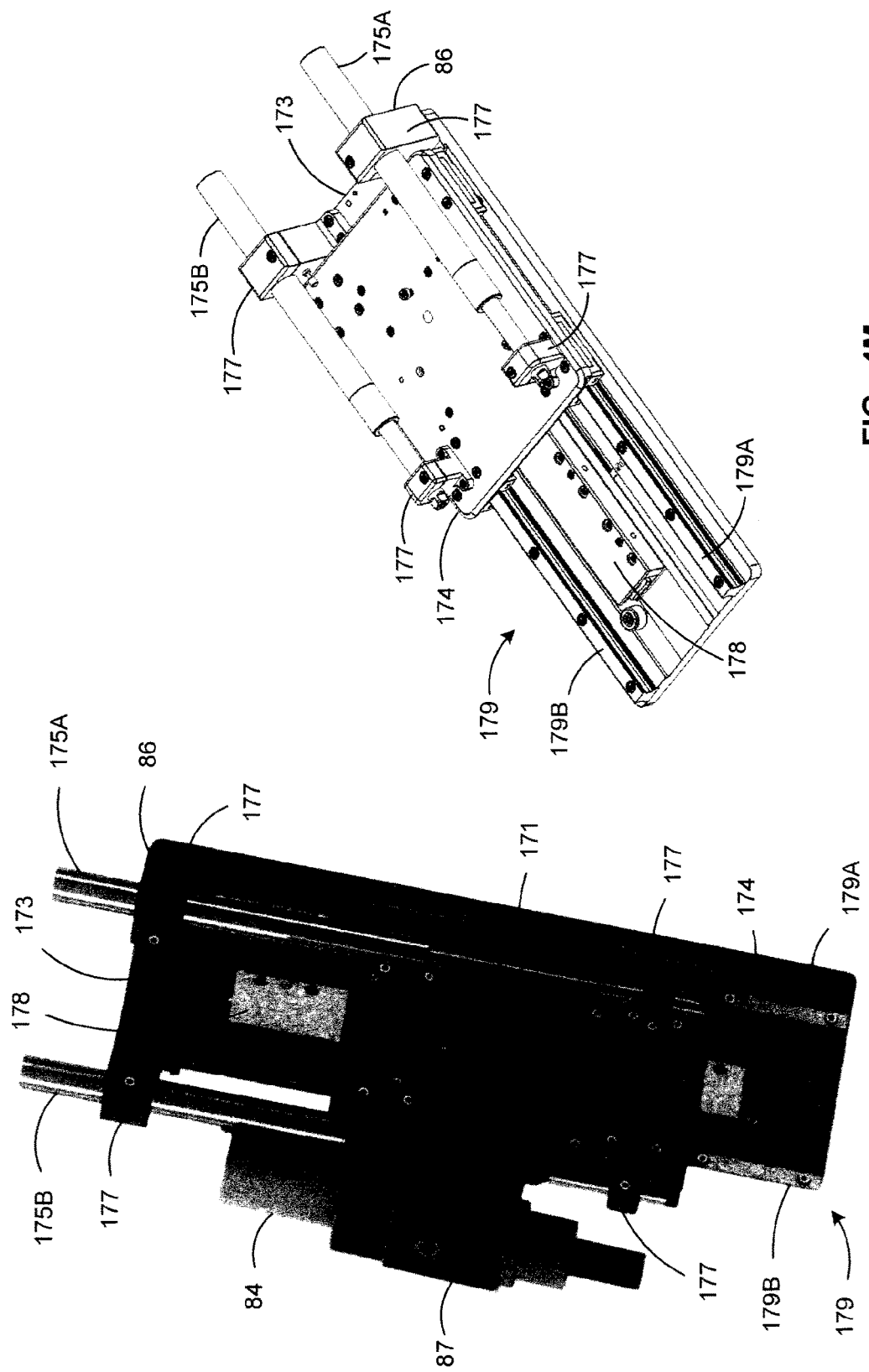

FIG. 6A
FIG. 6B
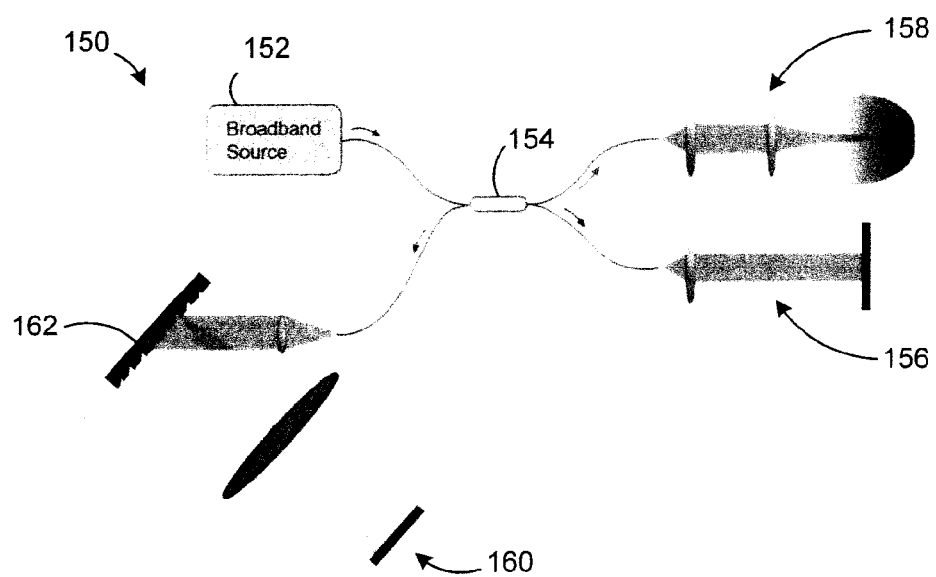
FIG. 6C

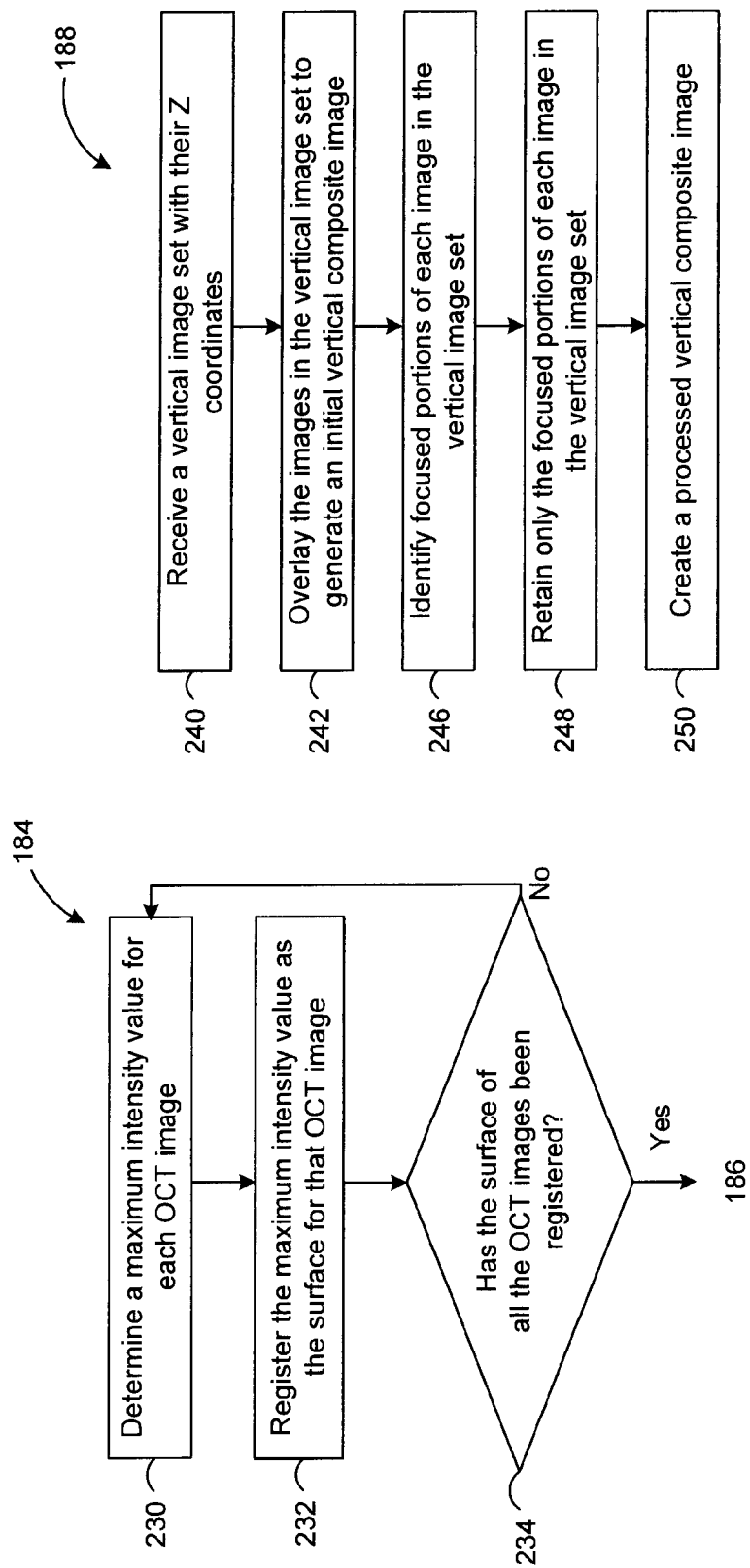

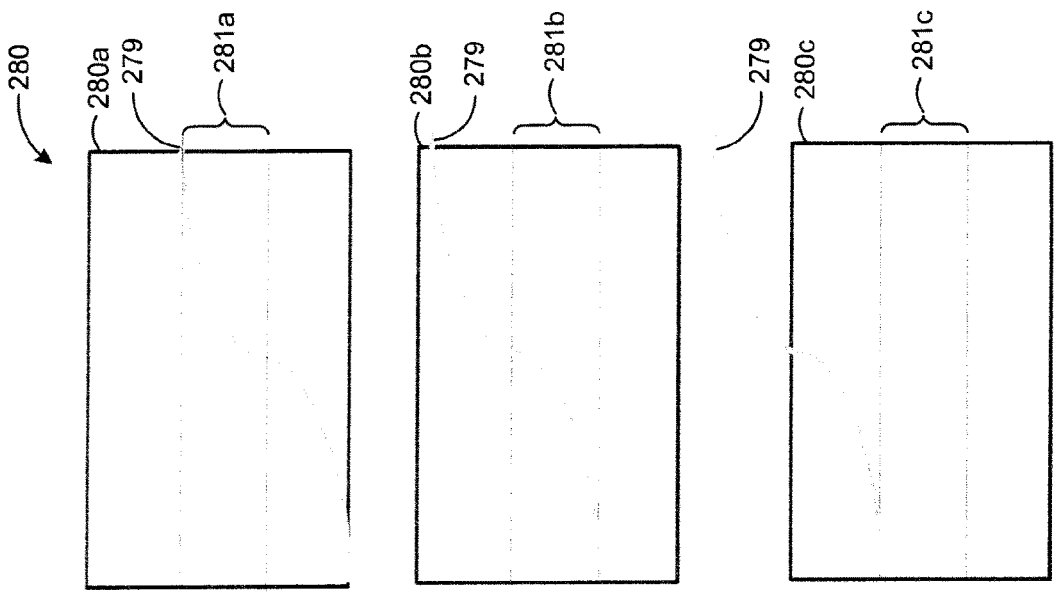
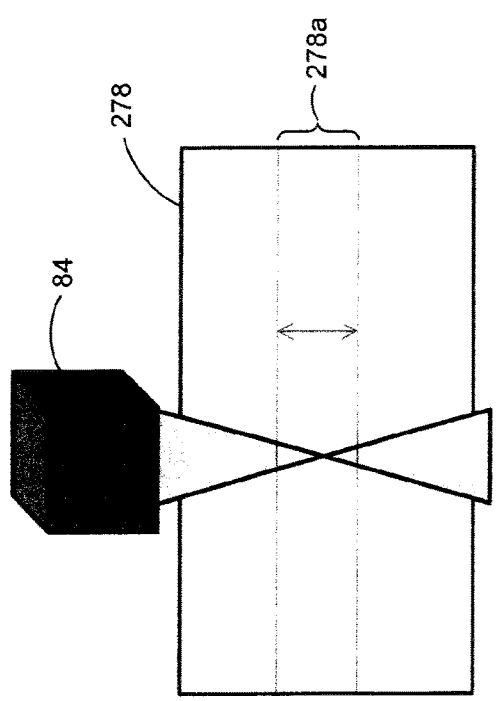
FIG. 8D
FIG. 8C

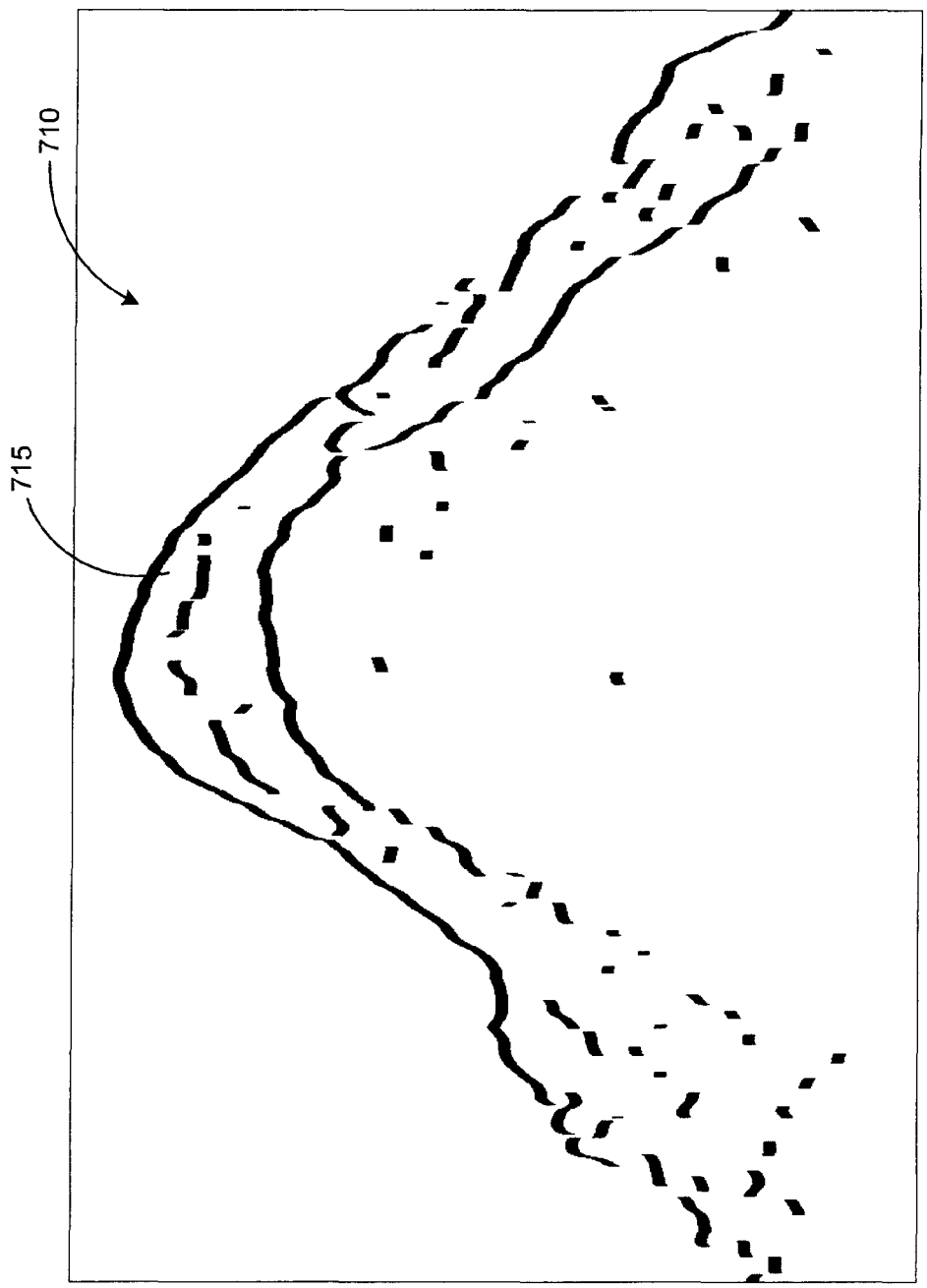

SYSTEM AND METHOD FOR GENERATING A WIDE-FIELD OCT IMAGE OF A PORTION OF A SAMPLE

FIELD

The various embodiments described herein generally relate to a system and method for obtaining Wide field OCT images.

BACKGROUND

Optical Coherence Tomography (OCT) imaging uses near-infrared light to produce high-resolution images of various objects such as, but not limited to tissue, for example. When OCT imaging is used on tissue, it is analogous to high-frequency ultrasound, except that the optical interferometry of OCT imaging is used for depth ranging rather than echo timing. OCT imaging is rapid, non-contact, non-invasive, and capable of generating 2D and 3D images at high resolution (~10 µm).

Current methods to measure margin width during lumpectomy procedures have been reported to result in reoperation rates of up to 20 to 60%, representing a significant and unmet need for improved margin assessment. High reoperation rates present both increased treatment risk to patients and an increased burden on healthcare systems. In the USA alone, over 150,000 lumpectomies are performed per year at an average cost of between $11,000 and $19,000 USD per procedure. Assuming an average repeat operation rate of 25%, potentially preventable repeat surgeries represent an approximate cost to the US healthcare system of $500M (USD) annually.

SUMMARY OF VARIOUS EMBODIMENTS

In a broad aspect, at least one embodiment described herein provides an imaging system for generating optical coherence tomography (OCT) images of a sample. The imaging system comprises a scanning area for receiving the sample; a scanning assembly disposed within the scanning area, the scanning assembly configured to acquire raw OCT data of at least a portion of the sample from at least two independent directions; and a processing module in electrical communication with the scanning assembly and operable to determine OCT imaging parameters for the raw OCT data, to control the scanning assembly according to the OCT imaging parameters to acquire the raw OCT data of at least the portion of the sample and to generate one or more corresponding OCT images.

In another broad aspect, at least one embodiment described herein provides a method for generating a wide field OCT image of a portion of a sample. The method comprises creating a surface map of the sample; acquiring raw OCT data of the portion of the sample based on the surface map; generating a plurality of OCT images from the raw OCT data; and combining two or more OCT images of the plurality of OCT images to create the wide field OCT image.

In another aspect, at least one embodiment described herein provides a system for generating a wide field OCT image of a portion of a sample. The system comprises an input port for receiving raw OCT data; a processing module configured to conduct the methods for generating a wide field OCT image of a portion of a sample in accordance with one or more of the embodiments described herein; and an output port to provide the wide-field OCT images to one of a user, a storage device and another computing device.

In another aspect, at least one embodiment described herein provides a computer-readable medium storing computer-executable instructions that cause a processor to perform one or more of the methods for generating a wide field OCT image as described herein.

In another broad aspect, at least one embodiment described herein provides a method for generating a wide field OCT image of a portion of a sample. The method comprises receiving a set of OCT images corresponding to the portion of the sample, the set of OCT images including a first OCT image and a neighbouring OCT image; aligning the first OCT image with the neighbouring OCT image; and overlaying a portion of the first OCT image over a portion of the neighbouring OCT image to create the wide field OCT image.

In another broad aspect, at least one embodiment described herein provides a method of assessing a degree of differentiation for a second region of an OCT image of a tissue sample with respect to a first region. The method comprises receiving OCT image data for the OCT image; identifying a boundary in the OCT image to identify the second region in the OCT image, the second region being disposed below the boundary; identifying a first set of OCT image data corresponding to the first region and a second set of OCT image data corresponding to the second region; generating a first optical dataset based on measurements of at least one first optical characteristic for the first set of OCT image data; generating a second optical dataset based on measurements of the at least one first optical characteristic for the second set of OCT image data; and comparing the first optical dataset and the second optical dataset to identify a degree of difference between the first region and the second region, wherein a high degree of difference indicates that the first region and the second region comprise different tissue types.

In another broad aspect, at least one embodiment described herein provides a system for assessing a degree of differentiation for a second region of an OCT image of a tissue sample with respect to a first region. The system comprises a data interface configured to receive OCT image data for the OCT image; a user interface configured to receive at least one input from a user and a display at least one output to the user; and a processing module coupled to the data interface and the user interface. The processing module coupled to the data interface and the user interface, the processing module being configured to identify a boundary in the OCT image to identify the second region in the OCT image, the second region being disposed below the boundary, to identify a first set of OCT image data corresponding to the first region and a second set of OCT image data corresponding to the second region, to generate a first optical dataset based on measurements of at least one first optical characteristic for the first set of OCT image data; to generate a second optical dataset based on measurements of the at least one first optical characteristic for the second set of OCT image data; and to compare the first optical dataset and the second optical dataset to identify a degree of difference between the first region and the second region, wherein a high degree of difference indicates that the first and second region comprise different tissue types In another broad aspect, at least one embodiment described herein provides a computer-readable medium storing computer-executable instructions that cause a processor to perform a method of assessing a degree of differentiation for a second region of an OCT image of a tissue sample with respect to a first region, the method comprising receiving OCT image data for the OCT image; identifying a boundary in the OCT image to identify the second region in the OCT image, the second region being disposed below the boundary; identifying a first set of OCT image data corresponding to the first region and a second set of OCT image data corresponding to the second region; generating a first optical dataset based on measurements of at least one first optical characteristic for the first set of OCT image data; generating a second optical dataset based on measurements of the at least one first optical characteristic for the second set of OCT image data; and comparing the first optical dataset and the second optical dataset to identify a degree of difference between the first region and the second region, wherein a high degree of difference indicates that the first and second region comprise different tissue types.

In another broad aspect, at least one embodiment described herein provides a sample container for containing a tissue sample and maintaining the tissue sample in a defined orientation. The container comprises an interface sleeve having one or more side walls which extend longitudinally between lower and upper open ends to define an interior volume for receiving the tissue sample, the one or more side walls collectively including a plurality of spaced apart retentive members distributed longitudinally between the lower and upper ends; a bottom sample support having an upper surface for supporting the tissue sample, the bottom sample support being releasably engageable with the interface sleeve for selectively closing the lower end; and a top sample support having a lower surface for supporting the tissue sample, the top sample support being sized to be received in the interior volume at a plurality of longitudinal positions corresponding to the plurality of spaced apart retentive members between the lower and upper ends of the interface sleeve, the top sample support including one or more retentive members that are releasably engageable with the retentive members of the interface sleeve to selectively lock the top sample support at a selected one of the plurality of longitudinal positions and hold the tissue sample firmly between the lower surface of the top sample support and the upper surface of the bottom sample support.

In another broad aspect, at least one embodiment described herein provides a sample container for containing a tissue sample and maintaining the tissue sample in a defined orientation. The container comprises an interface sleeve having one or more side walls which extend longitudinally between lower and upper open ends to define an interior volume for receiving the tissue sample, a bottom sample support configured to selectively close the lower end; and a top sample support selectively lockable at a plurality of longitudinal positions between the lower and upper ends to firmly hold a tissue sample in the interior volume between the bottom sample support and the top sample support.

DETAILED DESCRIPTION OF DRAWINGS

For a better understanding of the various embodiments described herein, and to show more clearly how these various embodiments may be carried into effect, reference will be made, by way of example, to the accompanying drawings which show at least one example embodiment, and in which:

FIG. 3A is a perspective view of an example embodiment of an imaging system;

FIG. 3B is a magnified view showing sterile controls of the imaging system;

FIG. 3C is a front view of the imaging system;

FIG. 3D is a magnified view of a wheel lock of the imaging system;

FIG. 3E is a rear perspective view of the imaging system;

Figure 4A:
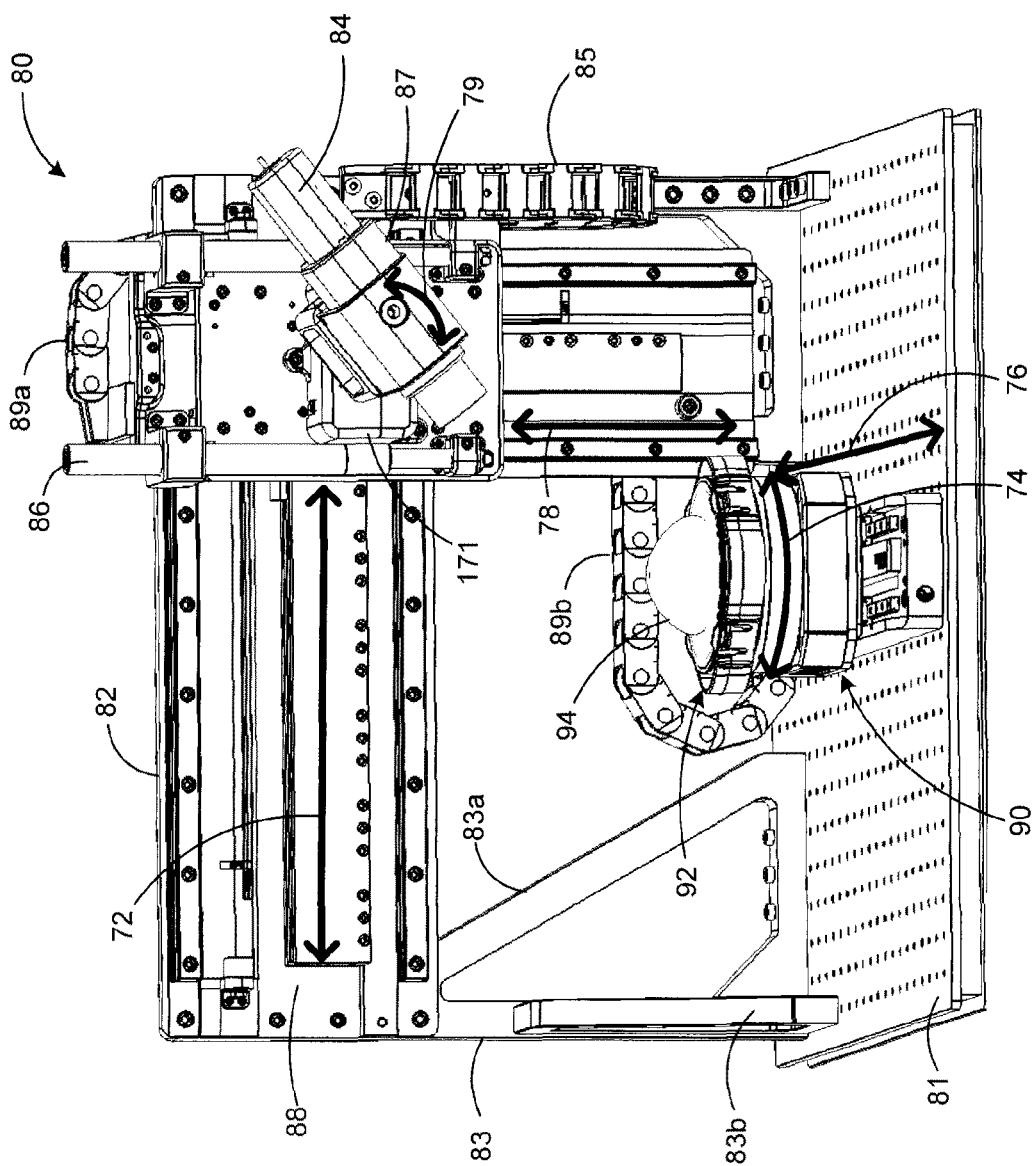
FIG. 4A is a front view of an example embodiment of a scanning assembly that may be used in the imaging system of FIGS. 3A to 3E for scanning a sample.
Figure 4B:
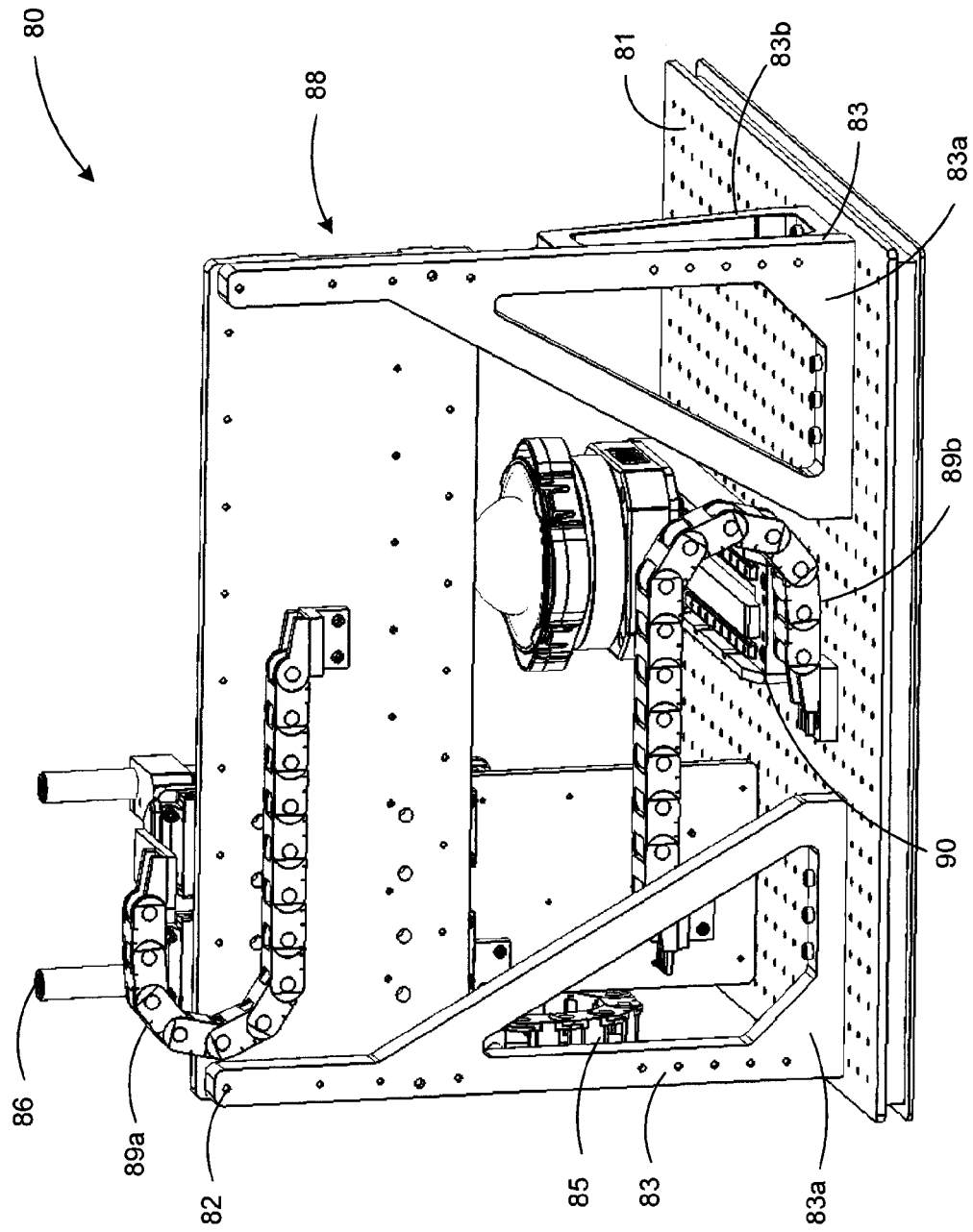
FIG. 4B is a rear view of the scanning assembly of FIG. 4A.
Figure 4C:
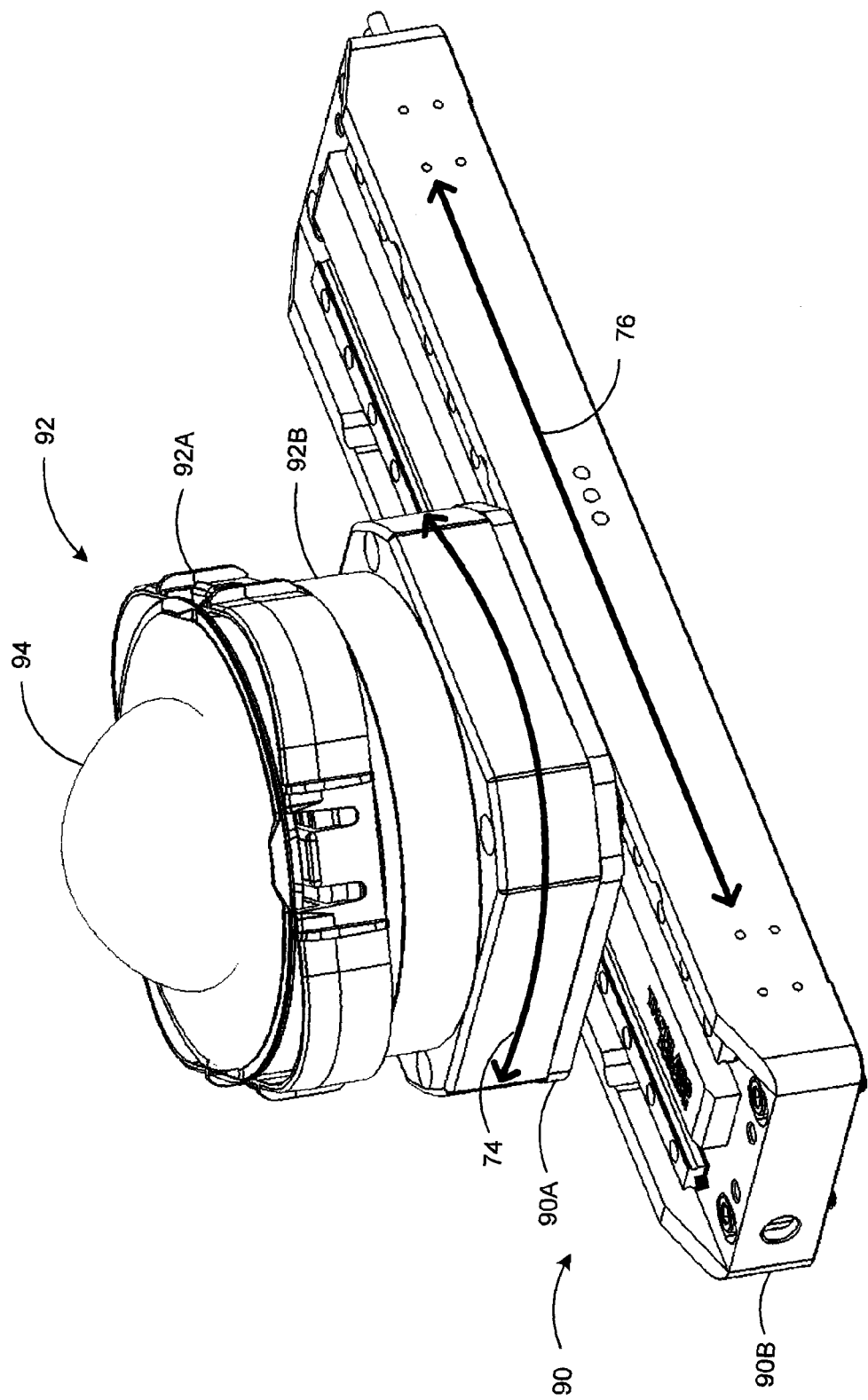
FIG. 4C is a perspective view of a trans-rotational mechanism and a support area in the scanning assembly of FIG. 4A.
Figure 4D:
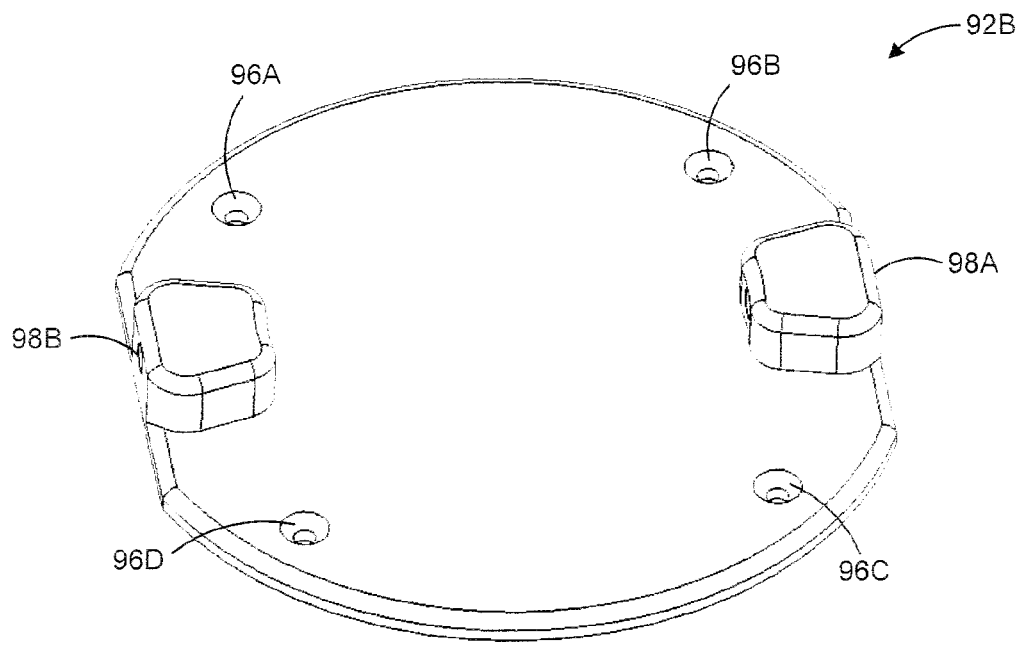
FIG. 4D is a perspective view of a container adapter for the scanning assembly of FIG. 4A.
Figure 4E:
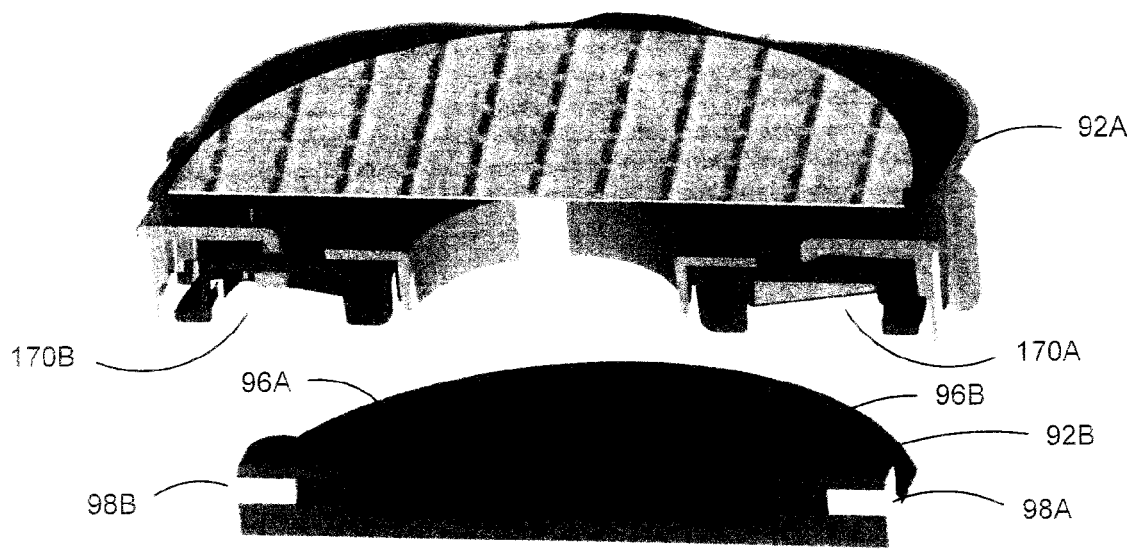
FIG. 4E is a cross-sectional exploded view of a container support and the container adapter of FIG. 4D for the scanning assembly of FIG. 4A.
Figure 4F:
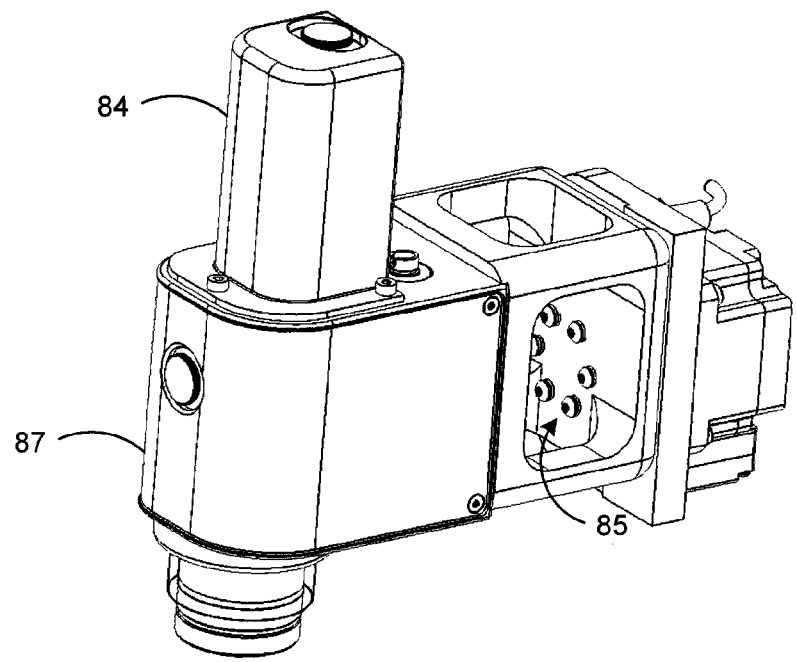
FIG. 4F is a front-side perspective view of a tilt mechanism and a scanning head for the scanning assembly of FIG. 4A.
Figure 4G:
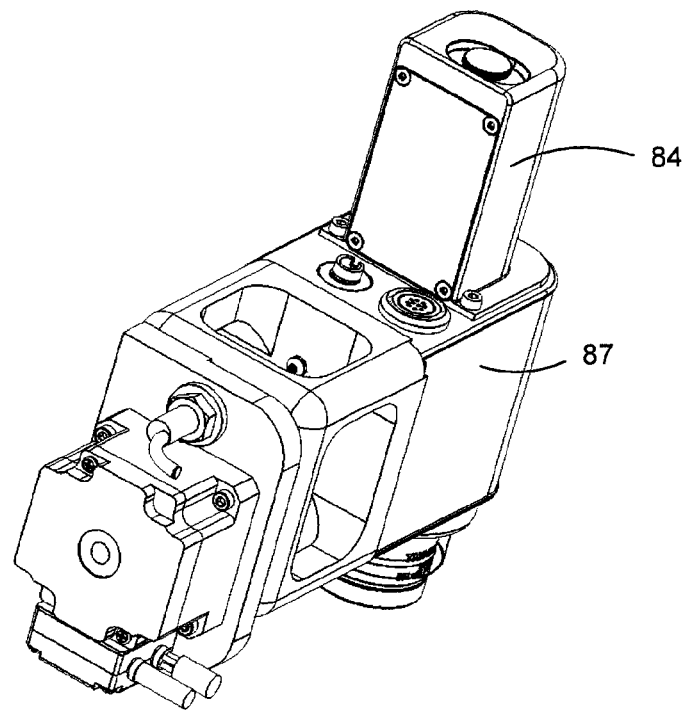
FIG. 4G is a rear perspective view of the tilt mechanism and the scanning head of FIG. 4F.
Figure 4H:
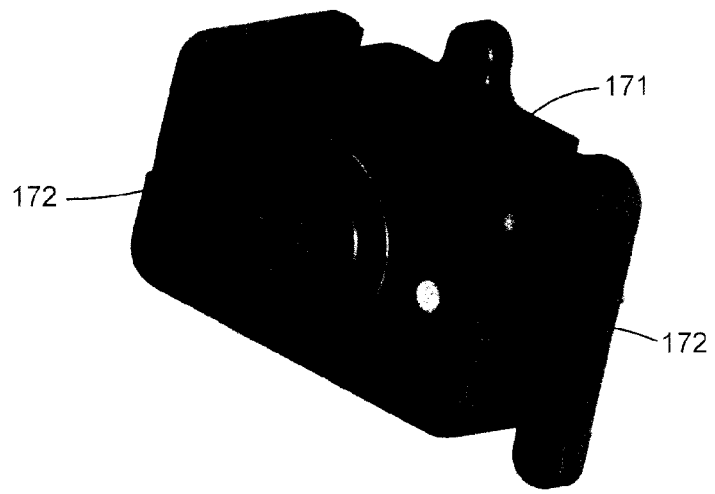
FIG. 4H is a perspective view of a home device for the scanning assembly of FIG. 4A.
Figure 4I:
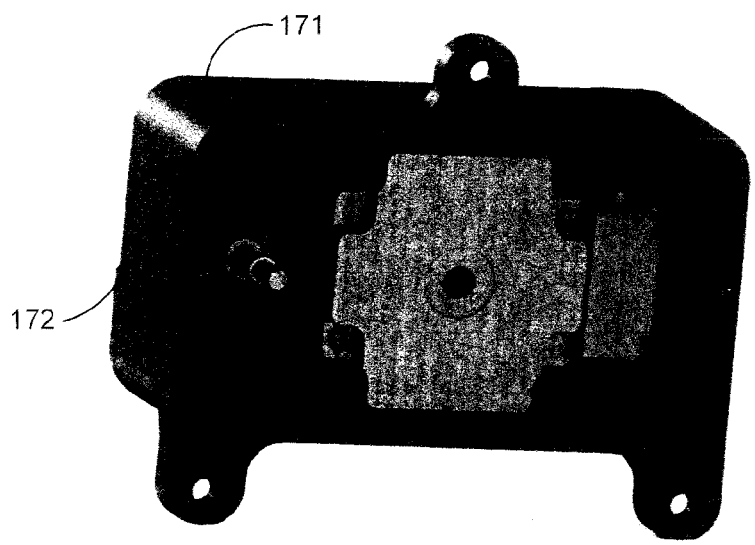
FIG. 4I is a rear perspective view of the home device of FIG. 4H.
Figure 4J:
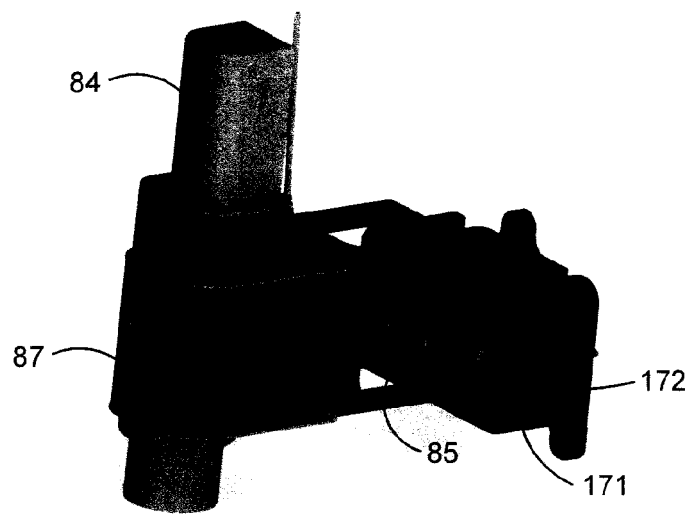
Figure 4K:
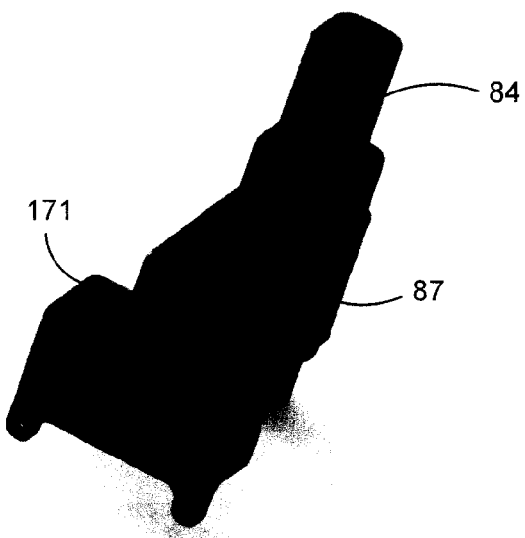
Figure 4N:
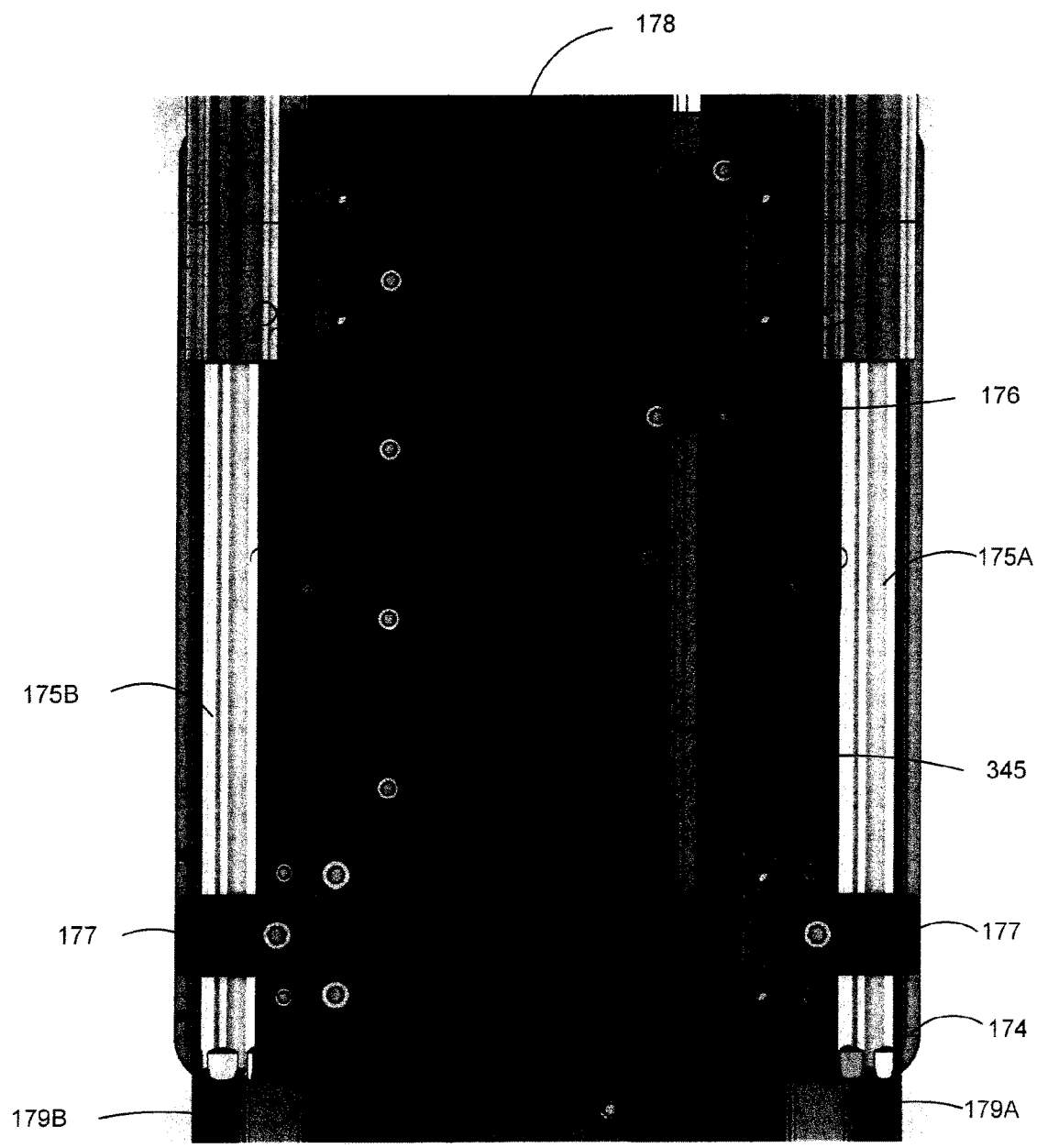
Figure 40:
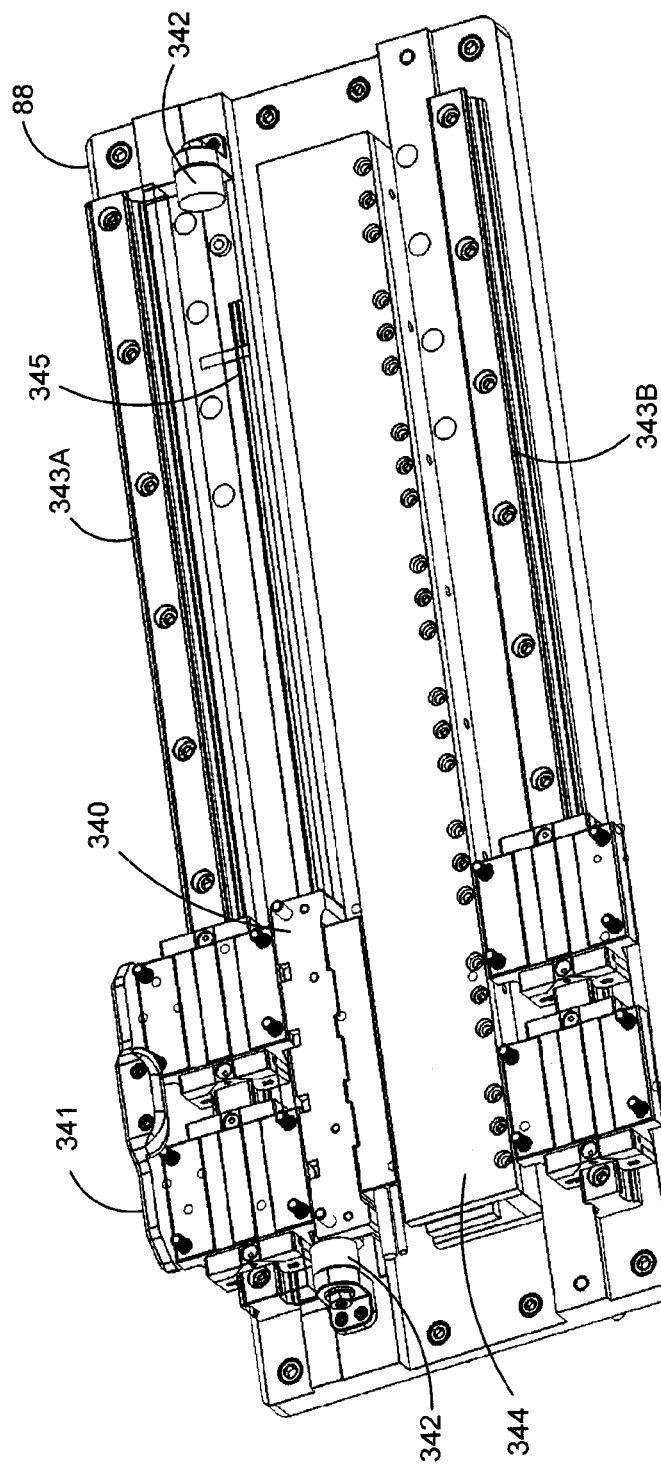
Figure 4P:
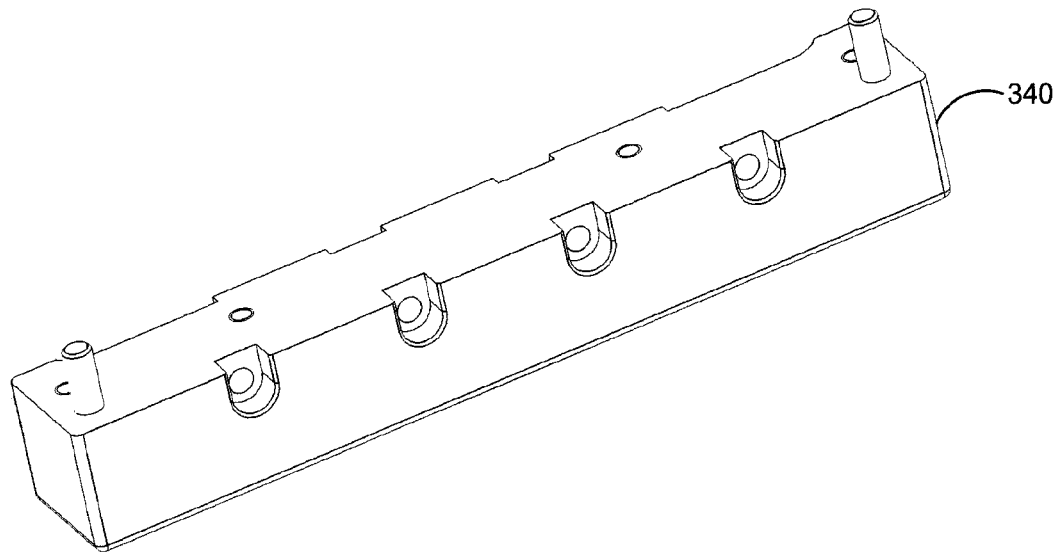
Figure 4Q:
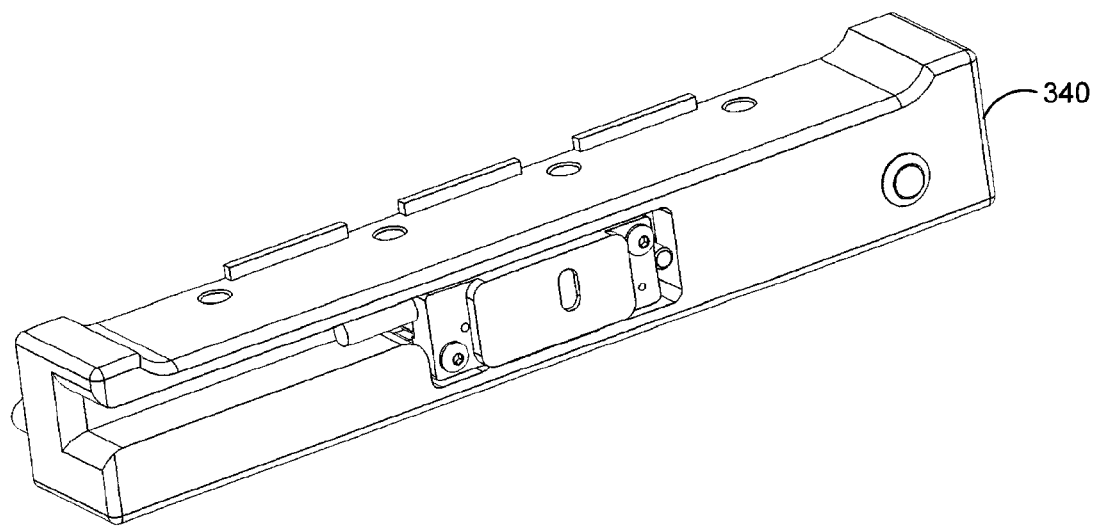
Figure 4R:
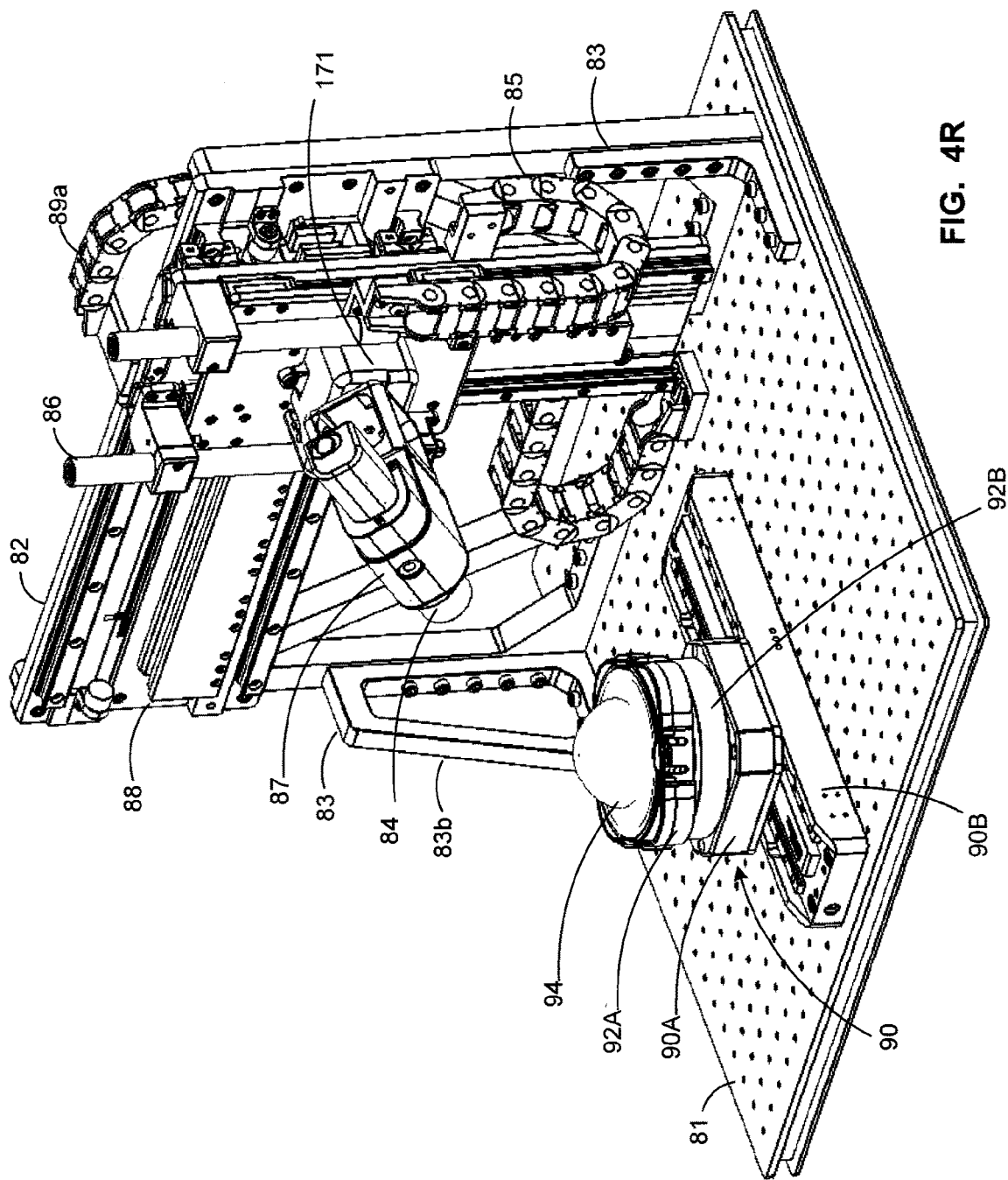
Figure 4S:
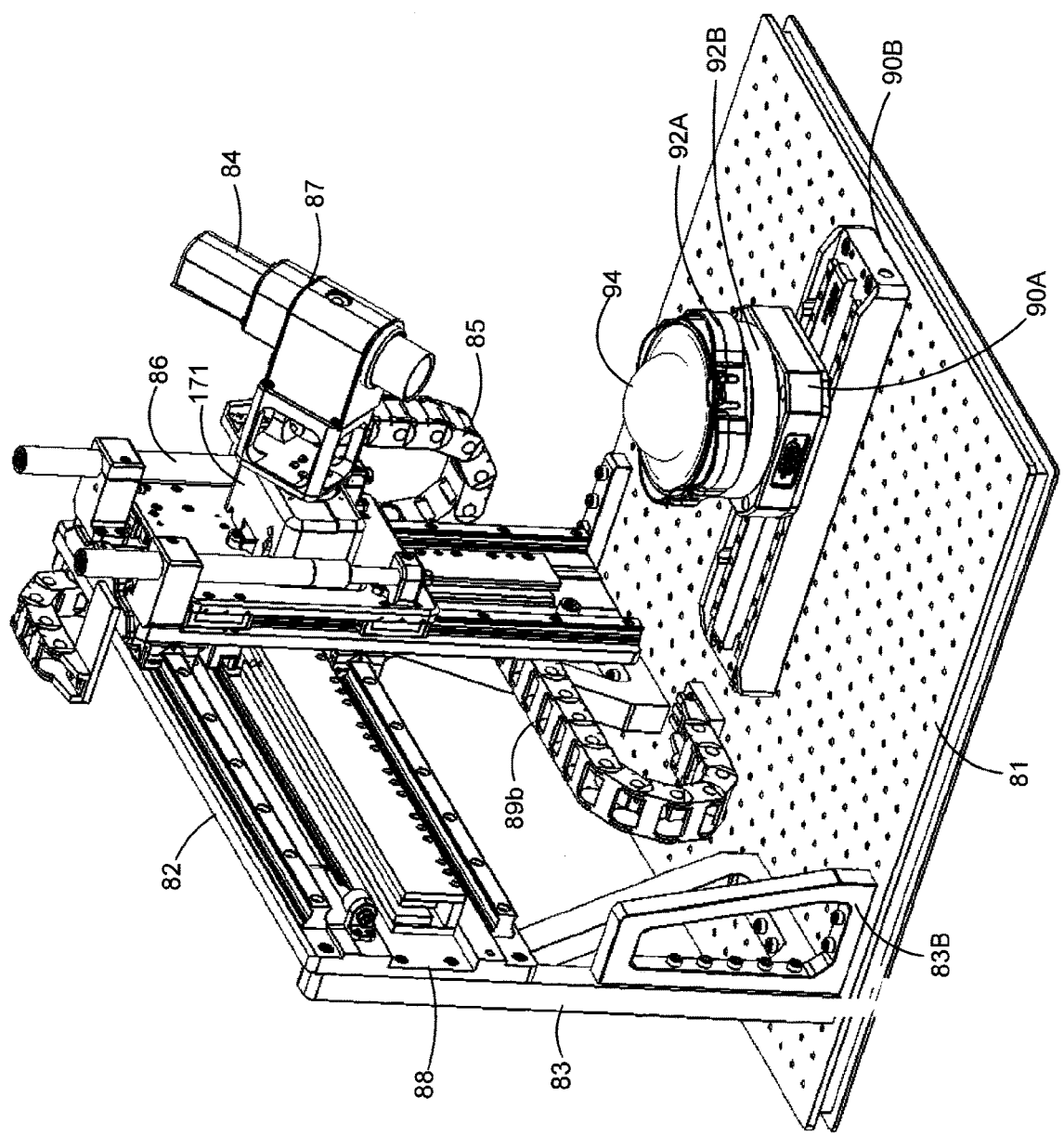
Figure 5:
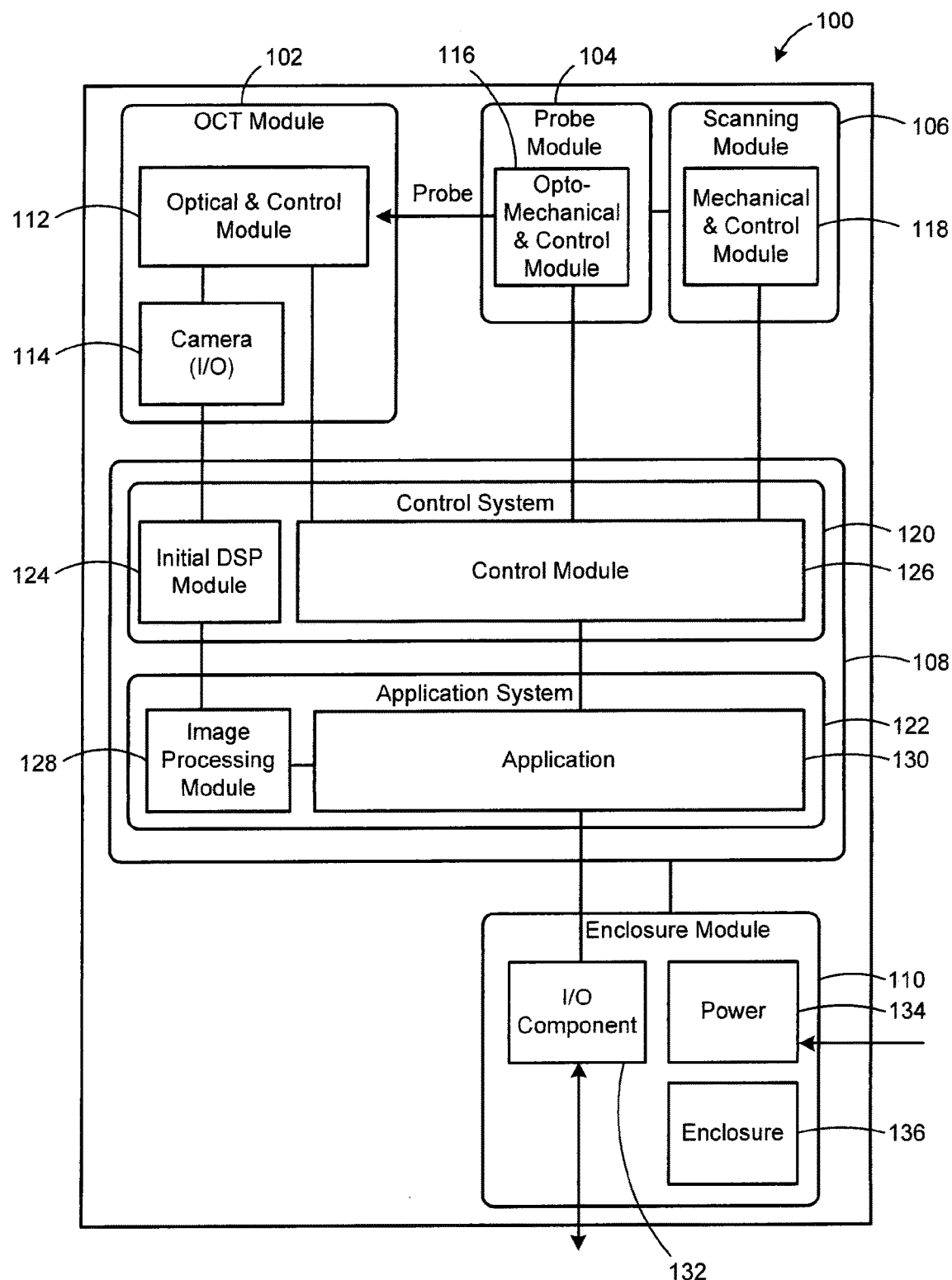
Figure 7A:
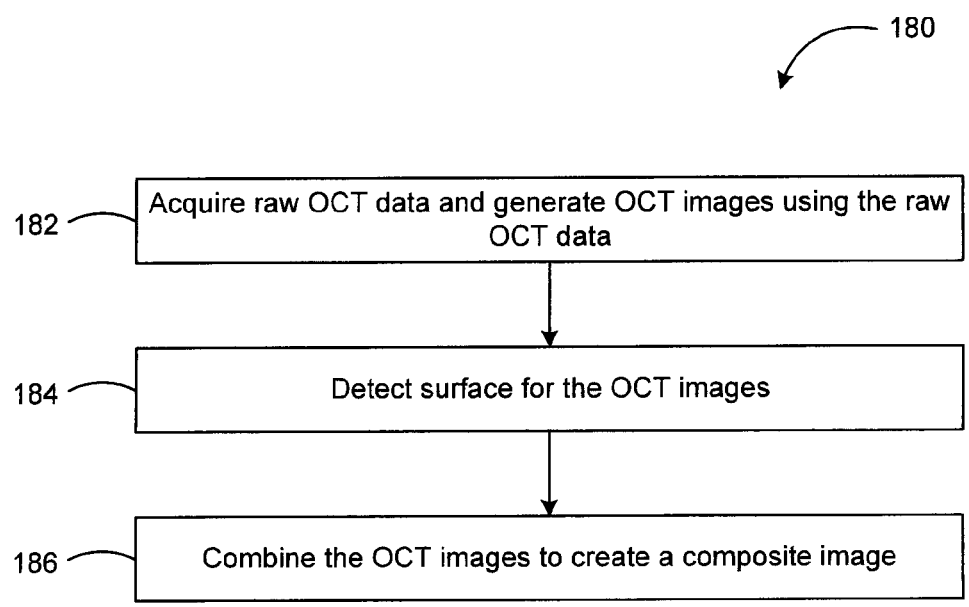
Figure 7B:
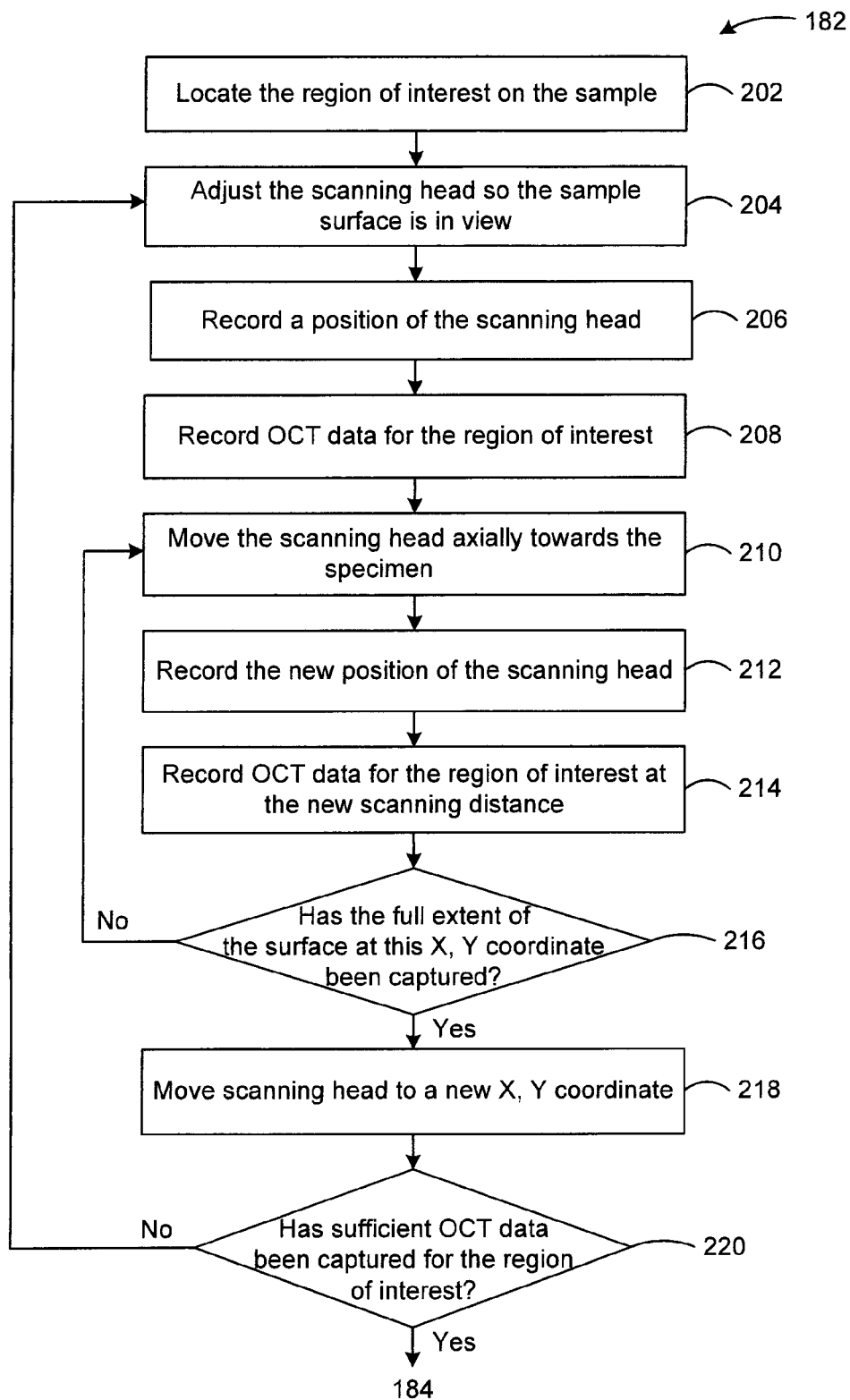
Figures 7E, 7F:
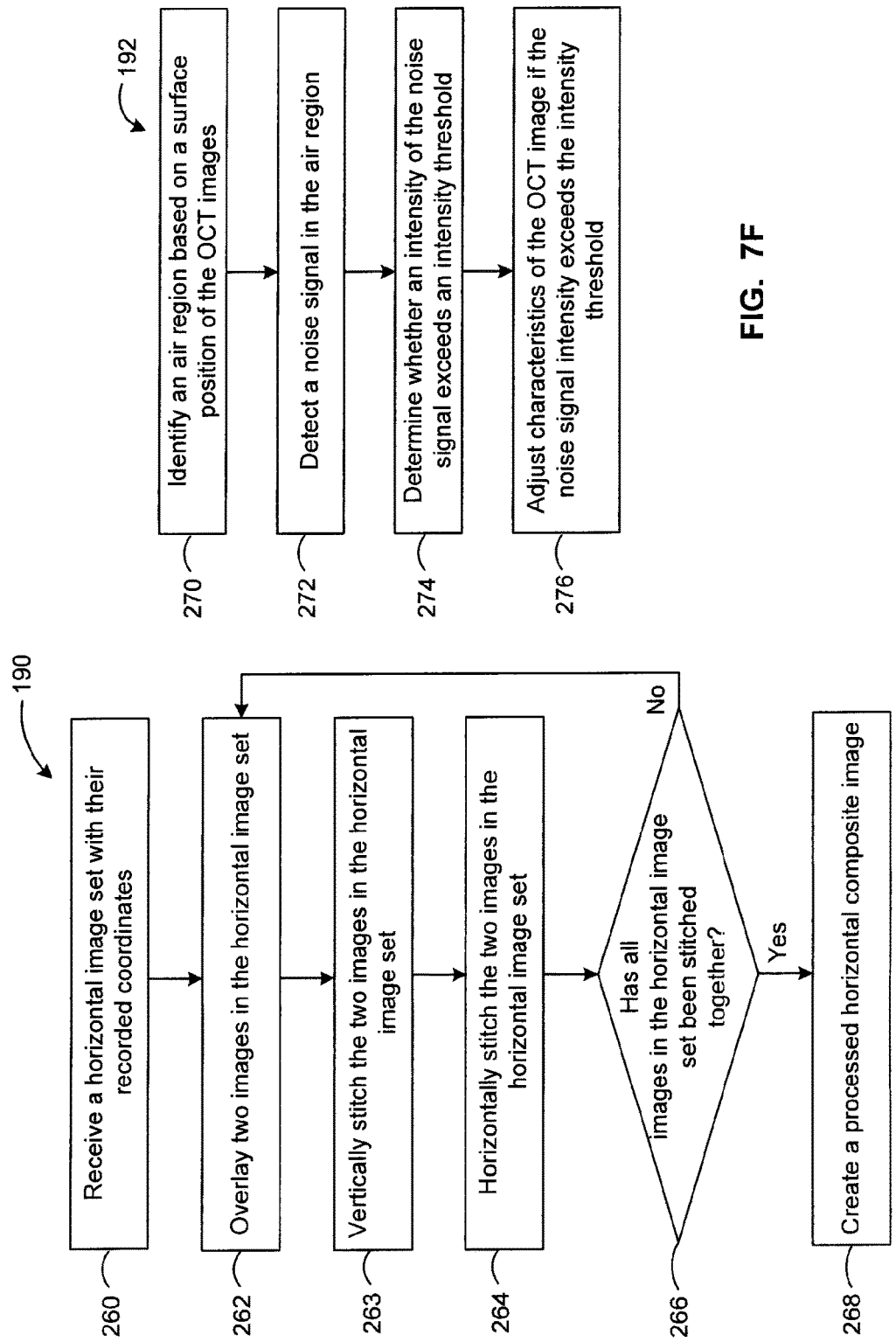
Figure 8B:
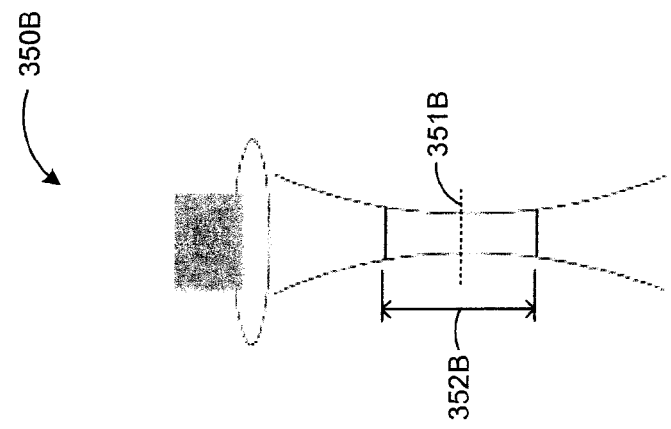
Figure 8A:
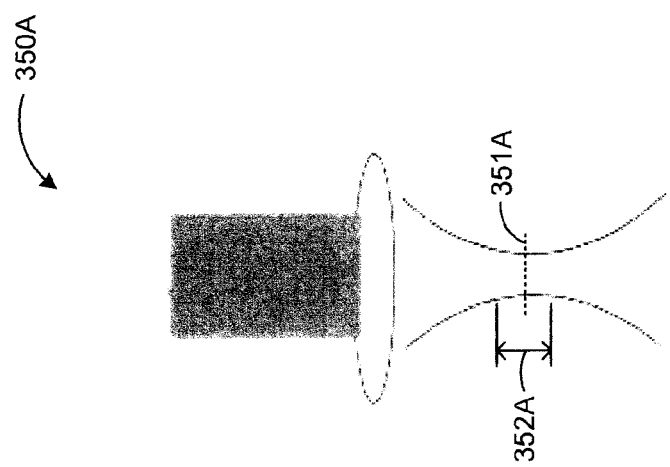
Figure 8E:
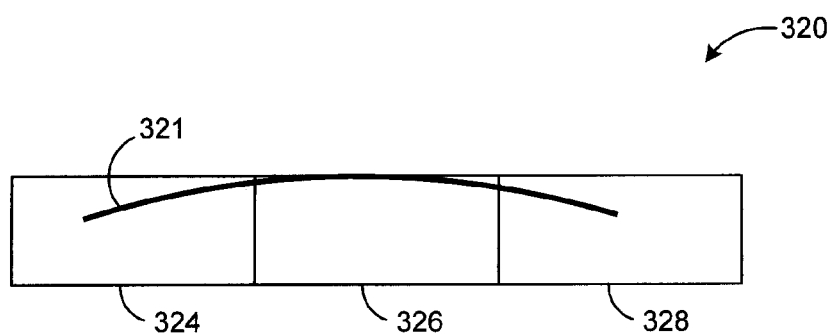
Figure 8F:
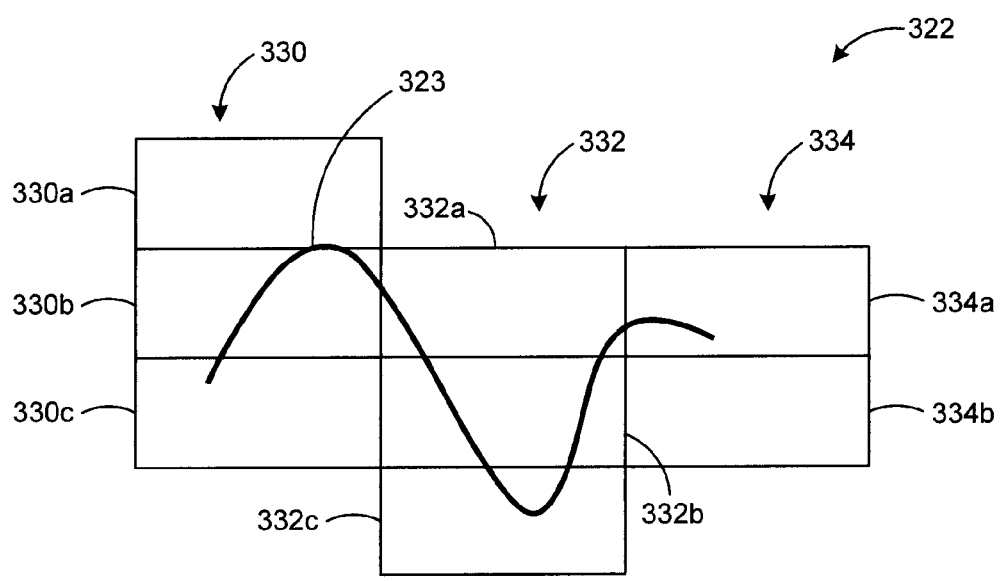
Figure 9C:
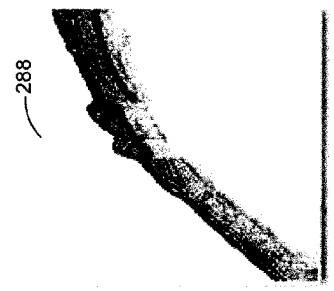
Figure 9B:
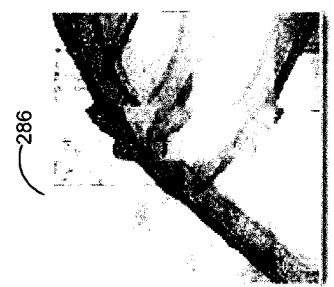
Figure 9A:
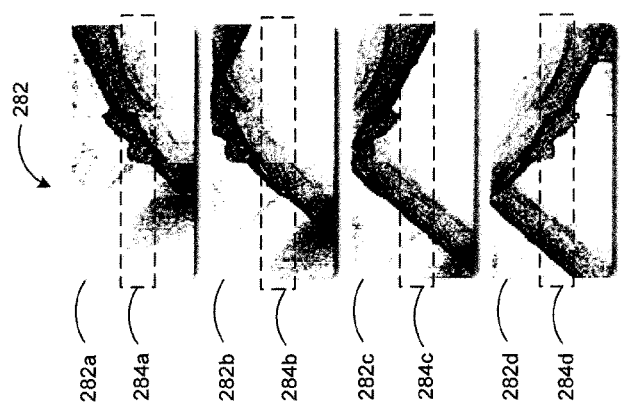
Figure 10C:
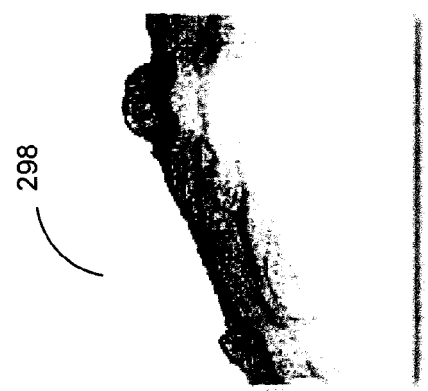
Figure 10B:
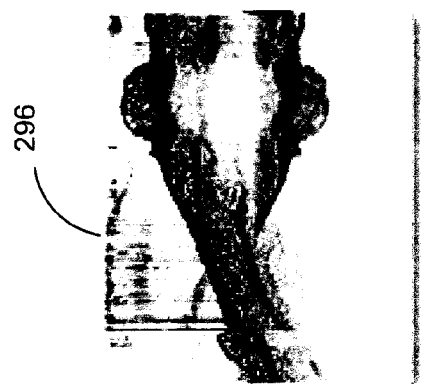
Figure 10A:
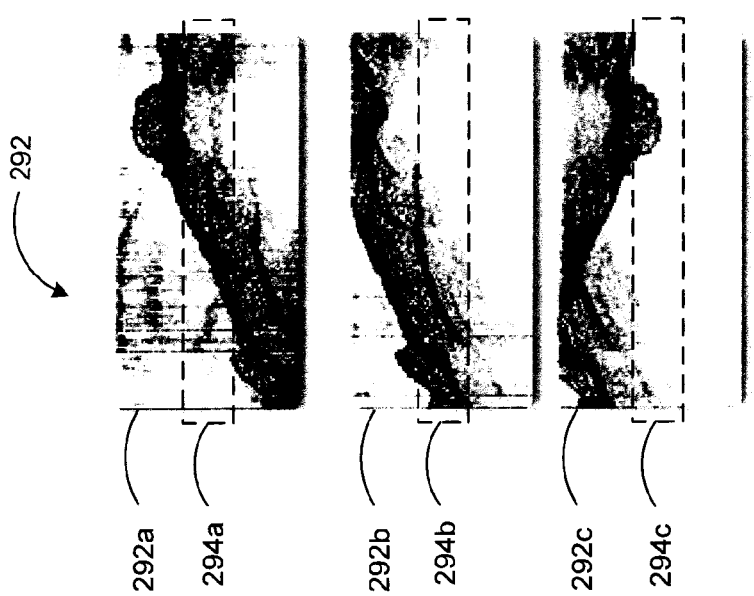
Figure 10F:
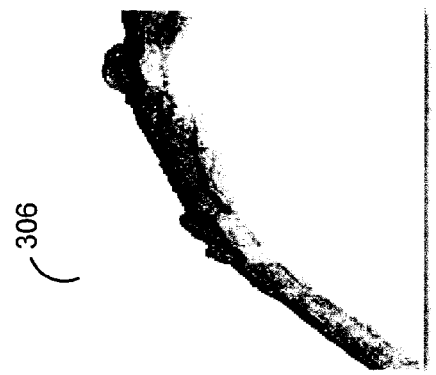
Figure 10E:
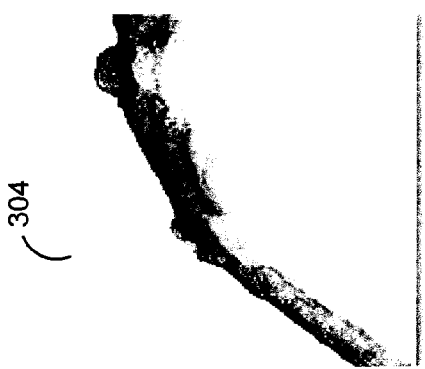
Figure 10D:
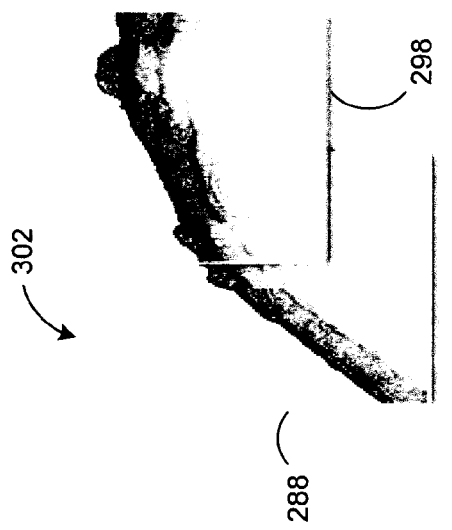
Figure 11A:
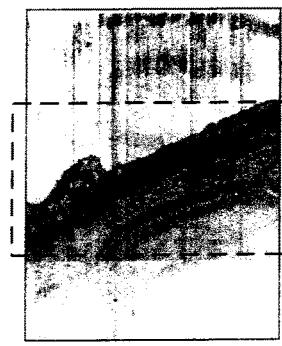
Figure 11B:
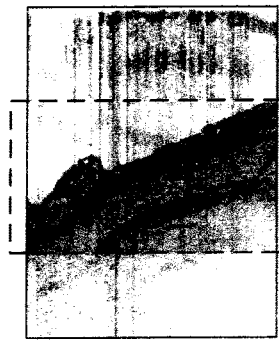
Figure 11C:
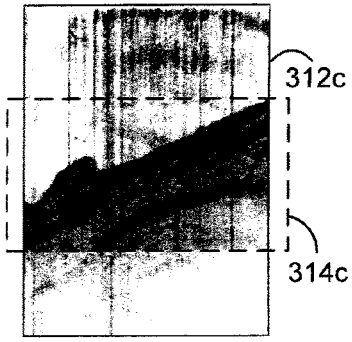
Figure 11D:
Figure 11E:
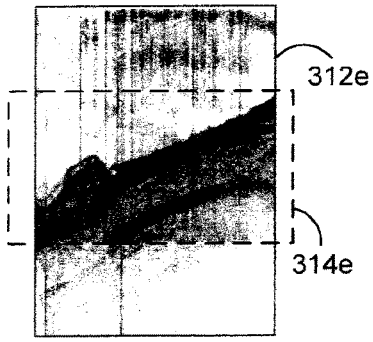
Figure 11F:
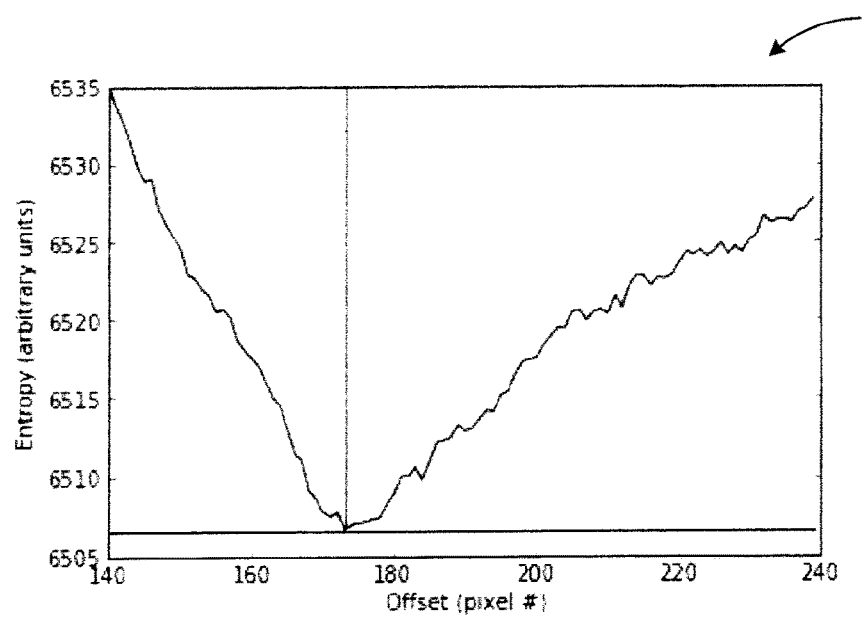
Figures 12A, 12B, 12C, 12D:
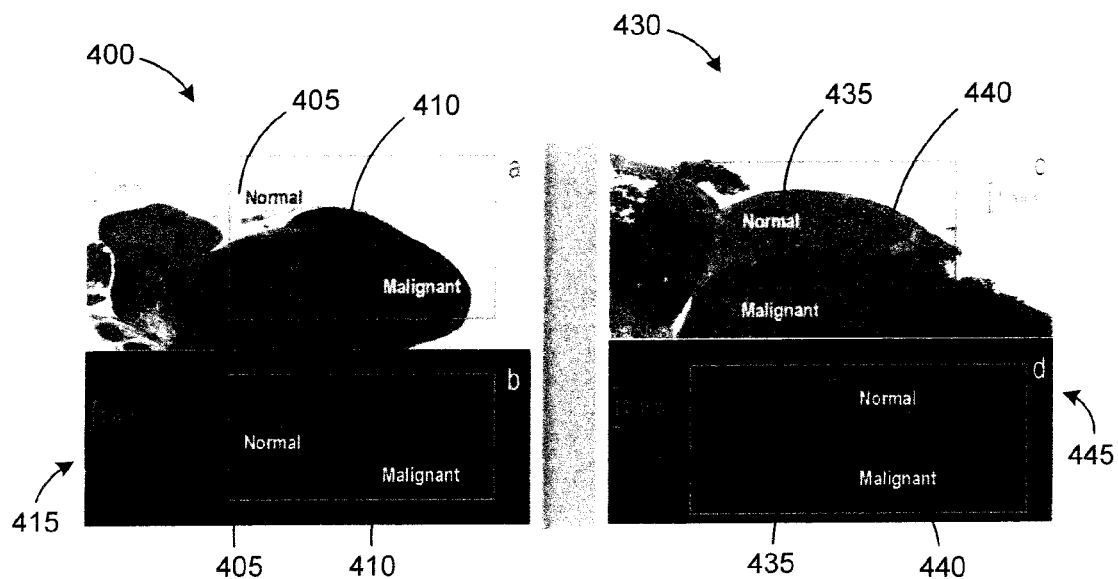
Figure 13A:
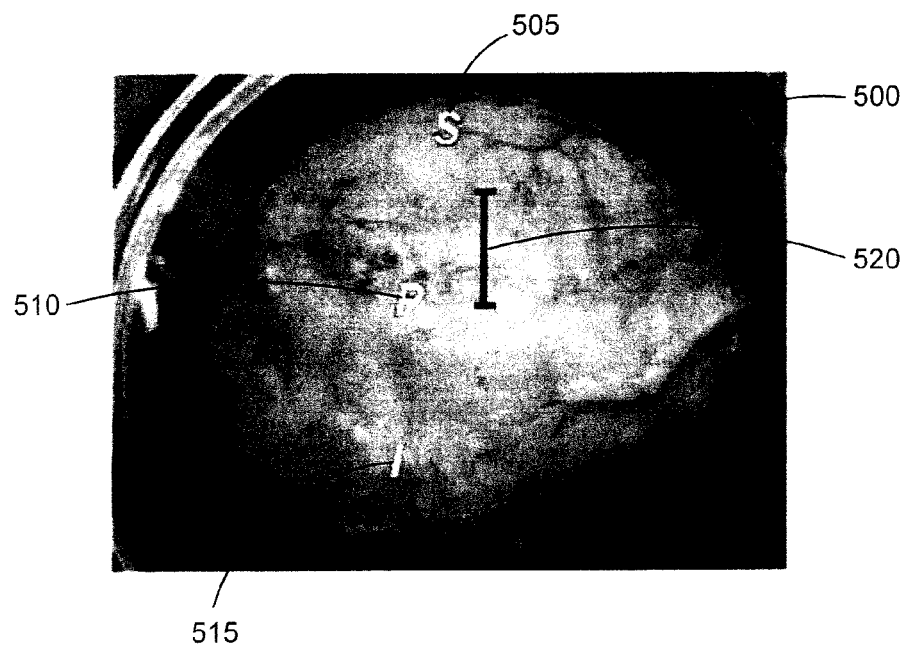
Figure 13B:
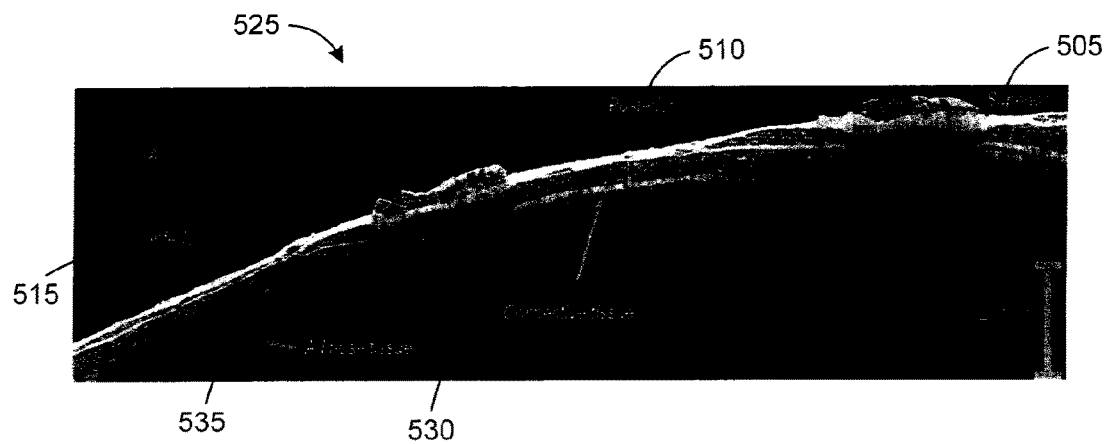
Figure 14A:
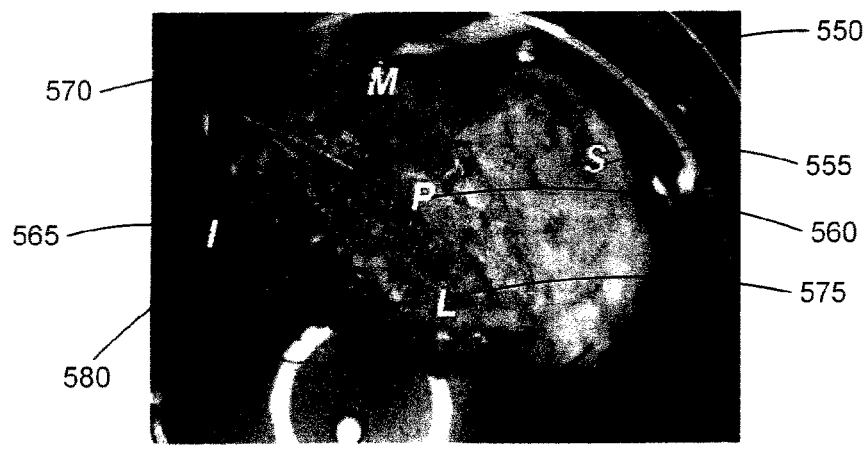
Figure 14B:
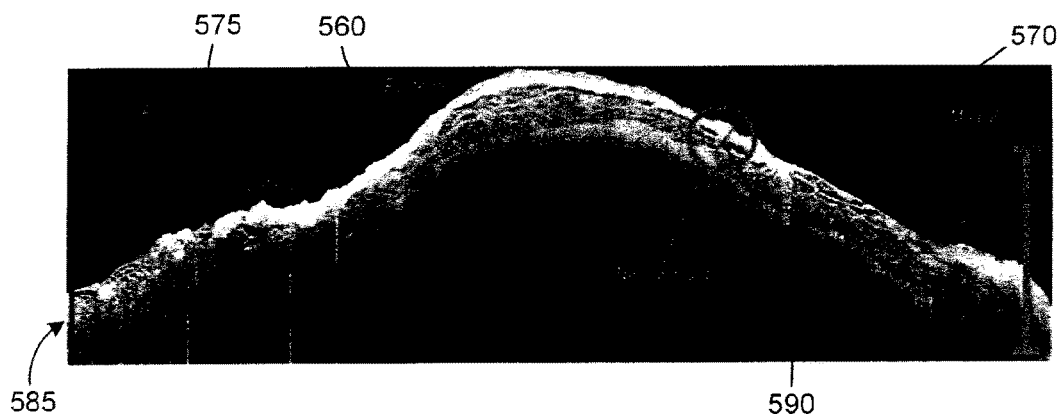
Figure 15A:
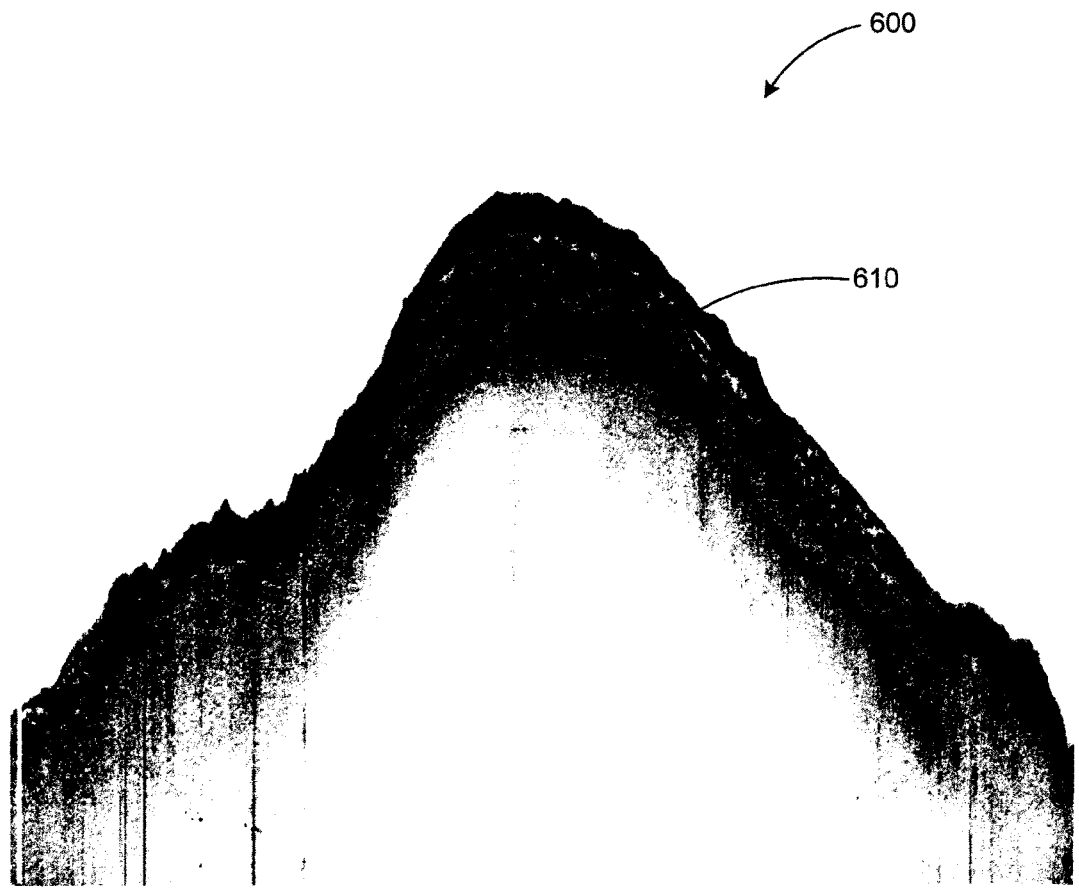
Figure 15B:
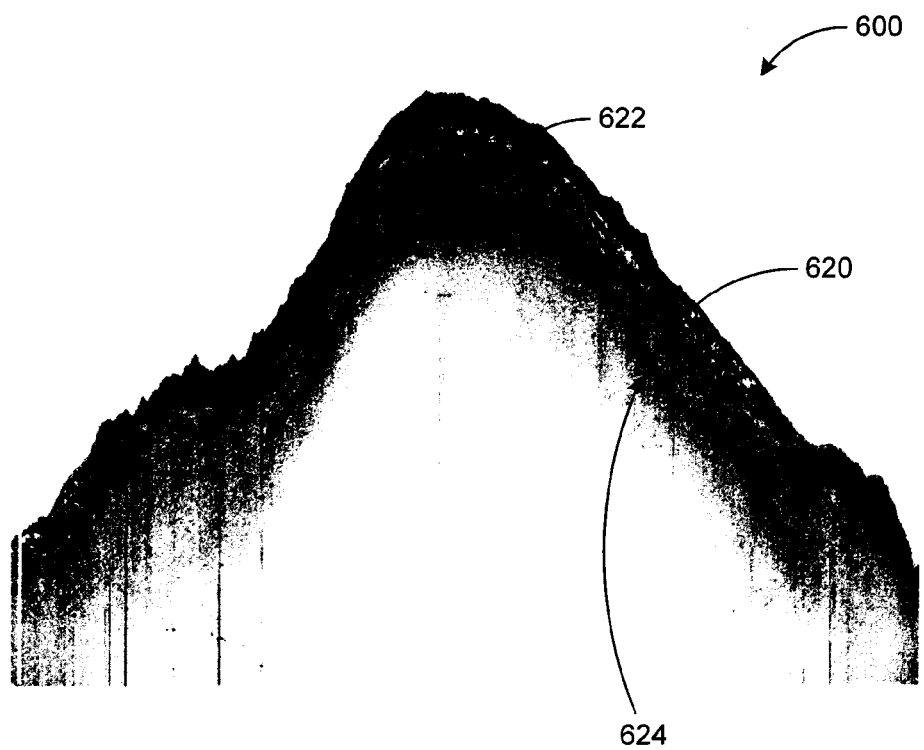
Figure 15C:
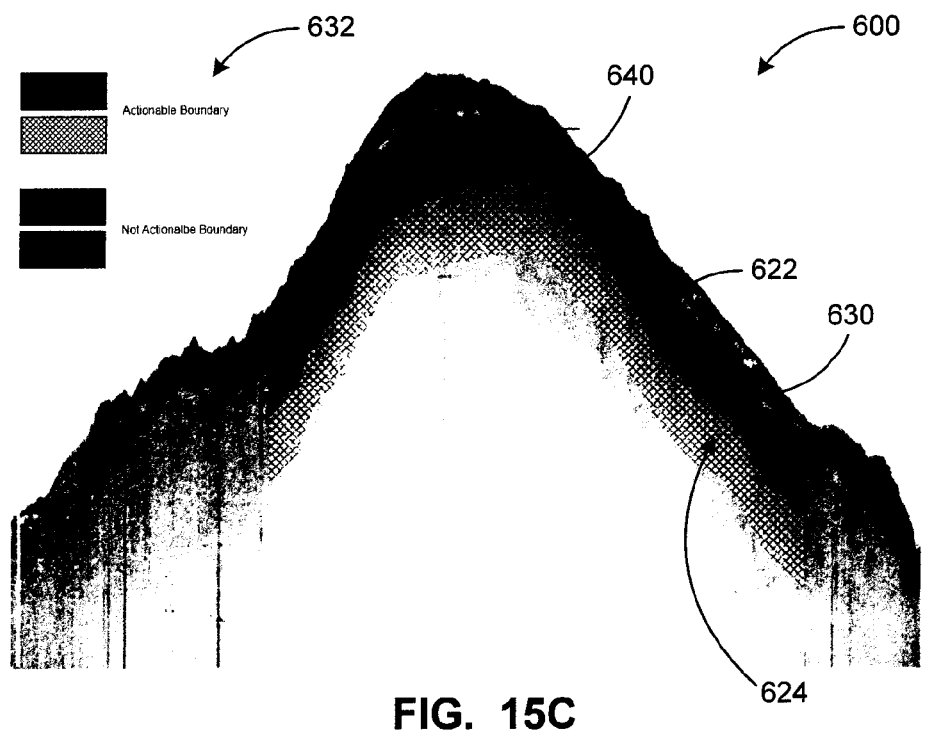
Figure 16:
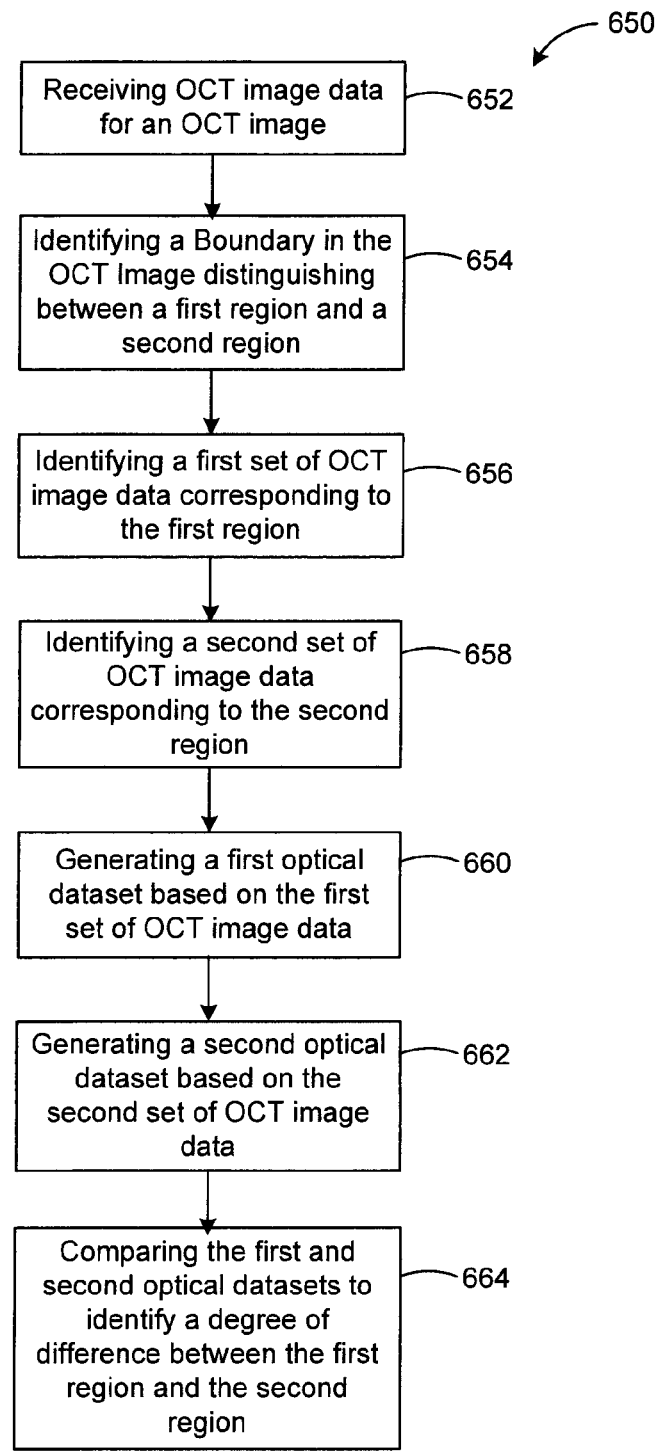
Figure 17:
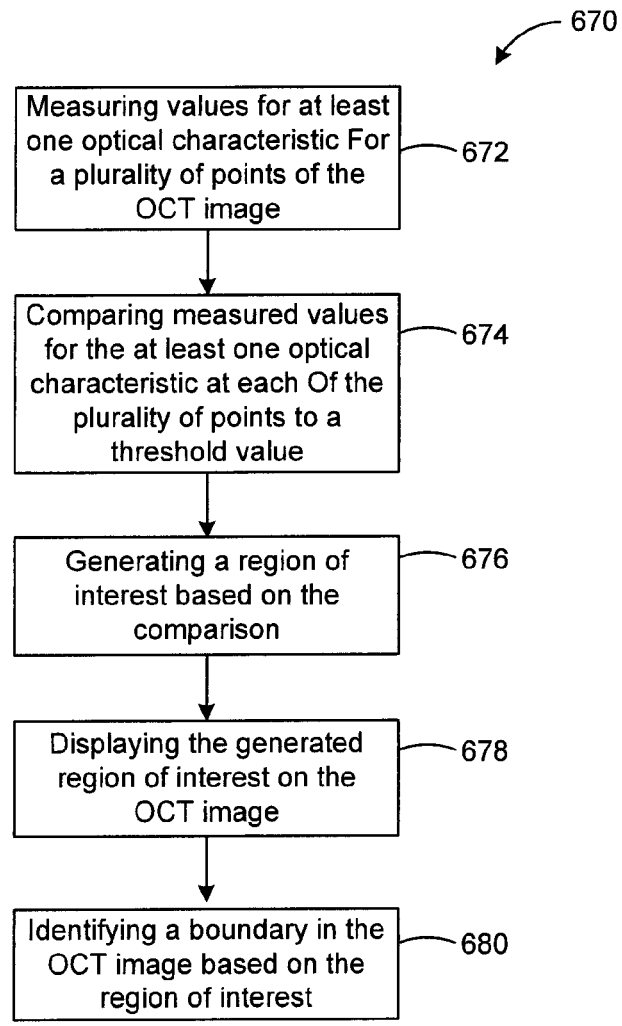
Figure 18A:
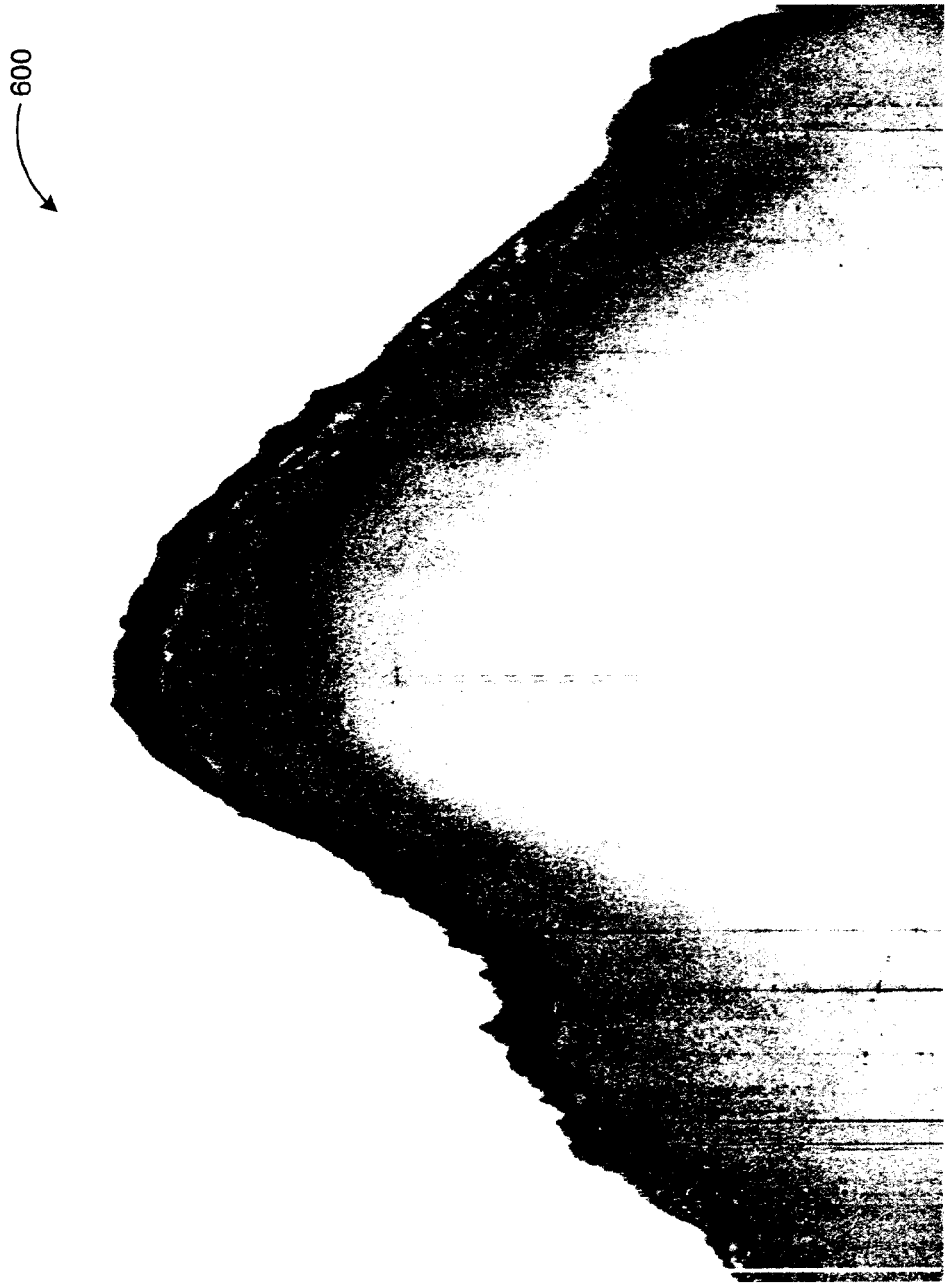
Figure 18B:
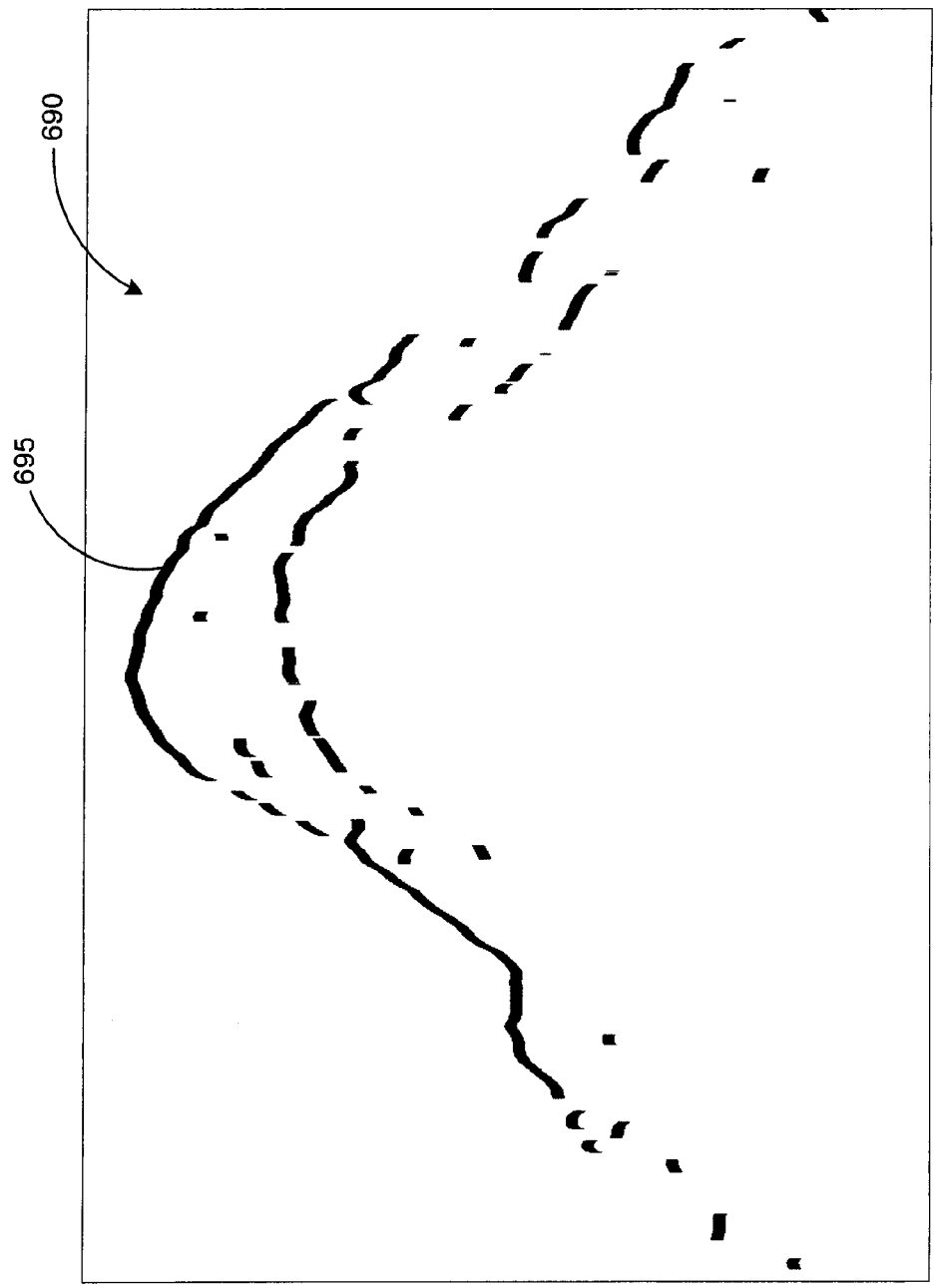
Figure 18C:
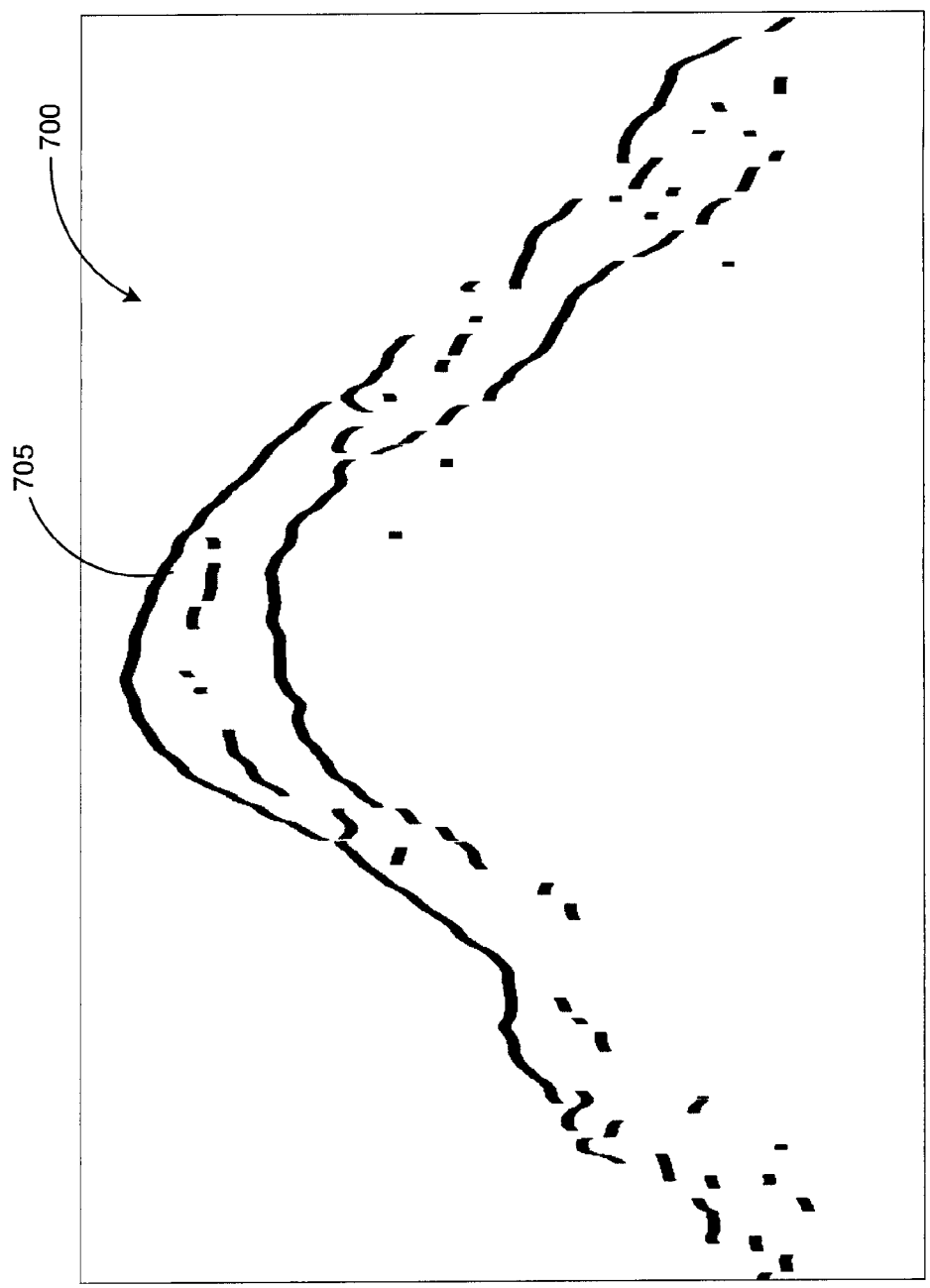
Figure 18E:
Figure 18F:
Figure 18G:
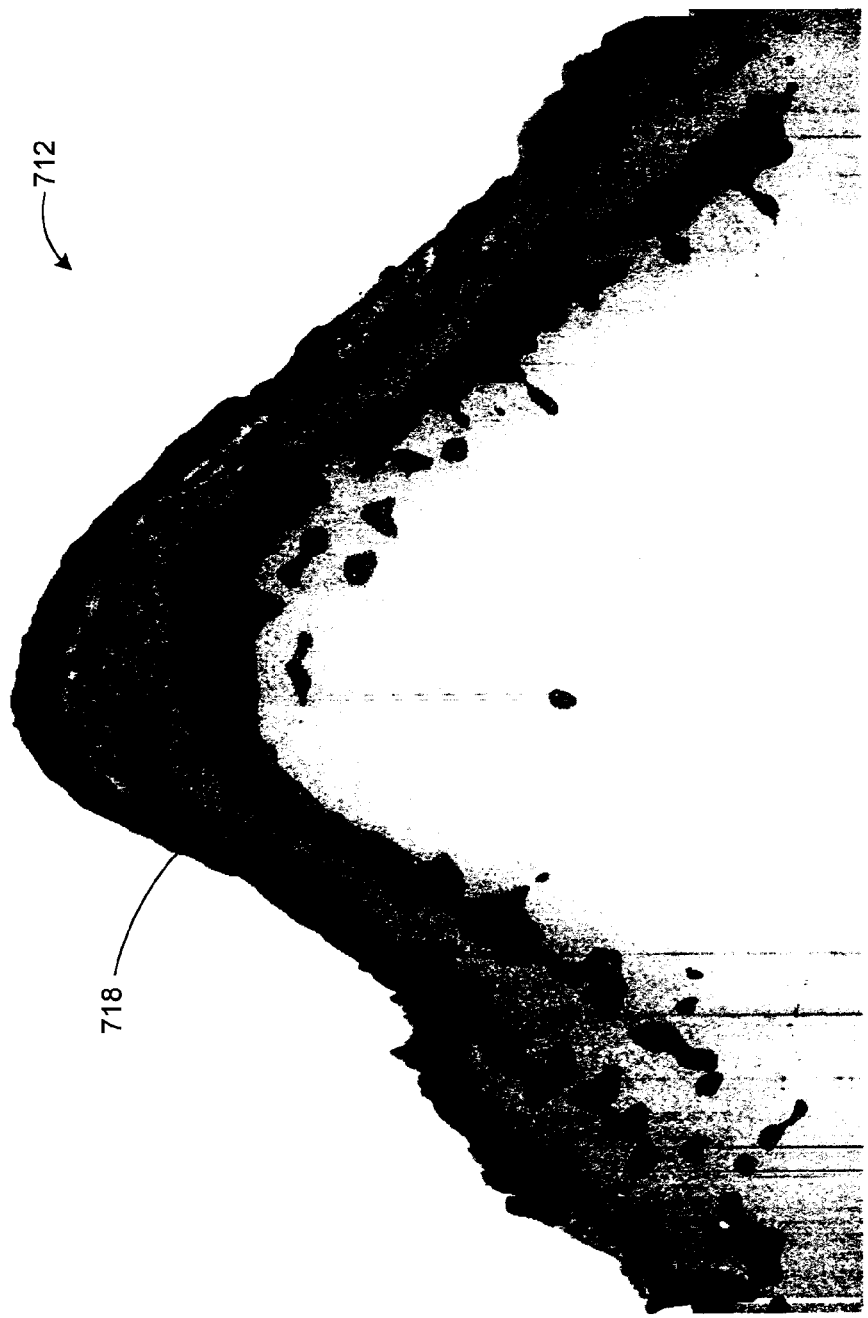
Figure 19A:
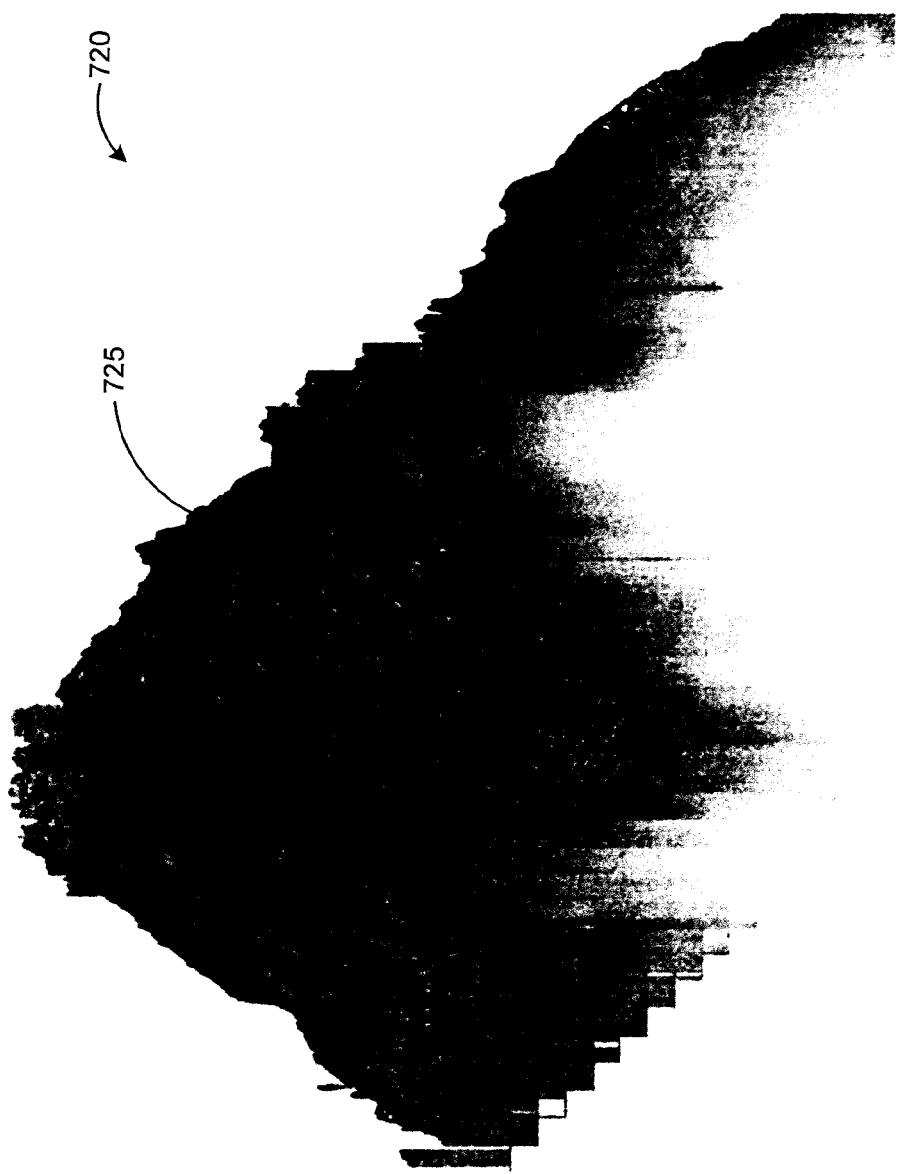
Figure 19B:
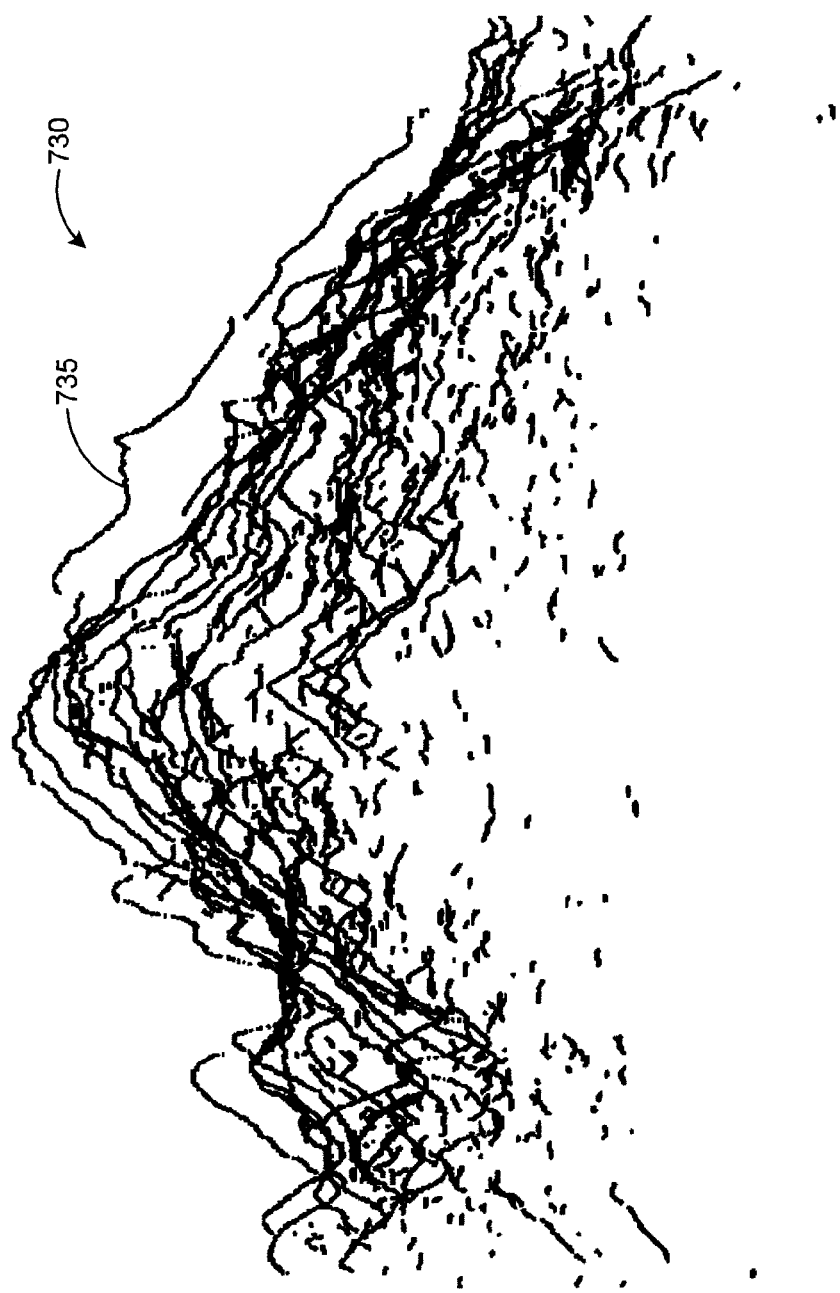
Figure 19C:
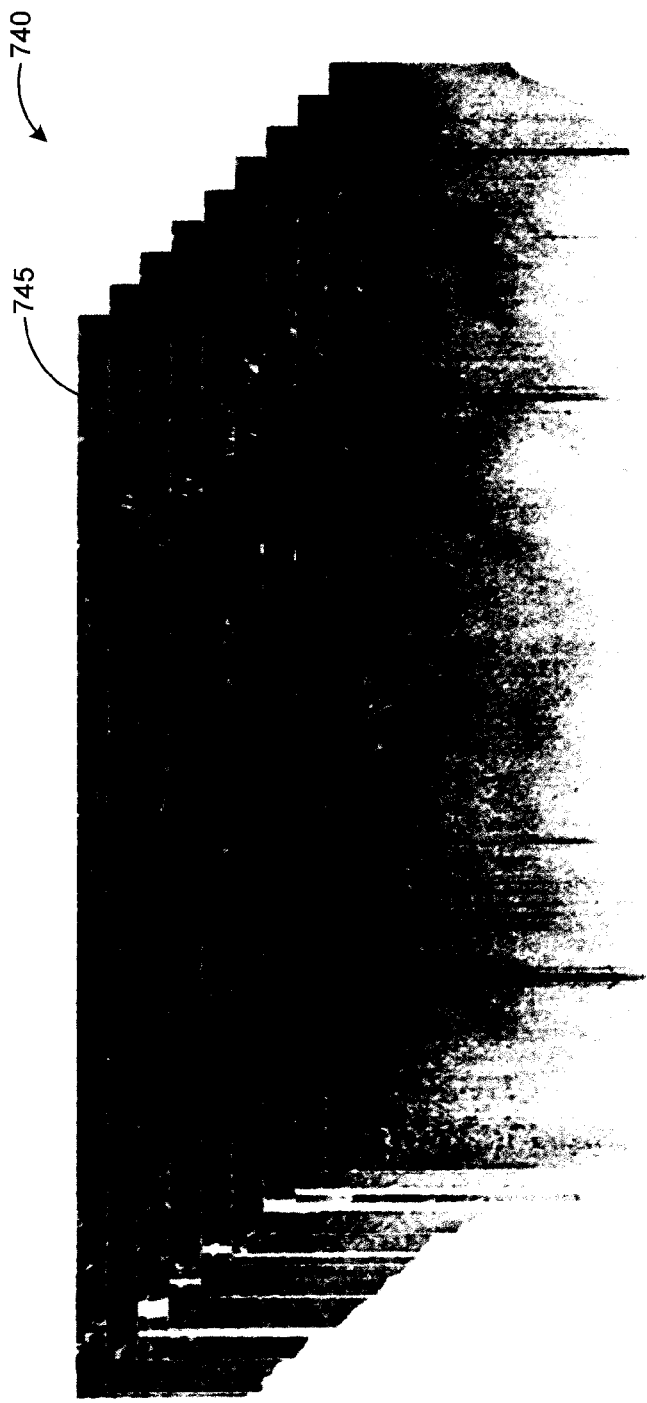
Figure 19D:
Figure 19E:
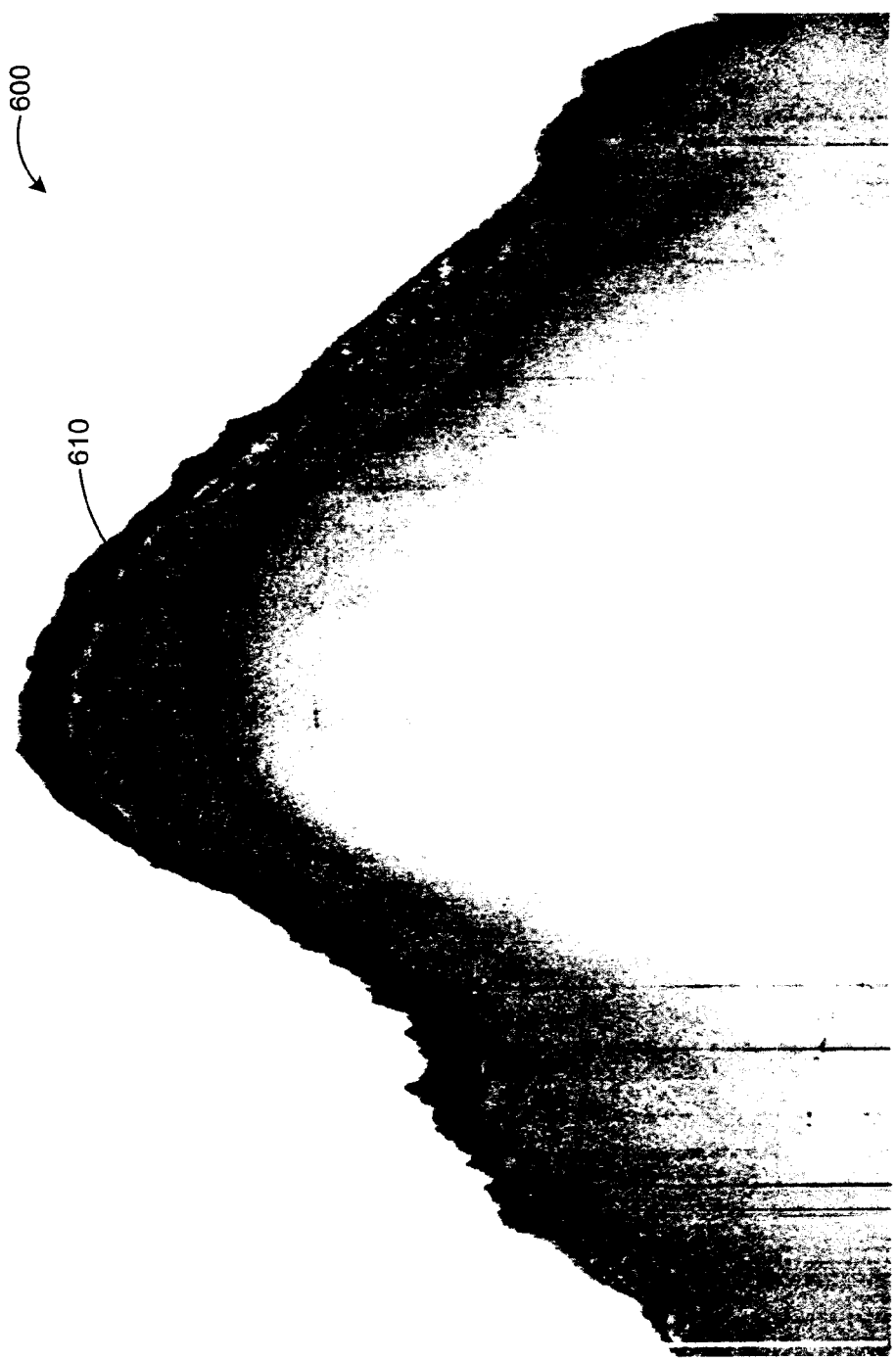
Figure 19F:
Figure 20A:
Figure 20B:
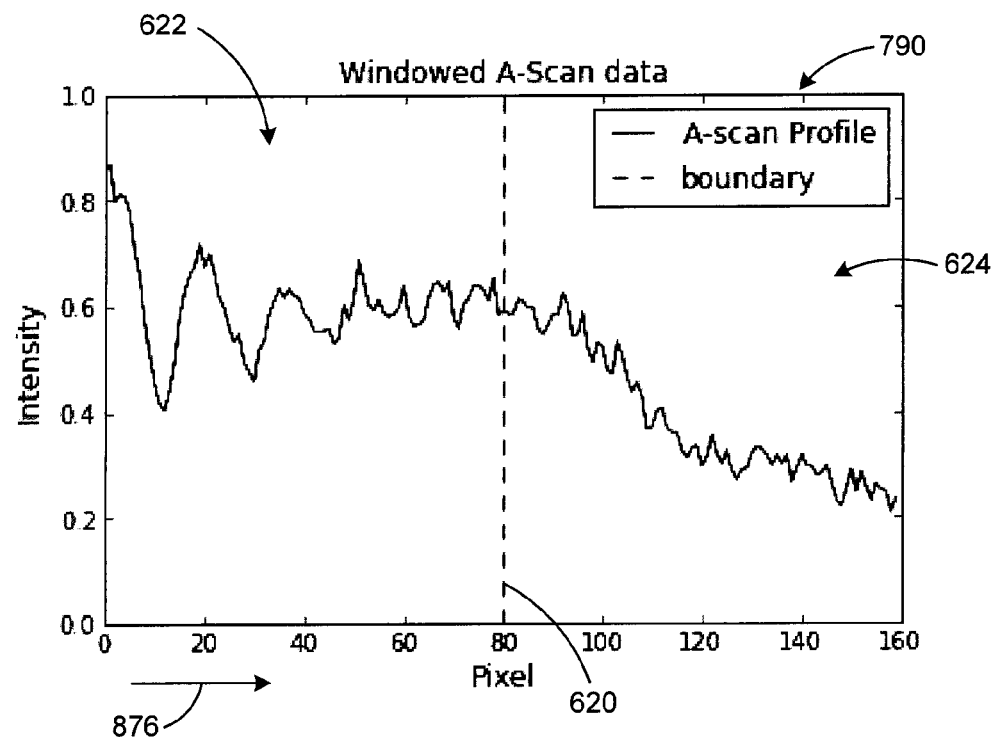
Figure 20C:
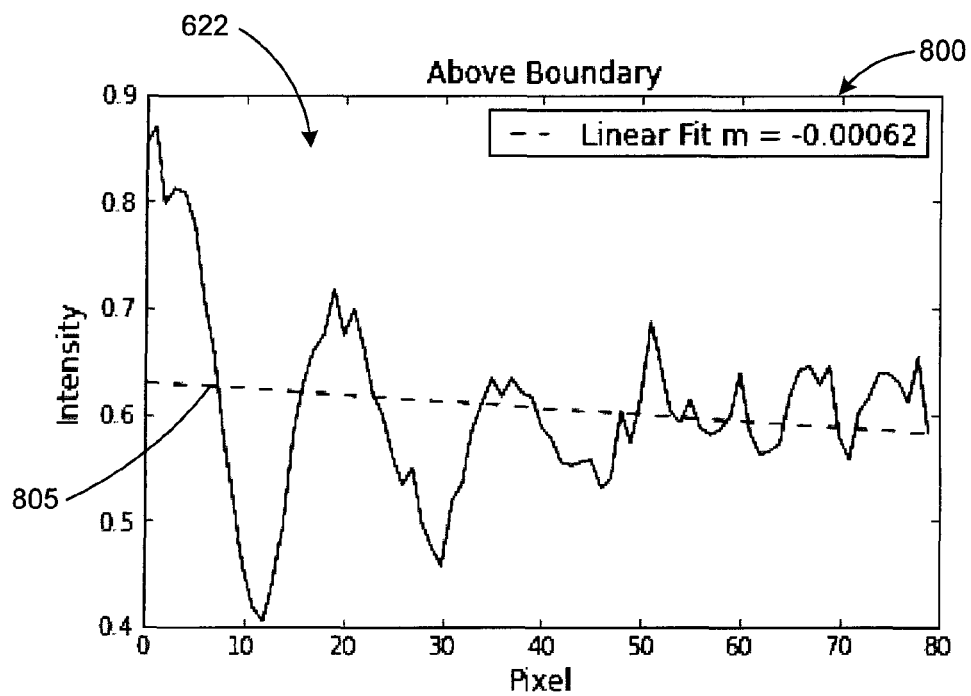
Figure 20D:
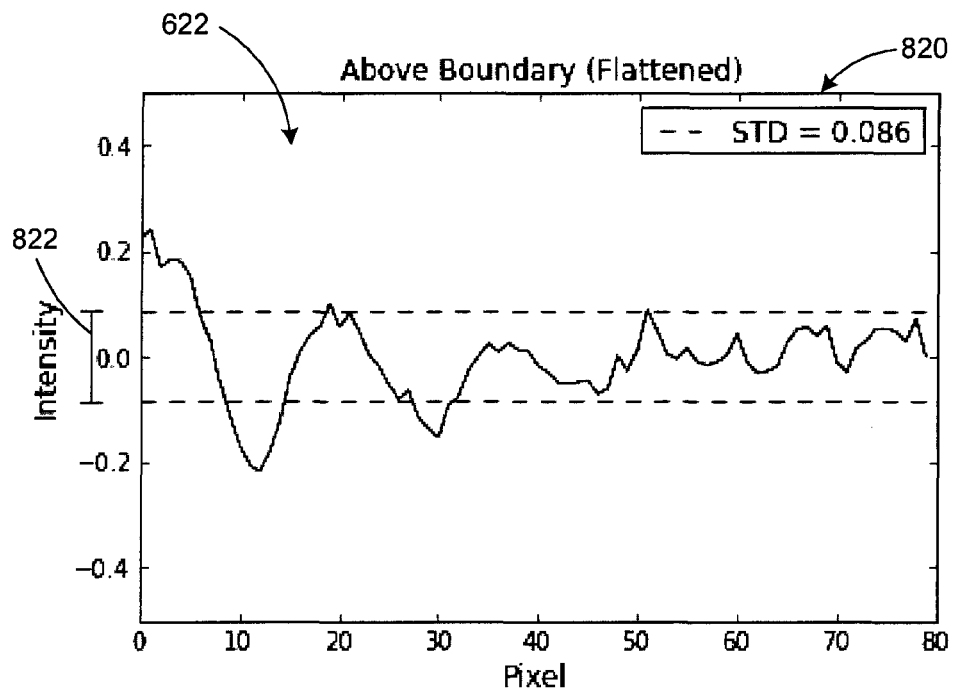
Figure 20E:
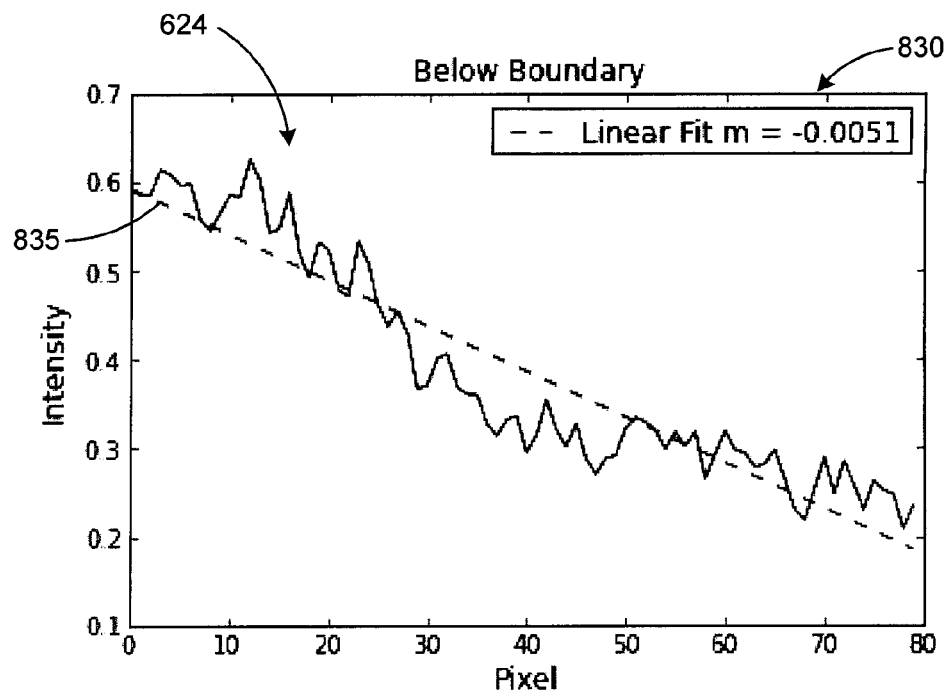
Figure 20F:
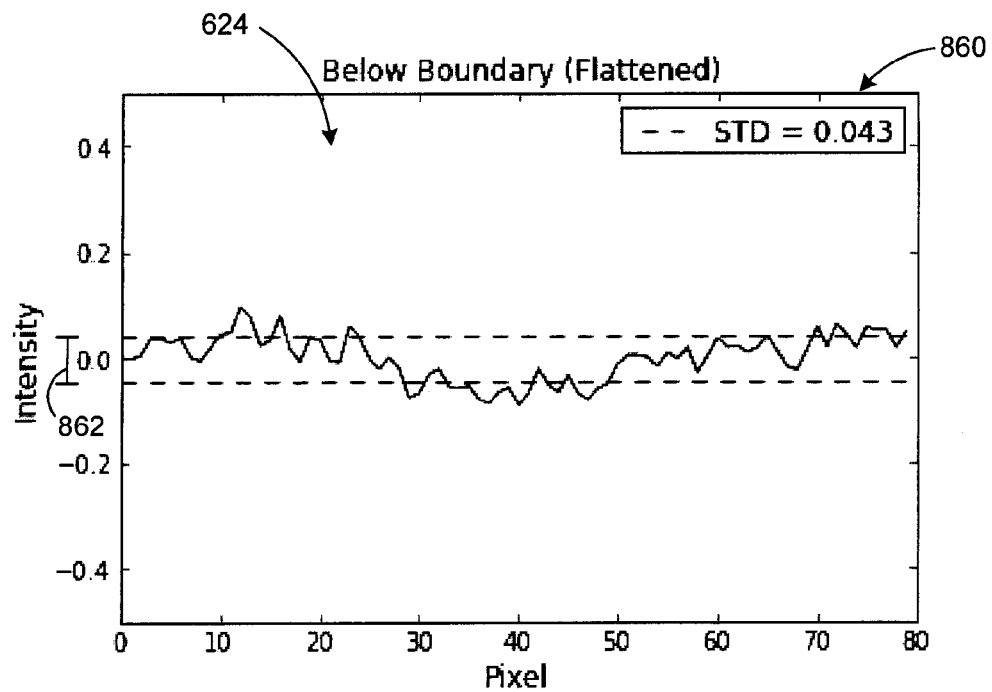
Figure 20G:
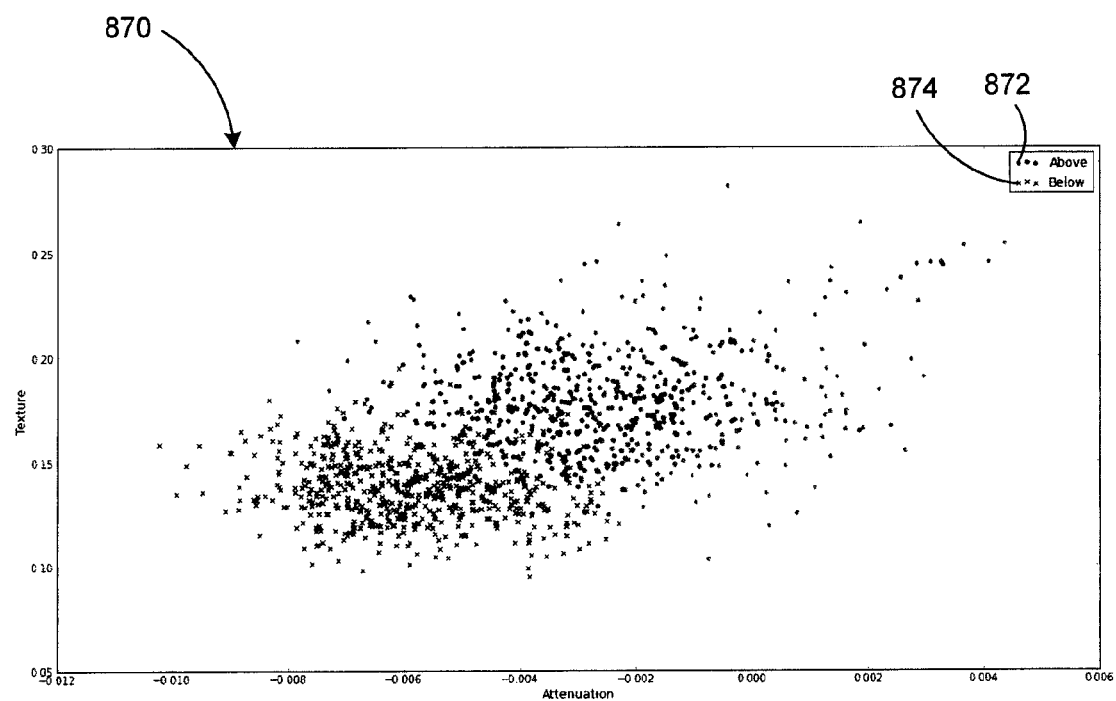
Figure 21A:
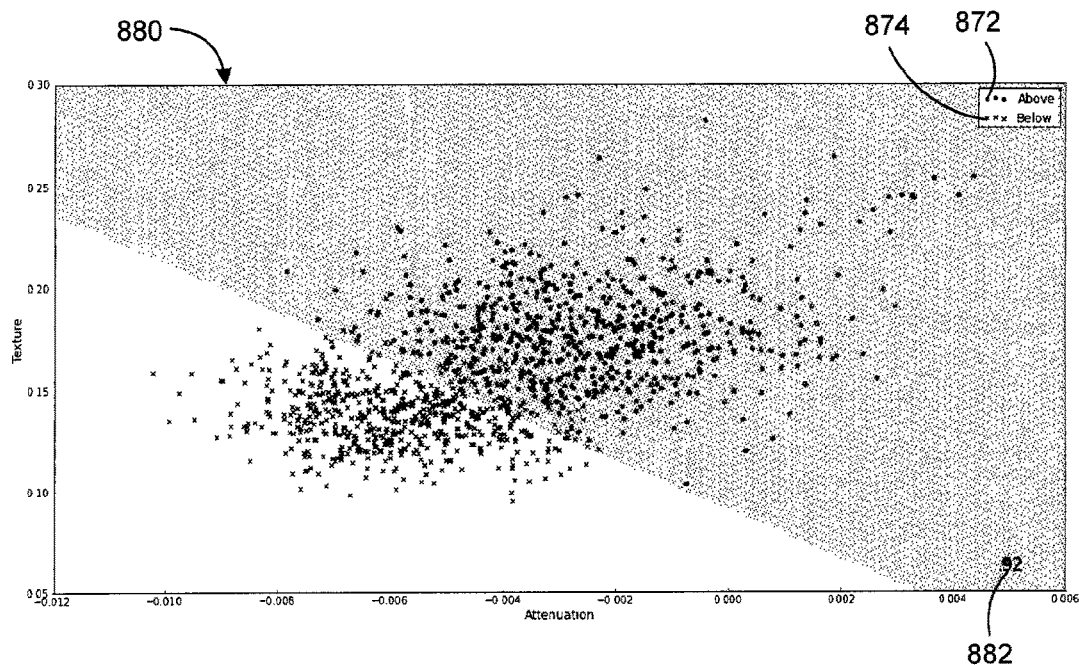
Figure 21B:
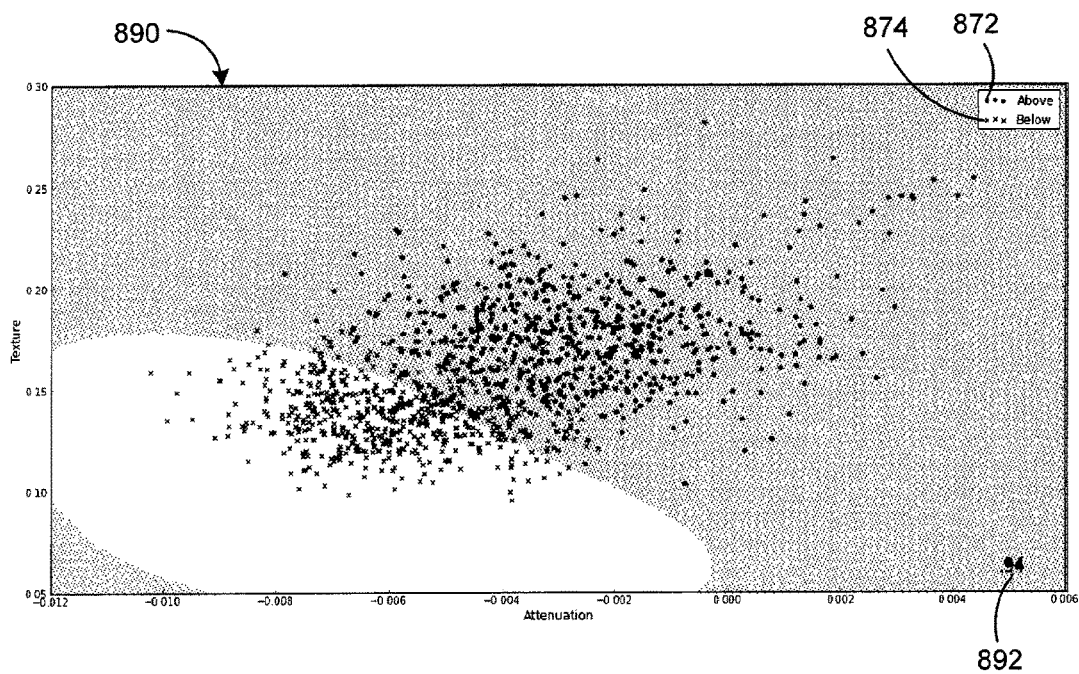
Figure 22A:
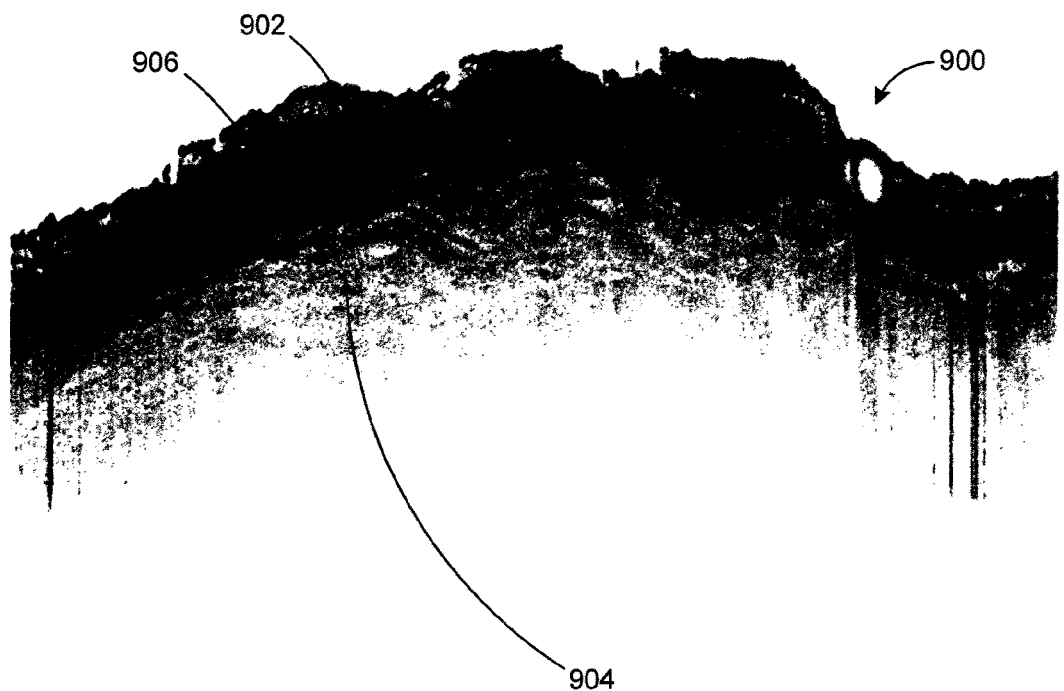
Figure 22B:
Figure 22C:
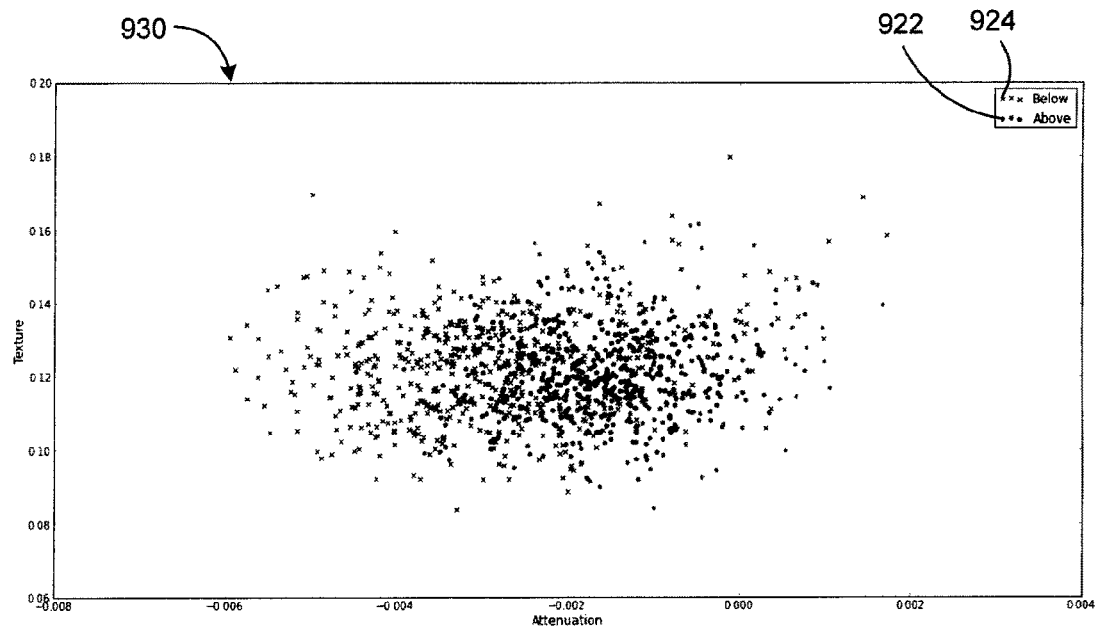
Figure 22D:
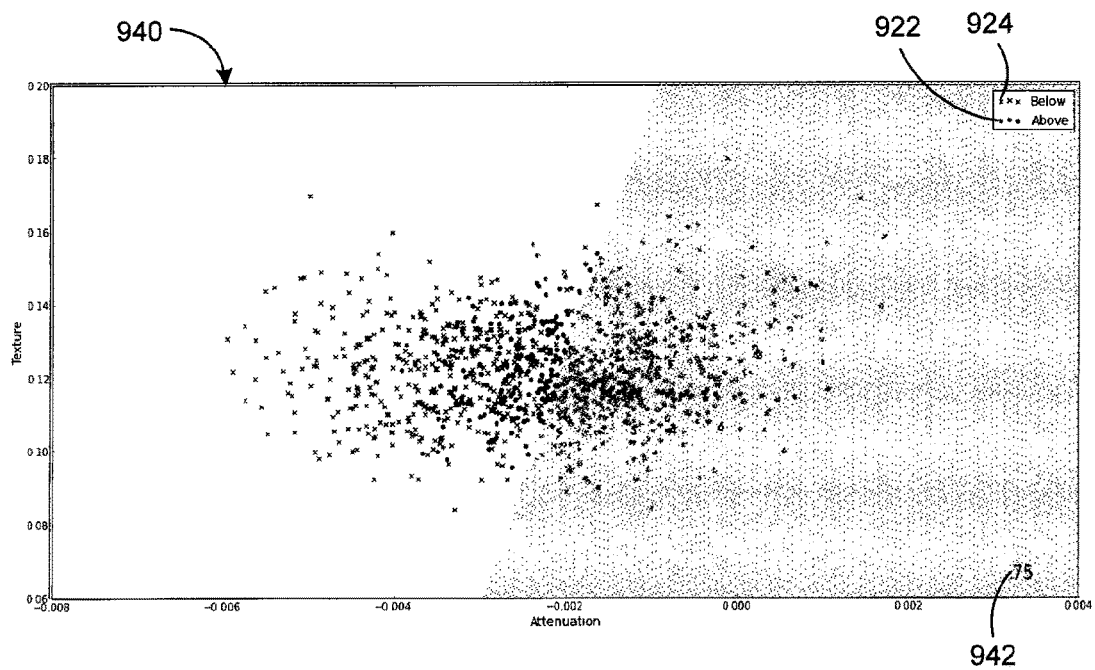
Figure 22E:
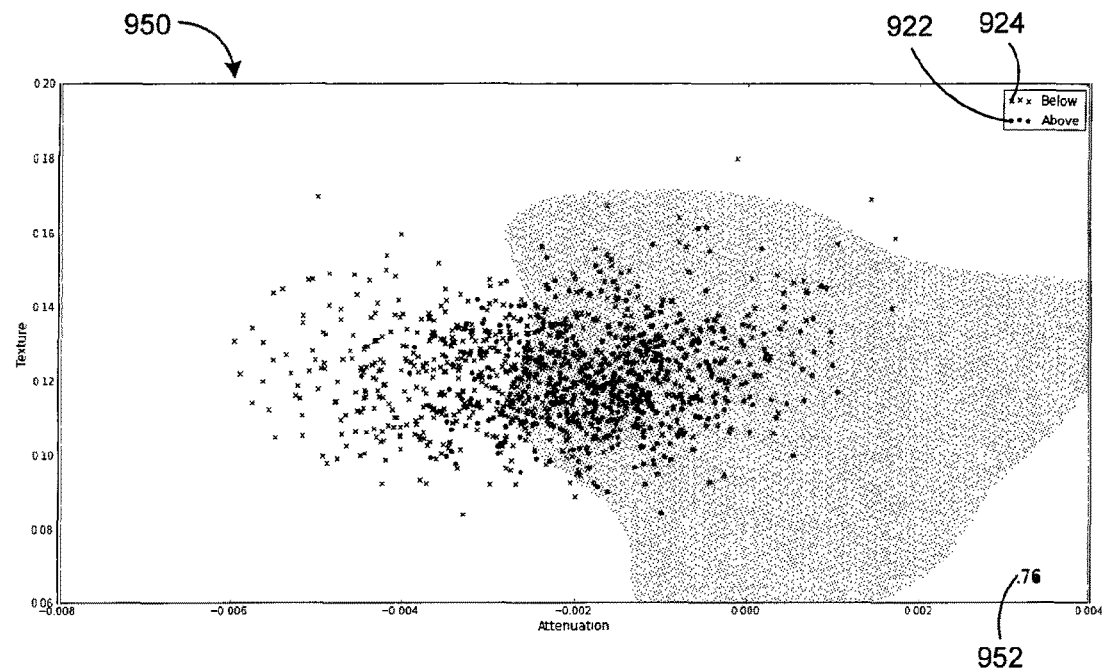
Figure 22F:
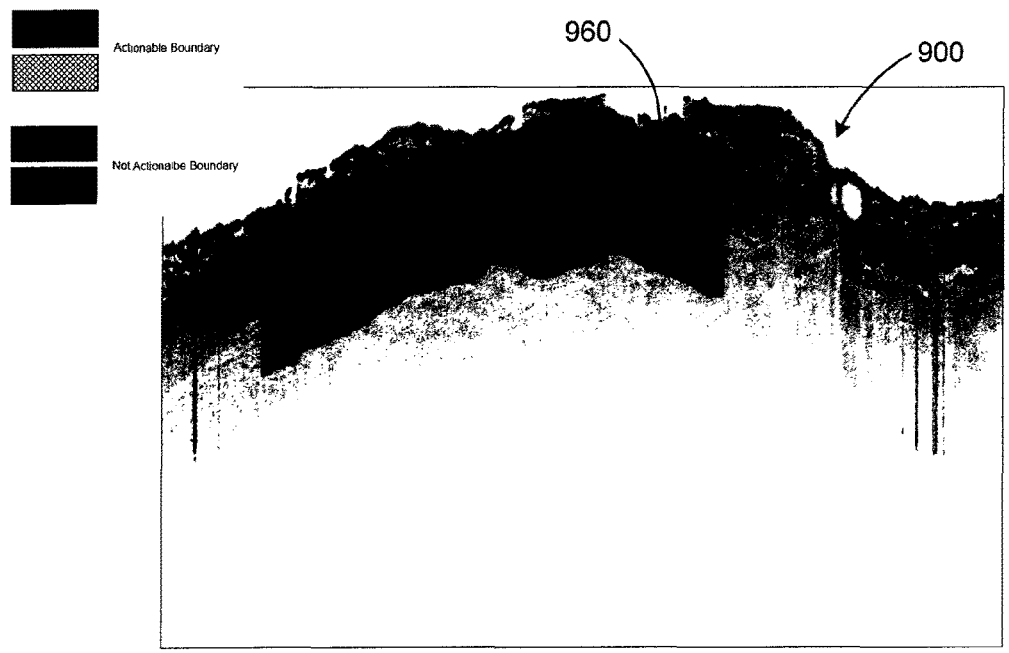
Figure 23A:
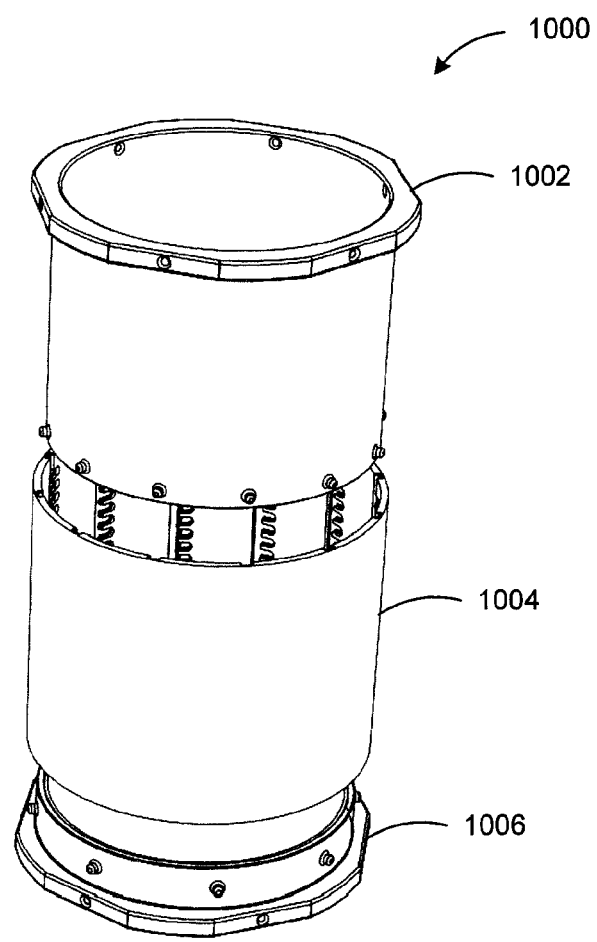
Figure 23B:
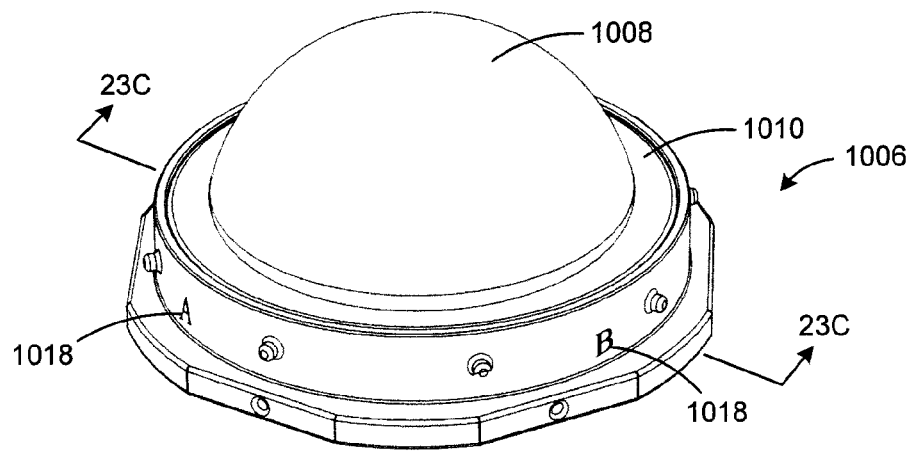
Figure 23C:
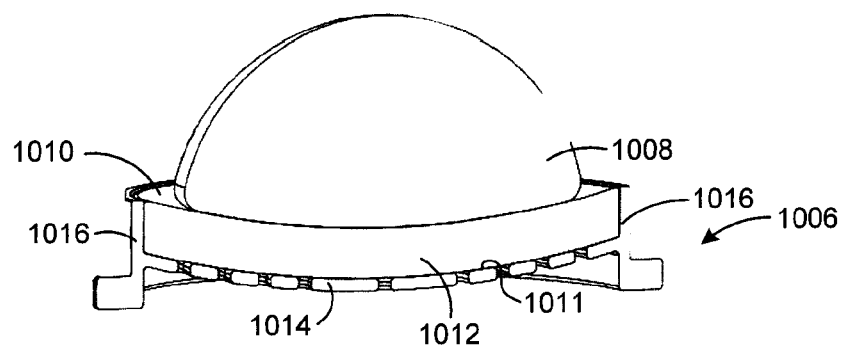
Figure 23D:
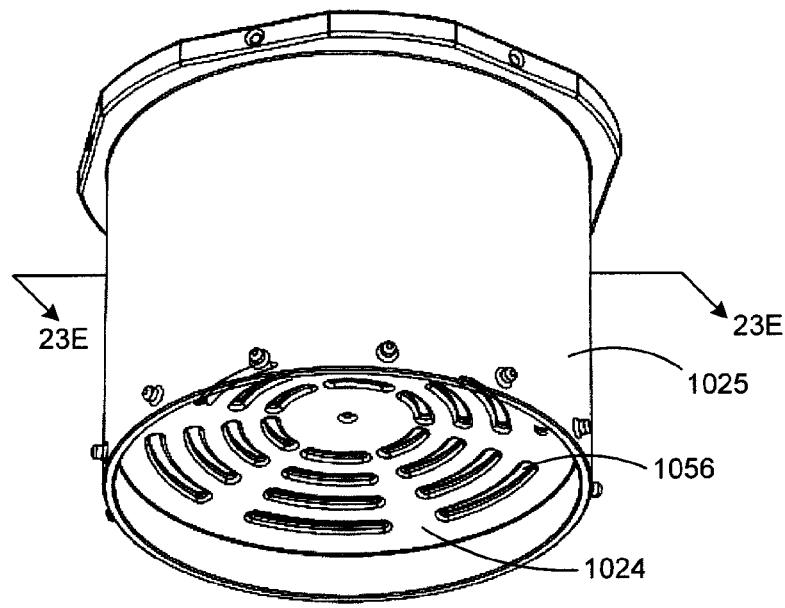
Figure 23E:
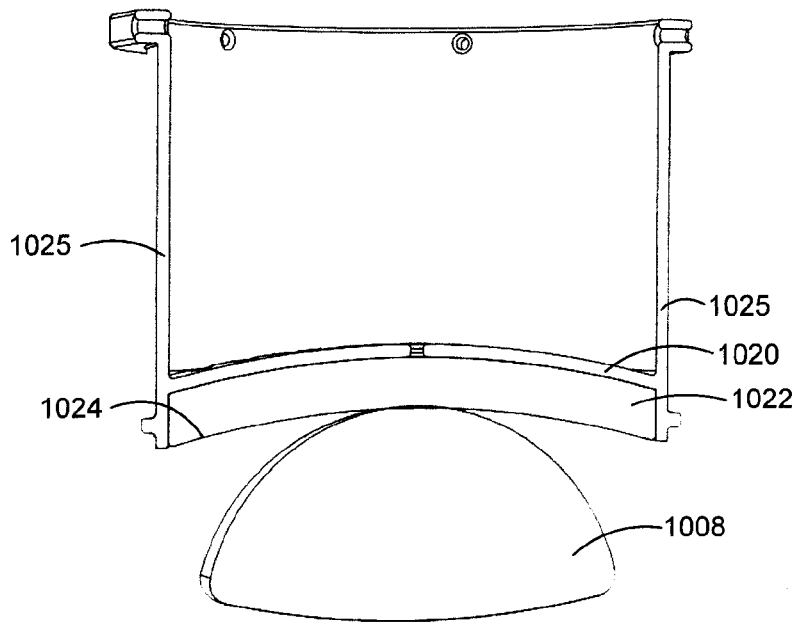
Figure 23F:
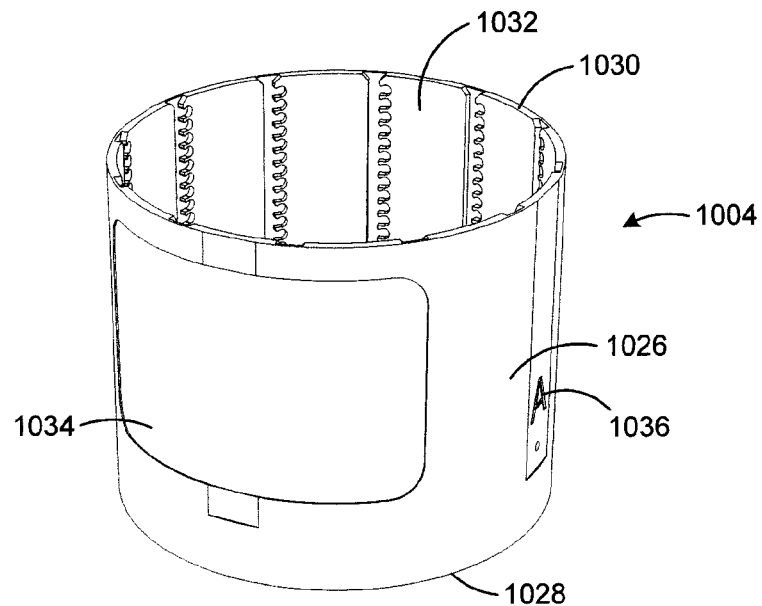
Figure 23G:
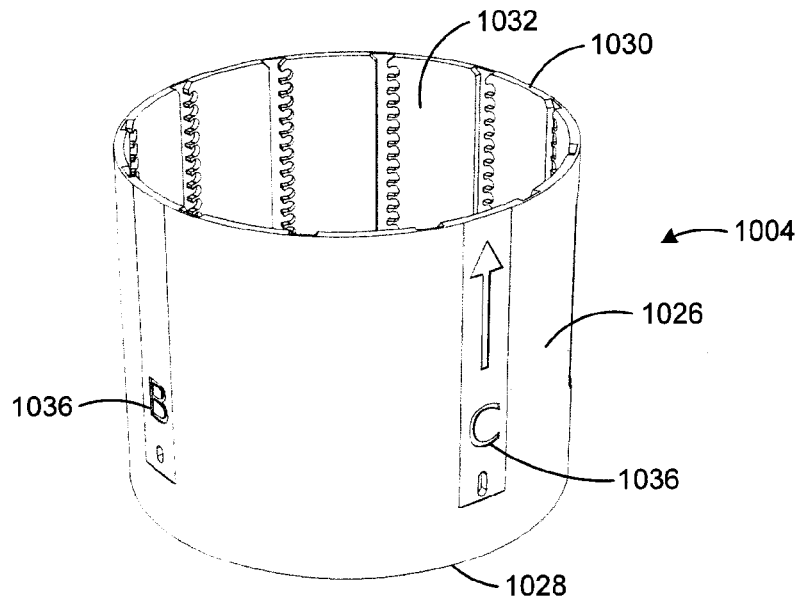
Figure 24A:
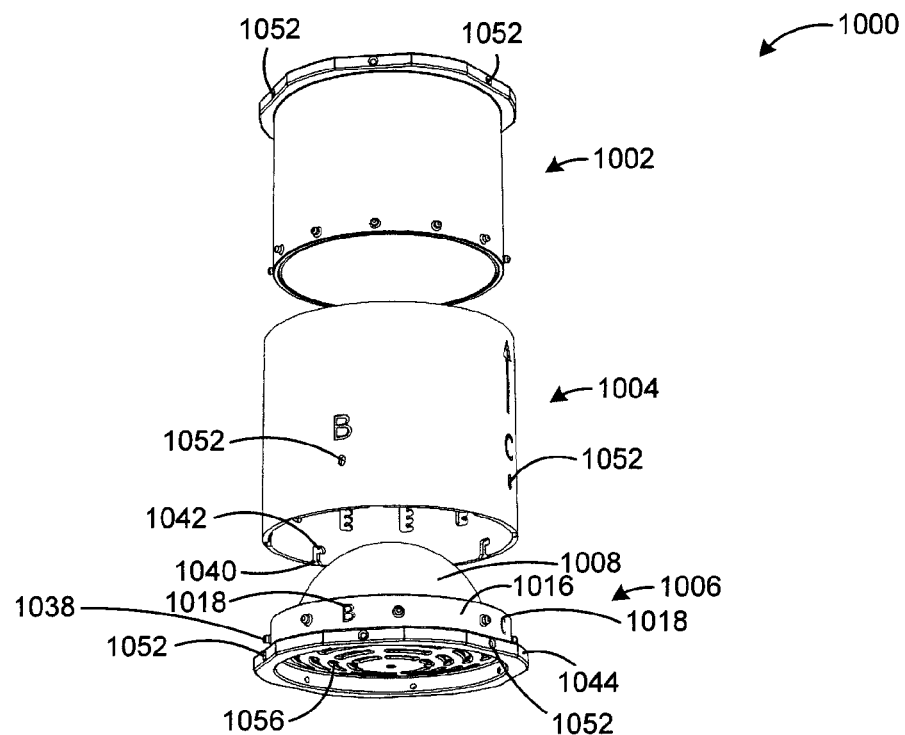
Figure 24B:
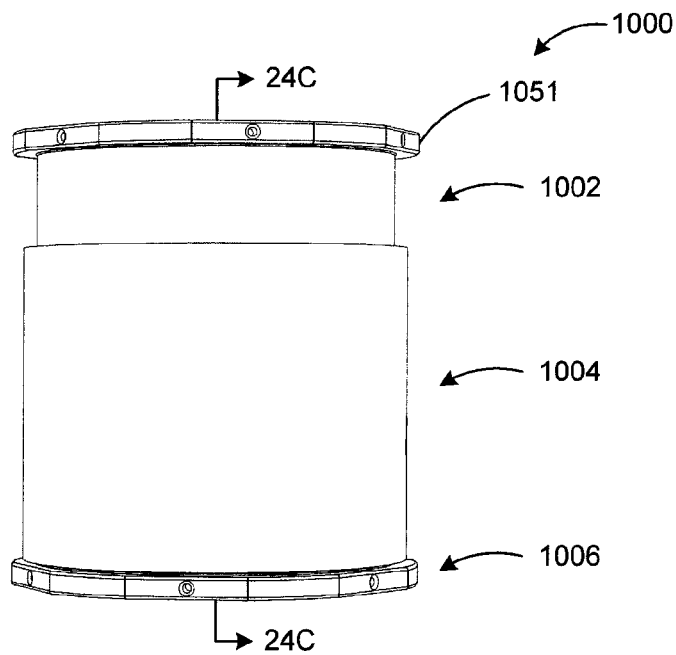
Figure 24C:
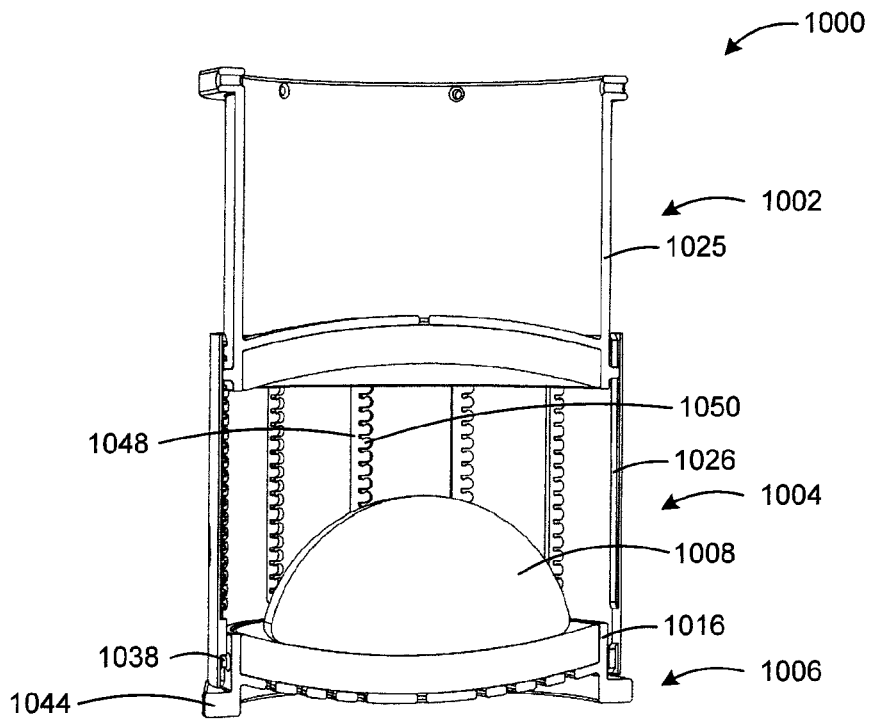
Figure 24D:
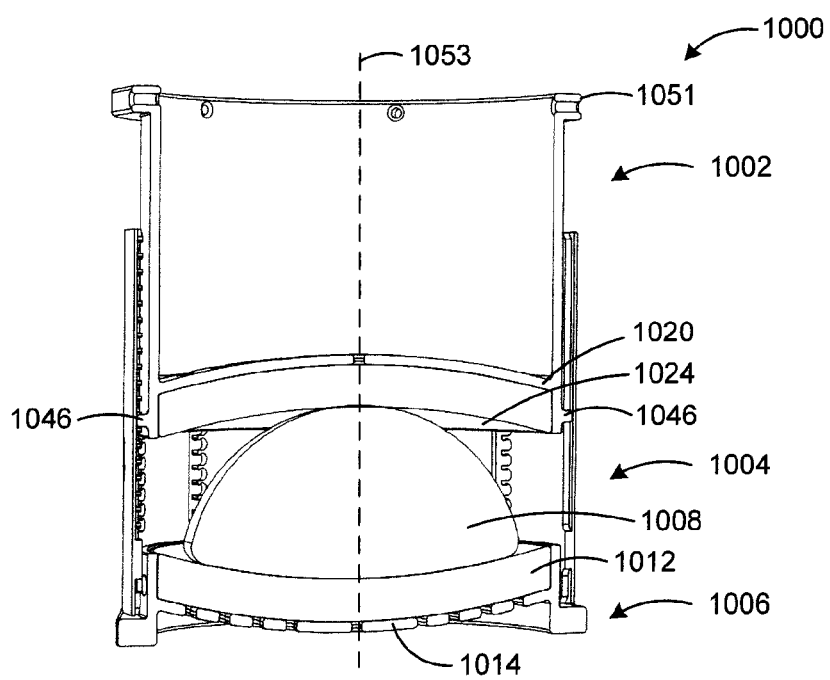
Figure 24E:
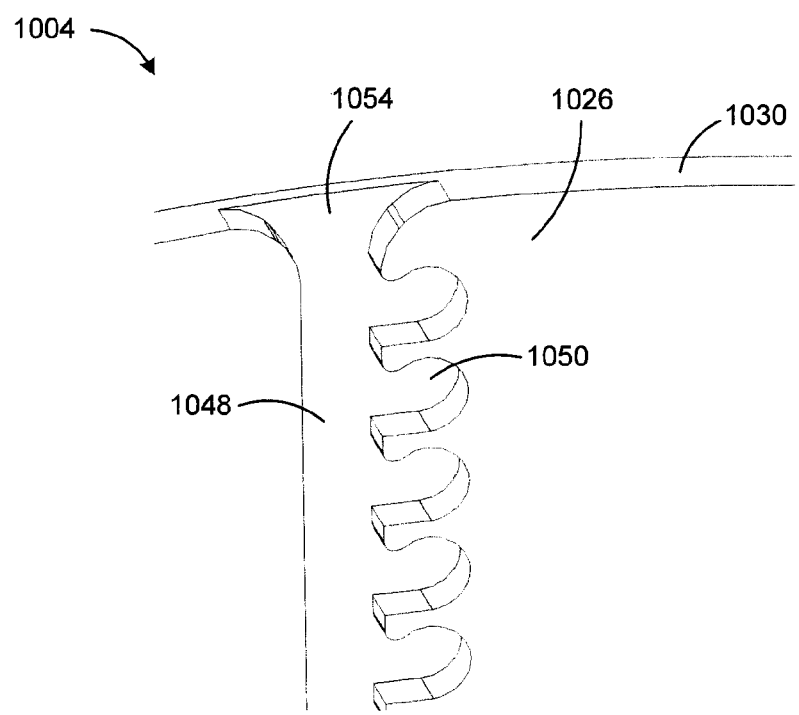
Figure 25A:
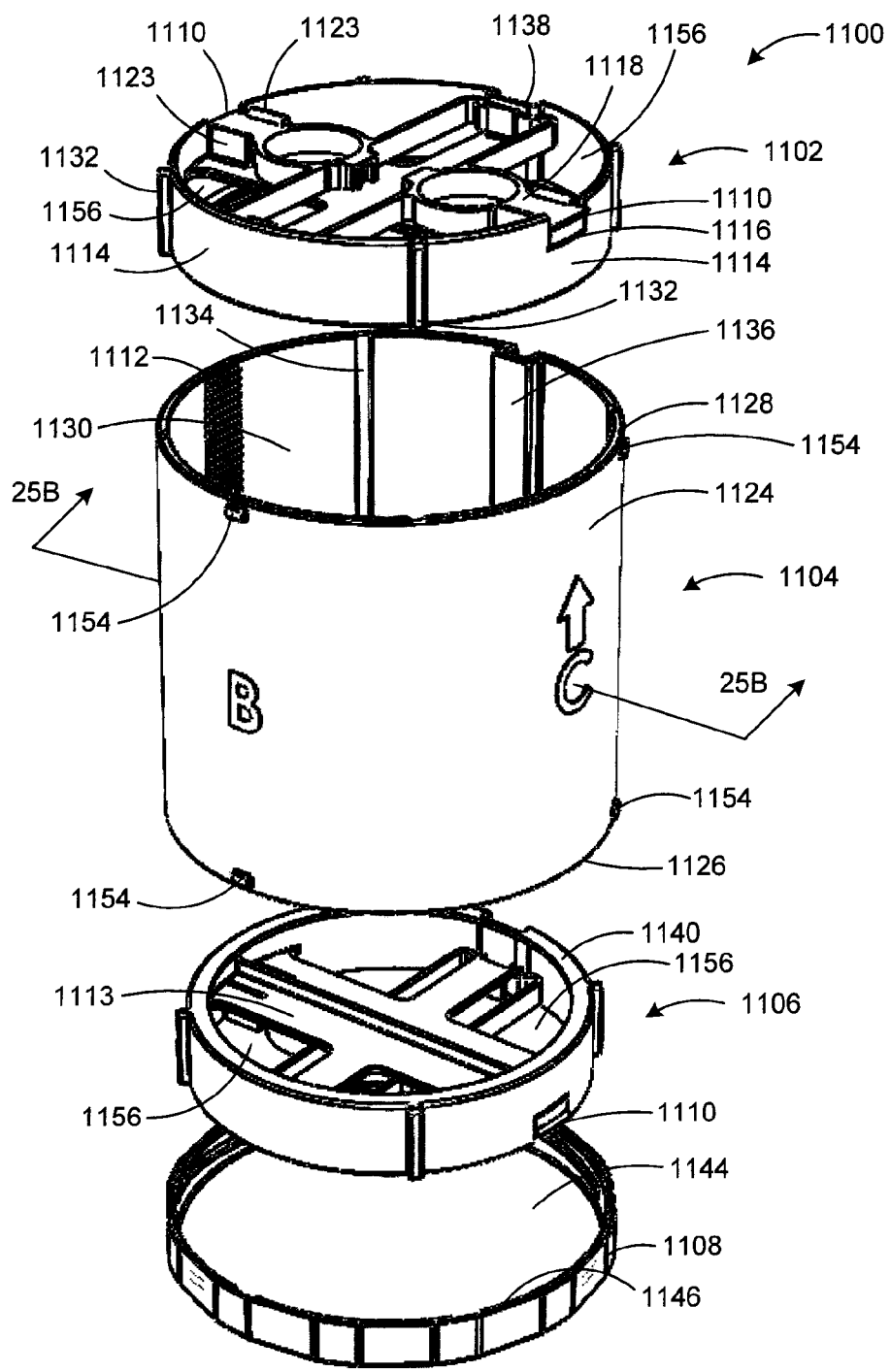
Figure 25B:
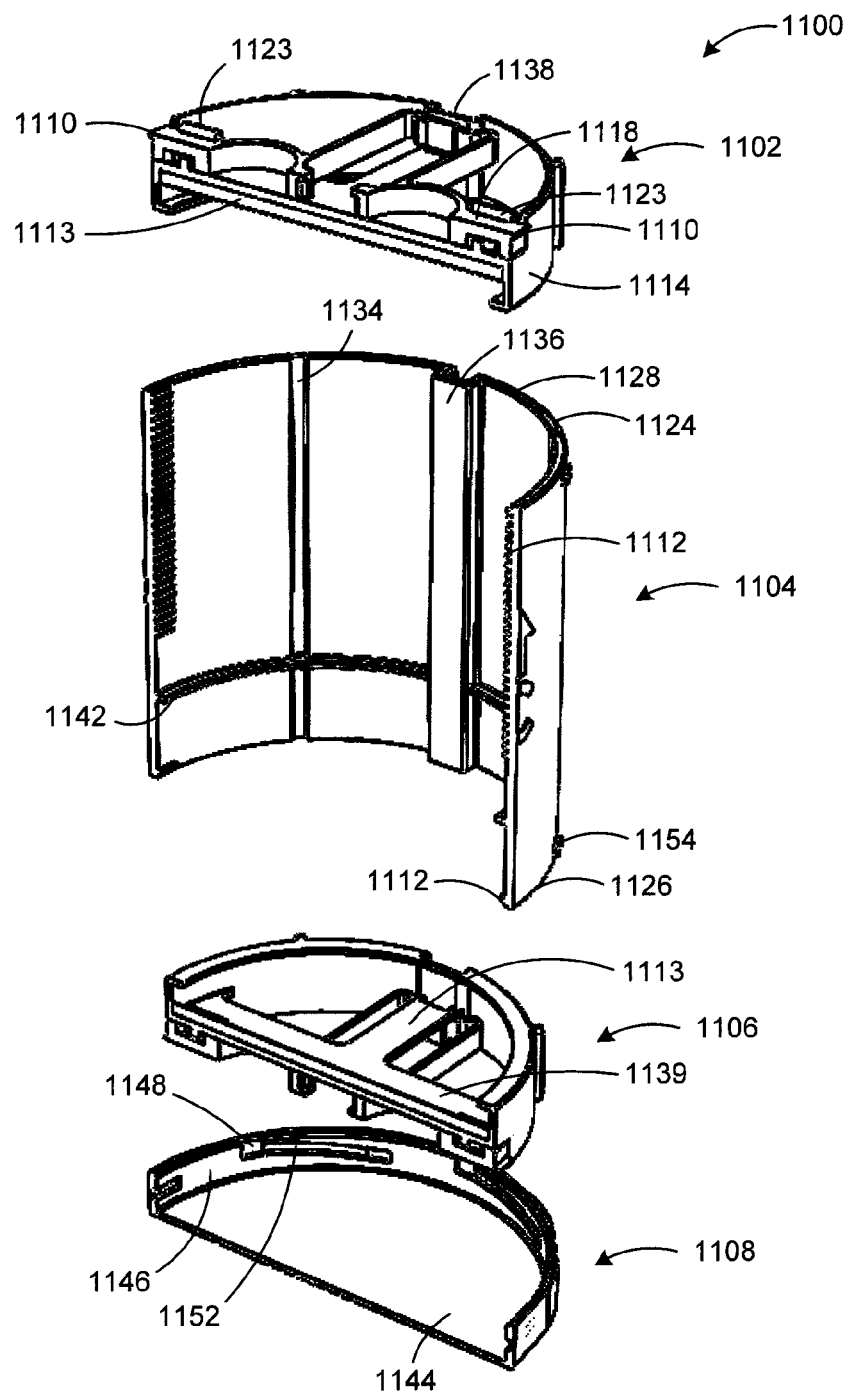
Figure 25C:
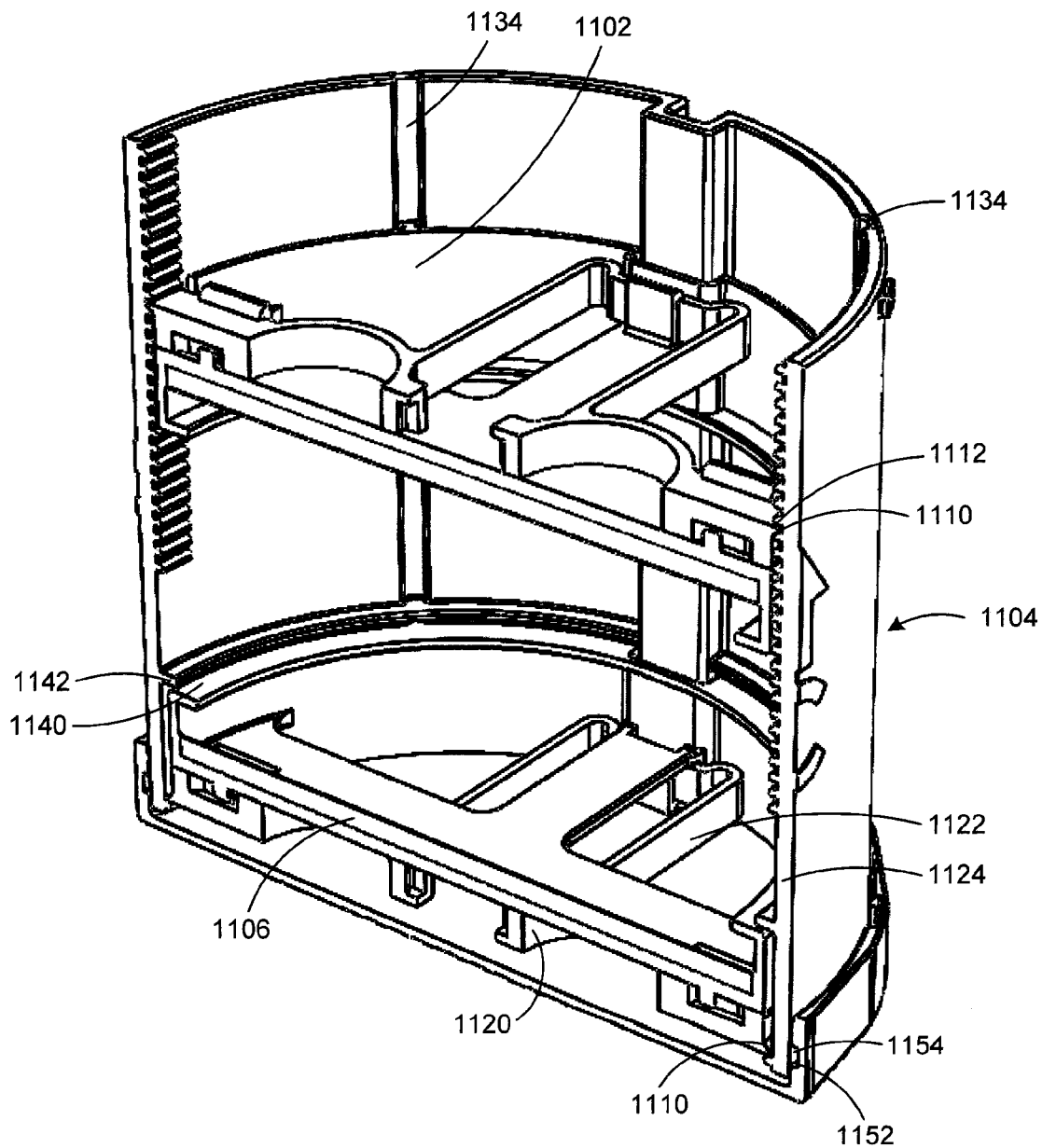
Figure 26A:
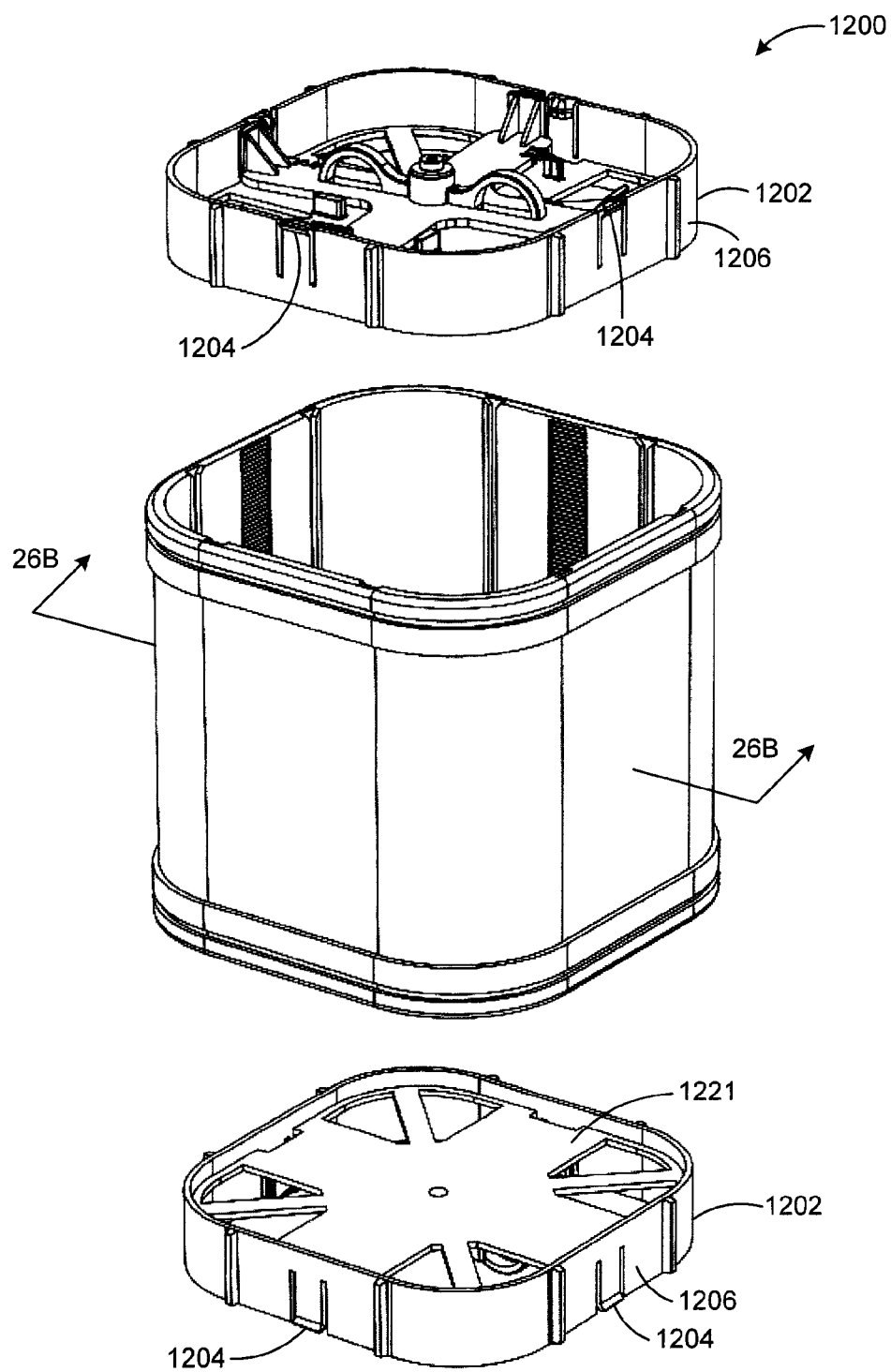
Figure 26B:
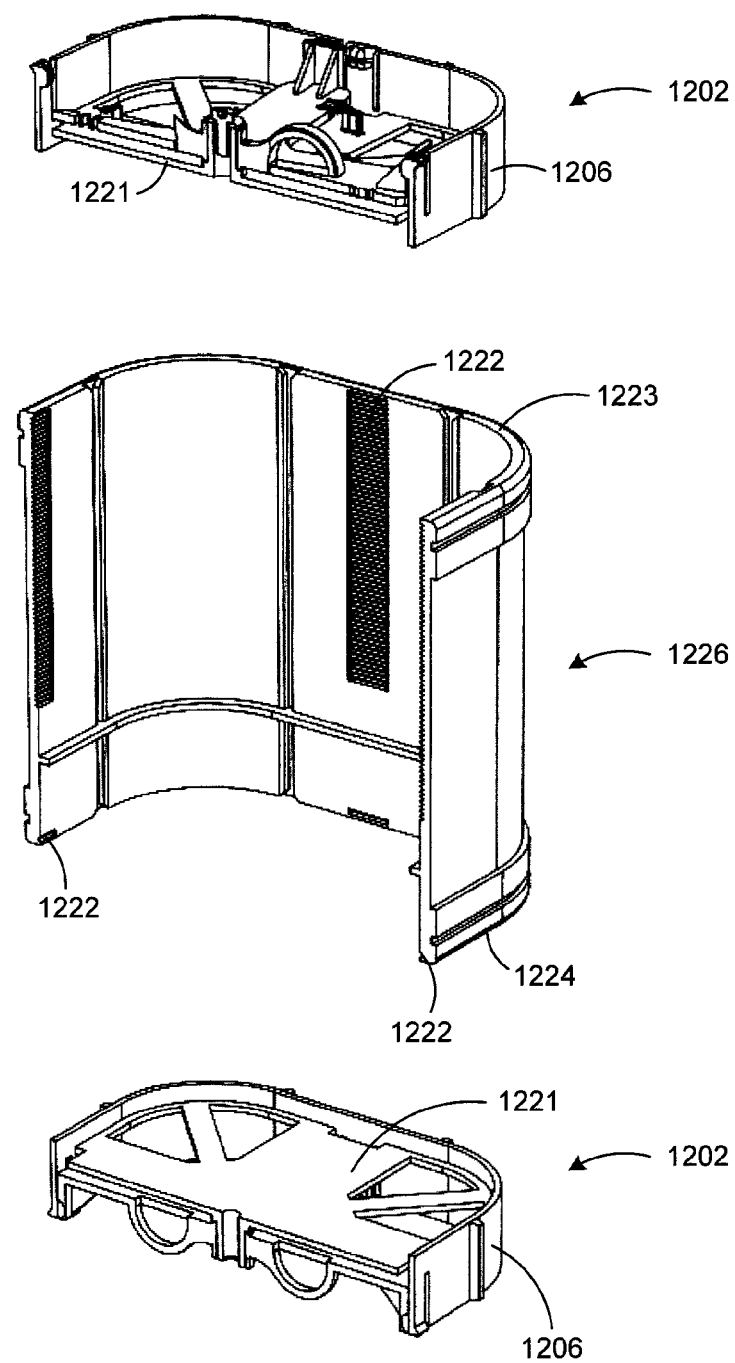
Figure 26C:
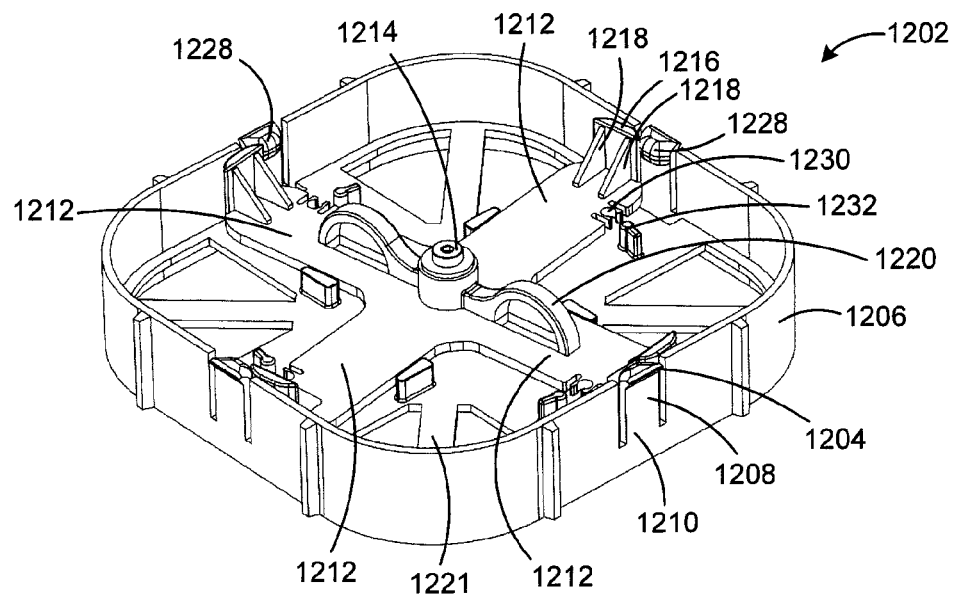
Figure 26D:
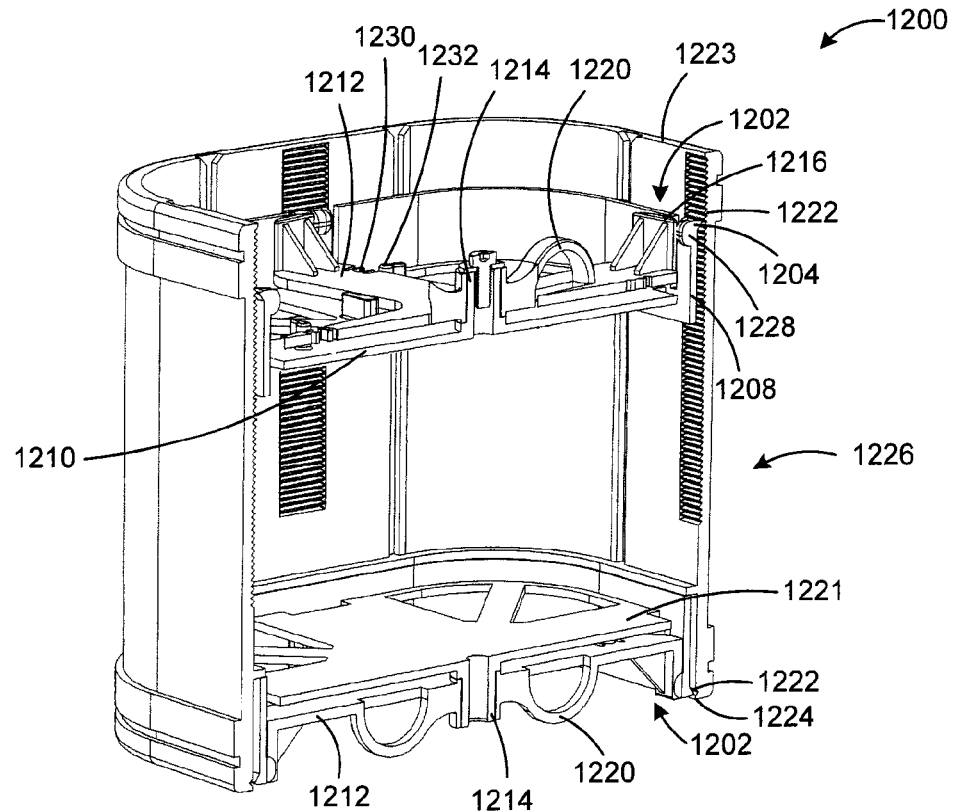
Figure 26E:
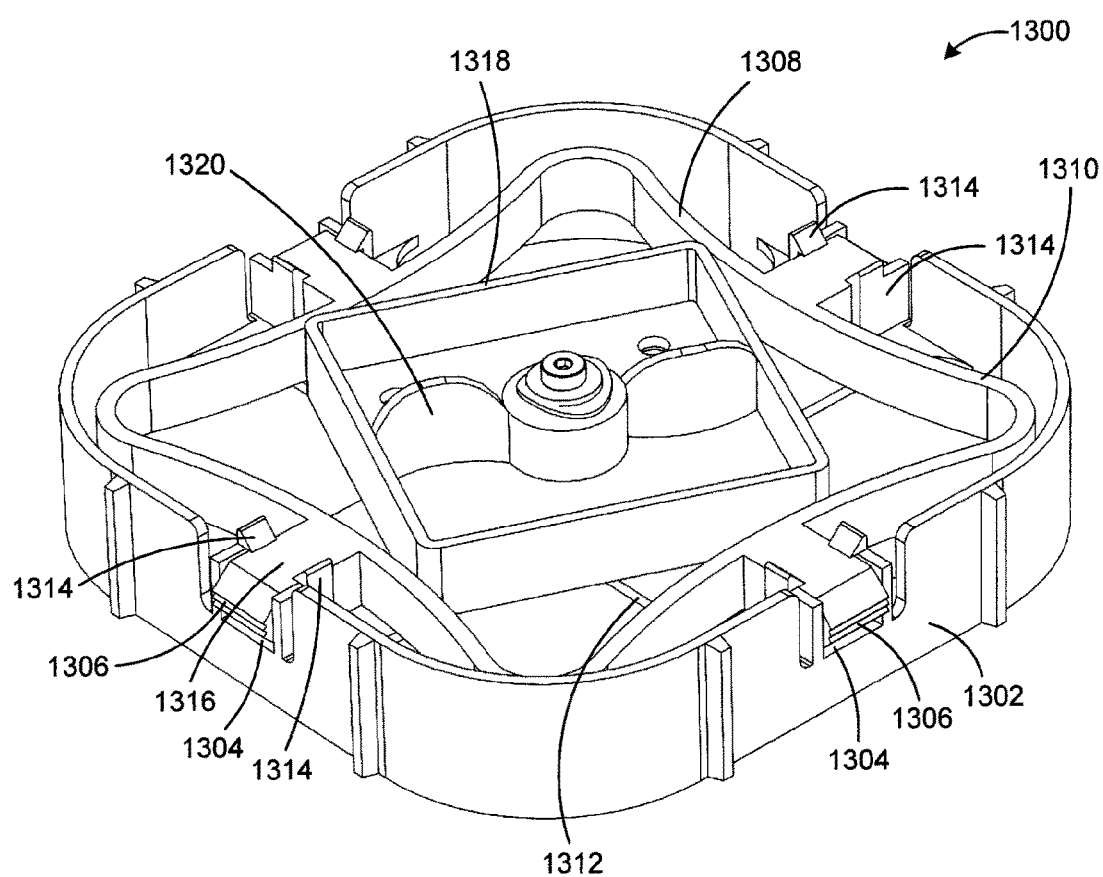

FIG. 4J a front-side perspective view of the tilt mechanism and the scanning head of FIG. 4F coupled of the home device of FIG. 4G;

FIG. 4K is a rear perspective view of FIG. 4J;

FIG. 4L is a perspective view of a first translation mechanism with a tilt mechanism and a scanning head for the scanning assembly of FIG. 4A;

FIG. 4M is a perspective view of the first translation mechanism of FIG. 4L;

FIG. 4N is a partial front view of the first translation mechanism of FIG. 4L illustrating components below a carriage plate;

FIG. 4O is a perspective view of a second translation mechanism for the scanning assembly of FIG. 4A;

FIGS. 4P and 4Q are different views of a horizontal encoder for the second translation mechanism of FIG. 4O;

FIG. 4R is a perspective view of support brackets for the scanning assembly of FIG. 4A;

FIG. 4S is a perspective view of the scanning assembly of FIG. 4A in accordance with an example embodiment;

FIG. 5 shows a block diagram of an example embodiment of hardware components that may be used with the imaging system;

FIGS. 6A and 6B show an example prototype of an imaging system for generating wide field OCT image data;

FIG. 6C shows an example schematic of a Spectral-Domain OCT system;

FIG. 7A shows a flowchart of an example embodiment of a wide field OCT imaging method;

FIG. 7B shows a flowchart of an example embodiment of a wide field acquisition method;

FIG. 7C shows a flowchart of an example embodiment of a surface detection method for OCT images;

FIG. 7D shows a flowchart of an example embodiment of a vertical stitching method;

FIG. 7E shows a flowchart of an example embodiment of a horizontal stitching method;

FIG. 7F shows a flowchart of an example embodiment of a method for minimizing saturation artifacts;

FIG. 8A shows a schematic of an optical path for a lens in accordance with an example embodiment;

FIG. 8B shows a schematic of an optical path for another lens in accordance with an example embodiment;

FIG. 8C shows a schematic of a scanning head capturing an OCT image in accordance with an example embodiment;

FIG. 8D shows a series of OCT images for a sample surface in accordance with an example embodiment;

FIG. 8E shows a series of OCT images for another sample surface in accordance with an example embodiment;

FIG. 8F shows a series of OCT image for yet another sample surface in accordance with an example embodiment;

FIGS. 9A to 9C show an example of how a series of OCT images may be combined for creating a wide field OCT image;

FIGS. 10A to 10C show an example combination of another series of OCT images for creating a wide field OCT image;

FIGS. 10D to 10F show an example combination of the wide field OCT image of FIG. 9C and the wide field OCT image of FIG. 10C for creating yet another wide field OCT image;

FIGS. 11A to 11E show various overlaid OCT images with different offset distances in accordance with an example embodiment;

FIG. 11F is a plot of the entropy associated with the overlaid OCT images of FIGS. 11A to 11E;

FIG. 12A shows an image of a histopathology sample of a rat ovary tumor that is derived from a human breast cancer cell line (MT-1) xenograft;

FIG. 12B shows a reconstructed OCT image of the rat ovary tumor sample of FIG. 12A;

FIG. 12C shows an image of another histopathology sample of a rat ovary tumor that is derived from a human breast cancer cell line (MT-1) xenograft;

FIG. 12D shows a reconstructed OCT image of the rat ovary tumor sample of FIG. 12C;

FIG. 13A shows a white light image of a lumpectomy specimen illustrating a B-scan path;

FIG. 13B shows a reconstructed OCT image of the lumpectomy specimen shown in FIG. 13A over the B-scan path;

FIG. 14A shows a white light image of a lumpectomy specimen illustrating a B-scan path;

FIG. 14B shows a reconstructed OCT image of the lumpectomy specimen shown in FIG. 14A over the B-scan path;

FIG. 15A is an example embodiment of a reconstructed OCT image with the borders of regions of interest identified;

FIG. 15B is an example embodiment of a reconstructed OCT image with a boundary distinguishing two regions identified;

FIG. 15C is an example embodiment of a reconstructed OCT image with a mask that can be used to show actionable boundaries and non-actionable boundaries;

FIG. 16 is a flowchart of an example embodiment of a tissue assessment method that may be used by a tissue imaging system or device to determine the degree of differentiation for different regions of a tissue sample;

FIG. 17 is flowchart of an example embodiment of a boundary identification method that may be used with the tissue assessment method of FIG. 16;

FIG. 18A is an example embodiment of a reconstructed OCT image for a portion of an excised tissue sample;

FIGS. 18B to 18D show examples of images indicating the borders of regions of interest for the reconstructed OCT image of FIG. 18A;

FIGS. 18E to 18G show examples of the OCT image of FIG. 18A along with various masks highlighting regions of high attenuation;

FIG. 19A shows an example of a plurality of B-scans for a reconstructed OCT image of an excised tissue sample;

FIG. 19B shows an example of an image indicating the borders for regions of interest for the plurality of B-scans in FIG. 19A;

FIG. 19C shows a plurality of flattened B-scan images corresponding to the plurality of B-scans shown in FIG. 19A;

FIG. 19D shows an example of an image indicating the borders for regions of interest for the plurality of flattened B-scan images of FIG. 19C;

FIG. 19E shows an example image of one of the plurality of B-scans of the FIG. 19A with a composite border for regions of interest;

FIG. 19F shows an example of an image indicating the composite border for regions of interest for the B-scan image in FIG. 19E;

FIG. 20A is an example image of a flattened window of a B-scan image for which a boundary has been accepted;

FIG. 20B shows an example of a plot of signal intensity for an A-scan of the B-scan image shown in FIG. 20A;

FIG. 20C shows a portion of the plot of signal intensity of FIG. 20B corresponding to a first region;

FIG. 20D shows an example of a normalized plot of signal intensity corresponding to the portion of the plot of signal intensity shown in FIG. 20C;

FIG. 20E shows a portion of the plot of signal intensity of FIG. 20B corresponding to a second region;

FIG. 20F shows an example of a normalized plot of signal intensity corresponding to the portion of the plot of signal intensity shown in FIG. 20E;

FIG. 20G shows an example plot of the measured attenuation and texture for two regions of the flattened B-scan window shown in FIG. 20A;

FIG. 21A shows an example plot of an output of an optimization method for the two regions of an OCT image of FIG. 20G;

FIG. 21B shows an example plot of another optimization method output for the two regions of an OCT image of FIG. 20G;

FIG. 22A is another example of an OCT image with a boundary distinguishing two regions;

FIG. 22B is an example of a flattened window of the OCT image of FIG. 22A for which the boundary was accepted;

FIG. 22C shows an example plot of the measured attenuation and texture in two regions of the flattened window of FIG. 22B;

FIG. 22D shows an example plot of an output of an optimization method for the two regions in the flattened OCT image of FIG. 22B;

FIG. 22E shows an example plot of an output of another optimization method for the two regions in the flattened OCT image of FIG. 22B;

FIG. 22F shows the OCT image of FIG. 22A with a mask;

FIG. 23A shows a perspective view of a sample container for containing a tissue sample, in accordance with at least one embodiment;

FIG. 23B shows a perspective view of a bottom sample support and a tissue sample, in accordance with at least one embodiment;

FIG. 23C shows a cross-sectional view taken along line 23C-23C in FIG. 23B;

FIG. 23D shows a perspective view of a top sample support, in accordance with at least one embodiment;

FIG. 23E shows a cross-sectional view taken along line 23E-23E in FIG. 23D, in accordance with another embodiment;

FIGS. 23F and 23G show front and rear perspective views of an interface sleeve, in accordance with at least one embodiment;

FIG. 24A shows a tissue sample placed on a bottom sample support, in accordance with at least one embodiment;

FIG. 24B shows a top sample support and a bottom sample support inserted into an interface sleeve, in accordance with at least one embodiment;

FIG. 24C shows a cross-sectional view taken along line 24C-24C in FIG. 24B;

FIG. 24D shows a cross-sectional view taken along line 24C-24C in FIG. 24B, after the top sample support has been further inserted into the interface sleeve;

FIG. 24E shows a portion of the upper end of an interface sleeve, in accordance with at least one embodiment;

FIG. 25A shows a perspective view of a sample container, in accordance with another embodiment;

FIG. 25B shows a cross-sectional perspective view taken along line 25B-25B in FIG. 25A;

FIG. 25C shows a cross-section view of the container of FIG. 25A with a top sample support, a bottom sample support, and a bottom lid engaged with an interface sleeve, in accordance with at least one embodiment;

FIG. 26A shows a perspective view of a sample container in accordance with another embodiment;

FIG. 26B shows a cross-sectional view taken along line 26B-26B in FIG. 26A;

FIG. 26C shows a perspective view of a top or bottom sample support, in accordance with at least one embodiment;

FIG. 26D shows a cross-sectional perspective view of the container of FIG. 26A; and FIG. 26E shows a perspective view of a top or bottom sample support in accordance with another embodiment.

DETAILED DESCRIPTION OF THE EMBODIMENTS

Various apparatuses or processes will be described below to provide an example of an embodiment of the claimed subject matter. No embodiment described below limits any claimed subject matter and any claimed subject matter may cover processes or apparatuses that differ from those described below. The claimed subject matter is not necessarily limited to apparatuses or processes having all of the features of any one apparatus or process described below or to features common to multiple or all of the apparatuses or processes described below. It is possible that an apparatus or process described below is not an embodiment of any claimed subject matter. Any subject matter disclosed in an apparatus or process described below that is not claimed in this document may be the subject matter of another protective instrument, for example, a continuing patent application, and the applicants, inventors or owners do not intend to abandon, disclaim or dedicate to the public any such invention by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or coupling as used herein can have several different meanings depending on the context in which these terms are used. For example, the terms coupled or coupling can have a mechanical, electrical or optical connotation. For example, depending on the context, the terms coupled or coupling may indicate that two elements or devices can be physically, electrically or optically connected to one another or connected to one another through one or more intermediate elements or devices via a physical, electrical or optical element such as, but not limited to a wire, fiber optic cable or waveguide, for example.

It should be noted that terms of degree such as "substantially", "about" and "approximately" as used herein mean a reasonable amount of deviation of the modified term such that the end result is not significantly changed. These terms of degree should be construed as including a deviation of up to ±10% of the modified term if this deviation would not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." The term "about" means up to ±10% of the number to which reference is being made.

In the following passages, different aspects of the embodiments are defined in more detail. Each aspect so defined may be combined with any other aspect or aspects unless clearly indicated to the contrary. In particular, any feature indicated as being preferred or advantageous may be combined with at least one other feature or features indicated as being preferred or advantageous.

Described herein are various example embodiments of a system and method that can be used to obtain wide field OCT images. Wide field OCT imaging has various applications such as, but not limited to, scanning of a tissue surface that is larger than the viewable area of a typical OCT system and scanning of tissue samples that demand interrogation of the tissue characteristics at depths exceeding the typical penetration depth of a typical OCT system. The imaging window of a typical OCT system is typically a 10 mm×3 mm (W×H) area and the maximum penetration depth of tissue is approximately 2 mm. However, a typical tissue sample has a surface area of approximately 200 cm$^2$. Furthermore, the surface of the tissue may be irregular.

An example application of an imaging system will now be described with simultaneous reference to FIGS. 1 and 2.

Figure 1:
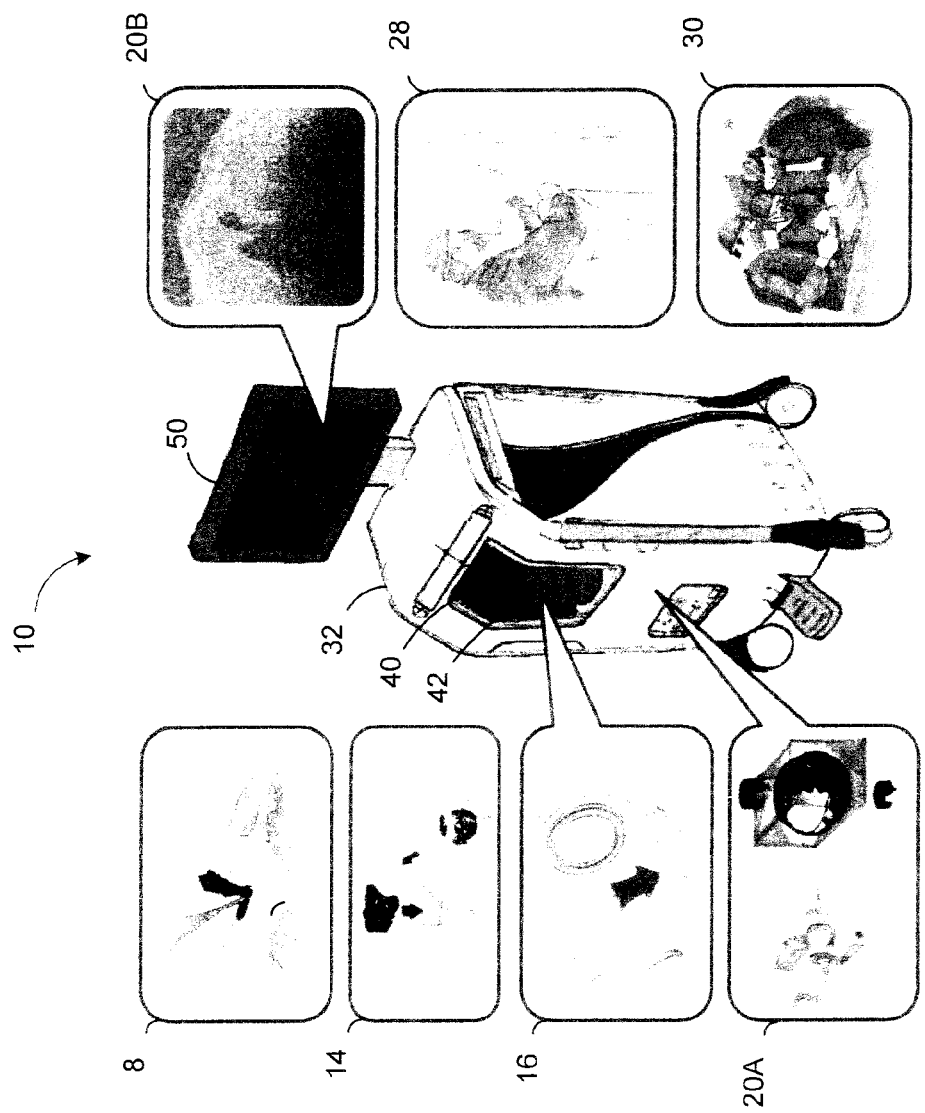
FIG. 1 shows an illustration of how an imaging system can be used in an operating room environment to assess resected tissue sample.
Figure 2:
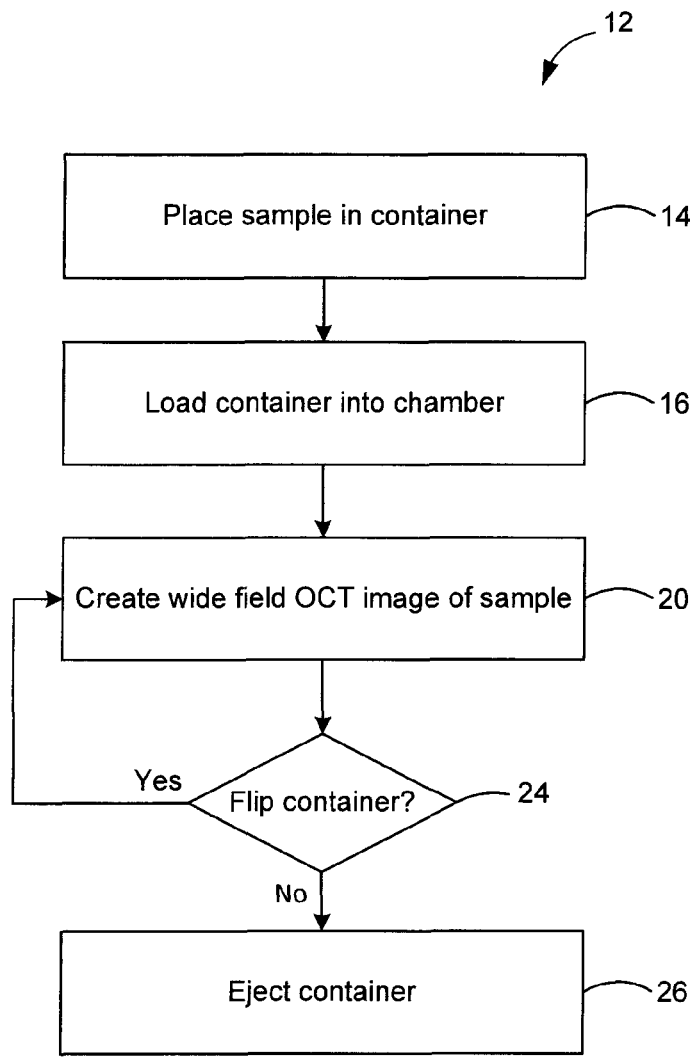
FIG. 2 shows a flowchart of an example embodiment of a method for using the imaging system to obtain wide field Optical Coherence Tomography (OCT) images of a sample.

FIG. 1 is an illustration of how an imaging system 10 can be used in an operating room environment to assess resected tissue samples. An example of the imaging system 10 may be a Margin Assessment Machine (a MAM). FIG. 2 is a flowchart of an example embodiment of a method 12 for using the imaging system 10 to obtain wide field OCT images of a sample. It should be noted that the flowchart illustrates only one example embodiment for the method 12 and there can be other embodiments in which different actions may be included or some actions may be removed depending on the particular application of the imaging system 10 (this also applies to the other flowcharts and block diagrams shown and described herein).

At 8 of FIG. 1, a specimen of excised tissue containing the tumor is resected. At 14, the tissue specimen can be placed into a consumable 42, which can also be called a container or sample container. The container 42 can be used to maintain the excised tissue in a particular orientation, as will be described with reference to FIGS. 23A to 26E.

At 16, the container 42 is placed in a chamber 40 of the imaging system 10 for imaging purposes. The container 42 can be used for a variety of purposes, including loading a sample into the imaging system 10, securing the sample during various types of imaging and scanning including OCT scanning, and transporting the sample through the clinical process. The sample may be a tissue specimen or other types of material requiring OCT imaging.

After the container 42 is placed inside the chamber 40, the imaging system 10 can then create wide field OCT images of the tissue specimen, such as at 20. For example, at 20A as shown in FIG. 1, the tissue specimen may be scanned by the imaging system 10 while inside the chamber 40 and then, at 20B as shown in FIG. 1, the imaging system 10 may generate a margin assessment width map or other image information about the tissue specimen.

In some embodiments, the imaging system 10 may operate based on input parameters provided by the user, such as a medical practitioner (e.g., a surgeon). Prior to generating images of the tissue specimen, the imaging system 10 may first receive input parameters from the user to specify various parameters for the OCT image data to be generated by the imaging system 10. The input parameters may include at least one of selecting regions of interest, selecting a scan density, and selecting a time constraint for three-dimensional (3D) OCT imaging of the tissue specimen.

Examples of various methods associated with creating the wide field OCT images of the sample according to the teachings herein will be described with reference to FIGS. 7A to 7F. Briefly, the methods of creating the wide field OCT images may involve creating a surface map trajectory for the sample, as will be described with reference to FIG. 7A. The surface map trajectory, and possibly other input data from the user, may be used to determine various positions for a scanning head of the scanning assembly in the imaging system 10 in order to generate desired images of the sample. For instance, the scanning head may be used for collecting raw OCT data of the sample, such as regions of interest as indicated by the input parameters provided by the user. As will be described with respect to FIG. 4A, the scanning head can be adjusted in various directions, such as each of the x, y and z directions in a Cartesian coordinate system, to obtain or capture the raw OCT data.

To create the wide field OCT images of the sample, the imaging system 10 can apply various stitching (i.e. combination or merging) methods to the OCT image data. The stitching methods may include horizontal stitching and vertical stitching. Vertical stitching may be needed depending on a variability of a height of the surface of the portion of the tissue sample being imaged, as will be generally described with reference to FIGS. 8E and 8F. For example, images associated with an object having a non-uniform surface may require vertical stitching due to the variations in height across its surface (such as the example shown in FIG. 8F). Alternatively, images associated with an object with a fairly uniform surface may not require vertical stitching (such as the example shown in FIG. 8E). Example embodiments of stitching methods will be described with reference to FIGS. 7D and 7E.

In some embodiments, the imaging system 10 may apply other image processing techniques to improve image quality of the wide field OCT images. These image processing techniques may be used, but not required, if aberrations typically inherent to OCT are present in the created OCT images. An example image processing technique will be described with reference to FIG. 7F.

At 24, the imaging system 10 determines whether the container 42 should be flipped (e.g. inverted) so that the imaging system 10 can capture additional OCT image data from another portion of the tissue specimen. For example, the container 42 can be flipped to switch hemispheres in order to image the entire surface of the sample. Whether or not the container 42 is flipped may depend on the input parameters provided by the user and/or default settings of the imaging system 10. If the imaging system 10 determines that the container 42 is to be flipped, the imaging system 10 allows for the operator of the imaging system 10 to access the container 42 and manually flip the container. The imaging system 10 can then repeat the creation of the wide field OCT images (at 20) for the flipped tissue specimen. If the imaging system 10 determines that no further OCT image data is needed, the imaging system 10 can eject the assembled container 42 (at 26 of FIG. 2).

It should be noted that there may be alternative embodiments in which flipping of the container is not performed.

At 28 of FIG. 1, the medical practitioner can review the margin assessment width map or other imaging information generated by the imaging system 10. The medical practitioner may manually review the results generated by the imaging system 10. Alternatively, in some embodiments, the imaging system 10 may provide an analysis of the results. For example, the imaging system 10 may apply detection methods that can detect various different tissue regions within the OCT image data. In some embodiments, the imaging system 10 may enable both manual analysis by the medical practitioner and also provide automated analysis of the images of the tissue specimen.

The imaging system 10 can provide the OCT image data and/or the analysis of the OCT image data to a display 50, for example. The OCT image data that may be displayed on the display 50 may include a margin assessment width map and/or other imaging information. The medical practitioner can then interpret the imaging result and determine an appropriate course of action. At 30, the routine in the operating room can continue. The routine may include routine pathology.

The imaging system 10 can be used for various different applications, such as one or more of OCT surface detection for optimizing an optical path scan, sample handling, automated OCT scanning of complex surface as well as wide field horizontal or vertical stitching of OCT images. As described with reference to FIGS. 1 and 2, the imaging system 10 can be used to receive a tissue specimen, such as a lumpectomy specimen or other complex specimens, perform scanning and surface profiling of the specimen, provide imaging results to a medical practitioner during a surgical procedure and eject the container 42 that contains the specimen.

The scanning of the samples may include selective high or low resolution scanning. Other embodiments may include scanning of the entire surface or a portion of the surface of the sample using another imaging modality, such as high frequency ultrasound. It will also be understood that the imaging system 10 is not limited to imaging of tissue samples, and that any sample that requires the surface to be profiled can be scanned by the imaging system 10. The various structures and techniques that allow the imaging system 10 to provide these features will now be discussed.

Generally, the imaging system 10 can generate OCT images of a sample. As shown in FIG. 1, the imaging system 10 can be provided in the form of a cart 32. The cart 32 can serve as an enclosure for housing a scanning area 40, such as a chamber within the imaging system 10. The scanning area 40 is dimensioned and configured for receiving the sample. The imaging system 10 also comprises a scanning assembly, which can include a sample handling system, within the scanning area 40 for obtaining the OCT image data of at least a portion of the sample. The imaging system 10 also comprises a processing module that is in electrical communication with the scanning assembly for at least controlling the scanning assembly according to certain OCT imaging parameters. An example embodiment of the scanning assembly will be described with reference to FIGS. 4A to 4S. The processing module is generally considered to have an input port through which the processing module receives input information such as data that is to be processed. Some examples of input ports include, but are not limited to, an input pin that is coupled to a bus or to a communication interface such as a radio, a network connection, a serial connection, a USB connection or a parallel connection. The processing module is also generally considered to have an output port through which the processing module sends outputs such as output data to a user, a storage element (e.g. RAM, ROM, etc.), a storage device (a hard drive, a flash drive, etc.) or another computing device, for example. Some examples of output ports include, but are not limited to, an output pin that is connected to a bus or to a display device, or a memory element, such as ROM, RAM, and the like.

Referring now to FIG. 3A, shown therein is a perspective view of an example embodiment of the imaging system 10 in the form of the cart 32. The cart 32 can be used, at least, to hold user interface elements, such as the display 50 and user input devices 52 and 54 (shown in FIG. 3B), such as, but not limited to, a keyboard and a mouse, and the like for example. The cart 32 also encloses the sample handling system in the scanning area 40 of the imaging system 10. The cart may present imaging results to at least one of the user interface elements, such as the display 50, to an operator of the imaging system 10. The user interface elements can be presented to the operator at an easily accessible height.

The user interface elements may be in electrical communication with the processing module. For example, the user interface elements can receive input values from the operator of the imaging system 10, such as the medical practitioner, that correspond to OCT imaging parameters for generating OCT images of the sample.

The user interface elements can enable an operator of the imaging system 10 to select regions of interest on a complex 3D object for OCT scanning. In an example in which the complex 3D object is a sample, the user interface elements can enable the operator to select the scan density and/or time constraint for 3D OCT imaging of that sample. In some embodiments, the user interface elements can include the display 50 or a printer so that the imaging system 10 can provide a 3D volume representation of the sample to the operator of the imaging system 10. In some embodiments, the user interface elements can be configured to provide a 3D representation of a portion of the sample and to allow the operator to interact with the OCT image data associated with that 3D representation. The OCT image data for that 3D representation may include margin assessment information.

Accordingly, the user interface elements may enable the operator or user of the imaging system 10 to acquire and assess OCT images, which can be used for a variety of purposes including, but not limited to, OCT margin assessment for cancerous tissue samples. The user interface elements can also enable key imaging specifications to be set prior to conducting the OCT scanning, and can apply various techniques to display the imaging results to the user and to allow the user to interact with the collected imaging data. In some embodiments, a manipulable 3D surface map or profile of the sample may be provided to allow the user to navigate through and select images of interest.

The processing module may receive OCT imaging parameters from the user interface elements, or from a data store such as a hard drive and the like, and control the operation of the scanning assembly in accordance with at least the OCT imaging parameters. In some embodiments, the processing module may also determine OCT imaging parameters for obtaining the OCT image data of the sample.

The user interface elements, such as user interface elements 50, 52, and 54, may be provided so that they are isolated from other components of the imaging system 10, such as the scanning area 40, in order to prevent contamination of the sample. An example configuration will now be described with reference to FIG. 3B.

FIG. 3B shows a magnified perspective view of the user input devices 52 and 54. The user input devices 52 and 54 may be sterile controls to minimize the chance of contamination during the use of the imaging system 10. The sterile controls 52 and 54 allow for a medical practitioner, such as a surgeon, to use the imaging system 10 during a medical procedure. Examples of the sterile controls 52, 54 may include, but are not limited to, a keyboard, a mouse, a trackball and a touch-sensitive screen.

As shown in FIG. 3B, the sterile controls 52 and 54 can be housed inside the cart 32. The sterile controls 52 and 54 can be slidably engaged with an interior surface of the cart 32 so that the sterile controls 52 and 54 can slide into and out of the cart 32 for various interactions with the operator, such as receiving the input values from the operator.

Referring now to FIG. 3C, shown therein is a front view of the imaging system 10. The cart 32 includes an access port 46 to the scanning area 40 of the imaging system 10. When opened, as shown in FIG. 3A, the access port 46 allows an operator to place the sample, such as a tissue specimen, into the imaging system 10. The tissue specimen may be provided inside a container 42 and the operator may place the container 42 inside the imaging system 10. When the access port 46 is closed, as shown in FIG. 3C, the access port 46 encloses the scanning area 40 to prevent contamination of the tissue specimen while it is inside the imaging system 10. The access port 46 may be closed during at least a part of the operation of the sample handling system. The access port 46 can also allow a maintenance person, or other operators, to service the imaging system 10.

Referring now to FIG. 3D, shown therein is a magnified view of a wheel lock 60 of the imaging system 10. The wheel lock 60 can be used to maintain the imaging system 10 at a fixed position by locking the wheels of the cart 32 at a desired location. The wheel lock 60 can prevent the cart 32 from engaging in any undesired movement that can affect the operation of the imaging system and negatively impact the quality of the OCT images.

Referring now to FIG. 3E, shown therein is a rear perspective view of the imaging system 10. The cart 32 may include a service access area 70 at the rear portion of the cart 32. The service access area 70 can allow the maintenance person, or other operators, to service the imaging system 10.

As briefly described, the imaging system 10 can include a scanning assembly within the scanning area 40 for facilitating the capture of OCT image data of the sample and the generation of corresponding OCT images of the sample. The sample may include a tissue specimen of a tumor or a sample having a complex 3D surface.

The scanning assembly can include a sample handling system that can manipulate the sample, or the container 42 holding the sample, in order to facilitate optical scanning of the surface of the sample while maintaining the integrity of the sample. The sample handling system can include a support area for receiving the sample or container 42, and various actuators for manipulating the sample via the support area by holding the sample in certain orientations during the imaging process.

In some embodiments, the scanning assembly may include a three-axis (X, Y, Z) stage for adjusting a position of at least one of the scanning head and the sample. The three-axis stage can facilitate various operation of the scanning assembly, such as surface scanning of a selected region of interest on the sample or an exposed surface of the sample. In some embodiments, the scanning assembly can include an attachment plate, or a container adapter, for securing the container 42 to the three-axis stage.

The scanning assembly can also include various mechanical modules or mechanisms for providing the necessary degrees of freedom for imaging the sample. The scanning assembly can also lock and control the speed at which the mechanisms operate. These features can be especially important in the case of power interruptions. The various types of mechanisms that can be used include, but are not limited to, at least one of powered safety brakes, constant force elements or counterbalances, and electrical energy storage elements, for example.

Referring now to FIGS. 4A to 4S, shown therein are illustrations of different views of an example embodiment of a scanning assembly 80 that can be used in the imaging system 10 for scanning the sample.

FIG. 4A is a front view of the scanning assembly 80 and FIG. 4B is a rear view of the scanning assembly 80 of FIG. 4A. As shown, the scanning assembly 80 includes a frame 82 upon which various actuators or translation mechanisms are coupled to provide various degrees of motion to the scanning assembly 80. With the various degrees of motion offered by the mechanisms, the scanning assembly 80 can acquire raw OCT data of the sample from at least two independent directions, as will be described.

The scanning assembly 80 also includes a scanning head 84, a first translation mechanism 86, a tilt mechanism 87, a second translation mechanism 88, and a trans-rotational mechanism 90. The various arrows 72, 74, 76, 78 and 79 in FIG. 4A show the various degrees of freedom of the scanning assembly 80.

The movement of each of the first translation mechanism 86 and the second translation mechanism 88 can be facilitated with a belt component. For example, as illustrated in FIGS. 4A, 4R and 4S, a belt component 85 can help control the translation motion of the first translation mechanism 86. Similarly, as shown in FIGS. 4A and 4B, the belt components 89a and 89b can be mounted on different portions of the scanning assembly 80, such as the base board 81 and the second translation mechanism 88, respectively, to control the translation motion of the second translation mechanism 88. The belt components 85, 89a and 89b can also help enhance the stability of the first translation mechanism 86 and the second translation mechanism 88 when they are in motion. It will be understood that other similar components may be used to control and stabilize the motion of the first translation mechanism 86 and the second translation mechanism 88.

The frame 82 includes several support brackets 83 to attach the second translation mechanism 88 to a base board 81 of the frame 82. The support bracket 83 may include a main support bracket 83a and a secondary support bracket 83b (shown also in FIG. 4R), for example.

The base board 81 may be an optical breadboard. The optical breadboard can be advantageous because it is generally associated with high-flatness and rigidity and thus, is appropriate for mounting the frame 82.

FIG. 4C is a perspective view of the trans-rotational mechanism 90 and a support area 92. The support area 92 may include a container adapter 92B for receiving the container 42 via a container support 92A on the container 42. The container support 92A, as shown in FIG. 4C, may hold a sample 94. Together, the container 42 and the support area 92 can hold the sample 94 in a stable manner during the operation of the scanning assembly 80.

The trans-rotational mechanism 90 may also include a rotational stage 90A attached to a linear stage 90B. As shown in FIGS. 4A and 4B, the linear stage 90B is mounted to the base board 81. The trans-rotational mechanism 90 is intended to manipulate the container 42 to apply at least one of a rotational movement and a translational movement, as generally illustrated by the respective arrows 74 and 76 in FIGS. 4A and 4C, to the container 42.

The rotational stage 90A may be driven by a direct-drive motor and may include an optical encoder for directing its rotational movement. One benefit of using the direct-drive motor is the elimination of backlash. The optical encoder can control the rotational movement of the rotational stage 90A by converting an angular position of the motor shaft to a digital code. The digital code corresponds to a rotational position for the rotational stage 90A. Therefore, when the rotational stage 90A receives the digital code from the optical encoder, the rotational stage 90A can rotate to the position corresponding to that digital code. In some embodiments, the optical encoder can provide an accuracy of +/−3.9 arcsec.

Generally, the linear stage 90B should be capable of translating the sample 94 a distance that approximately corresponds to a diameter of the sample 94. A typical diameter of samples may be about 120 mm. In some embodiments, the linear stage 90B may be a direct-drive linear motor stage, such as Model DDS220 by Thorlabs™. It will be understood that other mechanical devices that provide at least linear translation within the scanning assembly 80 may be used.

FIG. 4D is a perspective view of the container adapter 92B and FIG. 4E is a cross-sectional exploded view of the container support 92A and the container adapter 92B. As shown in FIG. 4D, the container adapter 92B has four holes, namely 96A to 96D, and two engagement members 98A, 98B, such as spring plungers or other similar engagement components. The engagement members 98A and 98B can be located at approximately opposite sides of the container adapter 92B. It will be understood that the illustrated number of holes 96 and engagement members 98 are merely examples and that fewer or greater number of holes 96 and engagement members 98 may be used.

Referring now to FIG. 4E, the container support 92A includes complementary latches 170A, 170B for securably engaging with corresponding engagement members 98A, 98B, respectively. For example, when spring plungers are used as the engagement members 98A, 98B on the container adapter 92B, the spring plungers 98A and 98B press against the latches 170A and 170B, respectively, to secure the container support 92A to the container adapter 92B. It will be appreciated that different spring plungers can exert a different range of forces, such as 1 to 2.5 lb-f, 2 to 5 lb-f or 4 to 10 lb-f. For securing the container support 92A to the container adapter 92B, spring plungers that can exert at least 4 lb-f can be used.

The scanning head 84 can obtain raw OCT data of the sample provided at the support area 92. As shown in FIG. 4A, the scanning assembly 80 has a gantry-like design that enables the scanning head 84 to effectively move about the sample at various angles and to acquire raw OCT data of the sample 94 at the various angles. In at least some embodiments, the scanning head 84 can be pivotally mounted to the frame 82 so that the scanning head 84 can pivot or rotate about an axis to vary the angle of view of the sample 94, such as shown by arrow 79. Accordingly, the scanning head 84 can be pivotally adjustable with respect to the sample 94.

FIG. 4F is a front-side perspective view of the scanning head 84 and the tilt mechanism 87 and FIG. 4G is a rear perspective view of the scanning head 84 and the tilt mechanism 87 of FIG. 4F. As shown in FIGS. 4J and 4K, the tilt mechanism 87 can be attached to a home device 171 (shown in FIGS. 4H and 4I) via fasteners shown generally at 85. As will be described, the tilt mechanism 87 can be attached to the first translation mechanism 86 via the home device 171.

The scanning head 84 may be a probe within the Telesto™ line of OCT imaging systems provided by Thorlabs, for example. It will be understood that other OCT imaging probes may be similarly used. As generally indicated by the arrow 79 in FIG. 4A, the tilt mechanism 87 can rotate the scanning head 84 within a range of approximately 0 to 180 degrees about an axis of rotation that is substantially perpendicular to a translation plane of the first translation mechanism 86 and the second translation mechanism 88. In some embodiments, the maximum rotational movement of the tilt mechanism 87 can be limited to a range of −2 to +182 degrees by including a ridge 172 at the home device 171 (as shown in FIGS. 4H and 4I, which illustrate different views of the home device 171).

The tilt mechanism 87 may include an actuator that is harmonic-driven. By using a harmonic-drive actuator, the tilt mechanism 87 is able to produce a high torque with minimal backlash and a very high accuracy in its movement. The harmonic-drive actuator can include an incremental-type encoder.

The scanning head 84 can also be operably coupled to each of the first translation mechanism 86 and the second translation mechanism 88 so that the scanning head 84 is shifted in a first linear direction and a second linear direction with respect to the sample 94. The first translation mechanism 86 allows the scanning head 84 to be shifted in the first linear direction with respect to the sample 94 at the support area 92, and the second linear translation mechanism 88 allows the scanning head 84 to be shifted in the second linear direction with respect to the sample at the support area 92. The second linear direction may be substantially perpendicular to the first linear direction and also co-planar with the first linear direction.

In the example shown in FIG. 4A, the first linear direction has an up and down or vertical orientation with respect to the sample 94 at the support area 92 and the second linear direction has a left and right or horizontal orientation with respect to the sample 94. Accordingly, the first translation mechanism 86 can raise and lower the scanning head 84 in the first linear direction, and the second translation mechanism 88 can shift the scanning head 84 left and right along the second linear direction.

The first translation mechanism 86 and the second translation mechanism 88 allow for various OCT images of the sample to be taken from a first plane, which is a two-dimensional (2D) imaging plane. The trans-rotational mechanism 90 allows the sample to be moved in a linear and rotational fashion in a second plane. The second plane is substantially perpendicular to the first plane. The trans-rotational mechanism 90 can move the sample 94 linearly towards and away from the first plane while also allowing the sample 94 to be rotated with respect to the scanning head 84. The scanning head 84 may also be pivotally adjustable about an axis of rotation that is substantially perpendicular to the first plane. As a result, the scanning head 84 can capture raw OCT data of various depths around various surfaces of the sample.

Each of the first translation mechanism 86 and the second translation mechanism 88 will now be described.

FIG. 4L is a perspective view of the first translation mechanism 86 with the tilt mechanism 87 and the scanning head 84, and FIG. 4M is a perspective view of the first translation mechanism 86.

The first translation mechanism 86 may include an encoder for directing the translation movement. The first translation mechanism 86 may also include one or more homing switches. The encoder may be an incremental type encoder or other similar encoders. The homing switch may facilitate calibration of the scanning assembly 80, which can help improve the accuracy of the spatial coordinates used with the scanning assembly 80. The first translation mechanism 86 should be capable of moving a distance that corresponds, at least, to a height of the sample 94. The distance may also take into account the movement of the tilt mechanism 87. For example, a sample 94 with a height of 80 mm may require a minimum translation movement of 180 mm by the first translation mechanism 86 since the operation of the tilt mechanism 87 can provide an additional vertical movement distance of approximately 100 mm. In general, the height of the first translation mechanism 86 should be minimized as much as possible so that the overall size of the scanning assembly 80 can be as small as possible.

As shown in FIG. 4M, the first translation mechanism 86 includes a base plate 173 and a carriage plate 174. The components of the first translation mechanism 86 are attached, either directly or indirectly, to the base plate 173, which is then attached to the frame 82 of the scanning assembly 80. The carriage plate 174 can securably receive the tilt mechanism 87 via the home device 171 (as shown in FIG. 4L).

As shown in FIGS. 4L and 4M, the first translation mechanism 86 includes a linear bearing structure 179 along which the carriage plate 174 is translated. The linear bearing structure 179 may be provided with an air-bearing or a crossed-roller bearing, for example, to ensure accuracy and smoothness in the movement. Another example linear bearing structure 179 may be linear guides, such as 179A and 179B shown in FIGS. 4L to 4N. The linear guides may be caged-ball linear guides. Compared with linear bearing structures 179 formed with the air-bearing or the crossed-roller bearing, the linear guides are less complicated to design and less expensive while also providing a fairly smooth and reliable translation movement.

The first translation mechanism 86 also includes a pair of linear actuators 175A, 175B. As shown in FIGS. 4L to 4N, the linear actuators 175A, 175B may be mounted to the base plate 173 with a slider clamp 177 to help absorb any shock or vibrations resulting from the movement of the linear actuators 175A, 175B or any other mechanical components in the scanning assembly 80.

The linear actuators 175A, 175B may be operated by a brushless linear motor, such as motor 178, to minimize back-lash. In some embodiments, the linear motor 178 can include ironless stator coils to further minimize vibration in order to maximize smoothness in the movement. Example motors may include motor model DX20B-C2, DX20B-C3 or DX20B-C4 by PBASystems™. Thermal resistance associated with the motor 178 during use may also be considered when selecting the motor for the first translation mechanism 86.

In some embodiments, the dimensions of the linear actuators 175A, 175B can be selected to accommodate the movement required for the first translation mechanism 86.

FIG. 4N is a partial front view of the first translation mechanism 86 illustrating components below the carriage plate 174. It will be understood that the carriage plate 174 appears transparent for the purpose of illustrating components underneath, and that the carriage plate 174 may or may not be formed of a transparent material.

As shown in FIG. 4N, the first translation mechanism 86 may include a linear encoder 176 for controlling the movement of the linear actuators 175A, 175B. In some embodiments, the linear encoder 176 can determine an intended position for the first translation mechanism 86 based on position information provided by the operator via a control system of the scanning assembly 80 (the control system will be described later). The linear encoder 176 can then initiate the operation of the motor 178 and the linear actuators 175A, 175B to move the first translation mechanism 86 to the intended position. The linear encoder 176 may also, in some embodiments, provide a feedback to the control system for verifying the position of the first translation mechanism 86.

Generally, the linear encoder 176 can provide a response speed of approximately 2 m/s, a resolution of approximately 1 μm and an accuracy of approximately 5 μm. In some embodiments, the linear encoder 176 can provide an accuracy of 1 μm, a resolution of 50 nm and a response speed close to 2 m/s. Example linear encoders 176 can include an encoder from the Mercury II™ 5000 series, for example. It will be understood that other similar encoders may be used.

The first translation mechanism 86 can also include a dowel pin 345 (see FIGS. 4N and 4O) to help align the first translation mechanism 86. The dowel pin 345 may also enable a larger interval of movement of the first translation mechanism 86.

In some embodiments, the first translation mechanism 86 may include a counterbalance component (not shown) for balancing the dynamics of the vertical axis. The counterbalance component may stabilize the scanning head 84 after the scanning head 84 has moved. For example, the counterbalance component can reduce the resonant effects caused by the stopping and starting of the movement of the scanning head 84. The counterbalance component may be a magnetic spring counterbalance. Magnetic spring counterbalances can be advantageous due to their passive nature, which can ensure a defined function or position of the device in a power-off condition. For example, a linear actuator 175A or 175B can be pushed in or pulled out with a constant force and to a predefined position. As a result, the counterbalance component may help ensure safety in the case of a power fault or interruption by locking and/or controlling the speed at which the first translation mechanism 86 operates.

In some embodiments, the counterbalance component may include dual counter-balances to accommodate any required forces and to minimize any abbe error.

Reference will now be made to FIGS. 4O to 4Q for describing the second translation mechanism 88. FIG. 4O is a perspective view of the second translation mechanism 88. FIG. 4P illustrates a bottom perspective view of a horizontal encoder 340 for the second translation mechanism 88 of FIG. 4O and FIG. 4Q illustrates a rear perspective view of the horizontal encoder 340.

Similar to the trans-rotational mechanism 90 and the first translation mechanism 86, the second translation mechanism 88 may be capable of translating the scanning head 84 at least along a diameter of the sample 94. As noted, the typical diameter of samples may be about 120 mm. The translation distance required for the second translation mechanism 88 may be longer in some embodiments to accommodate different factors, such as an optical focal length and horizontal movement due to the tilt mechanism 87.

The second translation mechanism 88 can include a horizontal base plate 341 for securably receiving the first translation mechanism 86. The second translation mechanism 88 can also include bumpers 342 at either edges of the second translation mechanism 88 to minimize any vibrations that may be caused by the translation movement and to limit the translation path of the second translation mechanism 88.

Many of the components provided in the second translation mechanism 88 are similar to those described with reference to the first translation mechanism 86, and therefore, will not be repeated. For example, the second translation mechanism 88 includes linear guides 343A and 343B that can be similar to the linear guides 179A and 179B of the first translation mechanism 86 and a linear motor 344 similar to the linear motor 178. The second translation mechanism 88 also includes the dowel pin 345 to help align the second translation mechanism 88.

It will be understood that although these components are similar for each of the first and second translation mechanisms 86, 88, they do not need to be the same in a particular scanning assembly 80.

Referring now to FIG. 4S, which is a perspective view of the scanning assembly 80 of FIG. 4A while in an example operation. As shown in FIG. 4S, the scanning head 84 is tilted by the tilt mechanism 87. The scanning head 84 is also translated to an edge of the second translation mechanism 88 and to approximately a lower middle portion of the first translation mechanism 86.

The scanning assembly 80 can also provide biasing of the mechanical movement to facilitate the typical image orientations expected across tissue margins. For example, the various actuation mechanisms can support rapid acquisition of raw OCT data for multiple parallel B-scans so that these images can be stacked parallel to each other to create a C-scan. In computed tomography, it is generally understood that a B-scan is a 2D slice through the sample and a C-scan is a typical 3D visualization of a volume of the sample.

As noted, the scanning assembly 80 is in electrical communication with the processing module and thus, the processing module can receive the raw OCT data captured by the scanning assembly 80 and generate wide field OCT images based on the received raw OCT data.

In some embodiments of the imaging system 10, the scanning head 84 may include a red wavelength laser source light for scanning and mapping human tissue samples. For example, in the application of scanning human breast tissue, the scanning head 84 may be a 660 nm laser.

The scanning head 84 may be a line scanner, for example. Furthermore, a minus 250 micron calibration in the height values may be used to account for any tissue penetration and the exposure that may be set on the line scanner to either automatically determine the necessary exposure time or that the exposure time should be set to roughly 300 µs for fatty tissue. It has also been found that height is not a contributing factor to the variation in measurements, so the distance that the sample is away from the line scanner may be determined by taking into account the expected height of the sample as well as the clearing distance of the beam.

Referring now to FIG. 5, shown therein is a block diagram 100 of an example embodiment of hardware components that can be used with the imaging system 10. The imaging system 10 can include an OCT module 102, a probe module 104, a scanning module 106, a processing module 108 and an enclosure module 110. It should be noted that the block diagram 100 is just one example embodiment for the imaging system 10 and that other configurations are possible. For example, some components can be grouped together, grouped differently and/or additional components may be used depending on the particular application of the imaging system 10.

The OCT module 102 can include an optical and control module 112 and a camera Input/Output (I/O) module 114. The optical and control module 112 can include optical hardware for capturing raw OCT data of the sample using the probe module 104 and a processor for controlling the optical hardware. The OCT module 102 generally controls the acquisition of the raw OCT data. For example, the camera 114 may be synced with a light source in the optical and control module 112 and with the probe module 104.

The probe module 104 can include an opto-mechanical control module 116. The opto-mechanical control module 116 may include opto-mechanical hardware, such as a scanning lens and imaging optics, for creating an OCT image of the sample and a processor for controlling the opto-mechanical hardware. The probe module 104 corresponds to the scanning head 84 shown in FIG. 4.

The probe module 104 can include a set of rastering mirrors that can scan the light source from the OCT module 102 along a surface of the sample. Each scan by the probe module 104 (or the scanning head 84) can include 1024 A-scans over a 15 mm range. In some embodiments, the probe module 104 can repeat the scan at 0.5 mm intervals to produce a low resolution volume image (i.e., a C-scan) over a 15×15 mm area. The probe module 104 can be coupled and synced with the scanning module 106. The probe module 104 can also alter a position of each C-Scan in order to capture raw OCT data for as much of the sample surface as possible.

The scanning module 106 can include a mechanical and control module 118. The scanning module 106 can include the scanning assembly 80 of FIG. 4A. For example, as described with reference to FIGS. 4A to 4S, the scanning assembly 80 includes various translation mechanisms, such as translation mechanisms 86, 88 and 90, that can position the scanning head 84 and/or the container 42 in various positions so that as much of the surface of the sample 94 can be imaged and images at various angles at a depth of a portion of the sample 94 can also be obtained. For example, the scanning module 106 can position the scanning head 84 over the sample 94 to capture a series of scans at various heights with respect to the surface of the sample 94. As will be described, the series of scans at different heights can ensure that as much useful data is captured for the sample 94.

As briefly described, the processing module 108 can control the operation of the imaging system 10. The processing module 108 generally includes a control system 120 and an application system 122.

The control system 120 can include a control module 126 and an initial digital signal processor (DSP) module 124. The control module 126, the initial DSP module 124 or the processing module may each include one or more processors or other dedicated circuitry depending on the configuration, purposes and computing requirements of the imaging system 10.

It should be understood that although only one control module 126 is shown within the control system 120 of FIG. 5, the control system 120 can include more control modules 126 depending on the design and configuration of the imaging system 10. For example, the control system 120 can include a separate control module 126 to operate with each of the OCT module 102, the probe module 104 and the scanning module 106. The number of control modules 126 provided in the control system 120 can also depend on the amount of computing power that is required by the processing module 108 and/or the imaging system 10 as a whole.

The initial DSP module 124 can control the relative motion between the scanning head 84 and the sample to obtain the raw OCT data for generating the wide field OCT images of the sample. The initial DSP module 124 can perform some initial digital signal processing on the raw OCT data that is provided by the OCT module 102 and generate pre-processed OCT data of the sample. The initial digital signal processing may include filtering and amplification.

The application system 122 includes an application 130 and an image processing module 128. The application system 122 can be an operating system, for example. In use, the processing module 108 can execute the application system 122 to run the application 130 for enabling capture of the raw OCT data by the OCT module 102, the probe module 104 and the scanning module 106. The image processing module 128 can use the acquired raw OCT data to create a wide field OCT image of the entire surface of the sample or specific regions of interest of the sample. The application system 122 can also manage user interactions and data storage.

The enclosure module 110 includes I/O components 132, a power module 134 and an enclosure 136. The I/O components 132 can include input and output devices, such as the user input devices 50 and 52. The I/O components 132 can include hardware for relaying I/O signals between an operator of the imaging system 10 and the imaging system 10. In some embodiments, the I/O components 132 may provide a user interface with which the operator can inspect generated OCT images.

As described, the enclosure 136, such as the cart 32, can house and protect the physical components of the imaging system 10. The power module 134 receives power from a power source, such as a three-phase mains line, a battery or a power generator, and transforms the received power so that it can be used by the various components of the imaging system 10.

An example operation of the imaging system 100 shown in FIG. 5 will now be described. After the imaging system 100 receives the container 42 holding a sample into the enclosure 136, the I/O component 132 can receive inputs from the operator. The inputs received via the I/O component 132 may include physical dimension data associated with the sample in the container 42. Alternatively, the input may indicate that a representation needs to be generated for the sample by the camera 114.

In response to the inputs received at the I/O component 132, the application 130 can process the received inputs to generate scanning parameters for the control module 126. Based on the scanning parameters, the control module 126 can forward the control commands to each of the OCT module 102, the probe module 104 and the scanning module 106 for controlling the operation of the imaging system 100. The control commands may include movement commands indicating how the probe module 104 should be moved by the scanning module 106 and data acquisition commands indicating the amount and type of raw OCT data that needs to be collected by the OCT module 102, for example.

The raw OCT data collected by the OCT module 102, the probe module 104 and the scanning module 106 can then be provided to the initial DSP module 124 for processing. The initial DSP module 124 can convert the raw OCT data into initial OCT images, for example. The initial OCT images can then be further processed at the image processing module 128. The processing of the initial OCT images will be described with reference to at least FIGS. 7A to 7F.

Reference will now be made to FIGS. 6A and 6B, which show different views of a prototype imaging system 140 for obtaining OCT image data. The prototype imaging system 140 includes a monitor 142 for displaying imaging results and/or analysis, and a prototype scanning assembly 148.

The prototype imaging system 140 was developed to facilitate preclinical and clinical studies. During those studies, the prototype imaging system 140 was used to collect quantitative imaging data from tissue-simulating phantoms and from animal-model and human tissue samples. Based on a review of the collected imaging data, the performance of the imaging system 140 was improved.

The prototype imaging system 140 shown in FIGS. 6A and 6B is based on Spectral-Domain OCT (SD-OCT), which can maximize the sensitivity and speed of scanning of an image. FIG. 6C shows an example schematic 150 of the SD-OCT system.

The SD-OCT system 140 includes a broadband light source 152, a beam splitter 154, a sample arm assembly 158, a reference arm assembly 156, a diffraction grating 162 and a detector array 160 that provides 'N' number of bins (or 'N' number of output samples). The broadband light source 152 is coupled through a fiber to the 50/50 beam splitter 154. The sample arm assembly 158 directs one half of the source light into the tissue sample which generates a reflected sample light signal. The second half of the source light is directed to a reference mirror in the reference arm assembly 156. The reference mirror can then generate a reflected reference light signal. In the context of the imaging system 10, the SD-OCT system 140 components may be part of the scanning head 84.

The light signals reflected from the reference mirror at the reference arm assembly 156 and from the tissue sample at the sample arm assembly 158 are then combined at the beam splitter 154 to form an interference pattern. The combined light is then sent to the detector array 160 where the interference between the reflected sample light signal and the reflected reference light signal can be measured. The output of the detector array 160 is then processed and used to create an OCT A-scan of the sample. The beam from the broadband light source 152 may then be swept across one or more different portions of the surface of the sample to generate complete or partial 2D or 3D OCT images.

Operation of the imaging system 10 for generating wide field OCT images will now be described with reference to FIGS. 7A to 11F.

With respect to analyzing tissue specimens, a wider view of the tissue specimen is generally useful in creating context for different tissue features. The field of view of a conventional OCT image reconstructed based on A-scans is limited in terms of the useful viewing range. With conventional techniques, the surface of the tissue specimen must be a certain distance from the OCT camera to make use of the full imaging window. However, the surface of the tissue specimen is often irregular, making it difficult to gather information over the entire surface. In addition, if the OCT camera is too close to the tissue specimen, then there will be undesirable effects in the OCT images, such as "wrap-around" effects, and if the OCT camera is too far from the tissue specimen, there will be little or no OCT signal.

To create a wide field OCT image, the imaging system 10 may be configured to scan the sample at different locations. The imaging system 10 may follow a certain scanning pattern, such as a raster pattern for example. The scanning pattern can generally be provided to the imaging system 10 as a series of control commands for adjusting a position of the scanning head 84. For example, the control commands can adjust a position of the series of mirrors at the probe module 104. In general, the scanning pattern can be uniquely generated to optimize scanning time and resolution in regions of interest of the sample 94. At each position of the surface of the sample (e.g., a position can be defined by a X,Y,Z coordinate in a Cartesian coordinate system), the imaging system 10 can collect raw OCT data at various distances from the surface of the sample. The imaging system 10 can also record spatial location for each OCT scan.

The imaging system 10 can then process the raw OCT data to generate OCT images that can then be combined together using one or more stitching processes that will be described with reference to FIGS. 7A to 11F to generate a composite OCT image. Example combination methods may include at least one of a wide field vertical stitching and horizontal stitching.

In some embodiments, as will be described with reference to FIG. 7F, the imaging system 10 may perform further processing so that the composite OCT image or the reconstructed OCT images have improved image quality.

Referring now to FIG. 7A, shown therein is a flowchart of an example embodiment of a wide field OCT imaging method 180. The imaging system 10 may apply various techniques, such as stitching of OCT images and other processing techniques for generating wide field OCT images of a sample.

At 182, the imaging system 10 can acquire raw OCT data of the sample and generate OCT images using the acquired raw OCT data.

In order to collect the raw OCT data over at least a portion of the sample, the imaging system 10 can operate the scanning assembly 80 along with a position measuring device. The position measuring device may include position sensors or cameras. For example, the position measuring device may be a laser based position sensor that is either a point-based measurement tool or a line scanner. For example, the laser based position sensor may be a laser position finder or scanner that is attached to the scanning head 84 or mounted separately, such as to a chassis, for example. Examples of cameras that may be used include, but are not limited to, one or more standard charge-coupled device (CCD) cameras that can capture images of the sample. The sample may also be rotated to facilitate the operation of the camera. The images captured by these cameras can be reconstructed to form a 3D representation of the sample. Like the laser based position sensor, the camera may be attached to the scanning head 84 or mounted separately. The 3D representation of the sample provides an indication of an overall surface of the sample to be imaged.

The position measuring device can measure and register at least a portion of the surface of the sample. Based on the measurements provided by the position measuring device, the scanning assembly 80 may generate a representation of the sample.

The representation of the sample may be a coarse spatial representation. The representation may include at least one of a surface map of the sample, a point cloud representation of the sample, and an interpolated surface of the point cloud representation. The representation of the sample may be generated using various triangulation methods that interpolate the surface positions provided by the position measuring device.

For example, the position measuring device can be a laser sensor. The laser sensor is positioned over a sample so that the laser sensor can measure a height from various positions along a surface of the sample. The various positions along the surface of the sample may correspond to X,Y coordinates in the Cartesian coordinate system. A representation of the surface of the sample may be generated by interpolating each of the measured height data based on the various positions along the surface of the sample.

The representation can facilitate the assessment of the specific regions at which high resolution raw OCT data is being captured. As will be described, the imaging system 10 may also use surface maps of the sample for maintaining focus throughout the OCT scanning process.

In some embodiments, the imaging system 10 can use the representation of the sample for developing a scan path for the scanning head 84 for capturing raw OCT data of a region of interest of the sample. The imaging system 10 can also use the representation for preventing collision of the scanning head 84 with the sample. The imaging system 10 can guide the scanning head 84 towards the sample in a safe manner. The collision detection method may be used during and after the scanning path has been created. For example, the imaging system 10 may require a minimum distance between the scanning head 84 and the sample so that the scanning head 84 does not collide with the sample or any of the other components of the scanning assembly 80, such as a portion of the frame 82 or any of the actuation mechanisms 86, 88 and 90.

Reference will now be made to FIG. 7B, which shows a flowchart of an example embodiment of a method 182 of acquiring raw OCT data. Generally, the imaging system 10 may operate the scanning assembly 80 to acquire the raw OCT data in order to generate a plurality of OCT images of at least a portion of the sample (i.e. the region of interest) based on at least the generated representation of the sample, such as the surface map. In some embodiments, the imaging system 10 may also operate the scanning assembly 80 in accordance with user inputs provided via the user interface elements. The user inputs may provide parameters for the wide field OCT images, for example.

At 202, the imaging system 10 can locate a portion of the sample that is to be imaged (e.g., a region of interest). The imaging system 10 may determine the region of interest based on user inputs provided via the user interface elements, for example.

At 204, the imaging system 10 can adjust the scanning head 84 so that a surface of the region of interest of the sample is within view of the scanning head 84. As noted, the imaging system 10 can operate the scanning assembly 80 according to at least one of the surface map and the user inputs. At 206, the imaging system 10 records the position of the scanning head 84. The position may be indicated using X, Y and Z coordinates in the Cartesian coordinate system, or other coordinate systems. At 208, the imaging system 10 can record the raw OCT data of the region of interest from the position of the scanning head 84.

At 210, once the imaging system 10 has recorded the raw OCT data associated with the region of interest, the imaging system 10 can adjust the position of the scanning head 84 axially towards the sample.

By adjusting the position of the scanning head 84 axially towards the sample, the imaging system 10 can capture the raw OCT data for a series of vertical OCT images that includes an initial OCT image and one or more vertical neighbouring OCT images. Each of the OCT images in the series of vertical OCT images is associated with a different scanning distance between the scanning head 84 and the surface of the sample. As will be described, the imaging system 10 may obtain the raw OCT data for the series of vertical OCT images such that the focus is maintained substantially constant.

In OCT systems, the interference signal between the sample signal, such as the signal from the sample arm assembly 158 of FIG. 6C, and the reference signal, such as the signal from the reference arm assembly 156 of FIG. 6C, increases in intensity as their respective optical path lengths of these arms match in distance. When the optical path lengths of each of the sample signal and the reference signal are matched, the reference arm (which can also be referred to as a delay line) is positioned at a zero delay position with respect to the sample arm.

The zero delay position corresponds to a position where the interference pattern is at a maximum. The resulting image quality at the zero delay position is therefore generally superior compared to the rest of the image. Conventional OCT imaging techniques generally involve positioning the reference arm with respect to a focal point of a sample so that the surface of the sample corresponds to an upper or top edge of an imaging window. The zero delay position in the imaging window for conventional OCT imaging systems would correspond to the upper edge of the image window In the methods and systems described herein, the zero delay position may be adjusted to be similar to the focal point position of the sample that is set at a predetermined distance below the surface of the sample. That is, the zero delay position may be below the surface of the sample, like that of the focal point position. Since the focal point position of the sample is generally a part of the region of interest, adjusting the zero delay position to be similar to the focal point position of the sample can improve the quality of the resulting OCT images by maximizing the interference signal in the region of interest of the sample. Generally, the zero delay position can be positioned at depths of penetration up to about 2 mm, for example. Adjustment of the reference arm assembly, such as reference arm assembly 156, can help adjust the focal point position, which is in the region of interest, so that it corresponds to a predefined region of the imaging window.

In some embodiments, wrap-around artifacts may appear in the region above the zero delay position of a given OCT image. The wrap-around artifacts may include the image rotated at 180 degrees. As will be described, further image processing and adjustments can be applied to the given OCT image to reduce wrap-around artifacts in the region above the zero delay position.

In order to maintain constant focus across a sample, the imaging system 10 can adjust the scanning head 84 based on the surface map of the sample. For example, for each X,Y position on the surface of the sample, the imaging system 10 can axially adjust the scanning head 84 so that the focus is initially at the surface of the sample. For samples with an uneven surface, the imaging system 10 may position the scanning head 84 at various different heights across the surface of the sample. The focal point positioning technique can be beneficial since the surface of most turbid samples is non-uniform which makes maintaining the focal point of the resulting OCT images at a constant depth a difficult task during OCT scanning. The focal point positioning technique described herein also avoids the use of dynamic surface tracking for focal point positioning, which is advantageous since dynamic surface tracking can be complex and computationally intensive.

Once the imaging system 10 has positioned the scanning head 84 so that the focus is at the surface of the sample, the imaging system 10 may further move the scanning head 84 by a scan adjustment distance towards the sample so that the focus is beneath the surface of the sample. The portions of the resulting OCT images that are in focus will generally correspond to a region at approximately a scan adjustment distance below the upper edge of the imaging window (examples of which are shown in the rectangular areas in the images of FIGS. 8D and 9A).

The scan adjustment distance may vary depending on the specifications of the imaging system 10 (e.g., type of lens, error estimation for the resulting images, etc.), the type of specimen (e.g., different tissue specimens may have different density), the purpose for the imaging (e.g., tissue differentiation for excised tissues with tumors, etc.), and other considerations. In some embodiments, the scan adjustment distance may be approximately half of the error estimation for the resulting images.

For example, as shown in FIGS. 8A and 8B, the scan adjustment distance may depend on a numerical aperture value associated with the lens of the imaging system 10. FIG. 8A is a schematic 350A of an optical path for a lens with a high numerical aperture and FIG. 8B is a schematic 350B of an optical path for a lens with a low numerical aperture. As is generally understood, a location of a focus can vary depending on the numerical aperture of the lens. As shown in FIGS. 8A and 8B, a lens with a higher numerical aperture will have a closer focus 351A compared to a focus 351B for a lens with a lower numerical aperture.

A region on either side of the focus can be referred to as a depth of field or a focused portion since the lens is able to capture the best image quality, or useful image data, from that region. The size of the depth of field also varies with the numerical aperture of the lens. As shown in FIG. 8A, for example, the depth of field 352A for a lens with the higher numerical aperture is smaller than the depth of field 352B for a lens with a lower numerical aperture (FIG. 8B).

Referring now to FIG. 8C, shown therein is a schematic of the scanning head 84 capturing an example OCT image 278. As described with reference to FIGS. 8A and 8B, a focused portion 278a for the OCT image 278 can vary based on a lens of the scanning head 84. Accordingly, in order for the imaging system 10 to capture sufficient raw OCT data at various depths of the sample, the imaging system 10 can adjust an axial position of the scanning head 84 so that different axial (i.e. vertical) regions of the sample appear in the focused portions 278a of the imaging window. The imaging system 10 may continue to adjust the axial position of the scanning head 84 until sufficient raw OCT data has been captured for the sample.

FIG. 8D illustrates a series 280 of OCT images for a sample surface 279. Each image 280a to 280c in the series 280 has a corresponding focused portion, namely 281a to 281c. After capturing the raw OCT data associated with the image 280a, the imaging system 10 can move the scanning head 84 closer to the sample surface 279 to capture the raw OCT data for the image 280b. As can be seen in images 280a and 280b, the respective focused portions 281a and 281b corresponds to a different vertical region along a depth of the sample. Similarly, raw OCT data for the image 280c can be captured by moving the scanning head 84 closer to the sample surface 279. By adjusting the scanning head 84 to different vertical positions with respect to the sample, the imaging system 10 can provide focused portions, namely 281a to 281c, for each vertical portion of the sample.

In some embodiments, the imaging system 10 can identify an initial scan position on the surface map that corresponds to a highest point of the surface of the sample and a final scan position on the surface map that corresponds to a lowest point of the surface of the sample. The imaging system 10 can adjust the position of the scanning head 84 so that each set of vertical OCT images corresponds to the raw OCT data that is captured within the range between the initial scan position and the final scan position, and so that there is at least one OCT image with each of the initial scan position and the final scan position at the upper edge of the imaging window.

The imaging system 10 may also determine a difference between the initial scan position and the final scan position of the surface of the sample to estimate the amount of raw OCT data that may be required for generating the wide field OCT image for the sample. As will be described with reference to FIGS. 8E and 8F, different types of surfaces may require a substantial difference in the amount of raw OCT data that is acquired in order to image provide a wide field image of the sample.

FIG. 8E shows a series 320 of OCT images for a sample surface 321 and FIG. 8F shows a series 322 of OCT images for a sample surface 323. Generally, if the difference between the initial scan position and the final scan position of the surface of the sample is fairly small, such as for the sample surface 321 in FIG. 8E, the imaging system 10 can determine that the surface of the sample is fairly flat and therefore, the imaging system 10 would not be required to capture data at too many different depths. As shown in FIG. 8E, the sample surface 321 can be captured with three horizontal OCT images 324, 326 and 328.

However, if the difference between the initial scan position and the final scan position of the surface of the sample is fairly large, such as in the case of the sample surface 323 in FIG. 8F, the imaging system 10 can determine that the surface of the sample is fairly uneven and the imaging system 10 would likely need to capture data corresponding to a greater number of heights to account for the unevenness of the surface. As shown in FIG. 8F, the sample surface 323 can be captured with three vertical sets of images, namely vertical image sets 330, 332 and 334. Each vertical image set 330, 332 and 334 includes more than one OCT image for different vertical regions of the sample. The vertical image set 330 includes images 330a to 330c, the vertical image set 332 includes images 332a to 332c and the vertical image set 334 includes images 334a and 334b.

It will be understood that, as described with reference to FIG. 8D, each of the images in FIGS. 8E and 8F may be a composite image formed from one or more images with a different vertical portion of the sample being the focused portion.

The focal point positioning technique described herein generally allows for, at least, the image quality of each of the OCT images of the sample to be equal throughout the imaging window; non-uniform surfaces to be scanned with no or insignificant degradation of image quality; and the imaging window to be extended along the Z-axis direction towards the sample to capture greater depth information.

Referring still to FIG. 7B, at 212, the imaging system 10 then records the new position of the scanning head 84, namely the new "Z" coordinate. At 214, the imaging system records the raw OCT data of the region of interest at a new scanning distance between the scanning head 84 and the surface of the sample.

At 216, the imaging system 10 determines whether a full extent of that portion of the sample has been captured. As noted, the imaging system 10 may, based on the surface map or from a visual review of the sample by an operator of the imaging system 10, determine whether additional raw OCT data is required at that portion of the sample. If the imaging system 10 determines that additional raw OCT data is required at that portion of the sample, the imaging system 10 repeats 210 to continue to capture the raw OCT data at a different vertical location of the sample. However, if the imaging system 10 determines that additional raw OCT data is not required at that portion of the sample, the imaging system 10 moves the scanning head 84 to a new horizontal region of the sample (e.g., a new X, Y coordinate of the sample) at 218. The portion of the sample may be a pre-set area.

At 220, the imaging system 10 determines whether sufficient raw OCT data has been captured for the region of interest. Again, depending on the surface map or from a visual review of the sample by an operator of the imaging system 10, it can be determined if the imaging system 10 has captured sufficient raw OCT data for the entire region of interest. The region of interest may be a pre-set area of a surface of the sample.

If the imaging system 10 determines that sufficient raw OCT data has been captured, the imaging system 10 proceeds to process the acquired raw OCT data of the sample at any one of 184 or 186 of FIG. 7A. If the imaging system 10 determines that there is an insufficient amount of raw OCT data for the region of interest (that is, there is an insufficient amount of raw OCT data for the sample), the imaging system 10 continues to capture additional raw OCT data by repeating 204 to 220 until sufficient raw OCT data has been captured for the region of interest.

After acquiring the raw OCT data of the sample, the imaging system 10 can generate OCT images based on the acquired raw OCT data. To generate the OCT images, the imaging system 10 may process the acquired raw OCT data using standard OCT reconstruction routines. For example, the imaging system 10 may process the raw OCT data acquired for every individual A-scan captured for the sample.

Referring again to FIG. 7A, at 184, the imaging system 10 can detect a surface for each of the OCT images being processed.

Once the imaging system 10 has acquired the raw OCT data and generated OCT images based on the raw OCT data for the sample, the imaging system 10 may process each OCT image to identify a surface position for each generated OCT image. The identification of the surface position can facilitate other image processing techniques that the imaging system 10 may apply to the generated OCT images. For example, the imaging system 10 can check for wrap-around artifacts in the generated OCT image based on the detected surface position and mitigate this risk by reversing a direction of the scanning head 84 upon detection of the wrap-around. It should be noted that the reference frame or coordinate system does not need to be transformed since the coordinate system is the same for data acquisition at 182 and surface detection at 184.

Referring now to FIG. 7C, shown therein is a flowchart of an example embodiment of a surface detection method 184 for the OCT images.

At 230 of the surface detection method 184, a maximum intensity value for each OCT image can be determined.

In some embodiments, the imaging system 10 may first overlay a series of OCT images based on the recorded height to generate a composite OCT image. As noted, the recorded height generally corresponds to an axial distance between the scanning head 84 and the surface of the sample. The imaging system 10 may then determine an average for the intensity values of each A-scan in the composite OCT image. Since the wrap-around artifacts are in the opposite direction as the OCT image data, the data associated with the wrap-around artifacts do not cumulatively add up in the averaged composite OCT image. The imaging system 10 may further apply a Gaussian filter to the averaged composite OCT image to reduce noise.

At 232, the imaging system 10 can register a depth position corresponding to the determined maximum intensity value as the surface for that OCT image.

The intensity of the signal at the surface of the sample is typically the highest for the sample. Therefore, the imaging system 10 can identify the surface position for the composite OCT image based on the determined maximum intensity value for each A-scan.

At 234 of the method 184, it is determined whether the surface of all of the OCT images has been detected and recorded.

If it is determined that the surface positions of all the OCT images have been registered, the imaging system 10 can proceed to combine the OCT images to create a composite image (at 186 of FIG. 7A). In some embodiments, once a surface position has been recorded for the OCT image, the imaging system 10 may further process the OCT image to clear the data associated with the pixels that are beyond the full viewing window. The imaging system 10 may clear the pixels outside the surface position by setting an intensity value of the corresponding pixels to zero, for example. This is one manner of eliminating any wrap-around artifacts that may exist in the OCT images.

If it is determined that not all of the surface positions of the OCT images have been registered, the method 184 can continue to determine the maximum intensity value for the remaining OCT images at 230.

Referring again to FIG. 7A, at 186, the imaging system 10 can combine the OCT images to create a wide field OCT image for a portion of the sample.

As briefly described, combining the OCT images may involve various different image processing techniques. Some techniques, in accordance with the teachings herein, will be described with simultaneous reference to FIGS. 7D to 7F, and 9A to 11F.

Referring now to FIGS. 9A to 9C, generally illustrated therein is an example combination of a series of OCT images for creating a wide field OCT image in accordance with the teachings herein. FIGS. 9A to 9C generally illustrate the results of various image processing techniques applied to a set of OCT images for generating a composite image. FIG. 9A illustrates a vertical OCT image set 282 including OCT images 282a, 282b, 282c and 282d. Each of the OCT images 282a, 282b, 282c and 282d is associated with the same position of the sample (that is, the same X,Y coordinate of the sample) but a different axial position of the scanning head 84. The focus of each of the OCT images 282a, 282b, 282c and 282d is constant. FIG. 9B is an initial vertical composite image 286 with each of the OCT images 282a, 282b, 282c and 282d combined together and is shown for example purposes. FIG. 9C is a processed vertical composite image 288 in which some processing techniques have been applied to the vertical OCT image set 282 to remove some of the noise seen in the initial vertical composite image 286.

In order to generate the initial vertical composite image 286 of FIG. 9B, the imaging system 10 combines each of the OCT images 282a, 282b, 282c and 282d by applying a vertical stitching process. An example vertical stitching process will be described with reference to FIGS. 7D and 11A to 11F. An example horizontal stitching process will be described with reference to FIGS. 7E and 10D to 10F.

Generally, the stitching methods in accordance with the teachings herein can be used to generate wide field 2D and 3D OCT images. The stitching methods described herein may also be used to combine OCT images that are acquired from non-uniform surfaces and equalize the image quality throughout the entire imaging window. As a result, the imaging system 10 can scan non-uniform surfaces without any degradation of image quality and the imaging system 10 can also extend the imaging window along the Z-axis further into the sample to capture greater depth information. It will also be noted that when used with the focal point positioning method in accordance with the teachings herein, the stitching methods described herein may also improve signal strength of the interference signal, and increase image quality and resolution at penetration depths of up to 2 mm beneath the surface of the sample. Accordingly, the imaging system 10 may employ the stitching methods described herein to scan through a range of depths to improve signal strength of the interference signal at all attainable depths.

It will be appreciated that the imaging system 10 may not be required to conduct both vertical and horizontal stitching methods when combining OCT images (as illustrated in the example shown in FIGS. 8E and 8F). When imaging small regions of interest, the imaging system 10 may only need to conduct vertical stitching in order to generate the wide field OCT image. On the other hand, the imaging system 10 may apply only the horizontal stitching method when imaging flat specimens or phantoms.

Generally, the vertical stitching method involves overlaying the OCT images based on associated spatial information (e.g., recorded height offsets), and fine-tuning an alignment of the OCT images. For two OCT images, the imaging system 10 may fine tune the alignment between the two OCT images by vertically shifting the alignment over a number of iterations and measuring the entropy associated with the overlap region of the two OCT images. The imaging system 10 can continue to repeat the alignment process for each OCT image. In some embodiments, the imaging system 10 may apply a weighted average to at least the overlap region between two OCT images in order to blend the overlap in order to further reduce horizontal step lines in the final combined OCT image and to further improve image quality.

Referring now to FIG. 7D, shown therein is a flowchart of an example embodiment of a vertical stitching method 188. For ease of exposition, the example vertical stitching method 188 will be described with reference to the vertical OCT image set 282 of FIG. 9A.

At 240, the imaging system 10 receives a vertical OCT image set, such as the vertical OCT image set 282 of FIG. 9A. The spatial information associated with each of the OCT images in the vertical OCT image set is also received by the imaging system 10 so that the imaging system 10 can align the OCT images accordingly.

At 242, the imaging system 10 overlays the images in the vertical image set. When overlaying an OCT image with a portion of a neighbouring OCT image, the imaging system 10 can determine entropy associated with the overlap region between the OCT image and the neighbouring OCT image in order to improve the alignment of the OCT image with the neighbouring OCT image. An example alignment process with now be described with reference to FIGS. 11A to 11E.

FIGS. 11A to 11E are various overlaid OCT images with different offset distances in accordance with an example embodiment. In this case, the offset is a height offset so the images are shifted vertically, either upwards or downwards, with respect to one another. For the purpose of consistency, the overlaid OCT images in FIGS. 11A to 11E correspond to the OCT images 282a and 282b of FIG. 9A. In this example, the OCT image 282b is the neighbouring OCT image of the OCT image 282a. In order to properly align the OCT images 282a and 282b together, the imaging system 10 can generate one or more intermediary composite images with a different amount of overlap, or offset distance, between the OCT images 282a and 282b. The offset distance may be in terms of pixels or any other suitable measurement. In some embodiments, the imaging system 10 may also determine an average for the overlapped region so that the intensity values at the overlapped region is not doubled.

FIG. 11A shows an intermediary composite image 312a with an offset distance of 150 pixels, FIG. 11B shows an intermediary composite image 312b with an offset distance of 160 pixels, FIG. 11C shows an intermediary composite image 312c with an offset distance of 170 pixels, FIG. 11D shows an intermediary composite image 312d with an offset distance of 180 pixels, and FIG. 11E shows an intermediary composite image 321e with an offset distance of 190 pixels. It will be understood that intermediary composite images can be generated for more offset distances and that only five offset distances are shown with FIGS. 11A to 11E for ease of exposition.

The imaging system 10 can then determine entropy for the overlap region of each of the intermediary composite images 312. Specifically, the imaging system 10 can measure the entropy associated with the overlap between the OCT images 282a and 282b in each of the intermediary composite images 312a to 312e. One example method to determine entropy will now be described. However, it will be understood that different methods of determining entropy are available and may be used instead of the technique described herein.

As is known in the art, entropy (H) is a statistical measure of randomness. The entropy of each of the intermediary composite images can be determined by measuring the standard deviation at the overlap in the intermediary composite images. In some embodiments, the entropy for an OCT image described herein can be defined using equation (1) below:

$$H = -\Sigma_{k=0}^{M-1} p_k \log_2(p_k) \quad (1)$$

where M is a number of gray levels of the OCT image (there are 65536 bins for 16 bit unsigned integers) and $p_k$ is the probability associated with a gray level k. The probability of each gray level, k, can be determined by creating a histogram of the gray level image intensity values. The number of bins in the histogram is equal to M. The probability of each gray level, k, can be calculated using equation (2) below:

$$p_k = \frac{n_k}{\Sigma n} \quad (2)$$

where $n_k$ is a count for gray level k and $\Sigma n$ is a total number of the counts for the gray levels.

Continuing with the example of FIGS. 11A to 11E, the imaging system 10 can identify which offset distance is most appropriate for aligning the OCT images 282a and 282b based on the entropy determined for each intermediary composite images 312a to 312e. Generally, the entropy for an image can be used to characterize the texture of that image. A lower entropy value can generally indicate that there is a greater order for a given overlap between the OCT images 282a and 282b and a higher entropy value can indicate that there is less order. Less order indicates that there is greater noise at the overlap between the OCT images 282a and 282b. The higher entropy value can indicate that the OCT images 282a and 282b are poorly aligned. The imaging system 10, therefore, identifies the intermediary composite image associated with the lowest entropy value as the composite image for the OCT images 282a and 282b. The imaging system 10 may also record the amount of overlap for that identified intermediary composite image for later use.

FIG. 11F is a plot 316 of the entropy associated with the intermediary composite images associated with the OCT images 282a and 282b at different offsets. As shown in the plot 316, the offset distance that is associated with the lowest entropy value is approximately 172 pixels. The imaging system 10 can therefore use the offset distance of 172 pixels for aligning the OCT images 282a and 282b to generate the composite image for the OCT images 282a and 282b.

The imaging system 10 can continue to overlay images from the vertical OCT image set 282 using the composite image generated for the OCT images 282a and 282b as an intermediary composite image. That is, the imaging system 10 can now overlap the OCT image 282c with the intermediary composite image generated for the OCT images 282a and 282b according to an offset as determined based on the minimum entropy technique described above to form another intermediary composite image. In general, the imaging system 10 can continue to overlay the images in the vertical OCT image set 282 to generate an initial vertical composite image 286 until the initial vertical composite image 286 fills an entire imaging window and/or until all the images in the vertical OCT image set 282 have been used.

In some embodiments, the image quality of the initial composite image can be improved. At 246, for example, focused portions for each OCT image in the vertical image set are identified. This may involve using the surface position determined individually for each OCT image to identify regions of the sample that are in focus. As described, the focused region for each OCT image is approximately the region located below the upper edge of the imaging window by a distance that corresponds to the scan adjustment distance. In some embodiments, the focused portions can correspond to a center portion of the imaging window for that OCT image.

Referring again to FIG. 9A, as shown, each of the OCT images 282a, 282b, 282c and 282d is associated with a corresponding focused portion 284a, 284b, 284c and 284d, respectively. The focused portion generally includes minimal noise and minimal artifacts.

At 248, only the focused portions of each of the OCT images are used to form the initial vertical composite image 286. For example, the imaging system 10 can remove the wraparound artifacts in each of the OCT images 282a, 282b, 282c and 282d by retaining only the respective focused portions 284a, 284b, 284c and 284d. The imaging system 10 may also remove any signal associated with the medium external to the surface of the sample based on the surface information previously registered for the OCT images 282a, 282b, 282c and 282d (in other words remove the signal outside of the surfaces for each of OCT images 282a, 282b, 282c and 282d).

At 250, the imaging system 10 generates a processed vertical composite image, such as the processed vertical composite image 288 of FIG. 9C by only using the focused portions 284a, 284b, 284c and 284d of each of the OCT images 282a, 282b, 282c and 282d after removing the signal outside of the each of the surfaces in the OCT images 282a, 282b, 282c and 282d (in an alternative embodiment, this removal step may not be done). The processed vertical composite image 288 is formed by shifting the focused portions 284a, 284b, 284c and 284d with respect to one another based on the offsets determined at 242 of method 188 to align each of the shifted focused portions 284a, 284b, 284c and 284d with each other.

Referring now to FIGS. 10A to 10C, shown therein is an example combination of another series of OCT images for creating a wide field OCT image. Similar to FIG. 9A, FIG. 10A illustrates a vertical OCT image set 292 including OCT images 292a, 292b, and 292c. Each of the OCT images 292a, 292b, and 292c is associated with the same position of the sample (that is, same X,Y coordinate of the sample) but a different axial or vertical position of the scanning head 84 with respect to the surface of the sample being imaged. The focus for each of the OCT images 292a, 292b, and 292c is constant. Each of the OCT images 292a, 292b, and 292c is also associated with a respective focused portion 294a, 294b and 294c.

FIG. 10B is an initial vertical composite image 296 with each of the OCT images 292a, 292b, and 292c combined together based on the offsets as determined by act 242 of method 188. The vertical stitching method as described with reference to FIG. 7D may be used for combining the OCT images 292a, 292b, and 292c.

Similar to FIG. 9C, FIG. 10C is a processed vertical composite image 298. The imaging system 10 can generate the processed vertical composite image 298 by retaining only the focused portions, namely focused portion 294a, 294b and 294c, of the OCT images 292a, 292b, and 292c. The imaging system 10 can also remove any signal associated with the medium external to the surface of the sample based on the surface position previously registered for the OCT images 292a, 292b, and 292c.

After applying the vertical stitching method to each of the vertical image sets, the imaging system 10 can apply a horizontal stitching to the processed vertical composite images. It should be again noted that the imaging system 10 can apply the horizontal stitching method to OCT images that were not previously vertically stitched together.

Generally, the horizontal stitching method can involve overlaying the OCT images based on associated spatial information (e.g., recorded positions along the surface of the sample) in a horizontal fashion. The spatial information may be the position data (e.g., X,Y coordinates) associated with the scanning head 84 as it moves horizontally along the surface of the sample when acquiring raw OCT data. Similar to the vertical stitching method described with reference to FIG. 7D, the imaging system 10 can continue to fine tune the overlap in the overlaid images by minimizing the entropy associated with the overlap between the horizontally overlaid images. In some embodiments, the imaging system 10 may further apply a weighted filter to the overlaid image to blend the overlap and further reduce noise at the overlap region. The imaging system 10 can continue to combine another neighbouring OCT image to the overlaid image and so on and so forth until all of the horizontal images have been combined or until the imaging window has been filled. Therefore, a series of OCT scans over the sample can be horizontally and/or vertically stitched to generate a composite macro view of a region of interest of the sample. This region of interest may be a small or a large portion of the sample.

Referring now to FIG. 7E, shown therein is a flowchart of an example embodiment of a horizontal stitching method 190. For ease of exposition, the example embodiment of the horizontal stitching method 190 will be described for the processed vertical composite images 288 and 298 of the respective FIGS. 9C and 10C with reference to FIGS. 10D to 10F. FIGS. 10D to 10F show an example combination of OCT images for generating a wide field OCT image.

At 260, the imaging system 10 can receive a horizontal image set along with associated position information. As described with reference to FIG. 7B, the position information may be associated with the position of the scanning head 84 as it captures the raw OCT data. The position information for each OCT image in the horizontal image set will include at least the X, Y coordinate.

In the example shown in FIGS. 10D to 10F, the horizontal image set 302 includes, at least, the processed vertical composite image 288 and the processed vertical composite image 298.

At 262, the imaging system 10 can overlay two images in the horizontal image set 302. Referring still to FIG. 10D, the processed vertical composite image 288 can be overlaid with the processed vertical composite image 298 to generate an initial horizontal composite image 304, as shown in FIG. 10E. To properly overlay the OCT images in the horizontal image set 302, the imaging system 10 may determine entropy associated with the overlap, as described with reference to FIGS. 7D and 11A to 11F, and select the offset distance associated with the lowest entropy value as the proper alignment for the processed vertical composite images 288 and 298.

Accordingly, the imaging system 10 may fine tune the alignment between the processed vertical composite images 288 and 298 by vertically shifting (if necessary) at 263 and horizontally shifting the images 288 and 298 at 264 over a number of iterations and measuring the entropy associated with the overlap of the processed vertical composite images 288 and 298. In some embodiments, such as the example shown in FIG. 10D, the processed vertical composite images 288 and 298 may have a vertical offset from each other that requires vertical stitching (i.e., based on the process described with reference to FIG. 7D) prior to horizontal stitching. Once the processed vertical composite images 288 and 298 are vertically aligned, the imaging system can horizontally align the images 288 and 298.

The imaging system 10 can continue to repeat the alignment process for each remaining OCT image in the horizontal image set 302.

At 266, the imaging system 10 determines whether all the images in the horizontal image set 302 have been stitched together. If the imaging system 10 determines that there are images in the horizontal image set 302 that have not been included into the initial horizontal composite image 304, the imaging system 10 returns to 262. If the imaging system 10 determines that all of the images in the horizontal image set 302 have been combined into the initial horizontal composite image 304, the imaging system 10 can perform further processing on the horizontal image set to generate a processed horizontal composite image (at 268), such as the processed horizontal composite image 306 shown in FIG. 10F.

As described, when combining the OCT images together, the imaging system 10 may also process the OCT images to remove artifacts. An example artifact is a saturation artifact which appears as streaks in the OCT image.

The saturation artifact is generally associated with a noise signal measured at a region outside the surface of the sample that exceeds a signal in air. The signal in air is an expected baseline signal for the region external to the surface of the sample. Generally, when obtaining raw OCT data, the scanning head 84 can become saturated when too much light is reflected back from the surface of the sample. The result of the saturation is a vertical streak through the OCT images and through the entire imaging window. To minimize the saturation artifact in the OCT images, the imaging system 10 can normalize the noise signal with reference to the signal in air.

Referring now to FIG. 7F, shown therein is a flowchart of an example method 192 for minimizing saturation artifacts.

At 270, the imaging system 10 can identify an external region based on a surface position of the OCT image. The external region borders the exterior of the surface of the sample. The imaging system 10 may determine the surface position based on the surface detection method described with reference to FIG. 7D, for example.

At 272, the imaging system 10 can detect a noise signal in the external region of the OCT image.

For example, an OCT image can be represented as a gray level image of 16 bit unsigned integers and u(x,y) can represent the grey level, or brightness, at the point (x,y) on the image. Therefore, noise in an area outside the region of the sample can be defined with the equation (4) as follows:

$$N_x = u(x, \bar{y})_{window} \quad (4)$$

where the y-values for the gray levels are averaged.

At 274, the imaging system 10 can determine whether an intensity of the noise signal exceeds an intensity threshold.

To reduce the saturation artifact, the noise signal can be analyzed. Generally, a certain amount of noise is expected in the external region. However, significant deviations from the signal in air may substantially impair the quality of the OCT image. Accordingly, if the imaging system 10 determines that the detected noise signal exceeds the intensity threshold, the imaging system 10 may need to process the OCT image in order to reduce the noise signal to minimize the saturation artifacts.

The intensity threshold may vary depending on the imaging window and leveling. Once the window and level has been set for an image set, the baseline signal can be expressed as $b_{air} = \bar{u}_{air}$. In some embodiments, the intensity threshold, $T_{air}$, may be at least three times the standard deviation of the expected signal in air, as expressed by equation (5) below;

$$T_{air} = 3*(\sigma_{\bar{u}_{air}}) \quad (5)$$

where $\sigma_{\bar{u}_{air}}$ represents the standard deviation of the expected signal in air.

At 276, the imaging system 10 can adjust characteristics of the OCT image if the intensity of the noise signal exceeds the intensity threshold. For example, the imaging system 10 may normalize the A-scan data corresponding to the OCT image with respect to the determined noise signal intensity to reduce the saturation artifacts. That is, the A-scan data can be normalized using equation (6) as follows:

$$u'(x, y) = \frac{u(x, y)}{N_x} (b_{air}) \quad (6)$$

By detecting the noise signal and adjusting the characteristics of the OCT image if the noise signal intensity exceeds the intensity threshold, the imaging system 10 can generate a high resolution OCT image with minimal artifacts.

In at least one embodiment of the imaging system 10, signal pre-processing may include techniques such as low pass filtering, rolling averages and nearest neighbor corrections to reduce the effect of outliers and holes in the acquired raw OCT data.

In at least one embodiment of the imaging system 10, using the surface mapper data, a path planning processing pipeline, based on a set of pre-programmed parameters, will know the midpoint of a selected area, how many c-scan areas to divide it into, and the slope of each region. With this information, the imaging system 10 can use the midpoints of each C-scan area as the location where the OCT probe will be placed and the imaging system 10 can get a rough idea about how the height changes over the area with the area dictating how many incremented depth scans to perform to penetrate equally over the entire surface or a portion of the surface of the sample as desired.

It should be noted that due to the various angles and depressions, the surface of the tissue specimen might skew the digital interpretation of the surface. Surface mapping can be modified to address this problem by having the operator place the sample's region of interest as normal to the OCT beam as possible. To facilitate this, instead of there being a pre-scan from the surface mapper, a square can be projected onto the sample with a low power light source. The operator, such as a surgeon for example, can then place the region of interest within that square ensuring that it is as flat as possible. The scanner can then scan the tissue specimen as it would have before.

Various embodiments are described herein that may be used to create wide field OCT images through appropriate combination of smaller, higher resolution OCT images through the use of guided mechanical movement and image alignment algorithms.

The various embodiments described herein may also facilitate clear and error-free communication of tissue orientation from tissue resection (by a surgeon, for example) for tissue analysis (by a pathologist, for example).

The various embodiments described herein may also minimally disrupt the workflow in the operating room by maintaining sterility, tissue integrity and orientation information of resected tissue samples.

With regards to assessing tumor margin widths, OCT imaging may be used to reduce the prevalence of repeat surgeries since it may provide a faster and more accurate intraoperative tool for assessing margin widths while a surgery is ongoing. For example, an OCT-based intraoperative imaging system may be used to provide near real-time imaging information about the internal structure of tissue samples excised during breast conserving surgery. The results of preclinical and initial clinical studies conducted with a prototype wide-field OCT imaging system are presented in further detail below with respect to FIGS. 12A to 14B.

Furthermore, OCT image processing methods may be implemented by an OCT-based intraoperative imaging system, or any other suitable image processing system, to provide additional information to assist in assessing tumor margin widths. For example, OCT image processing methods according to the teachings herein can be used to assist a surgeon in determining whether an actionable boundary exists in an excised tissue sample. An "actionable boundary" indicates that two regions above and below a defined boundary are sufficiently distinct, and that the boundary is within a defined depth from the surface. The various methods according to the teachings herein define a way to determine this level of difference to which may be used to assist a surgeon to determine whether sufficiently enough tissue has been removed (i.e. to remove a tumor).

When excising cancerous tissue a surgeon may want to have a continuous layer of healthy tissue surrounding the excised tumor. The healthy layer of tissue surrounding the excised tumor is referred to as the margin. The narrowest point of the margin is referred to herein as the margin width. A surgeon may prefer a larger margin to ensure that no residual cancer or other tumor is left in the patient after surgery. However, larger margins may come at the cost of cosmetic effects since more tissue than necessary is removed.

Furthermore, an acceptable margin width may change from surgeon to surgeon. For example, an acceptable margin width could be 1 mm or 2 mm depending on the surgeon. If the excised tissue does not have an acceptable margin width, additional tissue may have to be removed from a patient to ensure sufficient margin width.

If a boundary between non-tumor tissue and tumor tissue is detected that is less than an acceptable margin from the surface of the tissue, an "actionable boundary" is said to be detected. If it is actionable, the surgeon may choose to excise further tissue based on the information if more tissue is available. In some cases, there may be no more tissue available to be excised, for example where the tumor is close to the skin or where the tumor is close to the chest wall. There may also be other situations which prevent the surgeon from excising further tissue as is known to those skilled in the art.

Various OCT image processing methods are described herein that may be used to assist a surgeon in at least one of identifying if a boundary exists, indicating the depth of the boundary at various points in the tissue sample, determining the degree of difference between tissues on either side of the boundary, and determining whether an actionable boundary is detected. Some example embodiments of OCT image processing methods, which may be used for tissue assessment, are presented in further detail below with respect to FIGS. 15 to 22F. In some embodiments, the imaging system 10 may be configured to perform the OCT image processing methods for implement tissue assessment according to the teachings herein. In other embodiments, other computing devices, having similar hardware components needed for image processing (as shown in FIG. 5), may be used to perform these OCT image processing methods for tissue assessment.

While developing a wide field OCT imaging prototype for the imaging system 10, pre-clinical performance studies were first carried out in tissue-mimicking phantoms and in ex-vivo normal and tumor tissues from a rat model (see FIGS. 12A to 12D). This enabled the imaging prototype to be tested and improved as well as for comparisons to be made between the results from the reconstructed OCT images and from histopathology.

FIG. 12A shows an image of a histopathology sample 400 of a rat ovary tumor that is derived from a human breast cancer cell line (MT-1) xenograft. Normal tissue 405 and malignant tissue 410 can be distinguished in the histopathology sample 400.

FIG. 12B shows a reconstructed OCT image 415 corresponding to the histopathology sample 400. The normal tissue region 405 and the malignant tissue region 410 can be also identified in the reconstructed OCT image 415.

FIG. 12C shows an image of a second histopathology sample 430 of a rat ovary tumor that is derived from a human breast cancer cell line (MT-1) xenograft. Normal tissue 435 and malignant tissue 440 can be distinguished in the histopathology sample 430.

FIG. 12D shows a reconstructed OCT image 445 corresponding to the second histopathology sample 430. The normal tissue region 435 and the malignant tissue region 440 can also be identified in the reconstructed OCT image 445.

The results shown in FIGS. 12A to 12D are an example of the general findings in tissues that different layers of tissue and different types of tissue (e.g. adipose, connective, cancerous) can be identified in the OCT images and that tissue boundaries can be clearly defined and localized.

Referring now to FIGS. 13A to 14B, initial images were acquired of freshly excised human breast lumpectomy specimens. For this, the prototype imaging system was placed in the pathology lab and specimens were scanned during the cold ischemic time between excision and standard pathological processing.

FIG. 13A shows an image of a freshly excised breast lumpectomy specimen 500. The lumpectomy specimen 500 has a superior section 505, a posterior section 510 and an inferior section 515. An OCT image of the lumpectomy specimen 500 was obtained using the prototype imaging system over a B-scan path 520.

FIG. 13B shows a reconstructed OCT image 525 over the B-scan path 520 of the lumpectomy specimen 500. The superior section 505, posterior section 510 and inferior section 515 can be identified in the reconstructed OCT image 525.

Different types of tissue can be identified in reconstructed OCT images. For example, a layer of connective tissue 530 and a layer of adipose tissue 535 are identified in the reconstructed OCT image 525. Without any assistance or automated tools, the identification of tissue layers by a user on an OCT image may require specialized training and there may still be inaccurate results.

FIG. 14A shows an image of a second freshly excised breast lumpectomy specimen 550. The lumpectomy specimen 550 has a superior section 555, a posterior section 560, an inferior section 565, a medial section 570 and a lateral section 575. An OCT image of the lumpectomy specimen 550 was obtained using the prototype imaging system over B-scan path 580.

FIG. 14B shows a reconstructed OCT image 585 over the B-scan path 580 of the lumpectomy specimen 550. The posterior section 560, the medial section 570 and the lateral section 575 can be identified in the reconstructed OCT image 585.

OCT images can be used to identify when narrow margins exist in excised tissue. Narrow margins may exist when tumor tissue is present in an excised tissue sample and is closer to the surface of the excised tissue sample than is desired by a surgeon. A narrow margin that is less than a desired margin is indicative of an "actionable boundary". Often, a margin less than 2 mm is considered to be indicative of an "actionable boundary"; however acceptable margin width may differ depending on the surgeon.

In the OCT image 585, a narrow margin 590 has been identified. The identification of the narrow margin 590 in the OCT image 585 indicates that tumor tissue is present in the excised tissue sample and may be closer to the surface of the lumpectomy specimen 550 than is desired by a surgeon. This indicates that additional tissue may be excised.

The preliminary images seen in FIGS. 13A to 14B appear to demonstrate the capability of wide field OCT imaging to provide high-resolution, high-contrast subsurface images from within breast lumpectomy specimens that can be used to detect actionable boundaries.

In particular, the experimental work appears to demonstrate that: a) preclinical OCT images can be well correlated to standard pathology assessments, b) OCT provides images in which certain different tissue types can be distinguished from one another, and c) OCT is capable of providing subsurface images of human breast lumpectomy specimens that can be used to detect and localize the boundaries between various tissues in these specimens. The experimental results suggest that OCT imaging may be useful as a near-real time surgical assessment tool. This capability may be extended by using wide field OCT imaging as described herein which can be used to provide an increased field of view of a tissue sample.

Accordingly, in some embodiments of an OCT imaging system, a tissue assessment method may be used on OCT images that may or may not be wide field OCT images. Once an OCT image has been reconstructed, the tissue assessment method may be used to quantitatively measure the degree of difference between a region above and a region below an identified or highlighted boundary in the reconstructed OCT image by using various measures, such as but not limited to the optical characteristics of the sample. The tissue assessment method may then indicate whether a boundary is "actionable" or "non-actionable".

In some cases, a patient may be injected with a contrast agent prior to having a tissue sample excised. In some cases, a contrast agent may be applied to the tissue sample after it has been excised. A contrast agent may cause cancer cells to emit fluorescence. The use of fluorescence in conjunction along with at least one of the tissue assessment methods described herein may further improve the speed of assessing tumor margin widths.

Fluorescence may direct a user to a portion of a tissue sample where cancerous tissue is expected. In some cases, a user may only perform OCT imaging methods on that portion of the tissue sample near where the cancerous tissue is expected. In some cases, a user may also use the fluorescence after an OCT image has been reconstructed to select portions or regions of the OCT image to focus on in their review. For example, a user may only review those B-scan images or portions of B-scan images where fluorescence was detected. Similarly, regions indicated by fluorescence may be used to limit the portion or window of the OCT image for which a tissue assessment method is performed. Reducing the portion of the tissue sample for which OCT imaging methods and tissue assessment methods are performed may provide even faster intraoperative results.

Referring now to FIGS. 15A to 15C, shown therein is an example of a B-scan image 600 of an OCT image at various stages of processing by an example embodiment of a tissue assessment method in accordance with the teachings herein. As used herein, the term "B-scan image" refers to a reconstructed 2-D image based on raw OCT data collected for a 2-D slice of a tissue sample during OCT imaging. As noted, in computed tomography, it is generally understood that a B-scan is a 2D slice through the sample and a C-scan is a typical 3D visualization of a volume of the sample. The terms "C-scan image", "A-scan image" and 3D-OCT image used herein can be interpreted in a likewise manner as the term "B-scan image" in terms of being reconstructed from raw OCT data.

In an OCT imaging system, the raw OCT data is typically collected as interferometric data. The interferometric data can be detected, for example, as the number-of-photons for a given frequency. The number of photons for each given frequency can be recorded as the intensity for that frequency. The raw OCT data therefore comprises frequency data that can be processed to obtain an OCT image that indicates the intensity of the light reflected by the tissue sample at a plurality of points. For example, the raw OCT data can be converted to OCT signal intensity data using a Fourier transform at each point in space. An OCT image that is generated from the OCT signal intensity data may be referred to as a "reconstructed OCT image".

Raw OCT data is collected and may be organized as a series of B-scans or 2-D scans or "slices" of a tissue sample. The slices of raw OCT data may be collected at various resolutions which determine the distance between adjacent B-scans of the tissue sample. For example, in some cases adjacent B-scans may be separated by distances in the tens or hundreds of micrometers.

In general, OCT image data may be 3D image data that comprises a plurality of B-scan image data. Accordingly, B-scan images represent a 2-D slice of the 3D OCT image. Each B-scan image comprises a plurality of reconstructed A-scans. Each reconstructed A-scan represents OCT signal intensity data as a function of depth at a particular slice in a B-scan image.

The OCT image data that corresponds to a reconstructed OCT image may be obtained directly from the raw OCT data that was acquired by the imaging system 10 during operation. In some embodiments, the OCT image data may comprise processed OCT image data which corresponds to the raw OCT data after undergoing image pre-processing such as noise reduction for example.

FIG. 15A shows an example of B-scan image 600 with borders 610 indicating regions of interest in the B-scan image 600. The borders 610 may be identified based on a variety of optical characteristics of the tissue sample shown in the OCT image. In this example, the borders 610 highlighted in FIG. 15A represent the outline of regions having high attenuation in the B-scan image 600.

Regions of high attenuation can be determined by applying various processing techniques to the OCT image data. For example, the attenuation at a point in a tissue sample may be determined by calculating the rate of decay of the OCT signal intensity data at a point in the tissue sample. In some embodiments, a reconstructed A-scan can represent the OCT signal intensity data as a function of depth in a tissue sample for a slice of a B-scan image. The rate of decay of the OCT signal intensity data may then be calculated from the reconstructed A-scan using suitable methods such as, but not limited to, linear regression analysis.

Similarly, other optical characteristics such as, but not limited to, fluctuations in the OCT signal intensity data may be indicative of regions of interest. Fluctuations in the OCT signal intensity data can represent a measure of the texture of a tissue sample shown in an OCT image. An example method for determining the attenuation and texture in an OCT image is discussed in more detail with regard to FIGS. 20A to 20F.

In some embodiments, the regions of interest may themselves be highlighted in an OCT image. The regions of interest can be highlighted by applying a mask to the OCT image. In some embodiments, the mask may be generated to correspond directly to the values of the optical characteristics that indicate the regions of interest. For example, a color mask can be used where the RGB value of the mask at a pixel in the OCT image is based on one or more optical characteristics of the OCT image at that point.

In some embodiments, a mask may be generated to indicate whether values of optical characteristics are above certain thresholds. For example, a region having attenuation above an attenuation threshold may have a mask applied to that region, whereas regions where the attenuation is not above the threshold would not have the mask applied.

FIG. 15B shows an example of the same B-scan image 600 with a boundary 620 identified therein. The boundary 620 distinguishes a first region 622 from a second region 624. Once the boundary 620 has been identified in the B-scan image 600, a tissue assessment method can analyze the regions on both sides of the boundary 620 to determine the degree of difference or differentiation between the regions. This degree of difference may then be used to determine if the boundary is actionable.

In some embodiments, boundary 620 may be identified automatically. Automatic boundary identification can be based on various optical characteristics of the OCT image data. For example, in some embodiments, boundaries may be identified using the borders of regions of interest. Alternatively, in some embodiments, the optical characteristics used to identify borders of the regions of interest may provide a coarse indication of a boundary. In some embodiments, additional optical characteristics can be used to improve the selectivity of the identification of a boundary in the OCT image.

In some embodiments, the optical characteristics used to provide a coarse indication of a boundary may be the attenuation of the OCT signal intensity data and the fluctuation of the OCT signal intensity data. In some embodiments, the additional optical characteristics may include, but are not limited to, area under the profile of the A-scan, number of signal maxima in the OCT signal intensity data, mean distance between signal maxima in the OCT signal intensity data, standard deviation of the peak distance in the OCT signal intensity data, mean frequency of the OCT signal intensity data, and standard deviation of the frequencies in the OCT signal intensity data, for example In some embodiments of a tissue assessment method, a user can manually identify the boundary in a reconstructed OCT image. However, highlighting regions of interest and the borders of regions of interest in a reconstructed OCT image may assist a user in selecting an appropriate boundary.

Highlighting regions of interest and the borders of regions of interest in a reconstructed OCT image may have useful applications in training users that are unfamiliar with interpreting OCT images. Highlighting regions of interest using a mask on the OCT image or by identifying the borders of the region of interest, may direct users to more easily identify boundaries between different types of tissues.

Highlighting various optical characteristics in a reconstructed OCT image may also assist a user in identifying the particular type of tissue or tissues that are present in a reconstructed OCT image. Different tissue types typically have different optical properties, and using those optical properties to generate a color mask may assist a user in more easily identifying the different tissue types.

FIG. 15C shows an example of a B-scan image 600 after undergoing analysis by an example embodiment of a tissue assessment method in accordance with the teachings herein. In FIG. 15C, the B-scan image 600 has a mask 630 displayed thereon to indicate a degree of difference between a first region 622 and a second region 624. The mask 630 is displayed on the B-scan image 600 over a window in each of the regions 622 and 624 corresponding to the boundary margin width 640.

In FIG. 15C, the mask 630 is shown using cross-hatching to identify the different regions 622 and 624. The difference in the cross-hatching of the mask 630 in the first region 622 and in the second region 624 indicates that a high degree of difference has been detected between these two regions. As legend 632 indicates, the mask 630 shown in FIG. 15C is indicative of an actionable boundary. A tissue assessment method, in accordance with the teachings herein, may generate the mask 630 by comparing at least one optical characteristic of the first region 622 and the second region 624 on either side of the boundary 620.

It will be understood that in alternative embodiments, other types of masks may be used for the mask 630, such as a color mask that uses different colors or a shading mask that uses different levels of shading to indicate that the two regions have a certain degree of difference.

The boundary margin width 640 can be identified by a tissue assessment method as the narrowest distance between the tissue surface position and the boundary 620. The tissue surface position represents the exterior surface of the excised tissue sample being imaged. Depending on the method of OCT scanning, the exterior surface of the excised tissue sample may be adjacent to gel, air, water, glass and the like, as is known be those skilled in the art. With respect to OCT images or wide-field OCT images, in some embodiments the maximum value in an A-scan may be used to locate the estimated tissue surface position.

In accordance with the teachings herein, in at least one embodiment, a tissue assessment method can also provide a discrimination score indicating the degree of difference between the first and second regions on either side of a boundary. In some embodiments, the discrimination score may indicate the degree of difference on a continuous or incremental scale from 0 to 1 with a score of 0 representing almost identical regions, and a score of 1 representing regions with no similarity. In some embodiments, the discrimination score can be a binary value indicating whether the degree of difference is greater or less than a predefined threshold.

The predefined threshold can be defined and optimized using clinical data from known datasets. Accordingly, the threshold may change for different clinical data such as for one or more of different types of patients, different types of tissues or different types of tumors. In some cases, the predefined threshold may be adjusted depending on the density of tissue expected in the excised tissue. For example, younger patients typically have denser tissue so the threshold may be adjusted depending on the age of the patient.

In some embodiments, the margin width may be displayed on the OCT image. Furthermore, in at least some embodiments, when the tissue assessment method indicates a high degree of difference between the two regions and the margin of the tissue is less than an acceptable width, an indication of an actionable boundary is presented to a user of the imaging system 10.

Referring now to FIG. 16, shown therein is a flowchart of an example embodiment of a tissue assessment method 650. The tissue assessment method 650 may be implemented by any suitable image processing system, such as the imaging system 10, for example.

At 652, OCT image data for an OCT image is received. In some embodiments, the OCT image can be a reconstructed 3-D OCT image or a reconstructed 2-D OCT image of a tissue sample that may be reconstructed using conventional techniques or using the various wide field OCT imaging techniques described herein.

The OCT image data can be used for various aspects of tissue assessment. For example, the OCT image data can be used to identify regions of interest in the OCT image, identify boundaries distinguishing two regions in the OCT image and to determine the degree of difference between the regions in the OCT image.

At 654, a boundary is identified in the OCT image to distinguish between a first region and a second region. Referring now to FIG. 17, shown therein is a flowchart of an example embodiment of a boundary identification method 670 for identifying a boundary in an OCT image. It should be understood that this is one example and there may be other techniques that may be used for boundary identification as is known by those skilled in the art.

At 672, values for at least one optical characteristic for a plurality of points in the OCT image are measured by using the OCT image data corresponding to the plurality of points in the OCT image. The optical characteristics may be any optical characteristic derived from the OCT image data such as, but not limited to the slope of the OCT signal intensity data, the standard deviation of the OCT signal intensity data, the area under the profile of the A-scan, the number of signal maxima in the OCT signal intensity data, the mean distance between signal maxima in the OCT signal intensity data, the standard deviation of the peak distance in the OCT signal intensity data, the mean frequency of the OCT signal intensity data, and the standard deviation of the frequencies in the OCT signal intensity data, for example.

At 674, the measured values for the optical characteristics at each point in the plurality of points of the OCT image are compared to threshold values. In some embodiments, the threshold values may be adjusted by a user to adjust the sensitivity for identifying regions of interest.

In some cases, an optical characteristic may be measured at all points in the OCT image. In some cases, the average value and the standard deviation of the measured optical characteristic for all points in the OCT image may be calculated. A region threshold may be determined based on the average value and the standard deviation of the measured optical characteristic. For example, the region threshold may comprise two threshold values to identify data having particular large or particularly small amplitudes. For example, the threshold values may be the mean plus three standard deviations and the mean minus three standard deviations. Alternatively, another multiplier can be used such as X times so the threshold is the mean plus or minus X times the standard deviation where X is a variable that can be tuned. In general, a user can adjust the threshold values to adjust the sensitivity of the identification of a region of interest. For example, the thresholds can be adjusted to highlight the largest and smallest amplitudes that make up 20% of the data. Alternatively, the thresholds can be adjusted to highlight the largest and smallest amplitudes that make up 15% of the data. Alternatively, the thresholds can be adjusted to highlight the largest and smallest amplitudes that make up 10% of the data.

The comparison of the measured values for the optical characteristics to the threshold values can be used to identify a region of interest in the OCT image. Depending on the threshold values, different regions of interest will be identified in the OCT image. For example, FIG. 18A shows an example of B-scan image 600. FIGS. 18B to 18D show different borders for regions of interest identified in the B-scan image 600 when the threshold values are adjusted.

The borders of regions of interest shown in FIGS. 18B to 18D represent the borders of regions based on the optical characteristic of attenuation in the B-scan image 600. FIG. 18B shows an image 690 indicating the borders 695 for the regions of interest in the B-scan image 600 when the threshold for attenuation is set to identify regions with relatively high attenuation. FIG. 18C shows an image 700 indicating the borders 705 for regions of interest in B-scan image 600 when the threshold for attenuation is set to identify regions with lower levels of attenuation than that shown in FIG. 18B. FIG. 18D shows an image 710 indicating the borders 715 for regions of interest in B-scan image 600 when the threshold for attenuation is set to identify even lower values of attenuation as regions of interest as compared to the levels of attenuation shown in FIG. 18C.

FIGS. 18E to 18G show the OCT image of FIG. 18A with different masks showing different regions based on various levels of attenuation. In particular, the regions of interest shown in FIGS. 18E to 18G have borders that correspond to the borders of regions of various attenuation levels as determined in FIGS. 18B to 18D, respectively. As can be seen, adjustment of the region threshold that is used allows more or less boundaries to be detected and a boundary between layers indicates a region of interest.

FIG. 18E shows an OCT image 692 with a mask 698 indicating regions of attenuation in the B-scan image 600 when the threshold for attenuation is set to identify regions with relatively high attenuation as was done in FIG. 18B. FIG. 18F shows an OCT image 702 with a mask 708 indicating regions of attenuation in the B-scan image 600 when the threshold for attenuation is set to identify regions with mid-levels of attenuation as was done in FIG. 18C. FIG. 18F shows an OCT image 712 with a mask 718 indicating regions of attenuation in the B-scan image 600 when the threshold for attenuation is set for low levels of attenuation as was done in FIG. 18D.

A user may adjust the threshold values for detecting regions of interest to obtain more meaningful information that may indicate a valid boundary between two different regions of tissue. The threshold values may, for example, be adjusted based on the type(s) of tissue that is expected to be present in the excised tissue sample. The threshold may be increased in cases where the excised tissue sample is very dense (e.g. a tissue sample with a lower fat content). The threshold may be decreased when the tissue sample is less dense (e.g. a tissue sample with higher fatty tissue content).

For example, in one embodiment, there are various preset settings that the user may choose from to highlight particular regions of interest. These preset settings may correspond to be low, medium or high sensitivity that the user may want to select for various reasons.

For example, a user can select the threshold values based on the expected density of the tissue sample. Generally, tumor tissue is expected to be denser than non-tumor tissue; however the density of non-tumor tissue can vary amongst patients. Typically, younger and lower-weight patients have higher density tissue, while older and heavier patients have lower density tissue. Thus, in some cases a user may adjust the threshold values based on at least one of a patient's age and weight.

At 676, a region of interest is generated based on the comparison performed at 674. For a 3D OCT image comprising a plurality of B-scan images, regions of interest can be generated in each particular B-scan image. In some cases, there could be many regions of interests or there could be no regions of interest that are determined. Regions of interest can be used to identify where there is a region of suspicion in a tissue sample. Further boundary analysis may be used to make an assessment of a boundary to identify a first and a second region. In some cases, regions of interest may also be generated based on regions of fluorescence in an OCT image.

The regions of interest for a particular B-scan are generated based on the OCT image data corresponding to that particular B-scan. A consistent region of interest for the entire 3D OCT image may be generated by comparing the regions of interest identified in each B-scan image in the plurality of B-scan images, an example of which is illustrated in FIGS. 19A to 19D. In particular, FIGS. 19A to 19D show the progression of the generation of a consistent border for the regions of interest for a plurality of B-scan images in which the border is relatively consistent across all B-scan images.

FIG. 19A shows an example set 720 of a plurality of B-scan images 725. FIG. 19B shows a multi-boundary image 730 that shows the borders 735 of the regions of interest for each of the plurality of B-scan images 725 in the set 720 of B-scan images of FIG. 19A. In this particular example, the borders 735 of the regions of interest shown in FIG. 19B correspond to the borders of regions that have relatively high attenuation and high fluctuation in each B-scan image 725. In other embodiments, various other additional or alternative optical characteristics may be used to detect regions of interest for the B-scan image 725.

In FIG. 19C, a set 740 of a plurality of flattened B-scan images 745 corresponding to the B-scan images 725 is shown. A given flattened B-scan image 745 can be obtained by using the profile of the tissue surface for the slice of tissue sample shown in the given B-scan. A flattened B-scan image generally comprises all the OCT image data corresponding to the regions in the B-scan that are below the tissue surface. Accordingly, in a flattened B-scan image, all of the OCT image data above the tissue surface may be discarded and the surface registered to the same "height". This means that if an X,Y,Z coordinate system is used, then the surface of the specimen is brought to the same "height" or "Y" value by shifting all of the data in the A-scan so that all of the surface points are aligned at the same height (this is the "flattening").

The flattened B-scan images 745 may provide depth information about the borders 735 of the regions of interest across the set 720 of B-scan images 725. The depth information can be used to identify the margin width at a plurality of points in the B-scan images. In other words, the boundary margin can be determined by measuring the distance between an identified boundary and the tissue surface along the length of the boundary in each B-scan image. The boundary margin width for a given B-scan image may be determined as the shortest distance between the identified boundary and the tissue surface along the length of the boundary in the given B-scan image. If there is more than one margin identified (i.e. more than one B-scan with a margin) then the global minimum of all of the identified margins may be used as the margin for the whole specimen.

FIG. 19D shows an image 750 of the borders 755 of the regions of interest after undergoing the flattening process. The borders 755 and 735 of the regions of interest that are consistent throughout the sets 720 and 740 of the B-scan images 725 and 745, respectively, may be identified. The consistency of the regions of interest can be determined if the boundaries of the regions of interest are within a certain range of pixels of one another. For example, the borders 755 and 735 of the regions of interest in adjacent B-scan images may be considered to be consistent if the variation of the borders of corresponding regions of interest in adjacent B-scan images are within a certain physical threshold of one another such as 100 micrometers, for example, which corresponds to +/−X pixels where X is an integer that depends on the physical hardware. Accordingly, the number of pixels that are used in the threshold depends on the imaging resolution.

The threshold to determine a consistent border of a region of interest across a plurality of B-scan images may also be selected based on the physical distance between adjacent B-scan images. For example if adjacent scans are further apart, the threshold value may be higher because more variance between adjacent scans would be expected. In one embodiment, a threshold value for a consistent border may be determined as a function of the distance between adjacent scans in the OCT image, such as, but not limited to, a fractional value of the distance between adjacent scans.

Any B-scan images that are found not to have a consistent border may be discarded. Once consistent borders of the regions of interest are identified, they can be highlighted in each corresponding B-scan image. FIG. 19E shows an example of a B-scan image 600 where the border 610 for the regions of interest has been considered as being consistent with respect to the border of adjacent B-scan images. FIG. 19F shows an example of an image 770 displaying the profile of the consistent border 610 of the regions of interest. The other borders that are shown are due to noise as while the selection of a consistent boundary helps to reduce the number of detected boundaries, some unintended boundaries may still be retained.

At 678, the region of interest is displayed on the OCT image. In some embodiments, the borders of the regions of interest can be displayed on the OCT image. In some embodiments, the regions of interest may themselves be highlighted in an OCT image. Regions of interest can be highlighted, for example, by applying a mask to the OCT image. Example embodiments of OCT images with a mask highlighting regions of interest can be seen in FIGS. 18E to 18G.

A user may assess one B-scan at a time. Therefore, the different boundaries that are found to be consistent are retained and used with their corresponding B-scan image. The user may also pan through a series of B-scan images but the analysis is usually done on a B-scan-by-B-scan basis.

The boundary identification method 670 is considered to generally operate on a window of an OCT image. In the example just given, the window of the OCT image may comprise a series of B-scan images (as was just described above) or portions of one or more B-scan images. However, in each case the B-scan images (full or partial) comprise a collection of A-scans. For example, the window of the OCT image may comprise a series of A-scans from one B-scan image or multiple B-scan images for different scan paths, which may be linear or non-linear. The window can also be a different group of A-scans in a regular or irregular volume. In some cases, the window of the OCT image may be determined based on fluorescence emitted by a tissue sample. It should be understood that the boundary identification method 670 may operate on all of these different collections of A-scans.

At 680, a boundary in a given OCT image may be identified based on the region of interest generated at 676. In some embodiments, the identification of the boundary at 680 may occur automatically. To identify a boundary automatically, the boundary identification method 670 may measure the optical characteristics of a plurality of points in the regions of interest of the OCT image. Any suitable method may be used to detect the boundary, such as, but not limited to edge detection methods such as the Canny, Sobel and Prewitt edge detection methods. Other methods may also be used which use the measured optical characteristics.

In some alternative embodiments, the boundary identification at 680 may be based on an input that is received from a user indicating a boundary in the OCT image after the user views the identified regions of interest in an OCT image. In some embodiments, the user may indicate a boundary on the OCT image using a suitable input device. For example, if the OCT image is displayed on a touchscreen display, a user could identify the boundary using a stylus to draw the boundary based on the region of interest. A user could also use another suitable input device to indicate a boundary in the OCT image such as, but not limited to, a mouse, for example.

In some embodiments, a user may be able to identify a boundary without the generation of a region of interest. For example, a user experienced in analyzing OCT images may be able to detect a boundary in the OCT image without a highlighted region of interest but rather, by relying on certain visual features shown in the OCT image and the user's experience. In such a case, the user could indicate the boundary on the OCT image in any suitable manner, as discussed above.

Referring once more to FIG. 16, once a boundary along with corresponding first and second regions on either side thereof have been identified in the OCT image, the tissue assessment method 650 may proceed to analyze the first region and the second region. For a volume (e.g. a set of B-scans or a set of A-scans), the boundary can be defined by setting binary ones (for boundary points) and zeros (for non-boundary points) for each spatial point in the volume.

At 656, a first set of OCT image data is identified that corresponds to the first region in the OCT image. The OCT image data corresponding to the first region in the OCT image may comprise the portion of OCT image data from each portion of the A-scans that correspond to the first region in the OCT image for a 2D OCT image. For a 3D OCT image, the portions of the A-scans that correspond to the first region for each of the B-scans that make up the 3D OCT image may be used as the image data corresponding to the first region.

At 658, a second set of OCT image data is identified that corresponds to the second region in the OCT image. The OCT image data corresponding to the second region in the OCT image may comprise the portion of data representing the second region from each portion of the A-scans that correspond to the second region in the OCT image. In some cases, a standard window size can be used to determine the portion of the OCT image data from each of the first and second regions that will form the first and second sets of OCT image data. In some cases, where there is limited tissue above the boundary in the B-scan image, the first and second sets of OCT image data will comprise only that portion of the OCT image data corresponding to a window of the first and second region from the boundary with the same width as the boundary margin. The window size may be on the order of several hundreds of micrometers and the window size may be optimized based on a set of clinical data.

At 660, a first optical dataset is generated for the first set of OCT image data identified at 656. In some embodiments, the generation of the first optical dataset involves measuring at least one optical characteristic in the first set of OCT image data, which involves performing calculations on the first set of OCT image data identified at 656 to determine the at least one optical characteristic. For example, attenuation may be used as an optical characteristic. However, more accurate results may be achieved by using more than one optical characteristic such as, but not limited to, attenuation and fluctuation, for example.

Other examples of the at least one optical characteristic can include one or more of: area under the profile of an A-scan in the OCT signal intensity data, number of signal maxima in the OCT signal intensity data, mean distance between signal maxima in the OCT signal intensity data, standard deviation of the peak distance in the OCT signal intensity data, mean frequency of the OCT signal intensity data, standard deviation of frequencies in the OCT signal intensity data as well as various other optical properties of the OCT image.

At 662, a second optical dataset is generated based on the second set of OCT image data identified at 658. The generation of the second optical dataset can be performed in the same manner as described above with respect to the first optical dataset. The generation of the second optical dataset is performed so that the first optical dataset and second optical dataset comprise data representing the same optical characteristics for the first region and second regions respectively.

In an example embodiment, the tissue assessment method 650 can measure the optical properties of attenuation and fluctuation of the OCT signal intensity for each A-scan in the first and second regions of the OCT image data for a B-scan image. This may be extended to OCT image data for a C-scan image by considering each A-scan in the first and second regions of the OCT image data for all B-scans of the C-scan image. This may be extended to OCT image data for other volumes depending on the scan path that is used as previously described.

The attenuation of the OCT signal intensity data may be measured by using various techniques such as, but not limited to, a linear fit over a window in the A-scan signal intensity data, for example.

In some embodiments (not shown), the tissue assessment method 650 may also be used to detect the boundary margin which is the distance from the identified boundary to the surface. In some cases, the tissue assessment method may analyze each of the flattened B-scan images shown in FIG. 19C after a consistent boundary has been identified. The consistent boundary used for each flattened B-scan image will be the boundary in the flattened B-scan image that was found to be consistent with the boundaries in the adjacent flattened B-scan images to within an acceptable threshold as previously described. In some cases, the shortest distance between the consistent boundary and the tissue surface across the set of flattened B-scan images may be used as the boundary margin.

In another embodiment, a tissue assessment method may identify the shortest distance between the consistent boundary and the tissue surface across a set of non-flattened B-scan images to determine the boundary margin.

In another alternative embodiment, a tissue assessment method can further identify the average depth of the boundary margin for a single B-scan image or a set of B-scan images.

In some alternative embodiments, a tissue assessment method may compare the second region in a 2D or 3D OCT image to a known OCT image stored in a database which may allow the tissue assessment method 650 to identify the tissue type in the first, second or subsequent regions of the OCT image. For example, the database may store ideal cases of OCT image data known to correspond to various tissue types such as, but not limited to, adipose tissue, connective tissue, and tumor tissue, for example, and the given region of the OCT image may be found to be similar to one of these tissue types. In this case, the second region is defined herein as being the region under and the identified boundary which is being assessed to determine if it matches a particular type of tissue.

In some alternative embodiments, a tissue assessment method may determine that the boundary margin width is less than a margin threshold. This may indicate that the distance between the boundary and the tissue surface is too small to obtain meaningful information from the OCT image data for the first region. The first region is defined herein as being the region between the surface of the tissue and the identified boundary. In such a case, the OCT image data corresponding to the second region can be compared to known OCT image data corresponding to a stored OCT image. The second optical dataset generated for the second region would be compared with a known optical dataset based on measurements of the same one or more optical characteristics for a known set of OCT image data corresponding to a known region in the stored OCT image. This may assist a surgeon in determining if the tissue in the second region is cancerous. The second region is defined herein as being the region under the identified boundary.

In some alternative embodiments, a tissue assessment method may also detect a subsequent boundary in a 2D or 3D OCT image of a tissue specimen. A subsequent boundary can distinguish between the second region and a third region. In some cases, when a subsequent boundary is detected, the second region can be narrower than the first region. In such a case, the window may be determined to be the width of the second region at its narrowest point. Identification of a subsequent boundary is performed in the same manner as described above with regard to identification of a boundary distinguishing a first region and a second region.

Referring now to FIG. 20A, show therein is a flattened window of a B-scan image 600 using a window size that corresponds to the boundary margin width 640 where boundary 620 was identified. There is a window of data in both the first region 622 and the second region 624. If there is not much tissue above the boundary, then a smaller size may be used for the window for the first region 622. In some embodiments, the tissue assessment method 650 will analyze the first region 622 and the second region 624 for only that portion of the B-scan image where a consistent boundary was identified. A boundary is "accepted" for that portion of a B-scan image for which a consistent boundary was identified across adjacent B-scan images in a set of B-scan images. FIG. 20A also indicates identifiers for the first optical dataset 872 (the identifier is a circle) and the second optical dataset 874 (the identifier is an X).

FIG. 20B shows an example of an OCT signal intensity plot 790 of the signal intensity data obtained for an A-scan of the B-scan image 600. The A-scan represents an A-scan profile in the A-scan direction 876 for the flattened window of the B-scan image 600 shown in FIG. 20A. The boundary 620 is shown in the OCT signal intensity plot as well as the portions of the plot that correspond to the first region 622 and the second region 624.

FIG. 20C shows an example OCT signal intensity plot 800 for the portion of OCT signal intensity plot 790 corresponding to the window of the first region 622. A linear fit 805 was determined for the OCT signal intensity data in the OCT signal intensity plot 800. In some embodiments, the linear fit 805 can be determined using a linear regression analysis.

FIG. 20E shows an example OCT signal intensity plot 830 for the portion of the OCT signal intensity plot 790 corresponding to the window of the second region 624. A linear fit 835 was determined for the OCT signal intensity data in OCT signal intensity plot 830.

As can be seen from a comparison of FIG. 20C and FIG. 20E, the slope of the linear fit of the OCT signal intensity data may differ depending on the tissue region. For example, significant differences in signal attenuation between two regions may indicate different tissue types.

In some cases, the attenuation of the OCT signal intensity data can be determined from the low frequency component of the OCT signal intensity data alone. The low frequency component of the OCT signal intensity data can be isolated using any suitable signal processing technique such as, but not limited to, a low pass filter, a Gaussian filter and the like.

A Gaussian filter can also be used to normalize the OCT signal intensity plot 800. FIG. 20D shows a normalized OCT signal plot 820 corresponding to a normalization of OCT signal intensity plot 800 using a Gaussian filter. The low frequency data component identified using the Gaussian filter can be subtracted from the data shown in the OCT signal intensity plot 800 to generate a normalized OCT signal plot 820.

Similarly FIG. 20F shows a normalized OCT signal plot 860 corresponding to a normalization of the OCT signal intensity plot 830 for the second region using a Gaussian filter.

In some embodiments, the standard deviation of the normalized OCT signal plot is measured over a window from the boundary for each region. In FIG. 20D, the standard deviation 822 has been calculated for normalized OCT signal plot 820. Similarly, FIG. 20F shows the standard deviation 862 calculated for normalized OCT signal plot 860. The standard deviation of the normalized OCT signal plot is a measurement of signal variation (i.e. fluctuation of OCT signal intensity) through a region of interest for the tissue sample that provides an indication of the texture of the region of interest for the OCT image.

In some embodiments, both the attenuation and the texture of the OCT signal intensity data can be used as measured values for two optical characteristics o1 and o2 for the portion of each A-scan in the window in the first region and for the portion of each A-scan in the window in the second region and can be represented in the format (o11, o21) for the portion of the A-scan in the first region and (o12, o22) for the portion of the A-scan in the second region. In this example, the first index represents the optical measurement being made and the second index represents the region in which the measurement is made. For example, o11 is a measure of the first optical characteristic in the first region. A dataset can be generated based on these values for the first region and the second region by measuring these values for each portion of each A-scan in the first and second regions.

FIG. 20G shows an example of a scatter plot of measured optical data in which one measured optical characteristic (e.g. texture) is plotted along the y axis and a second measured optical characteristic (e.g. attenuation) is plotted along the x axis. The data from each portion of the A-scans provides a data point with x and y coordinates (e.g. (o11, o21) or (o21, o22)) that can be plotted on the scatter plot. Accordingly, the dataset plot 870 shows a plot of attenuation versus texture for the first optical dataset 872 and the second optical dataset 874. In some embodiments, different and further optical characteristics may also be used. Thus, a dataset can be generated for each region having a dimension depending on the number of measured optical characteristics and the data points can be plotted on a corresponding multi-dimensional scatter plot.

At 664, the first optical dataset and the second optical dataset are compared to identify a degree of difference between the first region and the second region. In some embodiments, the tissue assessment method 650 may calculate a discrimination score based on the comparison of the first optical dataset with the second optical dataset. A degree of difference between the first region and the second region can be identified based on the discrimination score. In some embodiments, the tissue assessment method 650 can use an optimization method or suitable machine learning method to calculate the discrimination score such as, but not limited to, a support vector machine method, a k-nearest neighbors method, a decision tree learning method, a random forest method, a native Bayes method and a quadratic decision boundary method, for example. In embodiments using a support vector machine, any suitable type of support vector machine can be used such as, but not limited to, a linear support vector machine and a radial bias function support vector machine.

Furthermore, it should be noted that the support vector machine method, as well as the other methods, is scalable to more or less dimensions where each dimension corresponds to a measurement of a different optical characteristic. By adding another optical characteristic so that there are three optical characteristics, the differentiation can be performed in more dimensions (i.e. three axes rather than two axes), or it can be performed in 1D (on a line, to find the optimal separation if only one optical measurement is used. However, it should be noted that with the different number of optical characteristics, there is a change in the threshold for what is defined as being "actionable". For example, the more optical characteristics (which can be considered to be variables for the optimization methods) that are used to make a differentiation, the easier it is to separate the variables. For example, if only one optical characteristic is used it may be difficult to get over 60% differentiation (in 1D separation). But if 3 or 4 different optical characteristics are used (i.e. in 3D or 4D), it is typically easier to get over 90 or 95% differentiation for the same area, provided that these areas are in fact different from one another. The thresholds used for differentiation are determined depending on the number of optical characteristics that are used.

As can be seen from FIG. 20G, the datasets corresponding to the two regions in the OCT image appear to have different optical characteristics. Regions with different optical characteristics may be indicative of an actionable boundary. Act 664 of the tissue assessment method 650 provides a discrimination score representing the maximum differentiability between the first and second optical datasets. Since the discrimination score represents the degree of difference between two regions, the discrimination score may be used to quantify the amount that the two regions differ from one another.

FIG. 21A shows an example scatter plot 880 where a linear support vector machine is used to determine a discrimination score 882 for the first optical dataset 872 and the second optical dataset 874. In the example shown in FIG. 21A, the two regions were determined to have a discrimination score of 0.92. In this case, the closer the value of the discrimination score is to 1, the higher the degree of differentiation between the first and second optical datasets meaning that the first and regions are more likely to be different from one another.

FIG. 21B shows an example scatter plot 880 where a support vector machine with a radial bias function is used to calculate a discrimination score 892 for the first optical dataset 872 and the second optical dataset 874. In the example shown in FIG. 21B, the two regions were determined to have a differentiation score of 0.94 indicating that there is a high degree of differentiation between the first and second optical datasets.

The degree of difference, provided by the discrimination score, may be used to identify when a boundary may be considered to be actionable by a surgeon. A high degree of difference may suggest that the two regions are different tissue types. Based on the degree of difference determined by the tissue assessment method 650, a surgeon may be able to decide whether further tissue must be excised intraoperatively. As described, in at least some embodiments, the tissue assessment method may also indicate the width of the margin for all points in the OCT image, which may further assist a surgeon in determining whether the boundary is actionable (i.e. if the width of the margin is less than a desired amount when the boundary is determined to be actionable).

FIGS. 22A to 22F show an example of output results from the tissue assessment method 650 for a tissue sample in which a non-actionable boundary is detected. The OCT images shown in FIGS. 22A to 22F correspond to the various acts of the tissue assessment method 650.

FIG. 22A shows a B-scan image 900 after a boundary 906 has been identified. The boundary 906 distinguishes a first region 902 from a second region 904.

FIG. 226 shows two windows of flattened B-scan image 920 for the region over which boundary 906 was accepted. The flattened B-scan image 920 is generated based on the identification of the surface of the tissue shown in the B-scan image 900. As can be seen from FIG. 22B, the window 926 over which each of the first and second regions is analyzed is the same.

FIG. 22C shows a scatter plot 930 of the measured optical characteristics for the two regions identified in FIG. 22B. The scatter plot 930 shows the optical datasets generated for the first region 922 and the second region 924 respectively. It seems that the measured optical characteristics of the two regions shown in FIG. 22C appear to be more similar to one another than the measured optical characteristics of the two regions plotted in FIG. 20G.

FIGS. 22D to 22E show the results of different optimization methods applied to the first and second datasets for the regions of interest shown in FIG. 22C. In FIG. 22D, a linear support vector machine method was used and in FIG. 22E a radial bias function support vector machine method was used. The linear support vector machine method output 940 of FIG. 22D determined a discrimination score 942 for the two regions of 0.75. The radial bias function support vector machine method output 950 shown in FIG. 22E determined a discrimination score 952 for the two regions of 0.76.

It is apparent that the outputs of the optimization methods used for the first and second regions in FIG. 22 indicate that these regions are more similar to one another than the two regions of tissue analyzed in FIG. 21. Since the optimization method indicated a lower degree of differentiability between the two regions, this suggests that an actionable boundary is not present in the tissue sample shown in a B-scan image 900.

FIG. 22F shows the B-scan image 900 with a mask 960 overlaid indicating the results of the tissue assessment method 650. The continuous hatching in mask 960 the first region and the second region indicates that there is not a high degree of difference between the first and second regions on either side of the boundary 906.

The tissue assessment method 650 may be modified to include other optical characteristics such as, area under the profile of an A-scan in the OCT signal intensity data, the number of signal maxima in the OCT signal intensity data, the mean distance between signal maxima in the OCT signal intensity data, the standard deviation of the peak distance in the OCT signal intensity data, the mean frequency of the OCT signal intensity data, the standard deviation of the frequencies in the OCT signal intensity data and various other optical properties of the OCT image. Different optical characteristics may be used in the tissue assessment method 650 since breast lumpectomy specimens have unique optical properties compared to other tissue samples such as blood vessel structures or retinal structures.

In some embodiments, the tissue assessment method 650 can be modified to identify a boundary in each B-scan image of the OCT image. For example, in these alternative embodiments, for each B-scan image, the modified tissue assessment method can identify a first and second set of OCT image data corresponding to the first and second regions of interest respectively in a B-scan image. The modified tissue assessment method can then generate first and second B-scan optical datasets for each B-scan image in the same manner as was described above. The tissue assessment method can then compare the first and second B-scan optical datasets for each B-scan image to determine the degree of difference between two regions in each B-scan.

In some embodiments, the tissue assessment method 650 may further be modified to determine the discrimination score for each B-scan image in a plurality of B-scan images. In some embodiments, the modified tissue assessment method can determine the degree of difference between the two regions in the 3D OCT image based on the average discrimination score for the plurality B-scan images that make up the 3D OCT image. In some embodiments, the data in the first and second B-scan optical datasets for all B-scan images may be compiled into first and second optical datasets for the OCT image. The first and second optical datasets can then be compared to determine the degree of difference between the first and second region for the OCT image.

In some embodiments, one of the first and second regions that are used in the tissue assessment method 650 may be from an identified image from a data store that has been previously been identified as being a particular type of tissue. The method would operate in a similar fashion since a boundary would still need to be detected but optical characteristics for the identified image would likely already have been measured and stored in the data store and the measured data can be accessed instead of re-determined for the identified image.

While OCT is an established medical imaging technique, it is also applicable and being increasingly used in industrial applications. Some of these industrial applications may include non-destructive testing (finding manufacturing defects, for example), welding quality assurance, material thickness measurements (for silicon wafers, for example), for industrial painting (e.g. verifying uniform thickness) and surface roughness characterization.

It should be noted that in alternative embodiments, the wide field OCT imaging methods described herein may be used for industrial applications, such as one or more of the aforementioned industrial applications, in terms of obtaining images of a greater portion of an object's surface and underlying layers that would otherwise not be possible based on the field of view of a conventional OCT imaging system.

It should also be noted that in alternative embodiments, the tissue assessment method may be used for industrial applications, such as one or more of the aforementioned industrial applications, in terms of determining whether two regions near an object's surface are different from one another or different in comparison to a region of a known material for the object. In these cases, the tissue assessment method can be referred to as an assessment method or a region assessment method.

The various embodiments of the tissue assessment method described herein may be implemented by the imaging system 10 including the associated hardware and software components shown in FIG. 5. However, more generally, the various embodiments of the tissue assessment methods described herein may be implemented using a combination of hardware and software. These embodiments may be implemented in part using computer programs executing on a programmable device that includes at least one processor, an operating system, one or more data stores (including volatile memory or non-volatile memory or other data storage elements or a combination thereof), at least one communication interface and/or user interface as well as any other associated hardware and software that is necessary to implement the functionality of the various embodiments described herein. For example, and without limitation, the computing device may be a server, a network appliance, an embedded device, a computer expansion module, a personal computer, a laptop, a personal data assistant, a smart-phone device, a tablet computer, a wireless device or any other computing device capable of being configured to carry out the tissue assessment methods described herein.

In some embodiments, the communication interface may be a network communication interface, a USB connection or another suitable connection as is known by those skilled in the art. In other embodiments, the communication interface may be a software communication interface, such as those for inter-process communication (IPC). In still other embodiments, there may be a combination of communication interfaces implemented as hardware, software, and a combination thereof.

In at least some of the embodiments described herein, program code may be applied to input data to perform at least some of the functions described herein and to generate output information. The output information may be applied to one or more output devices, for display or for further processing.

At least some of the embodiments described herein that use programs may be implemented in a high level procedural or object oriented programming and/or scripting language or both. Accordingly, the program code may be written in C, Java, SQL or any other suitable programming language and may comprise modules or classes, as is known to those skilled in object oriented programming. However, other programs may be implemented in assembly, machine language or firmware as needed. In either case, the language may be a compiled or interpreted language.

The computer programs may be stored on a storage media (e.g. a computer readable medium such as, but not limited to, ROM, magnetic disk, optical disc) or a device that is readable by a general or special purpose computing device. The program code, when read by the computing device, configures the computing device to operate in a new, specific and predefined manner in order to perform at least one of the methods described herein.

Furthermore, some of the programs associated with the various methods described herein are capable of being distributed in a computer program product comprising a computer readable medium that bears computer usable instructions for one or more processors. The medium may be provided in various forms, including non-transitory forms such as, but not limited to, one or more diskettes, compact disks, tapes, chips, and magnetic and electronic storage. In alternative embodiments the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

FIG. 23A shows a perspective view of an example embodiment of a sample container 1000 for containing a sample, such as a tissue sample or specimen. The container 1000 can be used for a variety of purposes including loading the sample into the imaging system 10, securing the sample during various types of imaging and scanning such as, but not limited to OCT scanning, for example, and transporting the sample through the clinical process.

The container 1000 may be used to provide a systematic means of communicating tissue sample orientation information relative to a reference point, such as on a patient's body for example, by using certain markers such as, but not limited to, radio opaque tags and imaging marking beads, for example. The container 1000 may also be used to prevent sample mix-up and enforce a single-usage policy through the use of mechanical tabs and/or RFID tags, for example. The container 1000, or a variant thereof, may also include a peel-off mechanism to expose a sterile portion of the container 1000 that interfaces with a tissue handling system of the imaging system 10. For example, a portion of the container 1000 may be initially covered by a material so that there is no direct contact between the operator and that portion of the container 1000 during the loading and assembly of the container 1000. The protected portion may then be exposed by peeling the protective material off of the container 1000 prior to loading the container into the imaging system 10. This may prevent blood or other fluids on the operator's gloves from being transferred into the scanning region of the imaging system 10. Furthermore, the container 1000, or a variant embodiment thereof, may provide a means of trimming a guide wire prior to scanning. This may be realized by a detachable wire cutter mechanism resembling a nail trimmer that is packaged as an integral part of the container 1000.

Some current methods for maintaining orientation information of tissue samples that are extracted from a human body, or other object, involve the application of coloring agents to the tissue sample to mark orientation, or the application of sutures to the tissue sample which act as fiducials. However, such methods rely upon a systematic application of these orientation cues by the surgeons. A failure to follow the orientation marking protocol results in the loss of the orientation information when the tissue specimen reaches various clinical members for detailed analysis of the tissue specimen. Amongst other reasons, this information is vital because the pathologist has to communicate the location of surfaces with suspicious margins back to the surgeon so that the surgeon can extract an additional amount of tissue from these specific regions if needed.

The container 1000, and variants thereof, may provide safe and consistent handling of a tissue sample when attempting to image its entire surface. For example, the container 1000 permits safe inversion of a contained tissue sample so that opposing surfaces can be imaged (or scanned). As another example, the container 1000 may include orientation cues (or fiducials) that may permit consistent handling of the contained tissue sample by preserving the orientation of the contained tissue sample. In some embodiments, the contained tissue sample may be uniquely associated with particular patient information through the use of bar-codes and/or RFID tags applied to the container 1000. This may provide a unique association between the patient information and the tissue sample that may reduce the mix-up of patient samples. In some example embodiments, the RFID tag or mechanical tabs can be further used to enforce single use of the container 1000 so that the potential for cross-contamination of tissue samples is minimized. Finally, the container 1000 may include an integrated trimmer tool that may be used to cut the guide wire, which is typically placed in a suspect region of the tissue sample as a pre-operative procedure, prior to imaging the tissue sample.

The container 1000 is shown including a top sample support 1002, an interface sleeve 1004 and a bottom sample support 1006. FIG. 23B shows a perspective view of the bottom sample support 1006 and a tissue sample 1008. As shown, the bottom sample support 1006 may be used as a platform to support the tissue sample 1008. FIG. 23C shows a cross-sectional view taken along line 23C-23C in FIG. 23B. In the example shown, the bottom sample support 1006 includes a base 1014, and side walls 1016 that depend therefrom.

As shown, an optional foam layer 1012 overlies the base 1014 between the side walls 1016 of the bottom sample support 1006 to define an upper surface 1010 for supporting the tissue sample 1008. In some cases, the foam layer 1012 may reduce the deformation of the tissue sample 1008 that is supported by the bottom sample support 1006. For example, the foam layer 1012 may compress beneath the tissue sample 1008 to at least partially conform to the shape of the tissue sample 1008. Still, in alternative embodiments, the bottom sample support 1006 does not include the foam layer 1012. In one example embodiment, the tissue sample 1008 may be directly supported by an upper surface 1011 of the base 1014.

In some examples, the base 1014 may be made from a rigid material (e.g. rigid plastic or metal). Alternatively, the base 1014 may be made from a compliant material (e.g. fabric, film, mesh, or foam). For example, the base 1014 may be suspended in tension between the side wall(s) 1016. In some cases, the base 1014 may be made of compliant material to reduce the deformation of the tissue sample 1008 that is supported by the bottom sample support 1006. For example, when the base 1014 is made of compliant material the base 1014 may stretch, compress, or otherwise deform to at least partially conform to the shape of the tissue sample 1008 supported thereon.

The bottom sample support 1006 as exemplified includes orientation markers 1018 for orienting the tissue sample 1008. In use, the surgical team may place an excised tissue sample 1008 onto the bottom sample support 1006 such that the orientation markers 1018 accurately correspond with the orientation of the tissue sample 1008 prior to excision in the patient's body. This may improve clinical workflow by maintaining and communicating the orientation of the tissue sample 1008 from the Operating Room (OR) to the pathology department. In turn, this may permit a margin analysis of the excised tissue sample 1008 by the pathology department to more accurately identify the location of additional tissue to be excised from the patient's body in the OR. Still, in alternative embodiments, the bottom sample support 1006 may not include the orientation markers 1018 but includes other orientation markers.

FIG. 23D shows a perspective view of the top sample support 1002. The top sample support 1002 may be used to support a tissue sample 1008. FIG. 23E shows a cross-sectional view taken along line 23E-23E in FIG. 23D, with the top sample support 1002 positioned above the tissue sample 1008 and additionally including an optional foam layer 1022. In the example shown, the top sample support 1002 includes a base 1020, and side wall(s) 1025 that depend therefrom.

FIG. 23E shows an embodiment of the top sample support 1002 including an optional foam layer 1022 that overlies the base 1020 between the side walls 1025 to define a lower surface 1024 for supporting the tissue sample 1008 when the container 1000 is inverted. In some cases, the foam layer 1022 may reduce the deformation of a tissue sample 1008 that is supported by the top sample support 1002. For example, the foam layer 1022 may compress to at least partially conform to the shape of the tissue sample 1008.

FIG. 23D shows an alternative embodiment of a top sample support 1002 that does not include the foam layer 1022. In the example shown, the base 1020 includes a lower surface 1024 that makes direct contact with a supported tissue sample 1008. In some examples, the base 1020 may be made from a rigid material (e.g. rigid plastic or metal). Alternatively, the base 1020 may be made from a compliant material (e.g. fabric, film, mesh, or foam). For example, the base 1020 may be suspended in tension between the side wall(s) 1025. In some cases, when the base 1020 is made of compliant material it may reduce the deformation of a tissue sample 1008 that is supported by the top sample support 1002. For example, when the base 1020 is made of compliant material it may stretch, compress, or otherwise deform to at least partially conform to the shape of the tissue sample 1008 supported there against.

FIGS. 23F and 23G show front and rear perspective views of an interface sleeve 1004, in accordance with at least one embodiment. In the example shown, the interface sleeve 1004 includes side wall(s) 1026 that extend between an open lower end 1028 and an open upper end 1030 of the interface sleeve 1004. As shown, the side wall(s) 1026 define an interior volume 1032 for receiving a tissue sample 1008. Optionally, a label 1034 or other identifying object, such as an RFID tag (not shown), for example, can be placed on an interface sleeve 1004 (e.g. on an exterior surface of the side wall(s) 1026). This may permit the container 1000 to provide information such as patient information, physician information, tissue sample information, and container usage information.

In some examples, an interface sleeve 1004 is substantially transparent to one or more imaging techniques. Some examples of imaging techniques include, without limitation, photography, radiography, magnetic resonance imaging (MRI), ultrasound, computed tomography (CT), and x-ray. This may permit the tissue sample 1008 to be imaged through the interface sleeve 1004 while being contained within the container 1000. In some examples, the interface sleeve 1004 may be transparent to light in the visible spectrum, which may permit imaging of a contained tissue sample 1008 by conventional photography and visual inspection by a medical practitioner. Alternatively or additionally, the interface sleeve 1004 may be radiographically transparent, which may permit imaging of a contained tissue sample 1008 by radiation-based imaging techniques (e.g. x-ray imaging). Still, in alternative embodiments, the interface sleeve 1004 may be substantially opaque to one or more imaging techniques. In these cases, imaging of the tissue sample 1008 contained within the container 1000 by certain imaging techniques may require the interface sleeve 1004 to be removed.

The interface sleeve 1004 as exemplified includes orientation markers 1036 distributed about the circumference of the interface sleeve 1004. The orientation markers 1036 may be included in addition to or as an alternative to the orientation markers 1018 on the bottom sample support 1006. In some examples, the orientation markers 1036 are at least partially opaque to one or more imaging techniques. This may permit an orientation marker 1036 to be automatically rendered in images produced by these one or more imaging techniques, thereby labeling the orientation on the rendered images. Still, in alternative embodiments, the interface sleeve 1004 does not include the orientation markers 1036.

Referring now to FIGS. 24A to 24F, shown therein are illustrations of how a tissue sample 1008 is placed in the container 1000 and the container 1000 is closed. FIG. 24A shows a tissue sample 1008 placed on the bottom sample support 1006. In some cases, the orientation of the tissue sample 1008 can be aligned with the orientation markers 1018 on the side walls 1016 of the bottom sample support 1006.

FIG. 24B shows the top sample support 1002 and the bottom sample support 1006 inserted into the interface sleeve 1004. FIG. 24C shows a cross-sectional view taken along line 24C-24C in FIG. 24B. As shown, the side walls 1016 and 1025 of the bottom sample support 1006 and the top sample support 1002 respectively, are sized to be received inside the interior volume 1032 between the side walls 1026 of the interface sleeve 1004. The side walls 1016, 1025, and 1026 as shown are cylindrical, and the outside diameter of side walls 1016 and 1025 is less than the inside diameter of side walls 1026. This may permit at least the portions of the top sample support 1002 and the bottom sample support 1006 defined by side walls 1016 and 1025 to slide inside of the interface sleeve 1004. In alternative embodiments, the side walls 1016, 1025, and 1026 have a different shape, such as cuboid for example.

In the example shown, the bottom sample support 1006 is releasably engageable with the interface sleeve 1004 for selectively closing the lower end 1028 of the interface sleeve 1004. In some embodiments, the bottom sample support 1006 and the interface sleeve 1004 may include one or more mating retentive members for releasably engaging the bottom sample support 1006 to the interface sleeve 1004. As shown, the bottom sample support 1006 includes a plurality of locking pins 1038 that extend radially outwardly from the side walls 1016. Further, the inner surface of the side walls 1026 of the interface sleeve 1004 is shown including a plurality of lower guide channels 1040 that extend from the lower end 1028 toward the upper end 1030. Each lower guide channel 1040 is sized to receive a locking pin 1038. A lower locking slot 1042 is shown extending tangentially from each lower guide channel 1040.

In use, the bottom sample support 1006 can be positioned below the lower end 1028 of the interface sleeve 1004 and rotated to align each locking pin 1038 with a lower guide channel 1040. The bottom sample support 1006 may then slide into the interface sleeve 1004 with each locking pin 1038 traveling inside a corresponding lower guide channel 1040. When each locking pin 1038 is positioned at an entry to a lower locking slot 1042, the bottom sample support 1006 can be rotated to move each locking pin 1038 into the corresponding lower locking slot 1042 thereby releasably engaging the bottom sample support 1006 with the interface sleeve 1004 and closing the lower end 1028. Together, each locking pin 1038 and lower locking slot 1042 may form a bayonette-style locking mechanism whereby each lower locking slot 1042 provides resistance to entry and exit of a locking pin 1038. This resistance can be overcome by an application of sufficient force.

Optionally, the bottom sample support 1006 includes a flange 1044 sized to prevent further insertion of the bottom sample support 1006 inside of the interface sleeve 1004. As shown, the flange 1044 extends radially outwardly from the side walls 1016 and has a diameter that is larger than the inside diameter of the side walls 1026 of the interface sleeve 1004. This may prevent the bottom sample support 1006 from becoming entirely received inside the interior volume 1032 of the interface sleeve 1004. In some cases, the flange 1044 provides a gripping surface for the hands of a user or the elements of a machine to grasp the bottom sample support 1006 (e.g. when engaging or disengaging the bottom sample support 1006 and the interface sleeve 1004). Still, in alternative embodiments, the bottom sample support 1006 may not include a flange 1044.

In the example shown, the top sample support 1002 is releasably engageable with the interface sleeve 1004 at a plurality of longitudinal positions between the upper end 1030 and the lower end 1028. In some embodiments, the top sample support 1002 and the interface sleeve 1004 include one or more mating retentive members for releasably engaging the top sample support 1002 to the interface sleeve 1004. As shown, the top sample support 1002 includes a plurality of locking pins 1046 that extend radially outwardly from side walls 1025. Further, the inner surface of the interface sleeve 1004 is shown including a plurality of upper guide channels 1048 that extend from the upper end 1030 toward the lower end 1028. A plurality of longitudinally distributed spaced-apart upper locking slots 1050 are shown extending tangentially from each upper guide channel 1048.

In the example shown, the locking pins 1046, upper guide channels 1048 and upper locking slots 1050 are configured analogously to the locking pins 1038, lower guide channels 1040, and lower locking slots 1042. In use, the top sample support 1002 is positioned above the upper end 1030 of the interface sleeve 1004, as shown in FIG. 24A, and rotated to align each locking pin 1046 with an upper guide channel 1048. The top sample support 1002 can then slide into the interface sleeve 1004 with each locking pin 1046 traveling inside a corresponding upper guide channel 1048, as shown in FIG. 24C. Upper locking slots 1050 provide a plurality of resting positions at which a locking pin 1046 can be releasably engaged. The top sample support 1002 can be moved longitudinally into the interface sleeve 1004 until the tissue sample 1008 is held firmly between the top sample support 1002 and the bottom sample support 1006, as shown in FIG. 24D. The top sample support 1002 can then be rotated to move each locking pin 1046 into a corresponding upper locking slot 1050 thereby releasably engaging the top sample support 1002 with the interface sleeve 1004 and closing the upper end 1030.

As shown, the top sample support 1002 is pressed downwards so that the top sample support 1002 and the bottom sample support 1006 firmly hold the tissue sample 1008 in place. Once, the locking pins 1038 and 1046 are moved into locking slots 1042 and 1050, locking slots 1042 and 1050 lock the position of the top and bottom sample supports 1002 and 1006 relative to the interface sleeve 1004 against both radial and axial forces. This may prevent the tissue sample 1008 from shifting within the container during handling when the top and bottom sample supports 1002 and 1006 are disposed to firmly engage the tissue sample 1008. In turn, this may preserve the relationship between the tissue sample 1008 and the orientation markers 1018 and/or 1036.

FIG. 24E shows a portion of the interface sleeve 1004 at the upper end 1030. As shown, an inside of side wall 1026 is provided with upper guide channels 1048 that extend longitudinally from the upper end 1030. In the example shown, upper guide channel 1048 has a radiused inlet 1054 at the upper end 1030. This may provide for easy insertion of a locking pin 1046 of the top sample support 1002. Similarly, lower guide channels 1040 provided at the lower end 1028 may have a similarly radiused inlet. In alternative embodiments, one or more (even all) of the guide channels 1040 and 1048 does not include a radiused inlet. For example, these guide channels 1040 and/or 1048 may include inlets having square-cut corners.

In some embodiments, one or both of the top and bottom sample supports 1002 and 1006 may include gasket(s) (e.g. o-rings, not shown) to achieve a liquid seal with the interface sleeve 1004. Alternatively or in addition, the interface sleeve 1004 may include gasket(s) (not shown) to support a liquid seal with one or both of the top and bottom sample supports 1002 and 1006. In other embodiments, none of the top and bottom sample supports 1002 and 1006, and the interface sleeve 1004 may include a gasket.

Referring again to FIGS. 24A to 24D, the top sample support 1002 optionally includes a flange 1051 sized to prevent further insertion of the top sample support 1002 inside of the interface sleeve 1004. As shown, the flange 1051 extends radially outwardly from the side walls 1025 and has a diameter that is larger than the inside diameter of the side walls 1026 of the interface sleeve 1004. This may prevent the top sample support 1002 from becoming entirely received inside the interior volume 1032 of the interface sleeve 1004. In some cases, the flange 1051 provides a gripping surface for the hands of a user or the elements of a machine to grasp the top sample support 1002 (e.g. when engaging or disengaging the top sample support 1002 and the interface sleeve 1004). Still, in alternative embodiments, the top sample support 1002 may not include a flange 1051.

In the example shown, each of the top sample support 1002 and the bottom sample support 1006 can be disengaged from the interface sleeve 1004 by twisting each relative to the interface sleeve 1004 to remove the locking pins 1038 and 1046 from the locking slots 1042 and 1050 and then moving each longitudinally away from the interface sleeve 1004 to withdraw each from the interface sleeve 1004.

As shown in FIG. 24D, the base 1014, base 1020, and the optional foam layers 1012 and 1022 are concave with respect to the tissue sample 1008. This may permit the top and bottom sample supports 1002 and 1006 to keep pressure on the tissue sample 1008 directed inwards towards the central axis 1053 of the container 1000. Still, in alternative embodiments, one or more (even all) of the base 1014, base 1020, and the optional foam layers 1012 and 1022 may not be concave with respect to the tissue sample 1008. For example, one or more of the base 1014, base 1020, and the optional foam layers 1012 and 1022 may be flat or convex with respect to the tissue sample 1008.

As exemplified in FIG. 24A, each of the top sample support 1002, interface sleeve 1004, and the bottom sample support 1006 may include machine interface features 1052. The machine interface features may permit the scanning assembly 80 of the imaging system 10 to systematically grip the container so that portions of it can be removed and re-attached as part of the scanning process. In the example shown, each machine interface feature 1052 comprises a bore for receiving a corresponding post of the tissue handling system. Alternatively, or in addition, one or more of the machine interface features 1052 may have a different structure that accommodates gripping by the tissue handling system, such as outwardly extending posts for example. Still, in alternative embodiments, one or more (even all) of the top sample support 1002, interface sleeve 1004, and the bottom sample support 1006 may not include the machine interface features 1052.

As shown most clearly in FIGS. 23D and 24A, the bases 1014 and 1020 are at least permeable to air. In the example shown, each of the bases 1014 and 1020 include a plurality of vent holes 1056. This may permit ambient air to permeate the container 1000 and thereby regulate the humidity inside the container 1000. In turn, this may help to prevent condensation from forming inside of the container 1000. Condensation can appear translucent or opaque to some imaging techniques and thus interfere with capturing clear images. In some cases, the vent holes 1056 may also permit gas or fluid from the tissue sample 1008 to escape the container 1000 (e.g. during scanning). In some embodiments, one or more of the foam layers 1012 and 1022 is also permeable to air. In alternative embodiments, one or more (even all) of the bases 1014 and 1020, and the foam layers 1012 and 1022 may be impermeable to air.

It will be appreciated that locking pins and locking slots are one of many examples of mating retentive members that permit the top and bottom sample supports 1002 and 1006 to releasably engage the interface sleeve 1004. Reference is now made to FIGS. 25A and 25B, which shows a container 1100 in accordance with another embodiment. FIG. 25A shows an exploded perspective view of the container 1100. FIG. 25B shows a cross-sectional view of the container 1100 taken along line 25B-25B in FIG. 25A.

In the example shown, the container 1100 includes a top sample support 1102, an interface sleeve 1104, a bottom sample support 1106, and a bottom lid 1108. As shown, the retentive members of the container 1100 include latches 1110 that can releasably engage notches (or teeth) 1112.

The top and bottom sample supports 1102 and 1106 as shown as being structurally identical. This may permit the top and bottom sample support 1102 and 1106 to be interchangeable. In alternative embodiments, the top and bottom sample supports 1102 and 1106 may not be structurally identical and thus not interchangeable. As shown, each sample support 1102 and 1106 includes a base 1113 and side walls 1114 that depend therefrom. A pair of latches 1110 are shown extending radially outwardly of the side walls 1114 through openings 1116 in the side walls 1114. As exemplified, each pair of latches 1110 may be biased in position by a biasing member 1118.

In the example shown, each biasing member 1118 includes a gripping member 1120 and two resilient arms 1122. A latch 1110 is shown extending radially outwardly from each gripping member 1120. As shown, each gripping member 1120 is held in sliding contact with the base 1113 by a pair of catches 1123 that limits the gripping member 1120 to movement in a radial direction. As exemplified, radially inward movement of each gripping member 1120 is effected by resilient bending of the corresponding pair of resilient arms 1122. Each latch 1110 can be withdrawn radially inwardly of the side walls 1114 by applying sufficient radial inward force to the gripping member 1120 to bend the resilient arms 1122. While bent, the resilient arms 1122 exert a biasing force urging the gripping member 1120 and the latch 1110 radially outwardly to return to the resting position shown in FIGS. 25A and 25B.

The interface sleeve 1104 as shown includes side walls 1124 which extend from an open lower end 1126 to an open upper end 1128 to define an interior volume 1130. As shown, a plurality of longitudinally spaced apart arranged notches (or teeth) 1112 are provided on an interior face of the side walls 1124.

In some embodiments, the sample supports 1102 and 1106, and the interface sleeve 1104 include mating alignment ribs and alignment channels. As shown, the sample supports 1102 and 1106 include alignment ribs 1132 that extend radially outwardly of the side walls 1114. Each alignment rib 1132 is sized and positioned to be received by a corresponding alignment channel 1134 provided on an interior of the side wall 1124 of the interface sleeve 1104. Further, the interior of the side wall 1124 of the interface sleeve 1104 includes a radially inwardly extending alignment rib 1136 that also extends longitudinally along the interior of the side wall 1124 and is sized and positioned to be received by a corresponding alignment channel 1138 provided on an outside of the side walls 1114.

In some embodiments, the alignment ribs and alignment channels of the container 1100 are configured to enforce an orientation relationship between each sample support 1102 and 1106, and the interface sleeve 1104. For example, each alignment rib and/or alignment channel of each sample support 1102 or 1104 may have a 1:1 correspondence with a corresponding alignment channel and/or alignment rib of the interface sleeve 1104. This may prevent the sample support 1102 or 1104 from being inserted into the interface sleeve 1104 except when the sample support 1102 or 1104 is rotated to align the alignment channels and alignment ribs.

In use, a tissue sample 1008 (not shown) can be placed on an upper surface 1139 of the base 1113 of the bottom sample support 1106. Optionally, a layer of foam (not shown) may be positioned above the base 1113, and the tissue sample 1008 may instead be placed on the layer of foam. Next, the bottom sample support 1106 can be positioned below the interface sleeve 1104 and rotated to align the alignment ribs 1132 with the alignment channels 1134, to align the alignment rib 1136 with the alignment channel 1138 and to align the latches 1110 with the notches 1112, as shown in FIGS. 25A and 25B. Next, the gripping members 1120 of the bottom sample support 1106 can be moved radially inwardly against the bias of the resilient arms 1122 to retract the latches 1110, and the bottom sample support 1106 can be moved upwardly into the interface sleeve 1104 through the lower end 1126 until an upper wall 1140 of the bottom sample support 1106 abuts a flange 1142 that extends inwardly from the side walls 1124, as shown in FIG. 25C. As shown, the flange 1142 is positioned to permit the bottom sample support 1106 to move into the interface sleeve 1104 a sufficient distance for the latches 1110 to clear the notches 1112. Afterwards, the gripping members 1120 can be released to move the latches 1110 radially outwardly under the bias of the resilient arms 1122. Thus, the bottom sample support 1106 is constrained inside the interface sleeve 1104. Longitudinal movement is constrained by the flange 1142 and the notches 1112, and rotationally movement is constrained by the alignment rib 1136 and the alignment channels 1134.

The top sample support 1102 interacts with the interface sleeve 1104 in an analogous manner as the bottom sample support 1106. The difference is that, in the example shown, the top sample support 1102 is moved into the interface sleeve 1104 through the upper end 1128, and can be positioned at a select longitudinal position, between the upper and lower ends 1128 and 1126. The gripping members 1120 can be released to move the latches 1110 radially outwardly under the bias of the resilient arms 1122 to between a pair of longitudinally spaced notches 1112. Thus the longitudinal position of the top sample support 1102 is constrained by the interaction of the latches 1110 between respective pairs of longitudinally spaced notches 1112. In practice, the longitudinal position of the top sample support 1102 may be selected to firmly hold a tissue specimen (not shown) between the top and bottom sample supports 1102 and 1106. As with the bottom sample support 1106, the top sample support 1102 can optionally include a foam layer that makes contact with the tissue sample instead of the upper surface of the base 1113 of the top sample support 1102.

In the example shown, the top and bottom sample supports 1102 and 1106 may be disengaged from the interface sleeve 1104 by using the gripping members 1120 to retract the latches 1110, and then withdrawing the sample supports 1102 or 1104 from the interface sleeve 1104.

The container 1100 is shown including an optional bottom lid 1108. The bottom lid 1108 as shown includes a circular base 1144 and a cylindrical side wall 1146 that depends from the base 1144. The side wall 1146 is sized to receive the lower end 1126 of the interface sleeve 1104. As shown, an interior of the side wall 1146 includes a plurality of guide channels 1148 that extend downwardly from an upper end 1150. A locking slot 1152 is shown extending tangentially from a bottom of each guide channel 1148.

In the example shown, the interface sleeve 1104 includes a plurality of locking pins 1154 extending radially outwardly from its side wall 1124 proximate the lower end 1126. In use, the bottom lid 1108 is positioned below the interface sleeve 1104 and rotated to align a guide channel 1148 with each locking pin 1154. The bottom lid 1108 can then be moved upwardly to receive the lower end 1126 of the interface sleeve 1104 between its side walls 1146, and receive each locking pin 1154 in one of its guide channels 1148. Next, the bottom lid 1108 can be rotated to move each locking pin 1154 into a locking slot 1152, thereby releasably engaging the bottom lid 1108 with the interface sleeve 1104.

In some cases, the bottom lid 1108 may prevent secretions (e.g. bodily fluid or blood) from a contained tissue sample from dripping out of the container 1100. In some embodiments, the container 1100 alternatively or additionally includes a top lid (not shown) similar to the bottom lid 1108 that releasably engages locking pins 1154 extending radially outwardly from the side wall 1124 proximate the upper end 1128. A top lid may be engaged to help preserve the sterility of the container 1100 prior to use, and/or to seal a specimen in the container 1000 during transportation and storage. In some embodiments, the top and bottom lids 1108 may form a liquid and air tight seal with the interface sleeve 1104. This may permit the interior volume 1130 containing a tissue sample (not shown) to be filled with a liquid preservative (e.g. formalin) to preserve the tissue sample. In some cases, one or both of the top sample support 1102 and the bottom sample support 1106 includes vent holes 1156 which may permit a liquid preservative to be poured into the interior volume 1130 while the tissue sample is optionally held firmly in place. As described above, with respect to the vent holes 1056 of container 1000, vent holes 1156 may also help to regulate humidity inside container 1100 (e.g. to prevent condensation from interfering with a clear image capture). Still, in alternative embodiments, the container 1100 may not include a top or bottom lid.

For example, one potential usage scenario of the container 1100 would involve placement of a specimen in the container 1100, scanning of the specimen using OCT, transmission of the container 1100 (still containing the specimen) to a radiology or MRI department, scanning of the container 1100 using X-RAY or MRI while the specimen is still in the container 1100, and then the submerging of the specimen in a preserving fluid such as formalin when the specimen is a tissue sample. The top and bottom lids 1108 of the container 1100 are sealable, so that the container 1100 may allow the specimen to be held in place within formalin until the specimen is later imaged, stored or otherwise processed.

It should be noted that once the specimen in the container 1100 is scanned using another modality, in addition to OCT, the imaging data from the other modality could be co-registered with the OCT image data since the specimen may be maintained in the same position when undergoing two or more types of imaging that are different from one another due to the upper and lower surfaces of the container 1100 firmly engaging the specimen in place, the interface sleeve being transparent for these different imaging modalities and the orientation markers on one or more of the interface sleeve, the bottom sample support and the top sample support can be imaged using the different imaging modalities (i.e. the orientation markers are opaque to these imaging modalities). The user could then view the two images on the same interface. For example, if the container 1100 underwent X-ray imaging after OCT imaging, a user could view the radiograph information alongside the OCT image data in the same interface. Alternatively, if the other modality is MRI Imaging, then hi resolution data for the surface of the MRI image could be obtained by overlaying the OCT image data on the MRI image data. It should be noted that this technique may be used with the other embodiments of the containers described herein.

Reference is now made to FIGS. 26A and 26B. FIG. 26A shows a perspective view of a container 1200 in accordance with another embodiment. FIG. 26B is a cross-sectional view taken along line 26B-26B in FIG. 26A. The container 1200 is substantially similar to container 1100, with some exceptions including that container 1200 has a cuboid shape, and its top and bottom sample supports 1202 have a different biasing mechanism for biasing the latches 1204 outwardly beyond the side walls 1206.

FIG. 26C shows a perspective view of a surface of a top or bottom sample support 1202 that is opposite the surface that is adjacent to the tissue sample in use. In the example shown, the latches 1204 extend outwardly from upstanding arms 1208 which are integrally formed with the side walls 1206. As shown, each arm 1208 is cantilevered at its base 1210 to resiliently bias the latches 1204 against radial movement to the position shown. The sample support 1202 is also shown including four integrally formed arms 1212 which pivot about a central post 1214. An upstanding cam 1216 is shown extending from a distal end of each arm 1212 and being supported in position by a pair of ribs 1218. Also, a gripping member 1220 is coupled to the integrally formed arms 1212.

FIG. 26D shows a perspective view of the container 1200 in a closed configuration. In use, a tissue sample (not shown) is placed on a base 1221 of a bottom sample support 1202. As in the embodiments described above, a foam layer (not shown) may optionally be positioned on the base 1221 and the tissue sample may be instead placed on the foam layer. Afterward, the top and bottom sample supports 1202 can be moved inside the upper and lower ends 1223 and 1224 of the interface sleeve 1226. The gripping member 1220 can then be grasped to rotate the arms 1212 about the post 1214. As shown, when the arms 1212 are rotated clockwise, each cam 1216 makes sliding contact with a radially inward protrusion 1228 on an upper end of each arm 1208. This contact urges each arm 1208 to bend radially outwardly, and in turn moves each latch 1204 radially outwardly into engagement with the notches (or teeth) 1222 of the interface sleeve 1226.

In the example shown, each arm 1212 includes a locking slot 1230 that is sized and positioned to mate with a corresponding locking pin 1232, which extends from a base 1221 of the sample support 1202. When the arms 1212 are rotated about the post 1214 to urge the latches 1204 to move radially outwardly, the locking slot 1230 receives the locking pin 1232 to lock the rotary position of the arms 1212. To disengage the sample support 1202 from the interface sleeve 1226, a user can grasp the gripping member 1220 to rotate the arms 1212 counterclockwise separating the locking slot 1230 from the locking pin 1232, separating the cam 1216 from the protrusion 1228, retracting the latches 1204 by the bias of the cantilevered arms 1208, and disengaging the latches 1204 from the notches 1222. Afterward, the sample support 1202 can be withdrawn from the interface sleeve 1226.

FIG. 26E shows a perspective view of a sample support 1300 in accordance with another embodiment. In some embodiments, the sample support 1300 substitutes one or both of the top and bottom sample support 1202 of the container 1200.

In the example shown, the sample support 1300 includes side walls 1302 sized and shaped to be received inside the interface sleeve 1226. The side walls 1302 as shown include a plurality of openings 1304, each of which is sized to receive a corresponding latch 1306. As shown, each latch 1306 extends radially outwardly of a central biasing member 1308 that biases the latches 1306 against radial movement to the position shown.

The biasing member 1308 as exemplified includes a generally rectangular frame 1310 that is secured to a base 1312 by a plurality of pairs of catches 1314. As shown, each pair of catches 1314 holds an arm 1316 in sliding contact with the base 1312. Further, each arm 1316 is shown connecting a corresponding latch 1306 to the frame 1310. Thus, the catches 1314 may restrict the movement of the arms 1316 and the latches 1306 to the radial direction.

In the example shown, the sample support 1300 also includes a rectangular cam 1318 that is rotatably mounted at its center to the base 1312. A gripping member 1320 is shown connected to the cam 1318 to facilitate hand-rotation of the cam 1318. In the example shown, the gripping member 1320 is formed by upstanding panels 1322 which extend from opposite sides of the cam 1318. As exemplified, the cam 1318 is sized and shaped to make sliding contact with the frame 1310 when rotated to bend the frame 1310 and urge the arms 1316 and the latches 1306 to move radially outwardly. In use, the gripping member 1320 can be manipulated to rotate the cam 1318 to urge the latches 1306 to move radially outwardly and engage the notches (or teeth) 1222 of the interface sleeve 1226. The gripping member 1320 can also be manipulated to rotate the cam 1318 out of contact with the frame 1310 to withdraw the latches 1306 under the bias of the frame 1310 and disengage the notches (or teeth) 1222.

While the applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without generally departing from the embodiments described herein.

The invention claimed is:

1. A method for generating a wide field optical coherence tomography (OCT) image of a portion of a sample, wherein the method comprises:
    creating a surface map of the sample;
    acquiring raw OCT data of the portion of the sample based on the surface map by identifying an initial scan position and a final scan position on the surface map, the initial scan position corresponding to a highest point of the surface of the portion of the sample and the final scan position corresponding to a lowest point of the surface of the portion of the sample, and for a given set of vertical OCT images, acquiring the raw OCT data to generate at least a first OCT image with an upper edge of an imaging window aligned with the initial scan position and a second OCT image with an upper edge of an imaging window aligned with the final scan position;
    generating a plurality of OCT images from the raw OCT data; and
    combining two or more OCT images of the plurality of OCT images to create the wide field OCT image.

2. The method of claim 1, wherein acquiring the raw OCT data further comprises:
    operating a scanning head to capture the raw OCT data; and
    adjusting a position of the scanning head with respect to a surface of the sample based on at least one of the surface map and OCT imaging parameters for the wide field OCT image.

3. The method of claim 2, further comprising adjusting the position of the scanning head from a first position to a second position that is different from the first position to accommodate unevenness at a surface of the portion of the sample.

4. The method of claim 1, wherein the focus used to acquire the raw OCT data used to generate the OCT images is substantially constant.

5. The method of claim 1, wherein the method further comprises detecting a surface position for each OCT image.

6. The method of claim 5, wherein detecting the surface position for a given OCT image comprises:
    identifying a signal portion associated with the given OCT image having a highest intensity value; and
    associating a depth position corresponding to the signal portion having the highest intensity value as the surface position.

7. The method of claim 1, wherein combining two or more OCT images comprises:
    aligning the first OCT image with a neighbouring OCT image; and
    overlaying a portion of the first OCT image over a portion of the neighbouring OCT image to create a composite OCT image.

8. The method of claim 7, wherein at least one of the first OCT image and the neighbouring OCT image is a composite OCT image resulting from the combination of at least two other OCT images.

9. The method of claim 7, wherein the neighbouring OCT image corresponds to a first section of a surface of the sample and the first OCT image corresponds to a second section of the surface of the sample that is different from the first section.

10. The method of claim 9, wherein the second section and the first section are from a horizontal image set obtained from the sample.

11. The method of claim 7, wherein the neighbouring OCT image and the first OCT image correspond to the same section of a surface of the sample and different depth positions of the sample.

12. The method of claim 7, wherein combining two or more OCT images further comprises:
    creating a plurality of intermediary composite images by overlaying a portion of the first OCT image over a portion of the neighbouring image, wherein each intermediary composite image includes a different amount of overlap between the OCT image and the neighbouring image;
    determining an entropy associated with each intermediary composite image; and
    selecting the intermediary composite image associated with a lowest entropy value as the composite OCT image for the first OCT image and the neighbouring OCT image and recording the amount of overlap associated with the selected intermediary composite image.

13. The method of claim 12, wherein combining two or more OCT images further comprises:
    identifying a focused portion in each of the first OCT image and the neighbouring OCT image based on the respective surface positions;
    overlaying the first OCT image and the neighbouring OCT image based on the recorded amount of overlap; and
    retaining, in the composite OCT image, only the focused portions from each of the first OCT image and the neighbouring OCT image.

14. The method of claim 1, wherein acquiring the raw OCT data further comprises minimizing saturation effects in at least one OCT image of the plurality of OCT images by:
    detecting a noise signal at a region proximate to an external surface of the sample in the at least one OCT image;

determining whether an intensity of the noise signal exceeds an intensity threshold; and adjusting characteristics of the at least one OCT image to reduce the intensity of the noise signal when the intensity of the noise signal exceeds the intensity threshold.

15. A system for generating a wide field optical coherence tomography (OCT) image of a portion of a sample, wherein the system comprises:

an input port for receiving raw OCT data;

an image processing module being configured to process the raw OCT data to generate wide field OCT images by creating a surface map of the sample; acquiring raw OCT data of the portion of the sample based on the surface map by identifying an initial scan position and a final scan position on the surface map, the initial scan position corresponding to a highest point of the surface of the portion of the sample and the final scan position corresponding to a lowest point of the surface of the portion of the sample, and for a given set of vertical OCT images, acquiring the raw OCT data to generate at least a first OCT image with an upper edge of an imaging window aligned with the initial scan position and a second OCT image with an upper edge of an imaging window aligned with the final scan position; generating a plurality of OCT images from the raw OCT data; and combining two or more OCT images of the plurality of OCT images to create the wide field OCT image; and an output port to provide the wide-field OCT images to one of a user, a storage device and another computing device.

16. The system of claim 15, wherein the image processing module is configured to acquire the raw OCT data by:

operating a scanning head to capture the raw OCT data;

adjusting a position of the scanning head with respect to a surface of the sample based on at least one of the surface map and OCT imaging parameters for the wide field OCT image; and adjusting the position of the scanning head from a first position to a second position that is different from the first position to accommodate unevenness at a surface of the portion of the sample.

17. The system of claim 15, wherein the image processing module is configured to maintain a substantially constant focus to acquire the raw OCT data used to generate the OCT images.

18. The system of claim 15, wherein the image processing module is configured to detect a surface position for each OCT image by:

identifying a signal portion associated with the given OCT image having a highest intensity value; and associating a depth position corresponding to the signal portion having the highest intensity value as the surface position.

19. The system of claim 15, wherein the image processing module is configured to combine two or more OCT images by:

aligning the first OCT image with a neighbouring OCT image; and overlaying a portion of the first OCT image over a portion of the neighbouring OCT image to create a composite OCT image.

20. The system of claim 19, wherein at least one of the first OCT image and the neighbouring OCT image is a composite OCT image resulting from the combination of at least two other OCT images.

21. The system of claim 19, wherein the neighbouring OCT image corresponds to a first section of a surface of the sample and the first OCT image corresponds to a second section of the surface of the sample that is different from the first section, and wherein the second section and the first section are from a horizontal image set obtained from the sample.

22. The system of claim 19, wherein the neighbouring OCT image and the first OCT image correspond to the same section of a surface of the sample and different depth positions of the sample.

23. The system of claim 19, wherein the image processing module is configured to combine two or more OCT images further by:

creating a plurality of intermediary composite images by overlaying a portion of the first OCT image over a portion of the neighbouring image, wherein each intermediary composite image includes a different amount of overlap between the OCT image and the neighbouring image;

determining an entropy associated with each intermediary composite image; and selecting the intermediary composite image associated with a lowest entropy value as the composite OCT image for the first OCT image and the neighbouring OCT image and recording the amount of overlap associated with the selected intermediary composite image.

24. The system of claim 23, wherein the image processing module is further configured to combine the two or more OCT images by:

identifying a focused portion in each of the first OCT image and the neighbouring OCT image based on the respective surface positions;

overlaying the first OCT image and the neighbouring OCT image based on the recorded amount of overlap; and retaining, in the composite OCT image, only the focused portions from each of the first OCT image and the neighbouring OCT image.

25. The system of claim 15, wherein the image processing module is configured to acquire the raw OCT data further by minimizing saturation effects in at least one OCT image of the plurality of OCT images by:

detecting a noise signal at a region proximate to an external surface of the sample in the at least one OCT image;

determining whether an intensity of the noise signal exceeds an intensity threshold; and adjusting characteristics of the at least one OCT image to reduce the intensity of the noise signal when the intensity of the noise signal exceeds the intensity threshold.

26. A non-transitory computer-readable medium storing computer-executable instructions, the instructions for causing an image processing module to perform a method for generating a wide field optical coherence tomography (OCT) image of a portion of a sample, wherein the method comprises:

creating a surface map of the sample;

acquiring raw OCT data of the portion of the sample based on the surface map by identifying an initial scan position and a final scan position on the surface map, the initial scan position corresponding to a highest point of the surface of the portion of the sample and the final scan position corresponding to a lowest point of the surface of the portion of the sample and for a given set of vertical OCT images, acquiring the raw OCT data to generate at least a first OCT image with an upper edge of an imaging window aligned with the initial scan position and a second OCT image with an upper edge of an imaging window aligned with the final scan position;

generating a plurality of OCT images from the raw OCT data; and combining two or more OCT images of the plurality of OCT images to create the wide field OCT image.

27. A method for generating a wide field optical coherence tomography (OCT) image of a portion of a sample, wherein the method comprises:

receiving a set of OCT images corresponding to the portion of the sample, the set of OCT images including a first OCT image and a neighbouring OCT image;

aligning the first OCT image with the neighbouring OCT image; and overlaying a portion of the first OCT image over a portion of the neighbouring OCT image to create the wide field OCT image by (1) creating a plurality of intermediary composite images based on the first OCT image and the neighbouring image, each intermediary composite image having a different amount of overlap between the OCT image and the neighbouring image, (2) determining an entropy associated with the overlap in each intermediary composite image; and (3) selecting the intermediary composite image associated with a lowest entropy value as the wide field OCT image for the first OCT image and the neighbouring OCT image and recording the overlap.

28. The method of claim 27, wherein the neighbouring OCT image corresponds to a first section of a surface of the sample and the first OCT image corresponds to a second section of the surface of the sample that is different from the first section, the second section and the first section are from a horizontal image set obtained from the sample and the method comprises using horizontal stitching to create the wide field OCT image.

29. The method of claim 27, wherein the neighbouring OCT image and the first OCT image correspond to the same section of a surface of the sample and different depth positions of the sample and the method comprises using vertical stitching to create the wide field OCT image.

30. The method of claim 27, wherein overlaying the portion of the first OCT image over the portion of the neighbouring OCT image further comprises:

identifying a focused portion in each of the first OCT image and the neighbouring OCT image based on respective surface positions;

overlaying the first OCT image and the neighbouring OCT image based on the recorded overlap to generate the wide field OCT image; and retaining, in the wide field OCT image, only the focused portions from each of the first OCT image and the neighbouring OCT image.

31. A method for generating a wide field optical coherence tomography (OCT) image of a portion of a sample, wherein the method comprises:

creating a surface map of the sample;

acquiring raw OCT data of the portion of the sample based on the surface map;

generating a plurality of OCT images from the raw OCT data;

combining two or more OCT images of the plurality of OCT images to create the wide field OCT image by:

aligning a first OCT image with a neighbouring OCT image;

creating a plurality of intermediary composite images by overlaying a portion of the first OCT image over a portion of the neighbouring image, wherein each intermediary composite image includes a different amount of overlap between the OCT image and the neighbouring image;

determining an entropy associated with each intermediary composite image; and selecting the intermediary composite image associated with a lowest entropy value as the composite OCT image for the first OCT image and the neighbouring OCT image and recording the amount of overlap associated with the selected intermediary composite image.

32. A system for generating a wide field optical coherence tomography (OCT) image of a portion of a sample, wherein the system comprises:

an input port for receiving raw OCT data;

an image processing module being configured to process the raw OCT data to generate wide field OCT images by creating a surface map of the sample; acquire raw OCT data of the portion of the sample based on the surface map; generate a plurality of OCT images from the raw OCT data; and combine two or more OCT images of the plurality of OCT images to create the wide field OCT image by:

aligning the first OCT image with a neighbouring OCT image;

overlaying a portion of the first OCT image over a portion of the neighbouring OCT image to create a composite OCT image;

creating a plurality of intermediary composite images by overlaying a portion of the first OCT image over a portion of the neighbouring image, wherein each intermediary composite image includes a different amount of overlap between the OCT image and the neighbouring image;

determining an entropy associated with each intermediary composite image; and selecting the intermediary composite image associated with a lowest entropy value as the composite OCT image for the first OCT image and the neighbouring OCT image and recording the amount of overlap associated with the selected intermediary composite image; and an output port to provide the wide-field OCT images to one of a user, a storage device and another computing device.

* * * * *